(12) United States Patent
Pearse et al.

(10) Patent No.: US 11,958,908 B2
(45) Date of Patent: *Apr. 16, 2024

(54) COMPOSITIONS AND METHODS FOR THE DEPLETION OF CD117+ CELLS

(71) Applicant: CRISPR THERAPEUTICS AG, Zug (CH)

(72) Inventors: Bradley R. Pearse, Watertown, MA (US); Michael Cooke, Brookline, MA (US); Anthony Boitano, Newton, MA (US); Rahul Palchaudhuri, Somerville, MA (US); Sean McDonough, Littleton, MA (US); Rajiv Panwar, Acton, MA (US); Jacob Glanville, South San Francisco, CA (US)

(73) Assignee: CRISPR THERAPEUTICS AG, Zug (CH)

( * ) Notice: Subject to any disclaimer, the term of this patent is extended or adjusted under 35 U.S.C. 154(b) by 137 days.

This patent is subject to a terminal disclaimer.

(21) Appl. No.: 17/103,866

(22) Filed: Nov. 24, 2020

(65) Prior Publication Data

US 2021/0206872 A1 Jul. 8, 2021

Related U.S. Application Data

(63) Continuation of application No. 16/168,823, filed on Oct. 23, 2018, now Pat. No. 10,899,843.

(Continued)

(51) Int. Cl.
*C07K 16/28* (2006.01)
*A61K 35/545* (2015.01)
(Continued)

(52) U.S. Cl.
CPC ........ *C07K 16/2896* (2013.01); *A61K 35/545* (2013.01); *A61K 47/6817* (2017.08);
(Continued)

(58) Field of Classification Search
None
See application file for complete search history.

(56) References Cited

U.S. PATENT DOCUMENTS

| 5,808,002 A | 9/1998 | Buhring et al. |
| 7,915,391 B2 | 3/2011 | Ng et al. |

(Continued)

FOREIGN PATENT DOCUMENTS

| EP | 1859811 B1 | 8/2011 |
| WO | 2007127317 A2 | 11/2007 |

(Continued)

OTHER PUBLICATIONS

Palchaudhuri et al., "Non-genotoxic conditioning for hematopoietic stem cell transplantation using a hematopoietic-cell-specific internalizing immunotoxin," Nat Biotechnol. 34(7):738-45 (22 pages) (2016).

(Continued)

*Primary Examiner* — Karl J Puttlitz
(74) *Attorney, Agent, or Firm* — Casimir Jones, S.C.; J. Mitchell Jones

(57) ABSTRACT

The invention provides compositions and methods useful for the depletion of CD117+ cells and for the treatment of various hematopoietic diseases, metabolic disorders, cancers, e.g., acute myeloid leukemia (AML) and autoimmune diseases, among others. Described herein are antibodies, antigen-binding fragments, and conjugates thereof that can be applied to effect the treatment of these conditions, for instance, by depleting a population of CD117+ cells in a patient, such as a human. The compositions and methods described herein can be used to treat a disorder directly, for instance, by depleting a population of CD117+ cancer cells or autoimmune cells. The compositions and methods described herein can also be used to prepare a patient for hematopoietic stem cell transplant therapy and to improve (Continued)

the engraftment of hematopoietic stem cell transplants by selectively depleting endogenous hematopoietic stem cells prior to the transplant procedure.

26 Claims, 37 Drawing Sheets

Specification includes a Sequence Listing.

Related U.S. Application Data

(60) Provisional application No. 62/638,053, filed on Mar. 2, 2018, provisional application No. 62/632,967, filed on Feb. 20, 2018, provisional application No. 62/596,569, filed on Dec. 8, 2017, provisional application No. 62/576,572, filed on Oct. 24, 2017.

(51) Int. Cl.

| | |
|---|---|
| *A61K 47/68* | (2017.01) |
| *A61P 35/00* | (2006.01) |
| *A61P 37/06* | (2006.01) |
| *C07K 7/64* | (2006.01) |
| *A61K 35/12* | (2015.01) |
| *A61K 38/00* | (2006.01) |
| *A61K 39/00* | (2006.01) |

(52) U.S. Cl.
CPC ...... *A61K 47/6831* (2017.08); *A61K 47/6849* (2017.08); *A61P 35/00* (2018.01); *A61P 37/06* (2018.01); *C07K 7/64* (2013.01); *C07K 16/2803* (2013.01); *A61K 2035/124* (2013.01); *A61K 38/00* (2013.01); *A61K 2039/505* (2013.01); *C07K 2317/21* (2013.01); *C07K 2317/52* (2013.01); *C07K 2317/55* (2013.01); *C07K 2317/71* (2013.01); *C07K 2317/73* (2013.01); *C07K 2317/92* (2013.01); *C07K 2317/94* (2013.01)

(56) References Cited

U.S. PATENT DOCUMENTS

| | | |
|---|---|---|
| 8,119,130 B2 | 2/2012 | Barry et al. |
| 10,111,966 B2 | 10/2018 | Nixon et al. |
| 10,280,225 B2 | 5/2019 | Scadden et al. |
| 10,570,207 B2 | 2/2020 | Scadden et al. |
| 2002/0127606 A1 | 9/2002 | Fritz et al. |
| 2003/0022345 A1 | 1/2003 | Olsen et al. |
| 2004/0067532 A1 | 4/2004 | Zhu et al. |
| 2008/0213251 A1 | 9/2008 | Sexton et al. |
| 2009/0318297 A1 | 12/2009 | Cappucilli et al. |
| 2010/0119516 A1 | 5/2010 | Wu et al. |
| 2010/0226927 A1 | 9/2010 | Weissman et al. |
| 2012/0288506 A1 | 11/2012 | Amatulli et al. |
| 2013/0004500 A1 | 1/2013 | Tanaka et al. |
| 2014/0193899 A1 | 7/2014 | Kim et al. |
| 2016/0151515 A1 | 6/2016 | Joubert et al. |
| 2016/0177390 A1 | 6/2016 | Feng et al. |
| 2016/0264651 A1 | 9/2016 | Freimoser-Grundschober et al. |
| 2017/0073414 A1 | 3/2017 | Weiskopf et al. |
| 2017/0114141 A1 | 4/2017 | Amann et al. |
| 2017/0121409 A1 | 5/2017 | Verona et al. |
| 2018/0043033 A1* | 2/2018 | Anderl ............... A61K 47/6831 |
| 2018/0127497 A1 | 5/2018 | Malik et al. |
| 2018/0193475 A1 | 7/2018 | Abrams et al. |
| 2019/0153114 A1 | 5/2019 | Pearse et al. |
| 2020/0148776 A1 | 5/2020 | Scadden et al. |

FOREIGN PATENT DOCUMENTS

| | | |
|---|---|---|
| WO | 2010115629 A3 | 4/2010 |
| WO | 2012041504 A1 | 4/2012 |
| WO | 2012119787 A1 | 9/2012 |
| WO | 2014135282 A1 | 9/2014 |
| WO | 2015057942 A1 | 4/2015 |
| WO | 2016071856 A1 | 5/2016 |
| WO | 2016142049 A1 | 9/2016 |
| WO | 2016164502 | 10/2016 |
| WO | 2016164637 A1 | 10/2016 |
| WO | 2016164745 A1 | 10/2016 |
| WO | 2017046658 A1 | 3/2017 |
| WO | 2017134197 A1 | 8/2017 |
| WO | 2017191579 A1 | 11/2017 |
| WO | 2017219029 A8 | 12/2017 |
| WO | 2018183613 A1 | 10/2018 |

OTHER PUBLICATIONS

Hamblett et al., Clinical Cancer Research, 2004, vol. 10, pp. 7063-7070.
Holliger and Hudson, Nature Biotechnology, 2005, vol. 23. pp. 1126-1136.
Abstract of Reis et al., Blood, 2015, vol. 126, No. 23, p. 2580.
Abrams et al., "Preclinical Antitumor Activity of a Novel Anti-c-KIT Antibody-Drug Conjugate against Mutant and Wild-type c-KIT-Positive Solid Tumors." Clin Cancer Res. vol. 24(17) p. 4297-4308 (2018).
LeFranc, MP. "Immunoglobulin and T cell receptor genes: IMGT® and the birth and rise of immunoinformatics." Frontiers in immunology, 2014 vol. 5, No. 22.

* cited by examiner

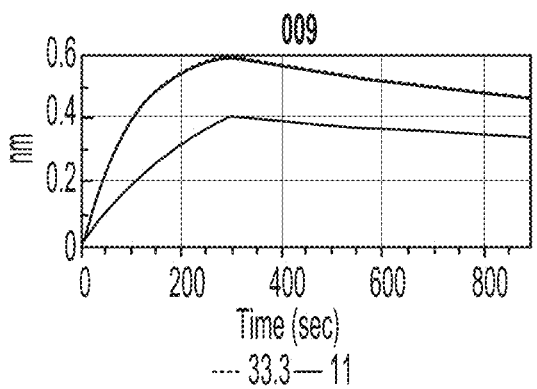
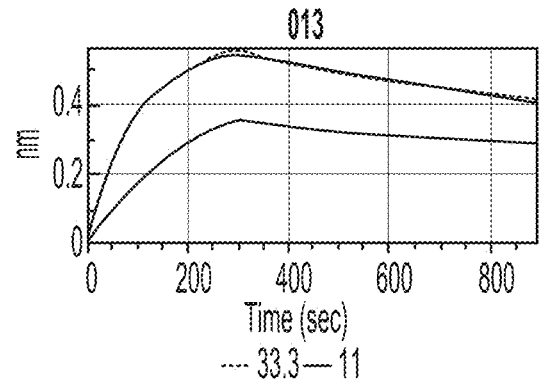
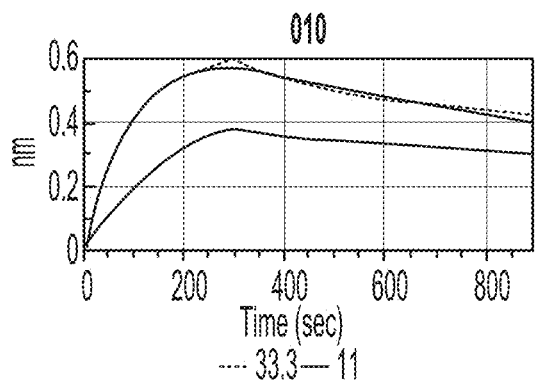
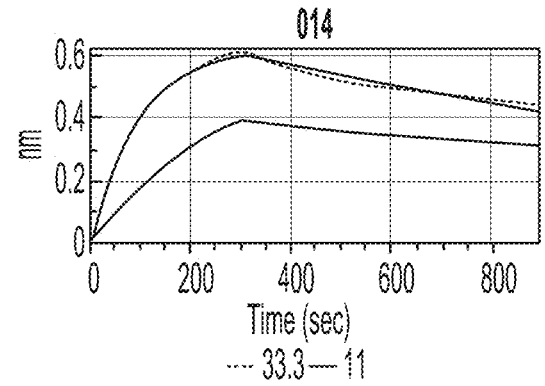
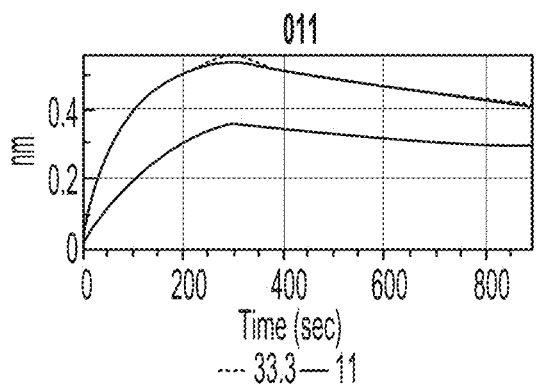
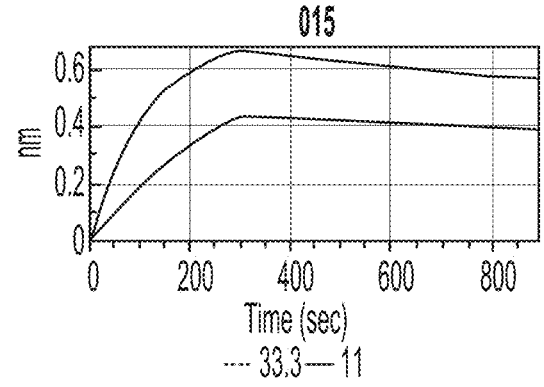
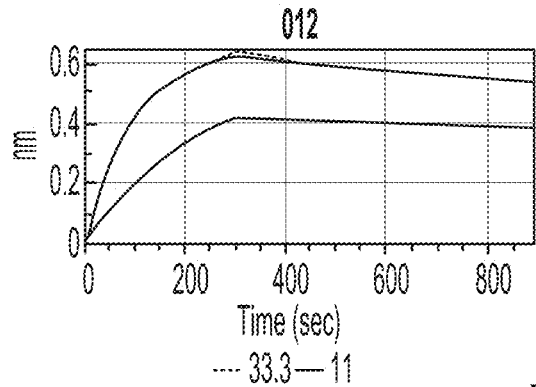
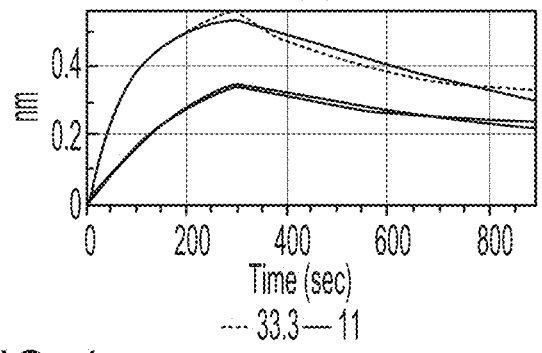
FIG. 1
CONTINUED

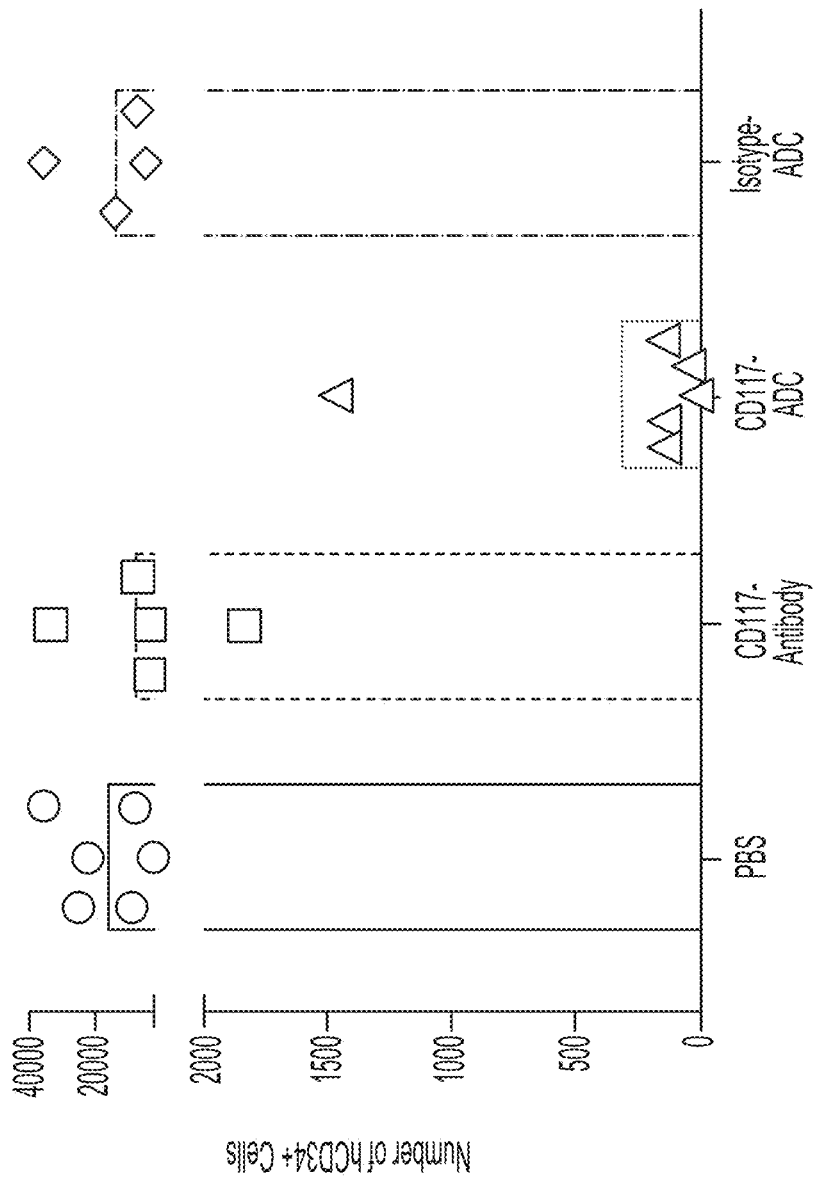

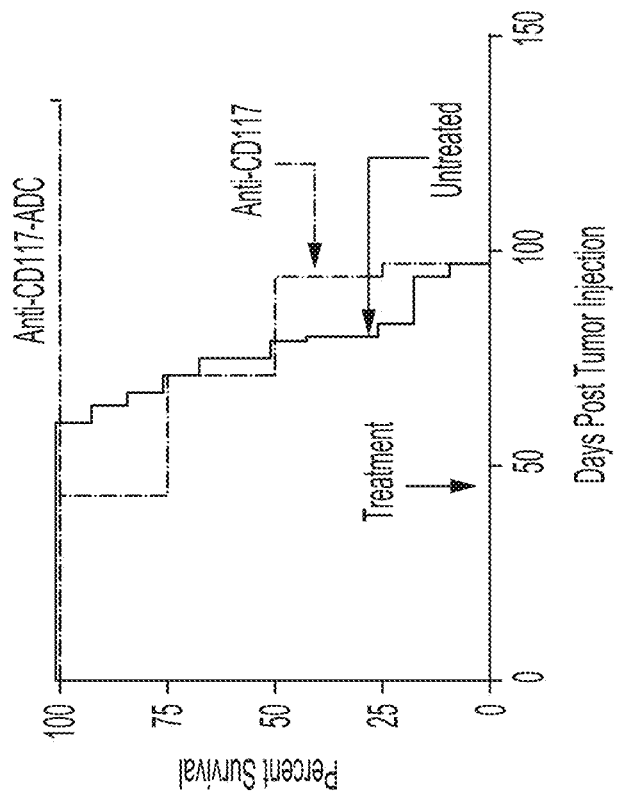
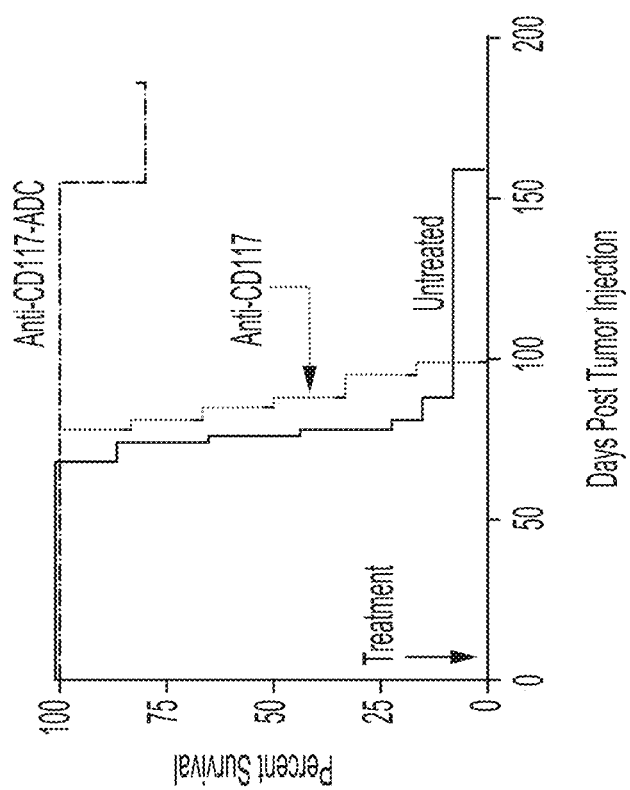
FIG. 4D
FIG. 4C

VH domains:

CK6   QVQLVQSGAEVKKPGESLKISCKGSGYRFTSYWIGWVRQMPGKGLEWMGIIYPGDSDTRYSPSFQGQVTISAGKSISTAYLQWSSLKASDTAMYYCARHGRGYNCYEGAFDIWGQGTMVTVSS
Ab85  EVQLVQSGAEVKKPGESLKISCKGSGYSFTNYWIGWVRQMPGKGLEWMAINPRDSDTRYRPSFQGQVTISADKSISTAYLQWSSLKASDTAMYYCARHGRGYEYEGAFDIWGQGTLVTVSS

FIG. 11A

VL domains:

CK6   AIQLTQSPSSLSASVGDRVTITCRASQGISSALAWYQQKPGKAPKLLIYDASSLESGVPSRFSGSGSGTDFTLTISSLQPEDFATYYCQQFNSYPLTFGGGTKVEIK
Ab85  DIQMTQSPSSLSASVGDRVTITCSSQGIRSDLGWYQQKPGKAPKLLIYDASNLETGVPSRFSGSGSGTDFTLTISSLQPEDFATYYCQQANGFPLTFGGGTKVEIK

FIG. 11B

VH domains:

CK6   QVQLVQSGAEVKKPGESLKISCKGSGYRFTSYWIGWVRQMPGKGLEWMGIIYPGDSDTRYSPSFQGQVTISAGKSISTAYLQWSSLKASDTAMYYCARHGRGYNCYEGAFDIWGQGTMVTVSS
Ab249 EVQLVQSGAEVKKPGESLKISCKGSGYRFTTSWIGWVRQMPGKGLEWMGIIYPGDSDTRYSPSFQGQVTISADKSISTAYLQWSSLKASDTAMYYCARHGLGYNGYEGAFDIWGQGTLVTVSS

FIG. 11C

VL domains:

CK6   AIQLTQSPSSLSASVGDRVTITCRASQGISSALAWYQQKPGKAPKLLIYDASSLESGVPSRFSGSGSGTDFTLTISSLQPEDFATYYCQQFNSYPLTFGGGTKVEIK
Ab249 DIQMTQSPSSLSASVGDRVTITCRASQGIGSSALAWYQQKPGKAPKLLIYDASNLETGVPSRFSGSGSGTDFTLTISSLQPEDFATYYCQQLNGYPLTFGGGTRLEIK

FIG. 11D

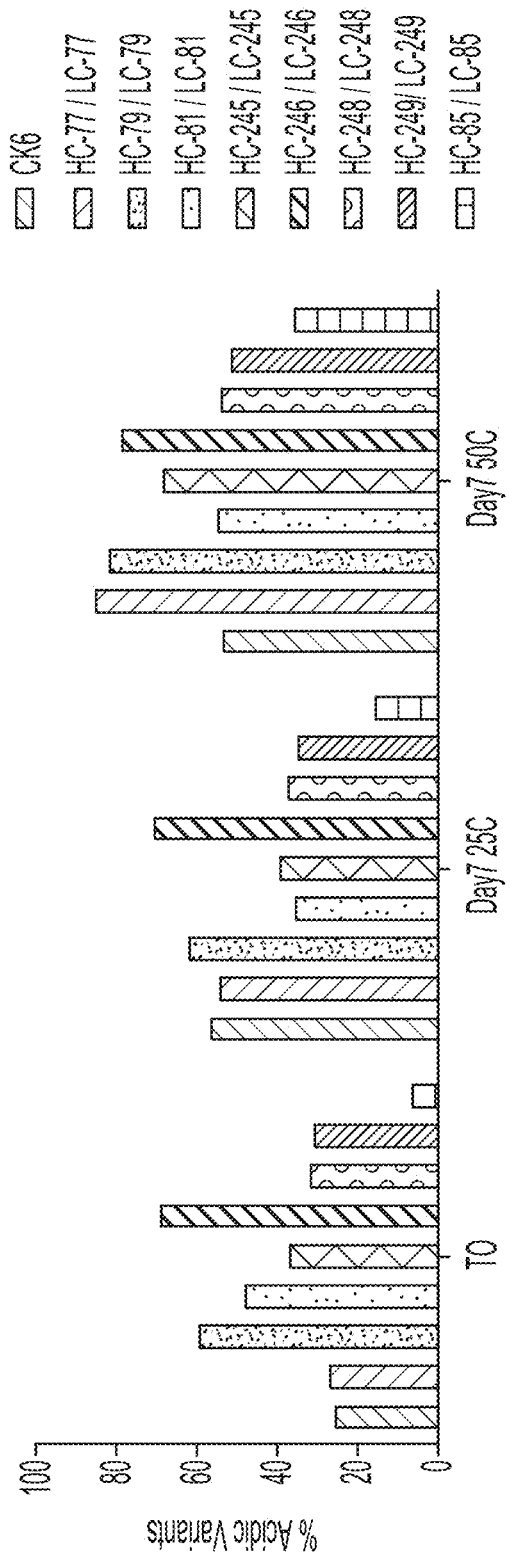
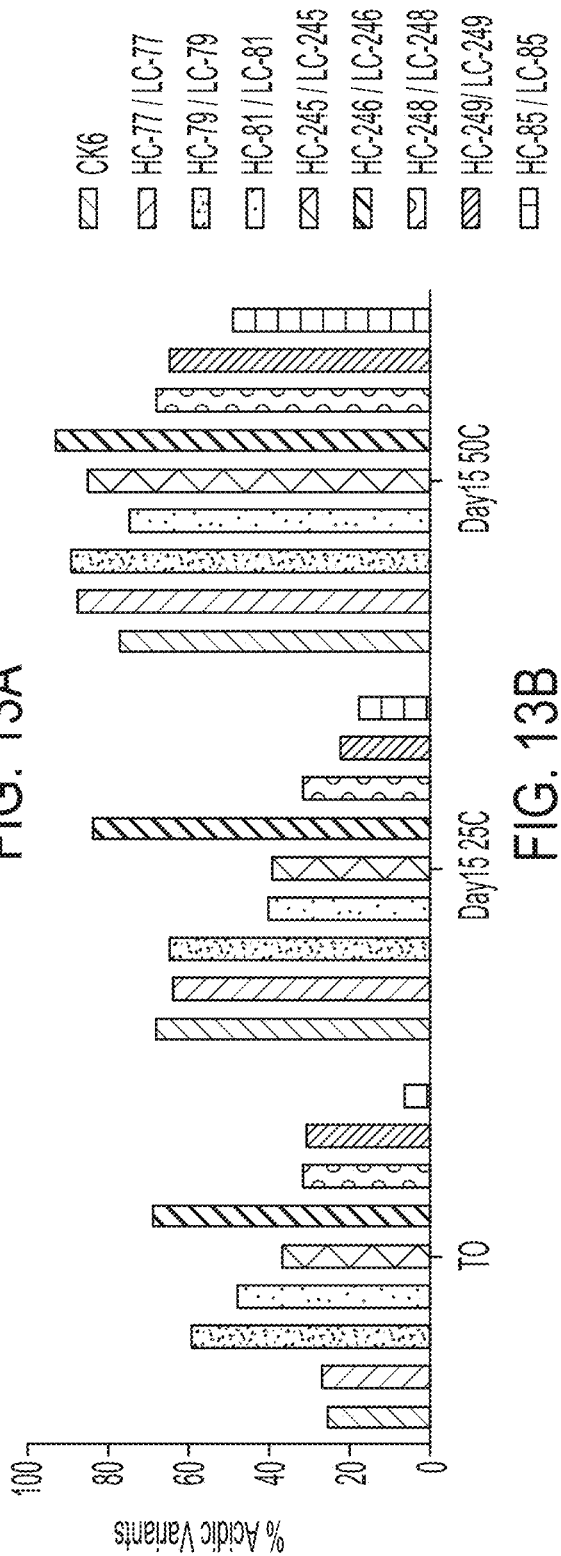
FIG. 13A
FIG. 13B

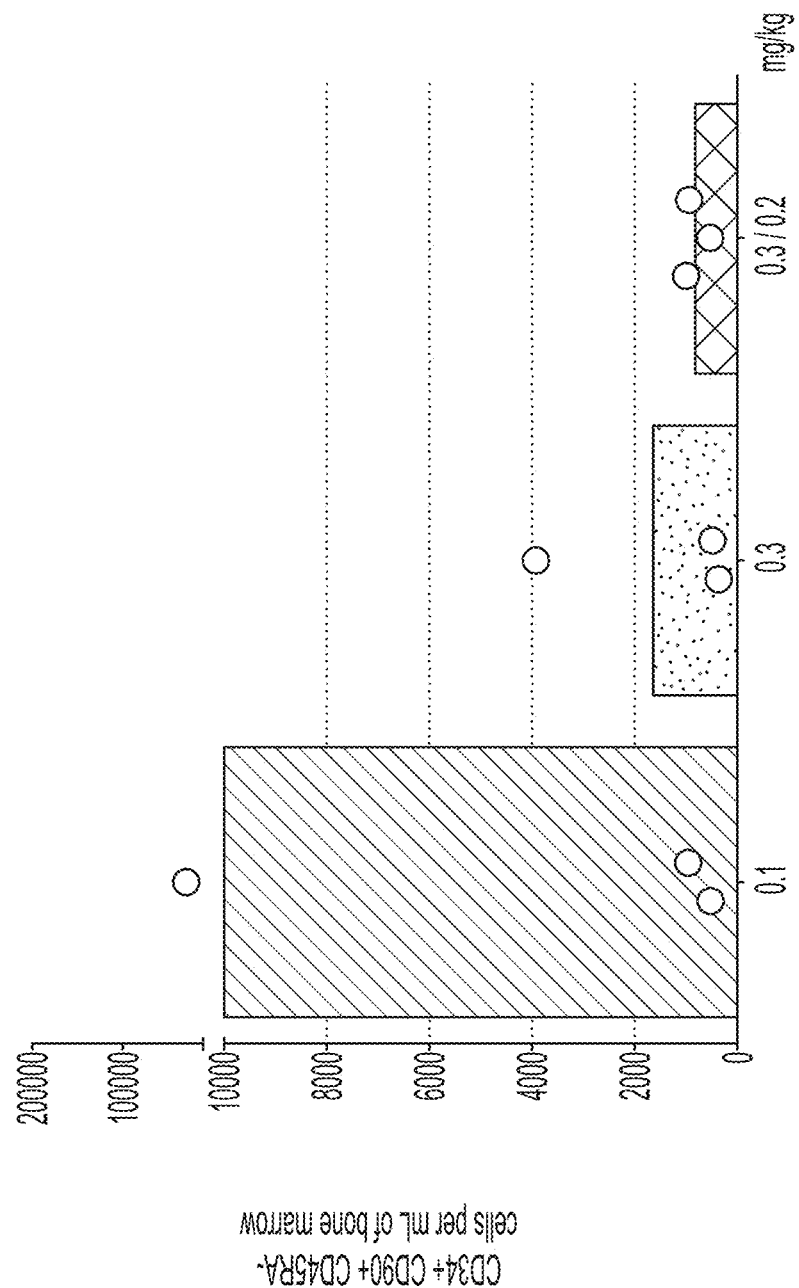

SEQUENCE LISTING

```
<160> NUMBER OF SEQ ID NOS: 189

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Tyr Trp Ile Gly
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Ile Tyr Pro Gly Asp Ser Asp Thr Arg Tyr Ser Pro Ser Phe Gln
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Gly Arg Gly Tyr Asn Gly Tyr Glu Gly Ala Phe Asp Ile
1               5                   10

<210> SEQ ID NO 4
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Gly Ile Ser Ser Ala Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ala Ser Ser Leu Glu Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Gln Gln Phe Asn Ser Tyr Pro Leu Thr
1               5                   10

<210> SEQ ID NO 7
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Ala Val Lys Lys Pro Gly Glu
1               5                   10                  15

Ser Leu Lys Ile Ser Cys Lys Gly Ser Gly Tyr Arg Phe Thr Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Gly Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Met Val Thr Val Ser Ser
        115                 120

<210> SEQ ID NO 8
<211> LENGTH: 107
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 8

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Thr Asp
            20                  25                  30

Leu Gly Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Ala Trp Tyr Gln Gln Lys Pro Gly Lys Thr Pro Lys Leu Leu Ile
        35                  40                  45
```

Tyr Asp Ala Ser Ser Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Asp Ile Lys
            100                 105

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asn Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Ser Asp Tyr
            20                  25                  30

Leu Ala Trp Phe Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105

<210> SEQ ID NO 13

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Ile Arg Met Thr Gln Ser Pro Ser Ser Leu Ser Ala Ser Val Gly
1               5                   10                  15

Asp Arg Val Ile Ile Ala Cys Arg Ala Ser Gln Gly Ile Gly Gly Ala
            20                  25                  30

Leu Ala Trp Tyr Gln Gln Lys Pro Gly Asn Ala Pro Lys Val Leu Val
        35                  40                  45

Tyr Asp Ala Ser Thr Leu Glu Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Leu Glu Ile Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Ala Met Thr Gln Ser Pro Ser Leu Ser Ala Phe Val Gly
1               5                   10                  15

Asp Arg Val Thr Ile Thr Cys Arg Ala Ser Gln Gly Ile Ile Ser Ser
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Arg Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Leu Glu Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

```
Leu Ala Trp Tyr Gln Gln Lys Ala Gly Lys Ala Pro Lys Val Leu Ile
            35                  40                  45

Ser Asp Ala Ser Ser Leu Glu Ser Gly Val Pro Ser Arg Phe Ser Gly
 50                  55                  60

Ser Gly Ser Gly Thr Asp Phe Thr Leu Ser Ile Ser Ser Leu Gln Pro
65                  70                  75                  80

Glu Asp Phe Ala Thr Tyr Tyr Cys Gln Gln Phe Asn Gly Tyr Pro Leu
                85                  90                  95

Thr Phe Gly Gly Gly Thr Lys Val Asp Ile Lys
            100                 105
```

```
<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Ile Arg Met Thr Gln Ser Pro Ser Ser Leu Ser Ala Ser Val Gly
1               5                   10                  15

Asp Arg Val Thr Ile Thr Cys Gln Ala Ser Gln Gly Ile Arg Asn Asp
            20                  25                  30

Leu Gly Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Phe Asn Ser Tyr Pro Leu
                85                  90                  95

Thr Phe Gly Gly Gly Thr Lys Leu Glu Ile Lys
            100                 105
```

```
<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asn Ile Gln Met Thr Gln Ser Pro Ser Ser Leu Ser Thr Ser Val Gly
1               5                   10                  15

Asp Arg Val Thr Ile Thr Cys Arg Ala Ser Gln Gly Ile Gly Thr Ser
            20                  25                  30

Leu Ala Trp Tyr Gln Gln Lys Pro Gly Lys Pro Pro Lys Leu Leu Ile
            35                  40                  45

Tyr Asp Ala Ser Ser Leu Glu Ser Gly Val Pro Ser Arg Leu Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Tyr Pro Ile
                85                  90                  95

Thr Phe Gly Gln Gly Thr Arg Leu Glu Ile Lys
            100                 105
```

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Asp Tyr
            20                  25                  30

Leu Thr Trp Tyr Gln Gln Lys Pro Gly Lys Ala Pro Lys Val Leu Ile
        35                  40                  45

Tyr Gly Ala Ser Ser Leu Gln Ser Gly Val Pro Pro Arg Phe Ser Gly
    50                  55                  60

Ser Gly Ser Gly Thr Asp Phe Thr Leu Thr Val Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Leu Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Arg Ser Thr
            20                  25                  30

Leu Ala Trp Tyr Gln Gln Lys Pro Gly Lys Ala Pro Lys Leu Leu Ile
        35                  40                  45

Tyr Asp Ala Ser Ile Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Gly Tyr Pro Leu
                85                  90                  95

Thr Phe Gly Gln Gly Thr Arg Leu Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp

```
            20                  25                  30

Leu Gly Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Leu Glu Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Phe
            20                  25                  30

Leu Ala Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Ala Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Leu
                85                  90                  95

Thr Phe Gly Gly Gly Thr Lys Val Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Ala
            20                  25                  30

Leu Ala Trp Tyr Gln Gln Lys Pro Gly Ile Gly Pro Lys Leu Leu Ile
        35                  40                  45

Tyr Asp Ala Ser Thr Leu Glu Ser Gly Val Pro Ala Arg Phe Ser Gly
    50                  55                  60

Ser Gly Ser Arg Thr Asp Phe Thr Leu Thr Ile Thr Ser Leu Gln Pro
65                  70                  75                  80

Glu Asp Phe Ala Thr Tyr Tyr Cys Gln Gln Phe Asn Gly Tyr Pro Leu
                85                  90                  95

Thr Phe Gly Gly Gly Thr Lys Leu Glu Ile Lys
```

```
                100             105

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Thr Ser Ala
            20                  25                  30

Leu Ala Trp Tyr Gln Glu Lys Pro Gly Lys Ala Pro Asn Leu Leu Ile
        35                  40                  45

Tyr Asp Ala Ser Ser Leu Glu Ser Gly Val Pro Ser Arg Phe Ser Gly
50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Asp Ile Lys
            100                 105

<210> SEQ ID NO 24
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Ile Gln Leu Val Gln Ser Gly Pro Glu Leu Arg Lys Pro Gly Glu
1               5                   10                  15

Ser Val Lys Ile Ser Cys Lys Ala Ser Gly Tyr Thr Phe Thr Asp Tyr
            20                  25                  30

Ala Met Tyr Trp Val Lys Gln Ala Pro Gly Lys Gly Leu Lys Trp Met
        35                  40                  45

Gly Trp Ile Asn Thr Tyr Thr Gly Lys Pro Thr Tyr Ala Asp Asp Phe
50                  55                  60

Lys Gly Arg Phe Val Phe Ser Leu Glu Ala Ser Ala Asn Thr Ala Asn
65                  70                  75                  80

Leu Gln Ile Ser Asn Leu Lys Asn Glu Asp Thr Ala Thr Tyr Phe Cys
                85                  90                  95

Ala Arg Ala Arg Gly Leu Val Asp Asp Tyr Val Met Asp Ala Trp Gly
            100                 105                 110

Gln Gly Thr Ser Val Thr Val Ser Ser
        115                 120

<210> SEQ ID NO 25
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25
```

```
Ser Tyr Glu Leu Ile Gln Pro Ser Ala Ser Val Thr Leu Gly Asn
1               5                   10                  15

Thr Val Ser Leu Thr Cys Val Gly Asp Glu Leu Ser Lys Arg Tyr Ala
                20                  25                  30

Gln Trp Tyr Gln Gln Lys Pro Asp Lys Thr Ile Val Ser Val Ile Tyr
                35                  40                  45

Lys Asp Ser Glu Arg Pro Ser Gly Ile Ser Asp Arg Phe Ser Gly Ser
            50                  55                  60

Ser Ser Gly Thr Thr Ala Thr Leu Thr Ile His Gly Thr Leu Ala Glu
65                  70                  75                  80

Asp Glu Ala Asp Tyr Tyr Cys Leu Ser Thr Tyr Ser Asp Asn Leu
                85                  90                  95

Pro Val Phe Gly Gly Gly Thr Lys Leu Thr Val Leu
                100                 105
```

<210> SEQ ID NO 26
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Glu Val Gln Leu Gln Gln Tyr Gly Ala Glu Leu Gly Lys Pro Gly Thr
1               5                   10                  15

Ser Val Arg Leu Ser Cys Lys Val Ser Gly Tyr Asn Ile Arg Asn Thr
                20                  25                  30

Tyr Ile His Trp Val Asn Gln Arg Pro Gly Glu Gly Leu Glu Trp Ile
                35                  40                  45

Gly Arg Ile Asp Pro Thr Asn Gly Asn Thr Ile Ser Ala Glu Lys Phe
            50                  55                  60

Lys Thr Lys Ala Thr Leu Thr Ala Asp Thr Ser Ser His Thr Ala Tyr
65                  70                  75                  80

Leu Gln Phe Ser Gln Leu Lys Ser Asp Asp Thr Ala Ile Tyr Phe Cys
                85                  90                  95

Ala Leu Asn Tyr Glu Gly Tyr Ala Asp Tyr Trp Gly Gln Gly Val Met
                100                 105                 110

Val Thr Gly Ser Ser
        115
```

<210> SEQ ID NO 27
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asn Lys Tyr
                20                  25                  30

Leu Asn Trp Tyr Gln Gln Lys Val Gly Glu Ala Pro Lys Arg Leu Ile
                35                  40                  45

Phe Lys Thr Asn Ser Leu Gln Thr Gly Ile Pro Ser Arg Phe Ser Gly
            50                  55                  60
```

```
Ser Gly Ser Gly Thr Asp Tyr Thr Leu Thr Ile Ser Ser Leu Gln Thr
 65                  70                  75                  80

Glu Asp Val Ala Thr Tyr Phe Cys Phe Gln Tyr Asn Ile Gly Tyr Thr
                 85                  90                  95

Phe Gly Ala Gly Thr Lys Val Glu Leu Lys
            100                 105

<210> SEQ ID NO 28
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Ser Ser Asn
            20                  25                  30

Tyr Arg Trp Asn Trp Ile Arg Lys Phe Pro Gly Asn Lys Val Glu Trp
        35                  40                  45

Met Gly Tyr Ile Asn Ser Ala Gly Ser Thr Asn Tyr Asn Pro Ser Leu
 50                  55                  60

Lys Ser Arg Ile Ser Met Thr Arg Asp Thr Ser Lys Asn Gln Phe Phe
 65                  70                  75                  80

Leu Gln Val Asn Ser Val Thr Thr Glu Asp Thr Ala Thr Tyr Tyr Cys
                 85                  90                  95

Ala Arg Ser Leu Arg Gly Tyr Ile Thr Asp Tyr Ser Gly Phe Phe Asp
            100                 105                 110

Tyr Trp Gly Gln Gly Val Met Val Thr Val Ser Ser
        115                 120

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Arg Met Thr Gln Ser Pro Ala Ser Leu Ser Ala Ser Leu Gly
1               5                   10                  15

Glu Thr Val Asn Ile Glu Cys Leu Ala Ser Glu Asp Ile Phe Ser Asp
            20                  25                  30

Leu Ala Trp Tyr Gln Gln Lys Pro Gly Lys Ser Pro Gln Leu Leu Ile
        35                  40                  45

Tyr Asn Ala Asn Ser Leu Gln Asn Gly Val Pro Ser Arg Phe Ser Gly
 50                  55                  60

Ser Gly Ser Gly Thr Arg Tyr Ser Leu Lys Ile Asn Ser Leu Gln Ser
 65                  70                  75                  80

Glu Asp Val Ala Thr Tyr Phe Cys Gln Gln Tyr Lys Asn Tyr Pro Leu
                 85                  90                  95

Thr Phe Gly Ser Gly Thr Lys Leu Glu Ile Lys
            100                 105

<210> SEQ ID NO 30
```

<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Gln Gln Tyr Gly Ala Glu Leu Gly Lys Pro Gly Thr
1               5                   10                  15

Ser Val Arg Leu Ser Cys Lys Leu Ser Gly Tyr Lys Ile Arg Asn Thr
            20                  25                  30

Tyr Ile His Trp Val Asn Gln Arg Pro Gly Lys Gly Leu Glu Trp Ile
        35                  40                  45

Gly Arg Ile Asp Pro Ala Asn Gly Asn Thr Ile Tyr Ala Glu Lys Phe
    50                  55                  60

Lys Ser Lys Val Thr Leu Thr Ala Asp Thr Ser Asn Thr Ala Tyr
65                  70                  75                  80

Met Gln Leu Ser Gln Leu Lys Ser Asp Asp Thr Ala Leu Tyr Phe Cys
                85                  90                  95

Ala Met Asn Tyr Glu Gly Tyr Glu Asp Tyr Trp Gly Gln Gly Val Met
            100                 105                 110

Val Thr Val Ser Ser
        115

<210> SEQ ID NO 31
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Gln Met Thr Gln Ser Pro Ser Phe Leu Ser Ala Ser Val Gly
1               5                   10                  15

Asp Ser Val Thr Ile Asn Cys Lys Ala Ser Gln Asn Ile Asn Lys Tyr
            20                  25                  30

Leu Asn Trp Tyr Gln Gln Lys Leu Gly Glu Ala Pro Lys Arg Leu Ile
        35                  40                  45

His Lys Thr Asp Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Phe Gln Tyr Lys Ser Gly Phe Met
                85                  90                  95

Phe Gly Ala Gly Thr Lys Leu Glu Leu Lys
            100                 105

<210> SEQ ID NO 32
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ala Val Tyr Trp Val Ile Gln Ala Pro Gly Lys Gly Leu Lys Trp Met
            35                  40                  45

Gly Trp Ile Asn Thr Tyr Thr Gly Lys Pro Thr Tyr Ala Asp Asp Phe
50                  55                  60

Lys Gly Arg Phe Val Phe Ser Leu Glu Thr Ser Ala Ser Thr Ala Asn
65                  70                  75                  80

Leu Gln Ile Ser Asn Leu Lys Asn Glu Asp Thr Ala Thr Tyr Phe Cys
                85                  90                  95

Ala Arg Gly Ala Gly Met Thr Lys Asp Tyr Val Met Asp Ala Trp Gly
            100                 105                 110

Arg Gly Val Leu Val Thr Val Ser
            115                 120

<210> SEQ ID NO 33
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ser Tyr Glu Leu Ile Gln Pro Pro Ser Ala Ser Val Thr Leu Gly Asn
1               5                   10                  15

Thr Val Ser Leu Thr Cys Val Gly Asp Glu Leu Ser Lys Arg Tyr Ala
            20                  25                  30

Gln Trp Tyr Gln Gln Lys Pro Asp Lys Thr Ile Val Ser Val Ile Tyr
            35                  40                  45

Lys Asp Ser Glu Arg Pro Ser Asp Ile Ser Asp Arg Phe Ser Gly Ser
50                  55                  60

Ser Ser Gly Thr Thr Ala Thr Leu Thr Ile His Gly Thr Leu Ala Glu
65                  70                  75                  80

Asp Glu Ala Asp Tyr Tyr Cys Leu Ser Thr Tyr Ser Asp Asp Asn Leu
                85                  90                  95

Pro Val Phe Gly Gly Thr Lys Leu Thr Val Leu
            100                 105

<210> SEQ ID NO 34
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Leu Val His Trp Val Arg Gln Pro Pro Gly Lys Thr Leu Glu Trp Val
            35                  40                  45

Gly Leu Met Trp Asn Asp Gly Asp Thr Ser Tyr Asn Ser Ala Leu Lys
        50                  55                  60

Ser Arg Leu Ser Ile Ser Arg Asp Thr Ser Lys Ser Gln Val Phe Leu
65                  70                  75                  80

```
Lys Met His Ser Leu Gln Ala Glu Asp Thr Ala Thr Tyr Tyr Cys Ala
             85                  90                  95

Arg Glu Ser Asn Leu Gly Phe Thr Tyr Trp Gly His Gly Thr Leu Val
            100                 105                 110

Thr Val Ser Ser
        115

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Met Thr Gln Ser Pro Ala Ser Leu Ser Ala Ser Leu Glu
1               5                   10                  15

Glu Ile Val Thr Ile Thr Cys Lys Ala Ser Gln Gly Ile Asp Asp Asp
            20                  25                  30

Leu Ser Trp Tyr Gln Gln Lys Pro Gly Lys Ser Pro Gln Leu Leu Ile
        35                  40                  45

Tyr Asp Val Thr Arg Leu Ala Asp Gly Val Pro Ser Arg Phe Ser Gly
    50                  55                  60

Ser Arg Ser Gly Thr Gln Tyr Ser Leu Lys Ile Ser Arg Pro Gln Val
65                  70                  75                  80

Ala Asp Ser Gly Ile Tyr Tyr Cys Leu Gln Ser Tyr Ser Thr Pro Tyr
                85                  90                  95

Thr Phe Gly Ala Gly Thr Lys Leu Glu Leu Lys
            100                 105

<210> SEQ ID NO 36
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Gln Gln Tyr Gly Ala Glu Leu Gly Lys Pro Gly Thr
1               5                   10                  15

Ser Val Arg Leu Ser Cys Lys Val Ser Gly Tyr Asn Ile Arg Asn Thr
            20                  25                  30

Tyr Ile His Trp Val His Gln Arg Pro Gly Glu Gly Leu Glu Trp Ile
        35                  40                  45

Gly Arg Ile Asp Pro Thr Asn Gly Asn Thr Ile Ser Ala Glu Lys Phe
    50                  55                  60

Lys Ser Lys Ala Thr Leu Thr Ala Asp Thr Ser Ser Asn Thr Ala Tyr
65                  70                  75                  80

Met Gln Phe Ser Gln Leu Lys Ser Asp Asp Thr Ala Ile Tyr Phe Cys
                85                  90                  95

Ala Met Asn Tyr Glu Gly Tyr Ala Asp Tyr Trp Gly Gln Gly Val Met
            100                 105                 110

Val Thr Val Ser Ser
        115

<210> SEQ ID NO 37
<211> LENGTH: 106
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Met Thr Gln Ser Pro Ser Phe Leu Ser Ala Ser Val Gly
1               5                   10                  15

Asp Arg Leu Thr Ile Asn Cys Lys Ala Ser Gln Asn Ile Asn Lys Tyr
            20                  25                  30

Leu Asn Trp Tyr Gln Gln Lys Leu Gly Glu Ala Pro Lys Arg Leu Ile
        35                  40                  45

Phe Lys Thr Asn Ser Leu Gln Thr Gly Ile Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Phe Gln Tyr Asn Ile Gly Phe Thr
                85                  90                  95

Phe Gly Ala Gly Thr Lys Leu Glu Leu Lys
            100                 105

<210> SEQ ID NO 38
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Leu Val Gln Ser Gly Arg
1               5                   10                  15

Ser Leu Lys Leu Ser Cys Ala Ala Ser Gly Phe Thr Val Ser Asp Tyr
            20                  25                  30

Tyr Met Ala Trp Val Arg Gln Ala Pro Thr Lys Gly Leu Glu Trp Val
        35                  40                  45

Ala Thr Ile Asn Tyr Asp Gly Ser Thr Thr Tyr His Arg Asp Ser Val
50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asp Tyr Gly Tyr His Tyr Gly Ala Tyr Tyr Phe Asp
            100                 105                 110

Tyr Trp Gly Gln Gly Val Met Val Thr Val Ser Ser
        115                 120

<210> SEQ ID NO 39
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Val Leu Thr Gln Ser Pro Ala Leu Ala Val Ser Leu Gly Gln
1               5                   10                  15

Arg Ala Thr Ile Ser Cys Arg Ala Ser Gln Thr Val Ser Leu Ser Gly
```

```
            20                  25                  30
Tyr Asn Leu Ile His Trp Tyr Gln Gln Arg Thr Gly Gln Gln Pro Lys
        35                  40                  45

Leu Leu Ile Tyr Arg Ala Ser Asn Leu Ala Pro Gly Ile Pro Ala Arg
    50                  55                  60

Phe Ser Gly Ser Gly Ser Gly Thr Asp Phe Thr Leu Thr Ile Ser Pro
65                  70                  75                  80

Val Gln Ser Asp Asp Ile Ala Thr Tyr Tyr Cys Gln Gln Ser Arg Glu
                85                  90                  95

Ser Trp Thr Phe Gly Gly Gly Thr Asn Leu Glu Met Lys
            100                 105

<210> SEQ ID NO 40
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ala Ile His Trp Val Lys Gln Ala Pro Gly Gln Gly Leu Arg Trp Met
        35                  40                  45

Ala Trp Ile Asn Thr Glu Thr Gly Lys Pro Thr Tyr Ala Asp Asp Phe
    50                  55                  60

Lys Gly Arg Phe Val Phe Ser Leu Glu Ala Ser Ala Ser Thr Ala His
65                  70                  75                  80

Leu Gln Ile Ser Asn Leu Lys Asn Glu Asp Thr Ala Thr Phe Phe Cys
                85                  90                  95

Ala Gly Gly Ser His Trp Phe Ala Tyr Trp Gly Gln Gly Thr Leu Val
            100                 105                 110

Thr Val Ser Ser
        115

<210> SEQ ID NO 41
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ser Tyr Glu Leu Ile Gln Pro Pro Ser Ala Ser Val Thr Leu Glu Asn
1               5                   10                  15

Thr Val Ser Ile Thr Cys Ser Gly Asp Glu Leu Ser Asn Lys Tyr Ala
            20                  25                  30

His Trp Tyr Gln Gln Lys Pro Asp Lys Thr Ile Leu Glu Val Ile Tyr
        35                  40                  45

Asn Asp Ser Glu Arg Pro Ser Gly Ile Ser Asp Arg Phe Ser Gly Ser
    50                  55                  60

Ser Ser Gly Thr Thr Ala Ile Leu Thr Ile Arg Asp Ala Gln Ala Glu
65                  70                  75                  80

Asp Glu Ala Asp Tyr Tyr Cys Leu Ser Thr Phe Ser Asp Asp Asp Leu
```

```
                     85                  90                  95

Pro Ile Phe Gly Gly Gly Thr Lys Leu Thr Val Leu
            100                 105

<210> SEQ ID NO 42
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ser Tyr Glu Leu Ile Gln Pro Pro Ser Thr Ser Val Thr Leu Gly Asn
1               5                   10                  15

Thr Val Ser Leu Thr Cys Val Gly Asn Glu Leu Pro Lys Arg Tyr Ala
            20                  25                  30

Tyr Trp Phe Gln Gln Lys Pro Asp Gln Ser Ile Val Arg Leu Ile Tyr
        35                  40                  45

Asp Asp Asp Arg Arg Pro Ser Gly Ile Ser Asp Arg Phe Ser Gly Ser
    50                  55                  60

Ser Ser Gly Thr Thr Ala Thr Leu Thr Ile Arg Asp Ala Gln Ala Glu
65                  70                  75                  80

Asp Glu Ala Tyr Tyr Tyr Cys His Ser Thr Tyr Thr Asp Asp Lys Val
                85                  90                  95

Pro Ile Phe Gly Gly Gly Thr Lys Leu Thr Val Leu
            100                 105

<210> SEQ ID NO 43
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Arg
1               5                   10                  15

Ser Met Lys Leu Ser Cys Lys Ala Ser Gly Phe Thr Phe Ser Asn Tyr
            20                  25                  30

Asp Met Ala Trp Val Arg Gln Ala Pro Thr Arg Gly Leu Glu Trp Val
        35                  40                  45

Ala Ser Ile Ser Tyr Asp Gly Ile Thr Ala Tyr Tyr Arg Asp Ser Val
    50                  55                  60

Lys Gly Arg Phe Thr Ile Ser Arg Glu Asn Ala Lys Ser Thr Leu Tyr
65                  70                  75                  80

Leu Gln Leu Val Ser Leu Arg Ser Glu Asp Thr Ala Thr Tyr Tyr Cys
                85                  90                  95

Thr Thr Glu Gly Gly Tyr Val Tyr Ser Gly Pro His Tyr Phe Asp Tyr
            100                 105                 110

Trp Gly Gln Gly Val Met Val Thr Val Ser Ser
        115                 120

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 44

Asp Ile Gln Met Thr Gln Ser Pro Ser Ser Met Ser Val Ser Leu Gly
1               5                   10                  15

Asp Thr Val Thr Ile Thr Cys Arg Ala Ser Gln Asp Val Gly Ile Phe
            20                  25                  30

Val Asn Trp Phe Gln Gln Lys Pro Gly Arg Ser Pro Arg Arg Met Ile
        35                  40                  45

Tyr Arg Ala Thr Asn Leu Ala Asp Gly Val Pro Ser Arg Phe Ser Gly
50                  55                  60

Ser Arg Ser Gly Ser Asp Tyr Ser Leu Thr Ile Ser Ser Leu Glu Ser
65                  70                  75                  80

Glu Asp Val Ala Asp Tyr His Cys Leu Gln Tyr Asp Glu Phe Pro Arg
                85                  90                  95

Thr Phe Gly Gly Gly Thr Lys Leu Glu Leu Lys
            100                 105

<210> SEQ ID NO 45
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Gln Gln Tyr Gly Ala Glu Leu Gly Lys Pro Gly Thr
1               5                   10                  15

Ser Val Arg Leu Ser Cys Lys Val Ser Gly Tyr Lys Ile Arg Asn Thr
            20                  25                  30

Tyr Ile His Trp Val Asn Gln Arg Pro Gly Lys Gly Leu Glu Trp Ile
        35                  40                  45

Gly Arg Ile Asp Pro Ala Asn Gly Asn Thr Ile Tyr Ala Glu Lys Phe
50                  55                  60

Lys Ser Lys Val Thr Leu Thr Ala Asp Thr Ser Ser Asn Thr Ala Tyr
65                  70                  75                  80

Met Gln Leu Ser Gln Leu Lys Ser Asp Asp Thr Ala Leu Tyr Phe Cys
                85                  90                  95

Ala Met Asn Tyr Glu Gly Tyr Glu Asp Tyr Trp Gly Gln Gly Val Met
            100                 105                 110

Val Thr Val Ser Ser
        115

<210> SEQ ID NO 46
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Phe Leu Ser Ala Ser Val Gly
1               5                   10                  15

Asp Ser Val Thr Ile Asn Cys Lys Ala Ser Gln Asn Ile Asn Lys Tyr
            20                  25                  30

Leu Asn Trp Tyr Gln Gln Lys Leu Gly Glu Ala Pro Lys Arg Leu Ile
        35                  40                  45

```
His Lys Thr Asn Ser Leu Gln Pro Gly Phe Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Val Ala Ala Tyr Phe Cys Phe Gln Tyr Asn Ser Gly Phe Thr
                85                  90                  95

Phe Gly Ala Gly Thr Lys Leu Glu Leu Lys
            100                 105
```

<210> SEQ ID NO 47
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Gly Trp Met Asn Pro His Ser Gly Asp Thr Gly Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser Ala Ser
        115                 120                 125
```

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asn Glu
                20                  25                  30

Leu Gly Trp Tyr Gln Gln Lys Pro Gly Lys Ala Pro Lys Leu Leu Ile
            35                  40                  45

Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asn Leu Pro Leu
                85                  90                  95

Thr Phe Gly Gln Gly Thr Lys Val Glu Ile Lys
            100                 105
```

<210> SEQ ID NO 49
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Leu His Trp Val Arg Gln Ala Pro Gly Gln Gly Leu Glu Trp Met
        35                  40                  45

Gly Trp Ile Asn Pro Asn Ser Gly Asp Thr Asn Tyr Ala Gln Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Leu
                85                  90                  95

Thr Phe Gly Gly Gly Thr Lys Val Glu Ile Lys
            100                 105

<210> SEQ ID NO 51
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Leu His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser Ala Ser
            115                 120                 125

<210> SEQ ID NO 52
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Asp Ala Ser Glu Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Ile
                85                  90                  95

Thr Phe Gly Gln Gly Thr Lys Val Glu Ile Lys
            100                 105

<210> SEQ ID NO 53
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Leu Asn Pro Ser Gly Gly Thr Ser Tyr Ala Gln Lys Phe
    50                  55                  60

```
Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Asp Gly Tyr Glu Gly Ala Phe Asp Ile
            100                 105                 110

Trp Gly Gln Gly Thr Leu Val Thr Val Ser Ser Ala Ser
            115                 120                 125
```

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Leu
                85                  90                  95

Thr Phe Gly Gly Gly Thr Lys Val Glu Ile Lys
            100                 105
```

<210> SEQ ID NO 55
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser Ala Ser
            115                 120                 125
```

```
<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Gly Phe Pro Leu
                85                  90                  95

Thr Phe Gly Gly Gly Thr Lys Val Glu Ile Lys
            100                 105

<210> SEQ ID NO 57
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Asn Thr Asn Tyr Ala Gln Asn Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Asn Ala Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Leu Ser Ala Ser Val Gly
```

-continued

```
                1               5                   10                  15
Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Asn Gly Tyr Pro Leu
                85                  90                  95

Thr Phe Gly Gly Gly Thr Lys Val Glu Ile Lys
                100                 105
```

<210> SEQ ID NO 59
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Asn Pro Thr Val Gly Gly Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Asn Glu Tyr Glu Gly Ala Phe Asp Ile
                100                 105                 110

Trp Gly Gln Gly Thr Leu Val Thr Val Ser Ser Ala Ser
        115                 120                 125
```

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asp Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Gly Asn Ser Phe Pro Leu
                    85                  90                  95

Thr Phe Gly Gly Gly Thr Lys Leu Glu Ile Lys
                100                 105

<210> SEQ ID NO 61
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Gln Ser Gly Ala Glu Val Lys Lys Leu Gly Ala
1               5                   10                  15

Ser Val Lys Val Ser Cys Lys Ala Ser Gly Tyr Thr Phe Ser Ser Tyr
                20                  25                  30

Tyr Met His Trp Val Arg Gln Ala Pro Gly Gln Gly Leu Glu Trp Met
            35                  40                  45

Gly Val Ile Asn Pro Asn Gly Ala Gly Thr Asn Phe Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Glu Gly Tyr Gly Ala Phe Asp Ile
                100                 105                 110

Trp Gly Gln Gly Thr Leu Val Thr Val Ser Ser Ala Ser
            115                 120                 125

<210> SEQ ID NO 62
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Tyr Met His Trp Val Arg Gln Ala Pro Gly Gln Gly Leu Glu Trp Met
            35                  40                  45

Gly Trp Ile Asn Pro Thr Gly Gly Thr Asn Tyr Ala Gln Asn Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Glu Gly Tyr Gly Ala Phe Asp Ile
                100                 105                 110

Trp Gly Gln Gly Thr Leu Val Thr Val Ser Ser Ala Ser
            115                 120                 125
```

```
<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Val Ser Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Ser Gly Tyr Pro Ile
                85                  90                  95

Thr Phe Gly Gln Gly Thr Lys Leu Glu Ile Lys
            100                 105

<210> SEQ ID NO 64
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Met Ile Asn Pro Ser Gly Gly Ser Thr Asn Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Asn Asp Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 65
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Glu Ala Ser Asn Leu Glu Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Val Glu Ile Lys
            100                 105

<210> SEQ ID NO 66
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Ala Tyr
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Ser Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Gly Gly Tyr Glu Gly Ala Phe Asp Ile
            100                 105                 110

Trp Asp Gln Gly Thr Leu Val Thr Val Ser Ser Ala Ser
        115                 120                 125

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Tyr
            20                  25                  30

Val Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Leu Asn Gly Tyr Pro Ile
                85                  90                  95

Thr Phe Gly Gln Gly Thr Arg Leu Glu Ile Lys
            100                 105

<210> SEQ ID NO 68
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Asp Asp Ser Asp Thr Arg Tyr Ser Pro Ser Phe
50                  55                  60

Gln Gly Gln Val Thr Ile Ser Val Asp Lys Ser Asn Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser Ala Ser
            115                 120                 125

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Tyr Phe Thr Leu Thr Ile Ser Ser Leu Gln Pro
65                  70                  75                  80

Glu Asp Phe Ala Thr Tyr Tyr Cys Gln Gln Gly Ala Ser Phe Pro Ile
                85                  90                  95

Thr Phe Gly Gln Gly Thr Lys Val Glu Ile Lys
            100                 105

<210> SEQ ID NO 70
<211> LENGTH: 125
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 70

Glu Val Gln Leu Val Gln Ser Gly Ala Glu Val Lys Lys Pro Gly Glu
1               5                   10                  15

Ser Leu Lys Ile Ser Cys Lys Gly Ser Gly Ser Ser Phe Pro Asn Ser
            20                  25                  30

Trp Ile Ala Trp Val Arg Gln Met Pro Gly Lys Gly Leu Glu Trp Met
        35                  40                  45

Gly Ile Ile Tyr Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Glu Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 71
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105

<210> SEQ ID NO 72
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asp Ser Tyr
            20                  25                  30
```

```
Trp Ile Gly Trp Val Arg Gln Met Pro Gly Lys Gly Leu Glu Trp Met
            35                  40                  45

Gly Ile Met Tyr Pro Gly Asp Ser Asp Thr Arg Tyr Ser Pro Ser Phe
 50                      55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Gly Arg Gly Tyr Asn Ala Tyr Glu Gly Ala Phe Asp Ile
            100                 105                 110

Trp Gly Gln Gly Thr Leu Val Thr Val Ser Ser Ala Ser
            115                 120                 125

<210> SEQ ID NO 73
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asn Asn Trp
            20                  25                  30

Leu Ala Trp Tyr Gln Gln Lys Pro Gly Lys Ala Pro Lys Leu Leu Ile
            35                  40                  45

Tyr Asp Ala Phe Ile Leu Gln Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Leu Asn Ser Tyr Pro Leu
                 85                  90                  95

Thr Phe Gly Pro Gly Thr Lys Val Asp Ile Lys
            100                 105

<210> SEQ ID NO 74
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Asn Trp
            20                  25                  30

Ile Ala Trp Val Arg Gln Met Pro Gly Lys Gly Leu Glu Trp Met Gly
            35                  40                  45

Ile Ile Tyr Pro Gly Asp Ser Glu Thr Arg Tyr Ser Pro Ser Phe Gln
 50                      55                  60

Gly Gln Val Thr Ile Ser Ala Asp Lys Ser Ile Ser Thr Ala Tyr Leu
 65                  70                  75                  80

Gln Trp Ser Ser Leu Lys Ala Ser Asp Thr Ala Met Tyr Tyr Cys Ala
                 85                  90                  95
```

```
Arg His Gly Arg Gly Tyr Tyr Gly Tyr Glu Gly Ala Phe Asp Ile Trp
            100                 105                 110

Gly Gln Gly Thr Leu Val Thr Val Ser Ser Ala Ser
        115                 120
```

<210> SEQ ID NO 75
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asp Asn
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ile Ser Phe Pro Leu
                85                  90                  95

Thr Phe Gly Gln Gly Thr Lys Val Glu Ile Lys
            100                 105
```

<210> SEQ ID NO 76
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
            20                  25                  30

Trp Ile Gly Trp Val Arg Gln Met Pro Gly Lys Gly Leu Glu Trp Met
        35                  40                  45

Gly Val Ile Tyr Pro Asp Asp Ser Glu Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser Ala Ser
        115                 120                 125
```

<210> SEQ ID NO 77
<211> LENGTH: 107
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Arg Asp Asp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 78
<211> LENGTH: 124
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 78

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Asn Thr Tyr
            20                  25                  30

Ile Gly Trp Val Arg Gln Met Pro Gly Lys Gly Leu Glu Trp Met Gly
        35                  40                  45

Ile Ile Tyr Pro Gly Asp Ser Gly Thr Arg Tyr Ser Pro Ser Phe Gln
    50                  55                  60

Gly Gln Val Thr Ile Ser Ala Asp Lys Ala Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg His Ser Arg Gly Tyr Asn Gly Tyr Glu Gly Ala Phe Asp Ile Trp
            100                 105                 110

Gly Gln Gly Thr Leu Val Thr Val Ser Ser Ala Ser
        115                 120

<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile

```
                35                  40                  45
Tyr Asp Ala Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Val
                 85                  90                  95

Thr Phe Gly Gln Gly Thr Lys Val Glu Ile Lys
            100                 105

<210> SEQ ID NO 80
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Asn Phe Thr Thr Tyr
                20                  25                  30

Trp Ile Gly Trp Val Arg Gln Met Pro Gly Lys Gly Leu Glu Trp Met
             35                  40                  45

Gly Ile Ile His Pro Ala Asp Ser Asp Thr Arg Tyr Asn Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser Ala Ser
         115                 120                 125

<210> SEQ ID NO 81
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Gln Met Thr Gln Ser Pro Ser Ser Leu Ser Ala Ser Val Gly
 1               5                  10                  15

Asp Arg Val Thr Ile Thr Cys Arg Val Ser Gln Gly Ile Ser Ser Tyr
                20                  25                  30

Leu Ala Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys
            100                 105
```

<210> SEQ ID NO 82
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Ser Asn Tyr
            20                  25                  30

Trp Ile Ala Trp Val Arg Gln Met Pro Gly Lys Gly Leu Glu Trp Met
        35                  40                  45

Gly Ile Ile Tyr Pro Asp Asn Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asp Gly Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 83
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Asp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Ser Phe Gly Gln Gly Thr Lys Val Glu Ile Lys
            100                 105

<210> SEQ ID NO 84
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Glu Val Gln Leu Val Gln Ser Gly Ala Glu Val Lys Pro Gly Glu
1               5                   10                  15

Ser Leu Lys Ile Ser Cys Lys Gly Ser Gly Tyr Arg Phe Ala Ser Tyr
                20                  25                  30

Trp Ile Gly Trp Val Arg Gln Met Pro Gly Lys Gly Leu Glu Trp Met
            35                  40                  45

Gly Ile Thr Tyr Pro Gly Asp Ser Glu Thr Arg Tyr Asn Pro Ser Gln
        50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg His Gly Arg Gly Tyr Gly Tyr Glu Gly Ala Phe Asp Ile Trp
            100                 105                 110

Gly Gln Gly Thr Leu Val Thr Val Ser Ser Ala Ser
            115                 120
```

<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105
```

<210> SEQ ID NO 86
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Glu Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60
```

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 87
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Leu
                85                  90                  95

Thr Phe Gly Gln Gly Thr Arg Leu Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ile Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 89

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Gly Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 91
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ile Ser Ala
            20                  25                  30
```

Leu Ala Trp Tyr Gln Gln Lys Pro Gly Lys Ala Pro Lys Leu Leu Ile
            35                  40                  45

Tyr Asp Ala Ser Ile Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Lys
            100                 105

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Arg Ser Ala
                 20                  25                  30

Leu Ala Trp Tyr Gln Gln Lys Pro Gly Lys Ala Pro Lys Leu Leu Ile
            35                  40                  45

Tyr Asp Ala Ser Ile Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Lys
            100                 105

<210> SEQ ID NO 93
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Val Gly Ser Ala
                 20                  25                  30

Leu Ala Trp Tyr Gln Gln Lys Pro Gly Lys Ala Pro Lys Leu Leu Ile
            35                  40                  45

Tyr Asp Ala Ser Ile Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Lys
            100                 105

```
<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ile Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 95
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ile Ser Ala
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
```

```
                20                  25                  30
Leu Ala Trp Tyr Gln Gln Lys Pro Gly Lys Ala Pro Lys Leu Leu Ile
            35                  40                  45

Tyr Asp Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105
```

<210> SEQ ID NO 97
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Gly Ser Ala
            20                  25                  30

Leu Ala Trp Tyr Gln Gln Lys Pro Gly Lys Ala Pro Lys Leu Leu Ile
            35                  40                  45

Tyr Asp Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105
```

<210> SEQ ID NO 98
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Thr Ser
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Leu Gly Tyr Asn Gly Tyr Glu Gly Ala Phe Asp Ile
```

```
                  100                 105                 110
Trp Gly Gln Gly Thr Leu Val Thr Val Ser Ser
            115                 120

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Ala
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Gly Tyr Pro Leu
                85                  90                  95

Thr Phe Gly Gln Gly Thr Arg Leu Glu Ile Lys
            100                 105

<210> SEQ ID NO 100
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Gly Ile Ser Asp Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 101
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Ala
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Leu
                85                  90                  95

Thr Phe Gly Gln Gly Thr Arg Leu Glu Ile Lys
            100                 105

<210> SEQ ID NO 102
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Ala
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Leu
                85                  90                  95

Thr Phe Gly Gln Gly Thr Arg Leu Glu Ile Lys
            100                 105

<210> SEQ ID NO 103
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
caggtgcagc tggtgcagag cggtgcggcg gtgaaaaaac ctggcgaaag cctgaaaatt      60
agctgcaaag cagcggcta tcgttttacc acctattgga ttggctgggt gcgtcagatg     120
ccgggcaaag gactggaatg gatgggcatt atctatccgg gcgatagcga tacccgttac    180
agccctagct ttcaggggca ggtgaccatt agcgcggaa aaagcattag caccgcgtat    240
ctgcagtgga gcagcttaaa agcgagcgac accgcgatgt attattgcgc gcgtcatggc    300
cgtggctata atggctatga aggcgcgttt gatatttggg gccagggac tatggttacc    360 gtgagcagcg ctagcaccaa gggcccca gc gtgttccctc tggccccag cagcaagagc    420

```
accagcggcg gaaccgccgc cctgggctgc ctggtgaagg actacttccc cgagcccgtg    480
accgtgtcct ggaacagcgg cgctctgacc agcggagtgc acaccttccc tgccgtgctg    540
cagagcagcg gcctgtactc cctgagcagc gtggtgaccg tgcccagcag cagcctgggc    600
acccagacct acatctgcaa cgtgaaccac aagccctcca acaccaaggt ggacaagaag    660
gtggagccta agagctgcga caagacccac acctgccctc ctgccccgc ccccgagctg     720 ctgggcggac ccagcgtgtt cctgttccct cccaagccca aggacaccct gatgatcagc    780 cgcaccccg aggtgacctg cgtggtggtg gacgtgagcc acgaggaccc cgaggtgaag     840
ttcaactggt acgtggacgg cgtggaggtg cacaacgcca agaccaagcc tcggaggag    900 cagtacaact ccacctaccg cgtggtgagc gtgctgaccg tgctgcacca ggactggctg    960
aacggcaagg agtacaagtg caaggtgagc aacaaggccc tgcccgctcc catcgagaag   1020
accatcagca aggccaaggg ccagccccgg gagcctcagg tgtacaccct gcccccagc    1080 cgcgacgagc tgaccaagaa ccaggtgagc ctgacctgcc tggtgaaggg cttctacccc   1140
tccgacatcg ccgtggagtg ggagagcaac ggccagcctg agaacaacta caagaccacc   1200
cctcccgtgc tggacagcga cggcagcttc ttcctgtaca gcaagctgac cgtggacaag   1260
tcccggtggc agcagggcaa cgtgttcagc tgcagcgtga tgcacgaggc cctgcacaac   1320
cactacaccc agaagagcct gagcctgagc cccggatagt aa                      1362
```

<210> SEQ ID NO 104
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
gccattcaac ttacacaaag tccgagtagt ctcagcgcga gcgtcgggga ccgggtaacc     60
ataacttgcc gagccagcca gggcgtctct agcgcattgg catggtatca acaaaaacct    120
ggaaaggctc ccaagctcct catttacgat gctagctccc ttgaatctgg cgtaccatcc    180
cgctttagtg gcagtgggtc tggaacagac tttactctta caatatcatc cctgcaacca    240
gaagattttg ctacctacta ctgtcaacag tttaatagtt acccactcac attcggcggg    300
ggtacgaaag tagaaataaa gcgaaccgtg gctgcgccta gcgtctttat ctttccccg     360 agcgatgaac agttgaaatc aggaactgct tctgtggtat gtttgcttaa taatttttac    420
ccacgggaag caaaagtgca gtggaaagta gacaatgcgc tccagtccgg caattctcaa    480
gagagtgtga ctgaacagga ttctaaggat agcacttatt cactgtcaag taccttgaca    540
ttgtcaaagg cggactatga gaaacataag gtttacgcct gtgaggtaac acaccaaggg   600
ctcagctcac ctgttacgaa atccttcaat aggggcgagt gt                        642
```

<210> SEQ ID NO 105
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105

```
gacatccagt tgacccagtc tccatcctcc ctgtctgcat ctgtgggaga cagagtcacc     60
atcacttgcc gggcaagtca gggcattaga actgatttag ctggtatca gcagaaacca    120
```

```
gggaaagctc ctaagctcct gatctatgat gcctccagtt tggaaagtgg ggtcccatca      180
aggttcagcg gcagtggatc tgggacagat ttcactctca ccatcagcag cctgcagcct      240
gaagattttg caacttatta ctgtcaacag tttaatagtt accctctcac tttcggcgga      300
gggaccaagg tggaaatcaa acggaccgtg gccgccccca gcgtgttcat cttccctccc      360
agcgacgagc agctgaagtc tggcaccgcc agcgtggtgt gcctgctgaa caacttctac      420
ccccgcgagg ccaaggtgca gtggaaggtg gacaacgccc tgcagagcgg caacagccag      480
gagagcgtga ccgagcagga ctccaaggac agcacctaca gcctgagcag cacccctgacc     540 ctgagcaagg ccgactacga aagcacaag gtgtacgcct gcgaggtgac ccaccaggga       600
ctgtctagcc ccgtgaccaa gagcttcaac cggggcgagt gctaa                     645
```

<210> SEQ ID NO 106
<211> LENGTH: 645
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 106

```
gccatccgga tgacccagtc tccatcctcc ctgtctgcat ctgtaggaga cagagtcacc      60
atcacttgcc gggcaagtca gggcattaga aatgatttag cctggtatca gcagaaacca     120
gggaaaactc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaatagtt acccgctcac tttcggcgga     300
gggaccaagg tggagatcaa acggaccgtg gccgccccca gcgtgttcat cttccctccc     360
agcgacgagc agctgaagtc tggcaccgcc agcgtggtgt gcctgctgaa caacttctac     420
ccccgcgagg ccaaggtgca gtggaaggtg gacaacgccc tgcagagcgg caacagccag     480
gagagcgtga ccgagcagga ctccaaggac agcacctaca gcctgagcag cacccctgacc   540 ctgagcaagg ccgactacga aagcacaag gtgtacgcct gcgaggtgac ccaccaggga     600
ctgtctagcc ccgtgaccaa gagcttcaac cggggcgagt gctaa                    645
```

<210> SEQ ID NO 107
<211> LENGTH: 645
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 107

```
gccatccaga tgacccagtc tccatcctcc ctgtctgcat ctgtaggaga cagagtcacc      60
atcacttgcc gggcaagtca gggcattaga aatgatttag gctggtatca acagaaacca    120
gggaaagccc ctaagctcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt accctctgac tttcggcgga    300
gggaccaaag tggatatcaa acggaccgtg gccgccccca gcgtgttcat cttccctccc    360
agcgacgagc agctgaagtc tggcaccgcc agcgtggtgt gcctgctgaa caacttctac    420
ccccgcgagg ccaaggtgca gtggaaggtg gacaacgccc tgcagagcgg caacagccag    480
```
gagagcgtga ccgagcagga ctccaaggac agcacctaca gcctgagcag caccctgacc    540
ctgagcaagg ccgactacga aagcacaag gtgtacgcct gcgaggtgac ccaccaggga    600
ctgtctagcc ccgtgaccaa gagcttcaac cggggcgagt gctaa                   645

<210> SEQ ID NO 108
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
aacatccaga tgacccagtc tccatcctca ctgtctgcat ctgtgggaga cagagtcacc    60
atcacttgtc gggcgagtca ggccattagc gattatttag cctggtttca gcagaaacca    120
gggaaagccc ctaagctcct gatctacgat gcatccaatt tggaaacagg ggtcccatca    180
aggttcagtg gaagtggatc tgggacagat ttcactctca ccatcagcag cctgcagcct    240
gaagattttg caacttatta ctgtcaacag cttaatagtt accccctcac tttcggcgga    300
gggaccaagg tggagatcaa acggaccgtg gccgccccca gcgtgttcat cttccctccc    360
agcgacgagc agctgaagtc tggcaccgcc agcgtggtgt gcctgctgaa caacttctac    420
ccccgcgagg ccaaggtgca gtggaaggtg gacaacgccc tgcagagcgg caacagccag    480
gagagcgtga ccgagcagga ctccaaggac agcacctaca gcctgagcag caccctgacc    540
ctgagcaagg ccgactacga aagcacaag gtgtacgcct gcgaggtgac ccaccaggga    600
ctgtctagcc ccgtgaccaa gagcttcaac cggggcgagt gctaa                   645

<210> SEQ ID NO 109
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
gccatccgga tgacccagtc tccatcctcc ctgtctgcat ctgtgggga cagagtcatt    60 atcgcttgcc gggcaagtca gggcatcggc ggtgctttag cctggtatca gcagaaacca    120
gggaatgctc ctaaggtcct ggtctatgat gcctccactt tggaaagtgg ggtcccatca    180
cggttcagcg gcggtggatc tgggacagat ttcactctca ccatcagcag cctgcagcct    240
gaagattttg caacttacta ctgtcaacag tttaatagtt accctctcac tttcggcgga    300
gggaccaagc tggagatcaa acggaccgtg gccgccccca gcgtgttcat cttccctccc    360
agcgacgagc agctgaagtc tggcaccgcc agcgtggtgt gcctgctgaa caacttctac    420
ccccgcgagg ccaaggtgca gtggaaggtg gacaacgccc tgcagagcgg caacagccag    480
gagagcgtga ccgagcagga ctccaaggac agcacctaca gcctgagcag caccctgacc    540
ctgagcaagg ccgactacga aagcacaag gtgtacgcct gcgaggtgac ccaccaggga    600
ctgtctagcc ccgtgaccaa gagcttcaac cggggcgagt gctaa                   645

<210> SEQ ID NO 110
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110

```
gacatcgcga tgacccagtc tccaccctcc ctgtctgcat ttgtagggga cagagtcacc        60
atcacttgcc gggcaagtca gggcattatc agttctttag cctggtatca gcagaaacca       120
gggaaagctc ctaagctcct gatctatgat gcctccagtt tggaaagtgg ggtcccatca       180
aggttcagtg gcagtggatc tgggacagat ttcactctca ccatccgcag cctgcagcct       240
gaagattttg ccacttatta ctgtcaacag tttaatagtt accctctcac tttcggcgga       300
gggaccaagc tggagatcaa acggaccgtg gccgccccca gcgtgttcat cttccctccc       360
agcgacgagc agctgaagtc tggcaccgcc agcgtggtgt gcctgctgaa caacttctac       420
ccccgcgagg ccaaggtgca gtggaaggtg gacaacgccc tgcagagcgg caacagccag       480
gagagcgtga ccgagcagga ctccaaggac agcacctaca gcctgagcag cacccctgacc     540
ctgagcaagg ccgactacga aagcacaag gtgtacgcct gcgaggtgac ccaccaggga       600
ctgtctagcc ccgtgaccaa gagcttcaac cggggcgagt gctaa                      645
```

<210> SEQ ID NO 111
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

```
gacatccaga tgacccagtc tccatcctcc ctgtctgcgt ctgttggaga cagagtcacc        60
atcacttgcc gggcaagtca gggcattagc agtgctttag cctggtatca gcagaaagca       120
gggaaagctc ctaaagtcct gatctctgat gcctccagtt tggaaagtgg ggtcccatca       180
aggttcagcg gcagtggatc tgggacagat ttcactctca gcatcagcag cctgcagcct       240
gaagattttg caacttatta ctgtcaacag tttaatggtt acccgctcac tttcggcgga       300
gggaccaaag tggatatcaa acggaccgtg gccgccccca gcgtgttcat cttccctccc       360
agcgacgagc agctgaagtc tggcaccgcc agcgtggtgt gcctgctgaa caacttctac       420
ccccgcgagg ccaaggtgca gtggaaggtg gacaacgccc tgcagagcgg caacagccag       480
gagagcgtga ccgagcagga ctccaaggac agcacctaca gcctgagcag cacccctgacc     540
ctgagcaagg ccgactacga aagcacaag gtgtacgcct gcgaggtgac ccaccaggga       600
ctgtctagcc ccgtgaccaa gagcttcaac cggggcgagt gctaa                      645
```

<210> SEQ ID NO 112
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112

```
gccatccgga tgacccagtc tccatcctcc ctgtctgcat ctgtaggaga cagagtcacc        60
atcacttgcc aggcgagtca gggcattaga aatgatttag gctggtatca gcagaaacca       120
gggaaagccc ctaagctcct gatctacgat gcatccaatt tggaaacagg ggtcccatca       180
aggttcagtg gaagtggatc tgggacagat tttactttca ccatcagcag cctgcagcct       240
gaagatattg caacatatta ctgtcaacag tttaatagtt acccgctcac tttcggcgga       300
```

```
gggaccaagc tggagatcaa acggaccgtg gccgccccca gcgtgttcat cttccctccc    360
agcgacgagc agctgaagtc tggcaccgcc agcgtggtgt gcctgctgaa caacttctac    420
ccccgcgagg ccaaggtgca gtggaaggtg gacaacgccc tgcagagcgg caacagccag    480
gagagcgtga ccgagcagga ctccaaggac agcacctaca gcctgagcag caccctgacc    540
ctgagcaagg ccgactacga gaagcacaag gtgtacgcct gcgaggtgac ccaccaggga    600
ctgtctagcc ccgtgaccaa gagcttcaac cggggcgagt gctaa                    645
```

<210> SEQ ID NO 113
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
aacatccaga tgacccagtc tccatcctcc ctgtctacat ccgtaggaga cagagtcacc     60
atcacttgcc gggcaagtca gggcattggc acttctttag cctggtatca gcagaagcca    120
gggaagcctc ctaagttact gatctatgat gcctccagtt tggaaagtgg ggtcccatca    180
aggctcagcg gcagtggatc tgggacagat ttcactctca ccatcagcag cctgcagcct    240
gaagattttg caacttatta ctgtcaacag tctaatagtt atccgatcac cttcggccaa    300
gggacacgac tggagattaa acggaccgtg gccgccccca gcgtgttcat cttccctccc    360
agcgacgagc agctgaagtc tggcaccgcc agcgtggtgt gcctgctgaa caacttctac    420
ccccgcgagg ccaaggtgca gtggaaggtg gacaacgccc tgcagagcgg caacagccag    480
gagagcgtga ccgagcagga ctccaaggac agcacctaca gcctgagcag caccctgacc    540
ctgagcaagg ccgactacga gaagcacaag gtgtacgcct gcgaggtgac ccaccaggga    600
ctgtctagcc ccgtgaccaa gagcttcaac cggggcgagt gctaa                    645
```

<210> SEQ ID NO 114
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
gccatccagt tgacccagtc tccatcctcc ctgtctgcat ctgtaggaga cagagtcacc     60
atcacttgcc gggcaagtca gagcattggc gactatttga cttggtatca gcagaaacca    120
ggcaaagccc ctaaggtcct gatctatggt gcatccagtt tgcaaagtgg ggtcccacca    180
aggttcagtg gcagtggttc tgggacagat ttcactctca ccgtcagcag tctgcaacct    240
gaagattttg caacttatta ctgtcaacag cttaatagtt accccctcac tttcggcgga    300
gggaccaagc tggagatcaa acggaccgtg gccgccccca gcgtgttcat cttccctccc    360
agcgacgagc agctgaagtc tggcaccgcc agcgtggtgt gcctgctgaa caacttctac    420
ccccgcgagg ccaaggtgca gtggaaggtg gacaacgccc tgcagagcgg caacagccag    480
gagagcgtga ccgagcagga ctccaaggac agcacctaca gcctgagcag caccctgacc    540
ctgagcaagg ccgactacga gaagcacaag gtgtacgcct gcgaggtgac ccaccaggga    600
ctgtctagcc ccgtgaccaa gagcttcaac cggggcgagt gctaa                    645
```

<210> SEQ ID NO 115
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 115

```
gacatccagt tgacccagtc tccatcctcc ctgtctgcat ctgtaggaga cagagtcacc      60
atcacgtgcc gggcaagtca gggcgttagg agtactttag cctggtatca gcagaaacca     120
gggaaagctc ctaagctcct gatctatgat gcctccattt tggaaagtgg ggtcccatca     180
aggttcagcg gcagtggatc tgggacagat ttcactctca ccatcagcag cctgcagcct     240
gaagattttg caacttatta ctgtcaacag tttaatggtt accctctcac cttcggccaa     300
gggacacgac tggagattaa acggaccgtg gccgccccca gcgtgttcat cttccctccc     360
agcgacgagc agctgaagtc tggcaccgcc agcgtggtgt gcctgctgaa caacttctac     420
ccccgcgagg ccaaggtgca gtggaaggtg acaacgccc tgcagagcgg caacagccag     480
gagagcgtga ccgagcagga ctccaaggac agcacctaca gcctgagcag caccctgacc     540
ctgagcaagg ccgactacga aagcacaag gtgtacgcct gcgaggtgac ccaccaggga     600
ctgtctagcc ccgtgaccaa gagcttcaac cggggcgagt gctaa                     645
```

<210> SEQ ID NO 116
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 116

```
gatattgtga tgactcagtc tccatcctcc ctgtctgcat ctgtaggaga cagagtcacc      60
atcacttgcc gggcaagtca gggcattaga aatgatttag gctggtatca gcagaaacca     120
gggaaagccc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaatagtt accctctcac tttcggcgga     300
gggaccaagc tggagatcaa acggaccgtg gccgccccca gcgtgttcat cttccctccc     360
agcgacgagc agctgaagtc tggcaccgcc agcgtggtgt gcctgctgaa caacttctac     420
ccccgcgagg ccaaggtgca gtggaaggtg acaacgccc tgcagagcgg caacagccag     480
gagagcgtga ccgagcagga ctccaaggac agcacctaca gcctgagcag caccctgacc     540
ctgagcaagg ccgactacga aagcacaag gtgtacgcct gcgaggtgac ccaccaggga     600
ctgtctagcc ccgtgaccaa gagcttcaac cggggcgagt gctaa                     645
```

<210> SEQ ID NO 117
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 117

```
gacatccagt tgacccagtc tccatcctcc ctgtctgcat ctgtaggaga cagagtcacc      60
```

| | | | |
|---|---|---|---|
| atcacttgcc gggccagtca gggcattagc agttttttag cctggtatca gcaaaaacca | 120 |
| gggaaagccc ctaagctcct gatctatgat gcatccactt tgcaaagtgg ggtcccatca | 180 |
| aggttcagcg gcagtgcatc tgggacagat ttcactctca ccatcagcag cctgcagcct | 240 |
| gaagattttg caacttatta ctgtcaacag cttaatggtt accctctcac tttcggcgga | 300 |
| gggaccaagg tggagatcaa acggaccgtg gccgccccca gcgtgttcat cttccctccc | 360 |
| agcgacgagc agctgaagtc tggcaccgcc agcgtggtgt gcctgctgaa caacttctac | 420 |
| ccccgcgagg ccaaggtgca gtggaaggtg gacaacgccc tgcagagcgg caacagccag | 480 |
| gagagcgtga ccgagcagga ctccaaggac agcacctaca gcctgagcag caccctgacc | 540 |
| ctgagcaagg ccgactacga aagcacaag gtgtacgcct gcgaggtgac ccaccaggga | 600 |
| ctgtctagcc ccgtgaccaa gagcttcaac cggggcgagt gctaa | 645 |

<210> SEQ ID NO 118
<211> LENGTH: 645
<212> TYPE: DNA
<213> ORGANISM: Artificial Sequence
<220> FEATURE:
<223> OTHER INFORMATION: Description of Artificial Sequence: Synthetic
 polynucleotide

<400> SEQUENCE: 118

| | | |
|---|---|---|
| gccatccagt tgacccagtc tccatcctcc ctgtctgcat ctgtaggaga cagagtcacc | 60 |
| atcacttgcc gggcaagtca gggcattggc agtgctttag cctggtatca gcagaaacca | 120 |
| gggataggtc ctaagctcct gatctatgat gcctcaactt tggaaagtgg ggtcccagca | 180 |
| aggttcagcg gcagtggatc taggacagat ttcactctca ccatcaccag cctgcagcct | 240 |
| gaagattttg caacttatta ctgtcaacag tttaatggtt accctctcac tttcggcgga | 300 |
| gggaccaagc tggagatcaa acggaccgtg gccgccccca gcgtgttcat cttccctccc | 360 |
| agcgacgagc agctgaagtc tggcaccgcc agcgtggtgt gcctgctgaa caacttctac | 420 |
| ccccgcgagg ccaaggtgca gtggaaggtg gacaacgccc tgcagagcgg caacagccag | 480 |
| gagagcgtga ccgagcagga ctccaaggac agcacctaca gcctgagcag caccctgacc | 540 |
| ctgagcaagg ccgactacga aagcacaag gtgtacgcct gcgaggtgac ccaccaggga | 600 |
| ctgtctagcc ccgtgaccaa gagcttcaac cggggcgagt gctaa | 645 |

<210> SEQ ID NO 119
<211> LENGTH: 645
<212> TYPE: DNA
<213> ORGANISM: Artificial Sequence
<220> FEATURE:
<223> OTHER INFORMATION: Description of Artificial Sequence: Synthetic
 polynucleotide

<400> SEQUENCE: 119

| | | |
|---|---|---|
| gccatccagt tgacccagtc tccatcctcc ctgtctgcat ctgtaggaga cagagtcacc | 60 |
| atcacttgcc gggcaagtca gggcattacc agtgctttag cctggtatca ggagaaacca | 120 |
| gggaaagctc ctaacctcct gatctatgat gcctccagtt tggaaagtgg ggtcccatca | 180 |
| aggttcagcg gcagtggata tgggacagat ttcactctca ccatcagcag cctgcagcct | 240 |
| gaagattttg caacttatta ctgtcaacag cttaatagtt accctctcac tttcggcgga | 300 |
| gggaccaaag tggatatcaa acggaccgtg gccgccccca gcgtgttcat cttccctccc | 360 |
| agcgacgagc agctgaagtc tggcaccgcc agcgtggtgt gcctgctgaa caacttctac | 420 |
| ccccgcgagg ccaaggtgca gtggaaggtg gacaacgccc tgcagagcgg caacagccag | 480 |

```
gagagcgtga ccgagcagga ctccaaggac agcacctaca gcctgagcag caccctgacc    540
ctgagcaagg ccgactacga aagcacaagg gtgtacgcct gcgaggtgac ccaccaggga    600
ctgtctagcc ccgtgaccaa gagcttcaac cggggcgagt gctaa                    645
```

<210> SEQ ID NO 120
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

```
cagatccagt tggtacagtc tggacctgag ctgaggaagc ctggcgagtc agtgaagatc     60
tcctgcaagg cttctggata taccttcaca gactatgcaa tgtattgggt gaaacaggct    120
ccaggaaagg gcttgaagtg gatgggctgg atcaacacct atactgggaa gccaacatat    180
gctgatgact tcaaaggacg atttgtcttc tctttggaag cctctgccaa cactgcaaat    240
ttgcagatca gcaacctcaa aaatgaggac acggctacat atttctgtgc aagagcccgc    300
ggattagtcg atgactatgt tatggatgcc tggggtcaag gacttcagt cactgtctcc    360 tct                                                                 363
```

<210> SEQ ID NO 121
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121

```
agctatgagc tgatccaacc accttcggca tcagtcactc tgggaaatac tgtctcactc     60
acttgtgtcg gagatgaatt atcaaaaaga tatgctcagt ggtatcaaca aaagccagac    120
aagaccattg tgtccgtgat atacaaagat agtgagcggc cctcaggcat ctctgaccga    180
ttctctggtt ccagctccgg gacaacagcc actctgacaa tccatggcac cctggctgag    240
gatgaggctg attattactg tttgtcaaca tatagtgatg ataatctccc tgttttcggt    300
ggtggaacca agctcactgt ccta                                          324
```

<210> SEQ ID NO 122
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
gaagtccagc tgcagcagta tggggctgag cttgggaaac ctggacctc agtcaggttg      60 tcttgcaagg tttctggcta taacattagg aatacctaca ttcactgggt gaatcagagg    120
cctggagagg gcctggaatg gataggaagg attgatccta caaacggaaa tactatatct    180
gctgagaaat tcaaaaccaa ggccacactg actgcagata tcgtcccca cacagcctac    240 ttgcagttca gccaactgaa atctgacgac acagcaatct atttttgtgc tctgaactat    300
gagggatatg cggattattg gggccaggga gtcatggtca caggctcctc c             351
```

<210> SEQ ID NO 123
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
gacatccaga tgacccagtc tccttcattc ctgtctgcat ctgtgggaga cagagtcact    60
atcaactgca aagcaagtca gaatattaac aagtacttaa actggtatca gcaaaaggtt   120
ggagaagctc ccaaacgcct gatatttaag acaaacagtt tgcaaacggg catcccatca   180
aggttcagtg gcagtggatc tggaacagat tatacactca ccatcagcag cctgcagact   240
gaagatgttg ccacatattt ctgctttcag tataacattg gtacacgtt tggagctggg    300 accaaggtgg agctgaaa                                                 318

<210> SEQ ID NO 124
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
gaggtgcagc ttcaggagtc aggacctggc cttgtgaaac cctcacagtc actctccctc    60
acctgttcgg tcactggata ctccatttcc agtaattata gatggaactg gatccggaag   120
ttcccaggaa ataaagtgga gtggatggga tatataaaca gtgcaggcag tactaactac   180
aatccgtctc tcaaaagtcg aatctccatg actagagaca catccaagaa tcagttcttc   240
ctgcaggtga actctgtaac aactgaggac acagccactt attactgtgc gagatcccta   300
agagggtata ttacggatta ttcaggcttc tttgattact ggggccaagg agtcatggtc   360
acagtctcct ca                                                       372

<210> SEQ ID NO 125
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
gatatccgga tgacacagtc tccagcttcc ctgtctgcat ctctgggaga gactgtcaac    60
atcgaatgtc tagcaagtga ggacatttc agtgatttag catggtatca gcagaagcca   120
gggaaatctc ctcaactcct gatctataat gcaaatagct tgcaaaatgg ggtcccttca   180
cggtttagtg gcagtggatc tggcacacgg tattctctca aaataaacag cctgcaatct   240
gaagatgtcg cgacttattt ctgtcaacaa tataagaatt atccgctcac gttcggttct   300
gggaccaagc tggagatcaa a                                             321

<210> SEQ ID NO 126
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

```
gaagtccagc tgcagcagta tgggctgag cttgggaaac ctgggacctc agtcaggttg      60
tcttgcaagc tttctggcta aagattagg aatacctaca tacactgggt gaatcagagg     120
cctggaaagg gcctggaatg gattgggagg attgatcctg caaatggaaa tactatctat    180
gctgagaagt tcaaaagcaa ggttacactg actgcagata tcgtccaa cacagcctac      240
atgcaactca gccaactgaa atctgacgac acagcactct attttgtgc tatgaactac     300
gaagggtatg aggattactg gggccaagga gtcatggtca cagtctcctc a             351
```

<210> SEQ ID NO 127
<211> LENGTH: 318
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 127

```
gacatccaga tgacccagtc tccttcattc ctgtctgcat ctgtgggaga cagcgtcact     60
atcaactgca aagcaagtca gaatattaac aagtacttaa attggtatca gcaaaagctt    120
ggagaagctc ccaaacgcct gatacataaa acagacagtc tgcaaacggg catcccatca    180
aggttcagtg gcagtggatc tggtacagat tacacactca ccatcagcag cctgcagcct    240
gaagatgttg ccacatactt ctgctttcag tataagagtg ggttcatgtt tggagctggg    300
accaagctgg aactgaaa                                                  318
```

<210> SEQ ID NO 128
<211> LENGTH: 363
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 128

```
cagatccagt tggtacagtc tggacctgag ctgaagaagc ctggagagtc agtgaagatc     60
tcctgcaagg cctctgggta taccttcaca gactatgcag tgtactgggt gatacaggct    120
ccaggaaagg gcttgaagtg gatgggctgg atcaacacct atactgggaa gccaacatat    180
gccgatgact tcaaaggacg gtttgtcttc tctttggaaa cctctgccag cactgcaaat    240
ttgcagatca gcaacctcaa aaatgaggac acggctacat atttctgtgc aagaggagcg    300
ggcatgacta aggactatgt tatggatgcc tggggtcgag gggttttagt cactgtctcc    360
tca                                                                  363
```

<210> SEQ ID NO 129
<211> LENGTH: 324
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 129

```
agctatgagc tgatccaacc accttcggcg tcagtcactc tgggaaatac tgtctcactc     60
acttgtgtcg gagatgaatt atcaaaaaga tatgctcagt ggtatcaaca aaagccagac    120
aagaccattg tgtccgtgat atacaaagat agtgagcggc cctcagacat ctctgaccga    180
```

```
ttctctggtt ccagctccgg acaacagcc actctgacaa tccatggcac cctggctgag    240
gatgaggctg attattactg tttgtcaaca tatagtgatg ataatctccc tgttttcggt    300
ggtggaacca agctcactgt ccta                                          324
```

<210> SEQ ID NO 130
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
caggtgcagc tgaaggagtc aggacctggc ctggtgcagc cctcacagac cctgtctctc    60
acctgcactg tctctggatt ctcattaacc agctatcttg ttcactgggt tcgacagcct    120
ccaggaaaaa ctctggagtg ggtgggatta atgtggaatg atggagacac atcatataat    180
tcagctctca aatcccgact gagcatcagc agggacacct ccaagagcca agttttctta    240
aagatgcaca gtcttcaagc tgaggacaca gccacttact actgtgccag agagagcaac    300
ttgggattta cttactgggg ccacggcact ctggtcactg tctcttca                348
```

<210> SEQ ID NO 131
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
gacatccaga tgacacagtc tcctgcctcc ctgtctgctt ctctggaaga aattgtcacc    60
atcacctgca aggcaagcca gggcattgat gatgactat catggtatca gcagaaacca    120
gggaaatctc ctcagctcct gatctatgat gtaaccagat ggcagatgg ggtcccatca    180 cggttcagcg gcagtagatc tggcacacag tattctctta agatcagcag accacaggtt    240
gctgattctg gaatctatta ctgtctgcag agttacagta ctccgtacac gtttggagct    300
gggaccaagc tggaactgaa a                                             321
```

<210> SEQ ID NO 132
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

```
gaagtccagc tgcagcagta tggggctgag cttgggaaac ctgggacctc agtcaggttg    60
tcttgcaagg tttctggcta taacattagg aatacctaca ttcactgggt gcatcagagg    120
cctggagagg gcctggaatg gataggaagg attgatccta caaacggaaa tactatatct    180
gctgagaagt tcaaaagcaa ggccacactg actgcagata catcgtccaa tacagcctac    240
atgcagttca gccaactgaa atctgacgac acagcaatct attttgtgc tatgaactac    300 gaagggtatg cggattattg gggccaagga gtcatggtca cagtctcctc c             351
```

<210> SEQ ID NO 133
<211> LENGTH: 318
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 133
gacatccaga tgacccagtc tccttcattc ctgtctgcat ctgtgggaga cagactcact    60
atcaactgca aagcaagtca gaatattaac aagtacttaa actggtatca gcaaaagctt   120
ggagaagctc ccaaacgcct gatatttaag acaaacagtt tgcaaacggg catcccatca   180
aggttcagtg gcagtggatc tggaacagat tacacactca ccatcagcag cctgcagcct   240
gaagatgttg ccacatattt ctgctttcag tataacattg gttcacgtt tggagctggg    300 accaagctgg agctgaaa                                                 318

<210> SEQ ID NO 134
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
gaggtgcagc tggtggagtc tggtggaggc ttagtgcagt ctggaaggtc cctaaaactc    60
tcctgtgcag cctcaggatt cactgtcagt gactattaca tggcctgggt ccgccaggct   120
ccaacgaagg ggctggagtg ggtcgcaacc attaattatg atggtagtac cacttaccat   180
cgagactccg tgaagggccg attcactatc tccaggata atgcaaaaag caccctatac    240
ctgcaaatgg acagtctgcg gtctgaggac acggccactt attactgtgc aagacatggg   300
gactatgggt atcactacgg ggcctattat tttgattact ggggccaagg agtcatggtc   360
acagtctcct ca                                                       372

<210> SEQ ID NO 135
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
gacattgtct tgacccagtc tcctgctttg gctgtgtctc tggggcagag ggccactatc    60
tcctgtaggg ccagccagac tgtcagttta tctggatata atcttataca ctggtaccaa   120
cagagaacag gacagcaacc caaactcctc atctatcgtg catccaatct agcacctggg   180
atccctgcca ggttcagtgg cagtgggtct gggacagact tcaccctcac catcagccct   240
gtgcagtctg atgatattgc aacctattac tgtcagcaga gtagggagtc gtggacgttc   300
ggtggaggca ccaacttgga aatgaag                                       327

<210> SEQ ID NO 136
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
cagatccagt tggtacagtc tggacctgag ctgaagaagc ctggagagtc agtgaagatc    60
```

```
tcctgcaagg cttctgggta taccttcaca gactatgcaa tacactgggt gaaacaggct    120
ccaggacagg gcttgaggtg gatggcctgg atcaacaccg aaactgggaa gcctacatat    180
gctgatgact tcaaaggacg gtttgtcttc tctttggagg cctctgccag cactgcacat    240
ttgcagatca gcaacctcaa aaatgaggac acggctacat ttttctgtgc aggcgggtcc    300
cattggtttg cttactgggg ccaaggcact ctggtcactg tctcttca                 348
```

<210> SEQ ID NO 137
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137

```
agctatgagc tgatccaacc accttcagca tctgtcactc tggaaaatac tgtctcaatc    60
acttgttctg gagatgaatt atcaaacaaa tatgctcatt ggtatcaaca aaagccagac    120
aagaccattt tggaagtgat ctacaacgat agtgagcggc cctcaggcat ctctgaccga    180
ttctctgggt ccagctcagg gacaacagcc attctcacaa tccgtgatgc ccaggctgag    240
gatgaggctg attattactg tttgtcaaca tttagtgatg atgatctccc tattttcggt    300
ggtggcacca agctcactgt ccta                                           324
```

<210> SEQ ID NO 138
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138

```
agctatgagc tgatccaacc accttcaaca tcagtcactc tgggaaatac tgtctcactc    60
acctgtgttg gaaatgaatt accaaaaaga tatgcttatt ggtttcaaca aaagccagac    120
cagtccattg tgagactgat atatgacgat gacaggcggc cctcaggcat ctctgaccga    180
ttctctgggt ccagctctgg gacaacagcc actctgacaa tccgtgacgc ccaggctgag    240
gatgaggctt attattactg tcactcaaca tatactgatg ataaagtccc tattttcggt    300
ggtggaacca agctcactgt ccta                                           324
```

<210> SEQ ID NO 139
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139

```
gaggtgcagc tggtggagtc tgggggaggc ttagtgcagc ctggaaggtc catgaaactc    60
tcctgtaagg cctcaggatt cactttcagt aactatgaca tggcctgggt ccgccaggct    120
ccaacgaggg gtctggagtg ggtcgcatcc attagttatg atggtattac cgcttactat    180
cgagactccg tgaagggccg attcactatc tccagagaga atgcaaaaag caccctatac    240
ctgcaattgg tcagtctgag atctgaggac acggccactt attactgtac aacagagggg    300
ggttatgtgt actccggacc acactacttt gattactggg gccaaggagt catggtcaca    360
```

```
<210> SEQ ID NO 140
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
gacattcaga tgacccagtc tccatcctcc atgtctgtgt ctctgggaga cacagtcact      60
attacttgcc gggcaagtca ggacgttggg atttttgtaa attggttcca gcagaaacca     120
gggagatctc ctaggcgtat gatttatcgt gcaacgaact ggcagatggg gtcccatca     180 aggttcagcg gcagtaggtc tggatcagat tattctctca ccatcagcag cctggagtct    240
gaagatgtgg cagactatca ctgtctacag tatgatgagt ttcctcggac gttcggtgga    300
ggcaccaagc tggaattgaa a                                              321

<210> SEQ ID NO 141
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
gaagtccagc tgcagcagta tggggctgag cttgggaaac ctgggacctc agtcaggttg     60
tcttgcaagg tttctggcta taagattagg aatacctaca tacactgggt gaatcagagg    120
cctggaaagg gcctggaatg gatagggagg attgatcctg caaatggaaa tactatatat    180
gctgagaagt tcaaaagcaa ggttacactg actgcagata catcgtccaa cacagcctac    240
atgcaactca gccaactgaa atctgacgac acagcactct attttgtgc tatgaactac    300 gaagggtatg aggattactg gggccaagga gtcatggtca cagtctcctc a             351

<210> SEQ ID NO 142
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
gacatccaga tgacccagtc tccttcattc ctgtctgcat ctgtgggaga cagcgtcact     60
atcaactgca aagcaagtca gaatattaat aagtatttaa actggtatca gcaaaagctt    120
ggagaagctc ccaaacgcct gatacataaa acaaacagtt tgcaaccggg cttcccatca    180
aggttcagtg gcagtggatc tggtacagat tacacactca ccatcagcag cctgcagcct    240
gaagatgttg ccgcatattt ctgctttcag tataacagtg ggttcacgtt tggagctggg    300
accaagctgg aactgaaa                                                  318

<210> SEQ ID NO 143
<211> LENGTH: 123
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 143

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Ala Ile Ile Asn Pro Arg Asp Ser Asp Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser
        115                 120

<210> SEQ ID NO 144
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Gly Ile Arg Ser Asp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Gly Phe Pro Leu
                85                  90                  95

Thr Phe Gly Gly Gly Thr Lys Val Glu Ile Lys
            100                 105

<210> SEQ ID NO 145
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asn Tyr Trp Ile Gly
1               5

<210> SEQ ID NO 146
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 146

Ile Ile Asn Pro Arg Asp Ser Asp Thr Arg Tyr Arg Pro Ser Phe Gln
1               5                   10                  15

Gly

<210> SEQ ID NO 147
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

His Gly Arg Gly Tyr Glu Gly Tyr Glu Gly Ala Phe Asp Ile
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Ser Ser Gln Gly Ile Arg Ser Asp Leu Gly
1               5                   10

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Asp Ala Ser Asn Leu Glu Thr
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln Gln Ala Asn Gly Phe Pro Leu Thr
1               5

<210> SEQ ID NO 151
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Val Gln Leu Val Gln Ser Gly Ala Glu Val Lys Lys Pro Gly Glu
```

```
                1               5                   10                  15
Ser Leu Lys Ile Ser Cys Lys Gly Ser Gly Tyr Ser Phe Thr Asn Tyr
                20                  25                  30

Trp Ile Gly Trp Val Arg Gln Met Pro Gly Lys Gly Leu Glu Trp Met
                35                  40                  45

Gly Ile Ile Tyr Pro Gly Asp Ser Asp Ile Arg Tyr Ser Pro Ser Leu
                50                  55                  60

Gln Gly Gln Val Thr Ile Ser Val Asp Thr Ser Thr Ser Thr Ala Tyr
 65                 70                  75                  80

Leu Gln Trp Asn Ser Leu Lys Pro Ser Asp Thr Ala Met Tyr Tyr Cys
                85                  90                  95

Ala Arg His Gly Arg Gly Tyr Asn Gly Tyr Glu Gly Ala Phe Asp Ile
                100                 105                 110

Trp Gly Gln Gly Thr Leu Val Thr Val Ser Ser
                115                 120
```

<210> SEQ ID NO 152
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

```
Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Gly Ile Gly Asp Ser
                20                  25                  30

Leu Ala Trp Tyr Gln Gln Lys Pro Gly Lys Ala Pro Lys Leu Leu Ile
                35                  40                  45

Tyr Asp Ala Ser Asn Leu Glu Thr Gly Val Pro Ser Arg Phe Ser Gly
                50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Leu Asn Gly Tyr Pro Ile
                85                  90                  95

Thr Phe Gly Gln Gly Thr Lys Val Glu Ile Lys
                100                 105
```

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

```
Ile Ile Tyr Pro Gly Asp Ser Asp Ile Arg Tyr Ser Pro Ser Leu Gln
 1               5                   10                  15

Gly
```

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Ala Ser Gln Gly Ile Gly Asp Ser Leu Ala
1               5                   10

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gln Gln Leu Asn Gly Tyr Pro Ile Thr
1               5

<210> SEQ ID NO 156
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Ile
                85                  90                  95

Thr Phe Gly Gln Gly Thr Lys Val Glu Ile Lys
            100                 105

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Arg Ala Ser Gln Gly Ile Arg Asn Asp Leu Gly
1               5                   10

<210> SEQ ID NO 158
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Val Gln Leu Val Gln Ser Gly Ala Glu Val Lys Lys Pro Gly Glu
1               5                   10                  15

```
Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Leu Thr Arg Tyr Ser Pro Ser Phe
 50                  55                  60

Gln Gly Gln Val Thr Ile Ser Ala Asp Lys Ser Ile Ser Thr Ala Tyr
65                   70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser
        115                 120
```

<210> SEQ ID NO 159
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

```
Ile Ile Tyr Pro Gly Asp Ser Leu Thr Arg Tyr Ser Pro Ser Phe Gln
1               5                   10                  15

Gly
```

<210> SEQ ID NO 160
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 160

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
65                   70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser
        115                 120
```

<210> SEQ ID NO 161
<211> LENGTH: 123
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 161

Gln Val Gln Leu Val Gln Ser Gly Ala Ala Val Lys Pro Gly Glu
1               5                   10                  15

Ser Leu Lys Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Gly Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Met Val Thr Val Ser Ser
        115                 120

<210> SEQ ID NO 162
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 162

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 163

Thr Tyr Trp Ile Gly
1               5

<210> SEQ ID NO 164
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 164

Arg Ala Ser Gln Gly Val Ile Ser Ala Leu Ala
1               5                   10

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Asp Ala Ser Ile Leu Glu Ser
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gln Gln Phe Asn Ser Tyr Pro Leu Thr
1               5

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Ala Ser Gln Gly Val Gly Ser Ala Leu Ala
1               5                   10

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asp Ala Ser Thr Leu Glu Ser
1               5

<210> SEQ ID NO 169
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 170
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 171
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Cys Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 172
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn Ala Tyr Thr
305                 310                 315                 320

Gln Lys Ser Leu Ser Leu Ser Pro Gly Lys
                325                 330

<210> SEQ ID NO 173
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
```

```
              115                 120                 125
Lys Pro Lys Asp Thr Leu Met Ile Ser Arg Thr Pro Glu Val Thr Cys
    130                 135                 140

Val Val Val Cys Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 174
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

Val Val Val Cys Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn Ala Tyr Thr
305                 310                 315                 320

Gln Lys Ser Leu Ser Leu Ser Pro Gly Lys
                325                 330

<210> SEQ ID NO 175
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Ala Ile Ile Asn Pro Arg Asp Ser Asp Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

```
Pro Ala Val Leu Gln Ser Ser Gly Leu Tyr Ser Leu Ser Ser Val Val
            180                 185                 190

Thr Val Pro Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 176
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Ala Ile Ile Asn Pro Arg Asp Ser Asp Thr Arg Tyr Arg Pro Ser Phe
    50                  55                  60

Gln Gly Gln Val Thr Ile Ser Ala Asp Lys Ser Ile Ser Thr Ala Tyr
```

```
            65                  70                  75                  80
Leu Gln Trp Ser Ser Leu Lys Ala Ser Asp Thr Ala Met Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 177
<211> LENGTH: 453
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 177

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Ala Ile Ile Asn Pro Arg Asp Ser Asp Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Cys Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
```

```
                385                 390                 395                 400
Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 178
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Ala Ile Ile Asn Pro Arg Asp Ser Asp Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Cys Val
            260                 265                 270

Ser His Glu Asp Pro Glu Val Lys Phe Asn Trp Tyr Val Asp Gly Val
        275                 280                 285
```

```
Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn Ala Tyr Thr Gln Lys Ser Leu Ser
        435                 440                 445

Leu Ser Pro Gly Lys
    450

<210> SEQ ID NO 179
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Thr Ser
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Leu Gly Tyr Asn Gly Tyr Glu Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Leu Gly Thr Gln Thr Tyr Ile Cys Asn Val
            195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 180
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Thr Ser
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
```

```
                    85                  90                  95
Ala Arg His Gly Leu Gly Tyr Asn Gly Tyr Glu Gly Ala Phe Asp Ile
                    100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 181
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 181

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Thr Ser
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Leu Gly Tyr Asn Gly Tyr Glu Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Cys Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
```

```
                    405                 410                 415
Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 182
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Thr Ser
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Leu Gly Tyr Asn Gly Tyr Glu Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Cys Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn Ala Tyr Thr Gln Lys Ser Leu Ser
            435                 440                 445

Leu Ser Pro Gly Lys
    450

<210> SEQ ID NO 183
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 184
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Gly Ile Arg Ser Asp
            20                  25                  30

```
Leu Gly Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Gly Phe Pro Leu
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 185
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Gly Ser Ala
                 20                  25                  30

Leu Ala Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Leu Asn Gly Tyr Pro Leu
                 85                  90                  95

Thr Phe Gly Gln Gly Thr Arg Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 186
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Thr Ser Trp Ile Gly
1               5

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

His Gly Leu Gly Tyr Asn Gly Tyr Glu Gly Ala Phe Asp Ile
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Ala Ser Gln Gly Ile Gly Ser Ala Leu Ala
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Cys Gln Gln Leu Asn Gly Tyr Pro Leu Thr
1               5                   10
```

COMPOSITIONS AND METHODS FOR THE DEPLETION OF CD117+ CELLS

RELATED APPLICATIONS

This application is a continuation of U.S. patent application Ser. No. 16/168,823, filed Oct. 23, 2018, which in turn claims priority to U.S. Provisional Application No. 62/576,572, filed on Oct. 24, 2017; U.S. Provisional Application No. 62/596,569, filed on Dec. 8, 2017; U.S. Provisional Application No. 62/632,967, filed on Feb. 20, 2018; and U.S. Provisional Application No. 62/638,053, filed on Mar. 2, 2018. The entire contents of each of the foregoing applications are hereby incorporated by reference.

SEQUENCE LISTING

The instant application contains a Sequence Listing which has been submitted electronically in ASCII format and is hereby incorporated by reference in its entirety. Said ASCII copy, created on Nov. 24, 2020, is named M103034_1100US_C1_SL.txt and is 211,920 bytes in size.

FIELD OF THE INVENTION

The invention relates anti-CD117 antibodies, antibody drug conjugates (ADCs), and antigen-binding fragments thereof, as well as methods of treating patients suffering from various pathologies, such as blood diseases, metabolic disorders, cancers, and autoimmune diseases, among others, by administration of an antibody, or antibody drug conjugate (ADC), capable of binding an antigen expressed by a hematopoietic cell, such as a hematopoietic stem cell.

BACKGROUND OF THE INVENTION

Despite advances in the medicinal arts, there remains a demand for treating pathologies of the hematopoietic system, such as diseases of a particular blood cell, metabolic disorders, cancers, and autoimmune conditions, among others. While hematopoietic stem cells have significant therapeutic potential, a limitation that has hindered their use in the clinic has been the difficulty associated with ensuring engraftment of hematopoietic stem cell transplants in a host.

There is currently a need for compositions that target specific endogenous stem cells that can be used as conditioning agents to promote the engraftment of exogenous hematopoietic stem cell grafts such that the multi-potency and hematopoietic functionality of these cells is preserved in the patient following transplantation.

CD117 (also referred to as c-kit or Stem Cell Factor Receptor (SCRF)) is a single transmembrane, receptor tyrosine kinase that binds the ligand Stem Cell Factor (SCF). SCF induces homodimerization of cKIT which activates its tyrosine kinase activity and signals through both the PI3-AKT and MAPK pathways (Kindblom et al., *Am J. Path.* 1998 152(5):1259).

CD117 was initially discovered as an oncogene and has been studied in the field of oncology (see, for example, Stankov et al. (2014) *Curr Pharm Des.* 20(17):2849-80). An antibody drug conjugate (KTN0158) directed to CD117 is currently under investigation for the treatment of refractory gastrointestinal stromal tumors (GIST) (e.g., "KTN0158, a humanized anti-KIT monoclonal antibody, demonstrates biologic activity against both normal and malignant canine mast cells" London et al. (2016) *Clin Cancer Res* DOI: 10.1158/1078-0432.CCR-16-2152).

CD117 is highly expressed on hematopoietic stem cells (HSCs). This expression pattern makes CD117 a potential target for conditioning across a broad range of diseases. There remains, however, a need for anti-CD117 based therapy that is effective for conditioning a patient for transplantation, such as a bone marrow transplantation.

SUMMARY OF THE INVENTION

Described herein are antibodies, and antigen binding portions thereof, that specifically bind human CD117 (also known as c-kit), as well as compositions and methods of using said antibodies. In particular, the antibodies and fragments described herein can be used in anti-CD117 antibody drug conjugates (ADCs).

In one embodiment, the present invention provides compositions and methods for the direct treatment of various disorders of the hematopoietic system, metabolic disorders, cancers, and autoimmune diseases, among others. The invention additionally features methods for conditioning a patient, such as a human patient, prior to receiving hematopoietic stem cell transplant therapy so as to promote the engraftment of hematopoietic stem cell grafts. The patient may be one that is suffering from one or more blood disorders, such as a hemoglobinopathy or other hematopoietic pathology, and is thus in need of hematopoietic stem cell transplantation. As described herein, hematopoietic stem cells are capable of differentiating into a multitude of cell types in the hematopoietic lineage, and can be administered to a patient in order to populate or re-populate a cell type that is deficient in the patient. The invention features methods of treating a patient with antibodies and antibody drug conjugates (ADCs) capable of binding proteins expressed by hematopoietic cells, such as CD117 (including, for example, GNNK+ CD117), so as to (i) directly treat a disease such as a blood disorder, metabolic disease, cancer, or autoimmune disease, among others described herein, by selectively depleting a population of cells that express CD117, such as an aberrant blood cell, cancer cell, or autoimmune cell, and/or (ii) deplete a population of endogenous hematopoietic stem cells within the patient. The former activity enables the direct treatment of a wide range of disorders associated with a cell of the hematopoietic lineage, as CD117 may be expressed by a cancerous cell, such as a leukemic cell, an autoimmune lymphocyte, such as a T-cell that expresses a T-cell receptor that cross-reacts with a self antigen, among other cell types. The latter activity, the selective depletion of hematopoietic stem cells, in turn creates a vacancy that can subsequently be filled by transplantation of an exogenous (for instance, an autologous, allogeneic, or syngeneic) hematopoietic stem cell graft. The invention thus provides methods of treating a variety of hematopoietic conditions, such as sickle cell anemia, thalassemia, Fanconi anemia, Wiskott-Aldrich syndrome, adenosine deaminase deficiency-severe combined immunodeficiency, metachromatic leukodystrophy, Diamond-Blackfan anemia and Schwachman-Diamond syndrome, human immunodeficiency virus infection, and acquired immune deficiency syndrome, as well as cancers and autoimmune diseases, among others.

In one aspect, the invention provides a method of depleting a population of CD117+ cells in a human patient by administering an effective amount of an antibody, antigen-binding fragment thereof, capable of binding CD117 where the antibody or fragment is conjugated to a cytotoxin (forming an ADC).

In another aspect, the invention provides a method of depleting a population of CD117+ cells in a human patient in need of a hematopoietic stem cell transplant by administering, prior to the patient receiving a transplant including hematopoietic stem cells, an effective amount of an antibody or antigen-binding fragment thereof capable of binding CD117 conjugated to a cytotoxin (an ADC).

In another aspect, the invention features a method, for example, of treating a human patient in need of a hematopoietic stem cell transplant, including administering to a human patient a transplant including hematopoietic stem cells, wherein the patient has been previously administered an antibody or antigen-binding fragment thereof capable of binding CD117 conjugated to a cytotoxin (forming an ADC) in an amount sufficient to deplete a population of CD117+ cells in the patient.

In an additional aspect, the invention features a method, for example, of treating a human patient in need of a hematopoietic stem cell transplant, including: administering to a human patient an antibody or antigen-binding fragment thereof capable of binding CD117 conjugated to a cytotoxin (forming an ADC) in an amount sufficient to deplete a population of CD117+ cells in the patient, and subsequently administering to the patient a transplant including hematopoietic stem cells.

In any of the above aspects, the cytotoxin may be, for example, *pseudomonas* exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, or an indolinobenzodiazepine dimer, or a variant thereof.

In some embodiments of any of the above aspects, the cytotoxin is an amatoxin or derivative thereof, such as α-amanitin, β-amanitin, γ-amanitin, ε-amanitin, amanin, amaninamide, amanullin, amanullinic acid, and proamanullin. In one embodiment, the cytotoxin is an amanitin.

In some embodiments of any of the above aspects, the cytotoxin is an amatoxin, and the antibody, or antigen-binding fragment thereof, conjugated to the cytotoxin is represented by the formula Ab-Z-L-Am, wherein Ab is the antibody, or antigen-binding fragment thereof, L is a linker, Z is a chemical moiety, and Am is the amatoxin. In some embodiments, the amatoxin is conjugated to a linker. In some embodiments, the amatoxin linker conjugate Am-L-Z is represented by formula (I)

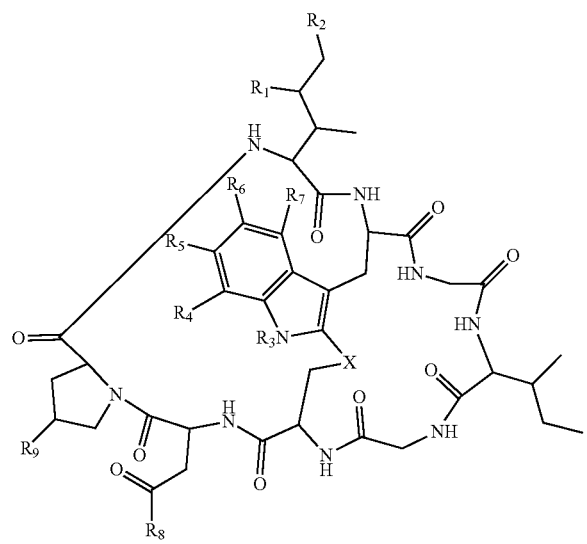

(I)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene; a dipeptide, —(C═O)—, a peptide, or a combination thereof; and
Z is a chemical moiety formed from a coupling reaction between a reactive substituent present on L and a reactive substituent present within an antibody, or antigen-binding fragment thereof, that binds CD117 (such as GNNK+ CD117).

In some embodiments, Am contains exactly one $R_C$ substituent.

In some embodiments, the linker L and the chemical moiety Z, taken together as L-Z, is

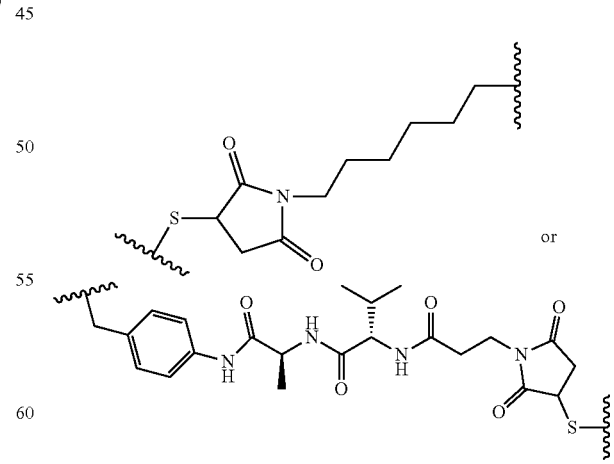

where S is a sulfur atom which represents the reactive substituent present within an antibody, or antigen-binding fragment thereof, that binds CD117 (e.g., from the —SH group of a cysteine residue).

In some embodiments, L-Z is
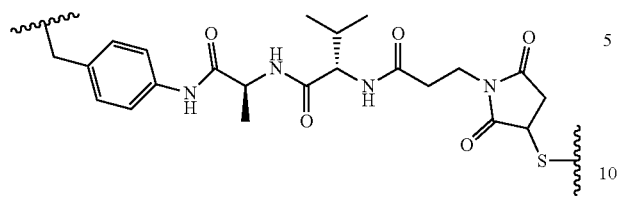
In some embodiments, Am-L-Z-Ab is one of:
(IV)
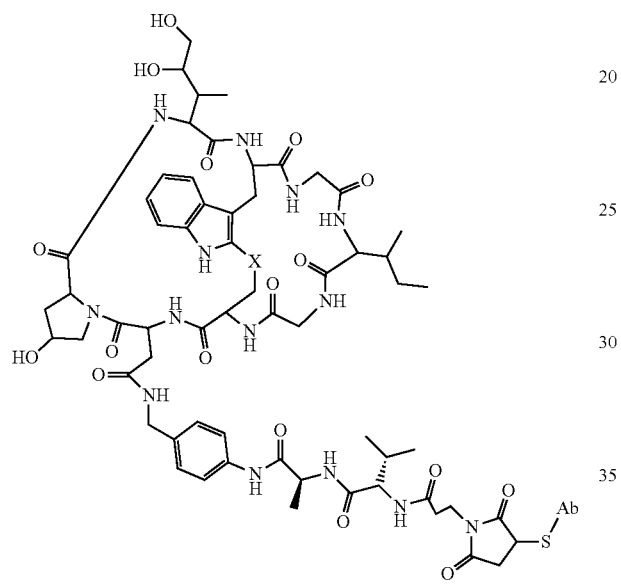
(IVA)
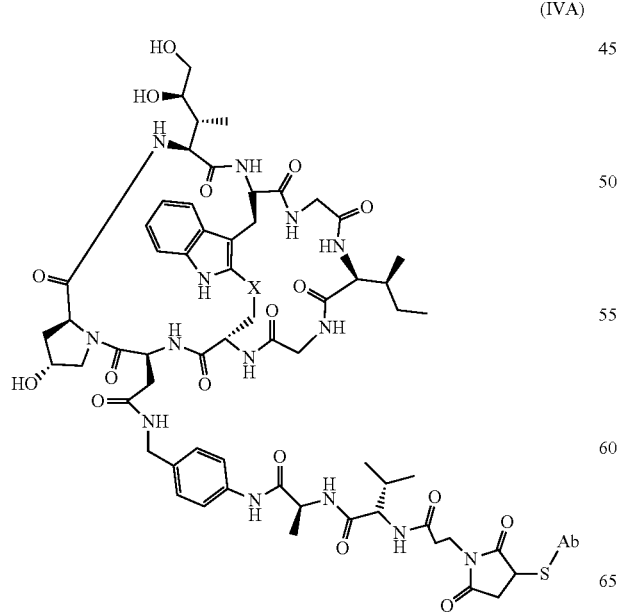
-continued
(IVB)
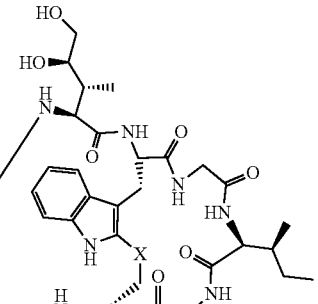
wherein X is —S—, —S(O)—, or —SO$_2$—.
In some embodiments, Am-L-Z-Ab is:
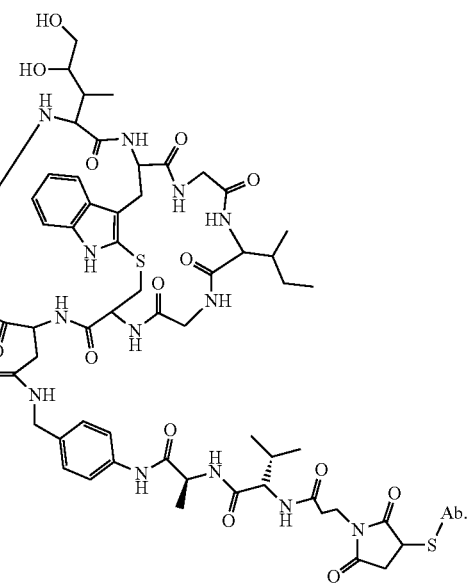

In some embodiments, Am-L-Z-Ab is:

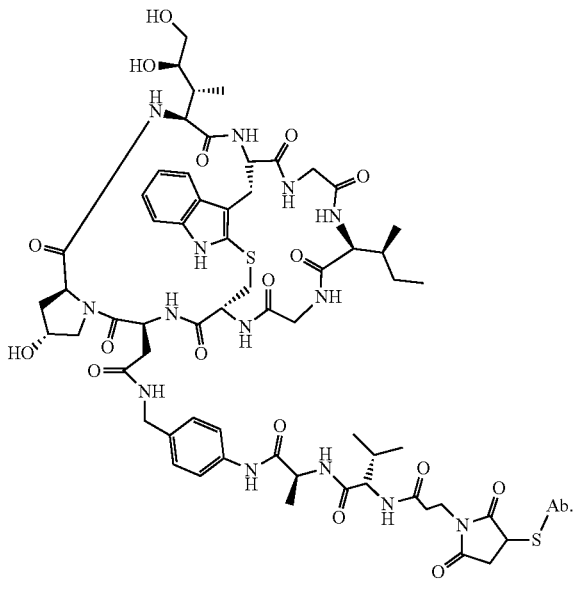

In some embodiments, Am-L-Z-Ab is:

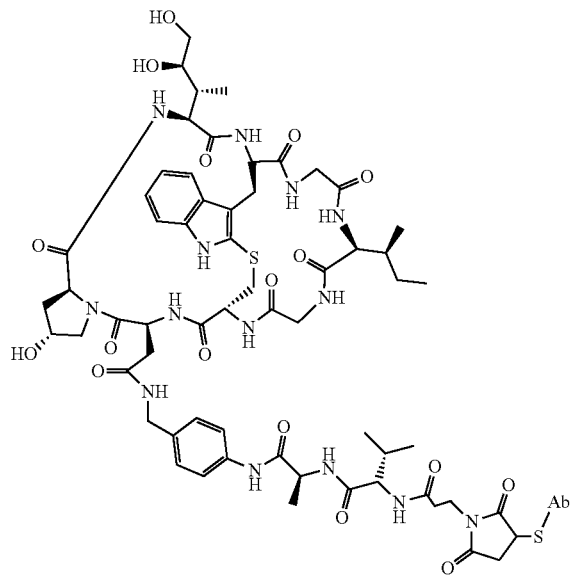

In some embodiments, Am-L-Z is represented by formula (IA)

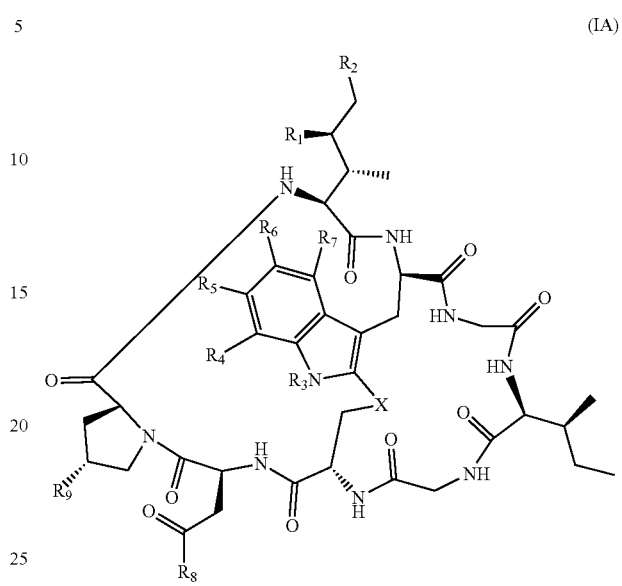

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a dipeptide, —(C═O)—, a peptide, or a combination thereof; Z is a chemical moiety formed from a coupling reaction between a reactive substituent present on L and a reactive substituent present within an antibody, or antigen-binding fragment thereof, that binds CD117 (such as GNNK+ CD117); and
wherein Am contains exactly one $R_C$ substituent.

In some embodiments, the linker L and the chemical moiety Z, taken together as L-Z, is

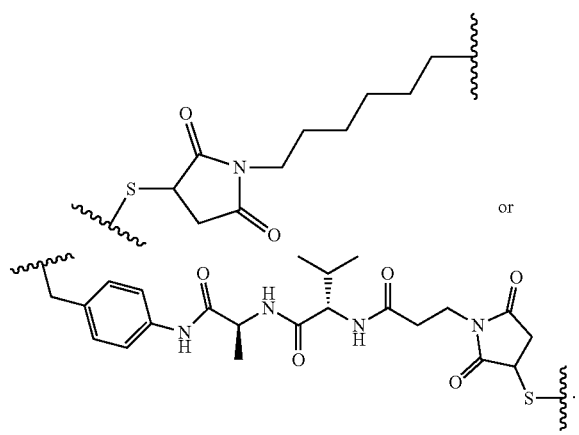

or

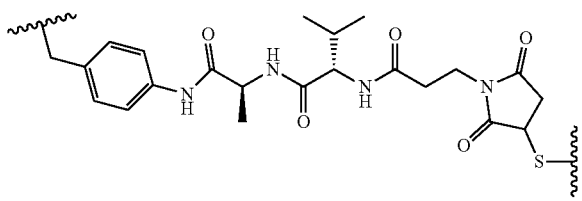

In some embodiments, L-Z is

In some embodiments, Am-L-Z is represented by formula (IB)

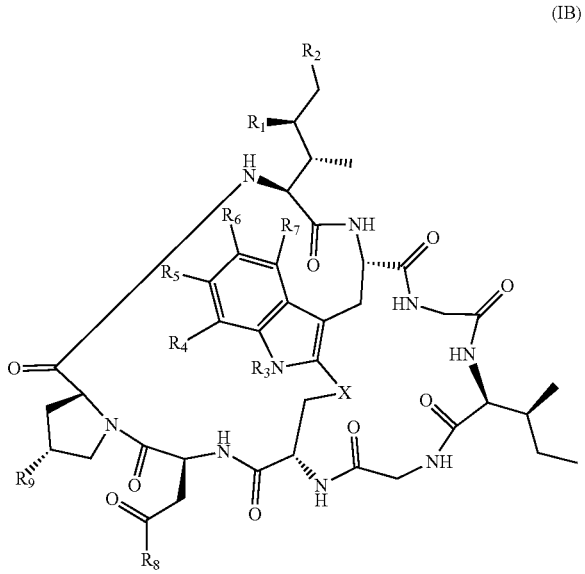
(IB)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a dipeptide, —(C=O)—, o a peptide, or a combination thereof;
Z is a chemical moiety formed from a coupling reaction between a reactive substituent present on L and a reactive substituent present within an antibody, or antigen-binding fragment thereof, that binds CD117 (such as GNNK+ CD117); and
wherein Am contains exactly one $R_C$ substituent.

In some embodiments, $R_A$ and $R_B$, together with the oxygen atoms to which they are bound, combine to form a 5-membered heterocycloalkyl group of formula:

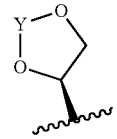

wherein Y is —(C=O)—, —(C=S)—, —(C=$NR_E$)—, or —(C$R_ER_{E'}$)—; and
$R_E$ and $R_{E'}$ are each independently optionally substituted $C_1$-$C_6$ alkylene-$R_C$, optionally substituted $C_1$-$C_6$ heteroalkylene-$R_C$, optionally substituted $C_2$-$C_6$ alkenylene-$R_C$, optionally substituted $C_2$-$C_6$ heteroalkenylene-$R_C$, optionally substituted $C_2$-$C_6$ alkynylene-$R_C$, optionally substituted $C_2$-$C_6$ heteroalkynylene-$R_C$, optionally substituted cycloalkylene-$R_C$, optionally substituted heterocycloalkylene-$R_C$, optionally substituted arylene-$R_C$, or optionally substituted heteroarylene-$R_C$.

In some embodiments, Am-L-Z is represented by formula (IA) or formula (IB), wherein $R_1$ is H, OH, $OR_A$, or $OR_C$;
$R_2$ is H, OH, $OR_B$, or $OR_C$;
$R_A$, and $R_B$, together with the oxygen atoms to which they are bound, combine to form:

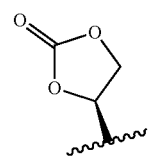 [SMILES: *[C@@H]1COC(=O)O1]

R$_3$ is H or R$_C$;
R$_4$ is H, OH, OR$_C$, OR$_D$, R$_C$, or R$_D$;
R$_5$ is H, OH, OR$_C$, OR$_D$, R$_C$, or R$_D$;
R$_6$ is H, OH, OR$_C$, OR$_D$, R$_C$, or R$_D$;
R$_7$ is H, OH, OR$_C$, OR$_D$, R$_C$, or R$_D$;
R$_8$ is OH, NH$_2$, OR$_C$, or NHR$_C$;
R$_9$ is H or OH; and
wherein R$_C$ and R$_D$ are each as defined above.

In some embodiments, Am-L-Z is represented by formula (IA) or formula (IB), wherein R$_1$ is H, OH, OR$_A$, or OR$_C$;
R$_2$ is H, OH, OR$_B$, or OR$_C$;
R$_A$ and R$_B$, together with the oxygen atoms to which they are bound, combine to form:

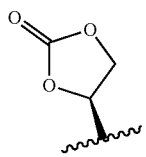 [SMILES: *[C@@H]1COC(=O)O1]

R$_3$ is H or R$_C$;
R$_4$ and R$_5$ are each independently H, OH, OR$_C$, R$_C$, or OR$_D$;
R$_6$ and R$_7$ are each H;
R$_8$ is OH, NH$_2$, OR$_C$, or NHR$_C$;
R$_9$ is H or OH; and
wherein R$_C$ is as defined above.

In some embodiments, Am-L-Z is represented by formula (IA) or formula (IB),
wherein R$_1$ is H, OH, or OR$_A$;
R$_2$ is H, OH, or OR$_B$;
R$_A$, and R$_B$, together with the oxygen atoms to which they are bound, combine to form:

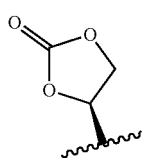 [SMILES: *[C@@H]1COC(=O)O1]

R$_3$, R$_4$, R$_6$, and R$_7$ are each H;
R$_5$ is OR$_C$;
R$_8$ is OH or NH$_2$;
R$_9$ is H or OH; and
wherein R$_C$ is as defined above.

In some embodiments, Am-L-Z is represented by formula (IA) or formula (IB),
wherein R$_1$ and R$_2$ are each independently H or OH;
R$_3$ is R$_C$;
R$_4$, R$_6$, and R$_7$ are each H;
R$_5$ is H, OH, or C$_1$-C$_6$ alkyl;
R$_8$ is OH or NH$_2$;
R$_9$ is H or OH; and
wherein R$_C$ is as defined above.

In some embodiments, Am-L-Z is represented by formula (IA) or formula (IB),
wherein R$_1$ and R$_2$ are each independently H or OH;
R$_3$, R$_6$, and R$_7$ are each H;
R$_4$ and R$_5$ are each independently H, OH, OR$_C$, or R$_C$;
R$_8$ is OH or NH$_2$;
R$_9$ is H or OH; and
wherein R$_C$ is as defined above.

In some embodiments, Am-L-Z is represented by formula (IA) or formula (IB),
wherein R$_1$ and R$_2$ are each independently H or OH;
R$_3$, R$_6$, and R$_7$ are each H;
R$_4$ and R$_5$ are each independently H or OH;
R$_8$ is OH, NH$_2$, OR$_C$, or NHR$_C$;
R$_9$ is H or OH; and
wherein R$_C$ is as defined above.

In some embodiments, the linker L and the chemical moiety Z, taken together as L-Z, is

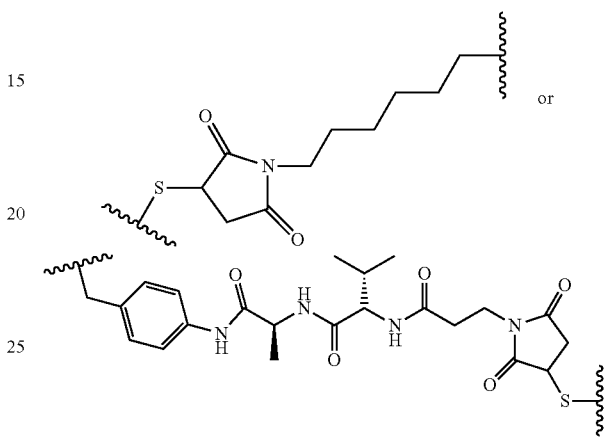

In some embodiments, L-Z is

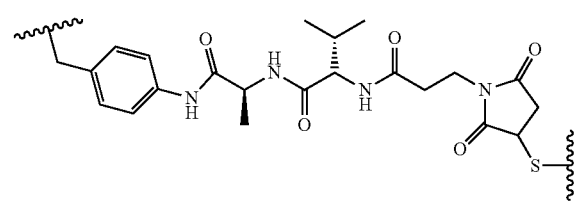

In some embodiments, Am-L-Z is represented by formula (II), formula (IIA), or formula (IIB)

(II)

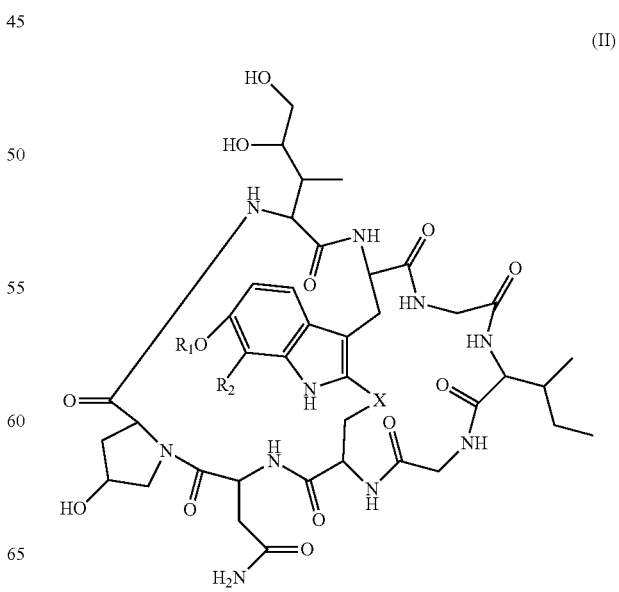

-continued (IIA)

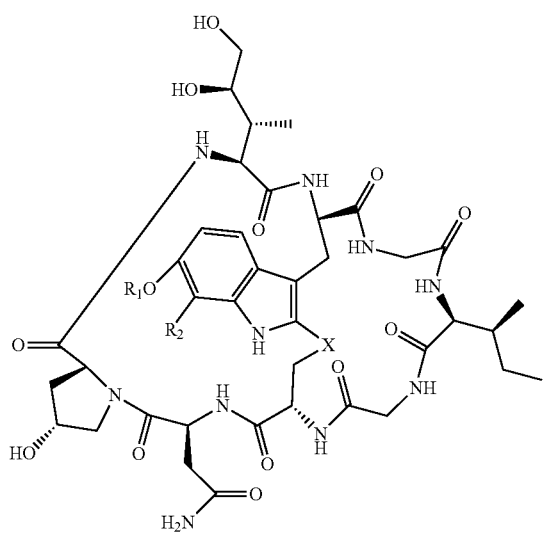

(IIB)

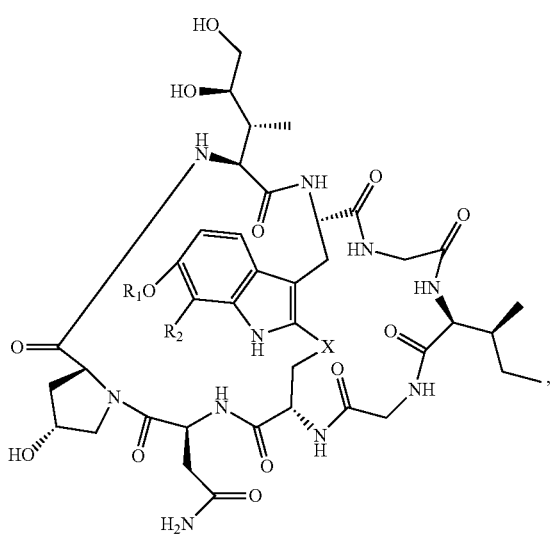

wherein X is S, SO, or SO$_2$; R$_1$ is H or a linker covalently bound to the antibody or antigen-binding fragment thereof through a chemical moeity Z, formed from a coupling reaction between a reactive substituent present on the linker and a reactive substituent present within an antibody, or antigen-binding fragment thereof; and R$_2$ is H or a linker covalently bound to the antibody or antigen-binding fragment thereof through a chemical moeity Z, formed from a coupling reaction between a reactive substituent present on the linker and a reactive substituent present within an antibody, or antigen-binding fragment thereof; wherein when R$_1$ is H, R$_2$ is the linker, and when R$_2$ is H, R$_1$ is the linker.

In some embodiments, the linker comprises a —(CH)$_{2n}$— unit, where n is an integer from 2-6.

In some embodiments, R$_1$ is the linker and R$_2$ is H, and the linker and chemical moiety, together as L-Z, is

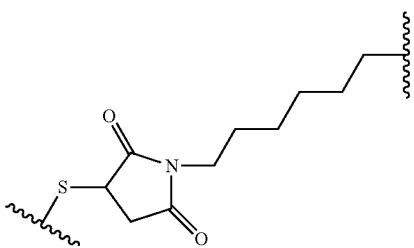 [SMILES: *CCCCCCN1C(=O)CC(S*)C1=O]

In some embodiments, Am-L-Z-Ab is:

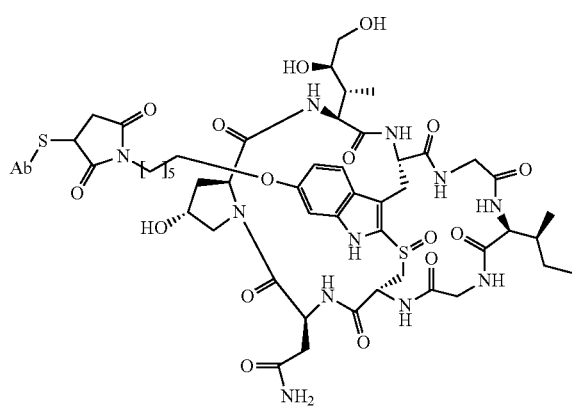

In some embodiments, Am-L-Z-Ab is:

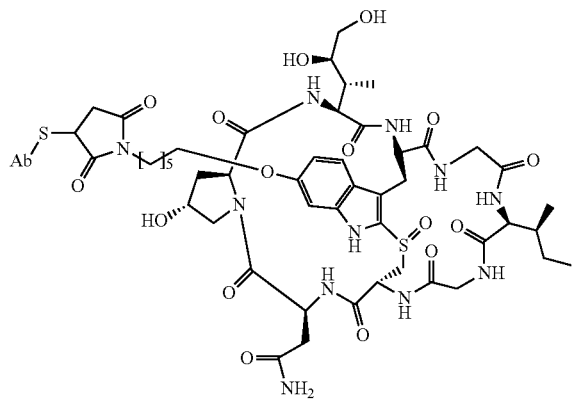

In some embodiments of any of the above aspects, the cytotoxin is a maytansinoid selected from the group consisting of DM1 and DM4. In some embodiments, the cytotoxin is an auristatin selected from the group consisting of monomethyl auristatin E and monomethyl auristatin F. In some embodiments, the cytotoxin is an anthracycline selected from the group consisting of daunorubicin, doxorubicin, epirubicin, and idarubicin.

In another aspect, the invention features a method of depleting a population of CD117+ cells in a human patient by administering an effective amount of an antibody, an antigen-binding fragment, or an ADC thereof capable of binding GNNK+ CD117.

In an additional, the invention features a method of depleting a population of CD117+ cells in a human patient in need of a hematopoietic stem cell transplant by administering, prior to the patient receiving a transplant containing hematopoietic stem cells, an effective amount of an antibody or antigen-binding fragment thereof, or ADC capable of binding GNNK+ CD117.

In another aspect, the invention features a method, for example, of treating a human patient in need of a hematopoietic stem cell transplant, including administering to a human patient a transplant containing hematopoietic stem cells, wherein the patient has been previously administered an antibody, antigen-binding fragment thereof, or ADC capable of binding GNNK+ CD117 in an amount sufficient to deplete a population of CD117+ cells in the patient.

In an additional aspect, the invention features a method, for example, of treating a human patient in need of a hematopoietic stem cell transplant, including: administering to a human patient an antibody, antigen-binding fragment thereof, or ADC capable of binding GNNK+ CD117 in an amount sufficient to deplete a population of CD117+ cells in the patient, and subsequently administering to the patient a transplant including hematopoietic stem cells.

In some embodiments of any of the above aspects, the antibody, antigen-binding fragment thereof, is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv. In some embodiments, the antibody has an isotype selected from the group consisting of IgG, IgA, IgM, IgD, and IgE.

In some embodiments of any of the above aspects, the antibody, or antigen-binding fragment thereof, is internalized by a hematopoietic cell, such as a hematopoietic stem cell, cancer cell, or autoimmune cell following administration to the patient. For instance, the antibody, or antigen-binding fragment thereof, or ADC may be internalized by hematopoietic stem cells, cancer cells, or autoimmune cells by receptor-mediated endocytosis (e.g., upon binding to cell-surface CD117, such as GNNK+ CD117). In some embodiments, a cytotoxin covalently bound to the antibody or antigen-binding fragment thereof may be released intracellularly by chemical cleavage (for instance, by enzymatic or non-specific cleavage of a linker described herein). The cytotoxin may then access its intracellular target (such as the mitotic spindle apparatus, nuclear DNA, ribosomal RNA, or topoisomerases, among others) so as to promote the death of an endogenous hematopoietic cell, such as an endogenous hematopoietic stem cell prior to transplantation therapy, an endogenous cancer cell, or an endogenous autoimmune cell, among others.

In some embodiments of any of the above aspects, the antibody, or antigen-binding fragment thereof, or ADC is capable of promoting necrosis of a hematopoietic cell, such as a hematopoietic stem cell, cancer cell, or autoimmune cell, among others. In some embodiments, the antibody or antigen-binding fragment thereof may promote the death of an endogenous hematopoietic stem cell prior to transplantation therapy, an endogenous cancer cell, or an endogenous autoimmune cell, among others, by recruiting one or more complement proteins, natural killer (NK) cells, macrophages, neutrophils, and/or eosinophils to the cell, such as a hematopoietic stem cell upon administration to the patient.

In some embodiments of any of the above aspects, the transplant containing hematopoietic stem cells is administered to the patient after the concentration of the antibody, antigen-binding fragment thereof, or ADC has substantially cleared from the blood of the patient.

In some embodiments of any of the above aspects, the hematopoietic stem cells or progeny thereof maintain hematopoietic stem cell functional potential after two or more days (for example, from about 2 to about 5 days, from about 2 to about 7 days, from about 2 to about 20 days, from about 2 to about 30 days, such as 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or more) following transplantation of the hematopoietic stem cells into the patient.

In some embodiments of any of the above aspects, the hematopoietic stem cells or progeny thereof are capable of localizing to hematopoietic tissue, such as the bone marrow, and/or reestablishing hematopoiesis following transplantation of the hematopoietic stem cells into the patient.

In some embodiments of any of the above aspects, upon transplantation into the patient, the hematopoietic stem cells give rise to recovery of a population of cells selected from the group consisting of megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes.

In some embodiments of any of the above aspects, the method is used to treat one or more disorders, such as by depleting a population of hematopoietic stem cells in a patient prior to hematopoietic stem cell transplant therapy so as to provide a niche to which the transplanted hematopoietic stem cells may home. Following transplantation, the hematopoietic stem cells may establish productive hematopoiesis, so as to replenish a deficient cell type in the patient or a cell type that is being actively killed or has been killed, for instance, by chemotherapeutic methods. For instance, the patient may be one that is suffering from a stem cell disorder. In some embodiments, the patient is suffering from a hemoglobinopathy disorder, such as sickle cell anemia, thalassemia, Fanconi anemia, aplastic anemia, and Wiskott-Aldrich syndrome. The patient may be suffering from an immunodeficiency disorder, such as a congenital immunodeficiency disorder or an acquired immunodeficiency disorder (e.g., human immunodeficiency virus or acquired immune deficiency syndrome). In some embodiments, the patient is suffering from a metabolic disorder, such as glycogen storage diseases, mucopolysaccharidoses, Gaucher's Disease, Hurlers Disease, sphingolipidoses, and metachromatic leukodystrophy. In some embodiments, the patient is suffering from a disorder selected from the group consisting of adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, and juvenile rheumatoid arthritis. In some embodiments, the patient is suffering from an autoimmune disease, such as scleroderma, multiple sclerosis, ulcerative colitis, Crohn's disease, ant Type 1 diabetes. In some embodiments, the patient is suffering from cancer or myeloproliferative disease, such as a hematological cancer. In some embodiments, the patient is suffering from acute myeloid leukemia (AML), acute lymphoid leukemia, chronic myeloid leukemia, chronic lymohoid leukemia, multiple meloma, diffuse large B-cell lymphoma, or non-Hodgkin's lymphoma. In some embodiments, the patient is suffering from a myelodysplastic disease, such as myelodysplastic syndrome.

In some embodiments of any of the above aspects, the method is used to directly treat a cancer, such as a cancer characterized by CD117+ cells (e.g., a leukemia characterized by CD117+ cells), by administration of an antibody, or antigen-binding fragment thereof, or ADC that depletes a population of CD117+ cancer cells in the patient and/or by administration of an antibody, or antigen-binding fragment thereof, so as to deplete a population of endogenous hematopoietic stem cells prior to hematopoietic stem cell transplantation. In the latter case, the transplantation may in turn re-constitute, for example, a population of cells depleted during the process of eradicating cancer cells. The cancer may be a hematological cancer, such as acute myeloid leukemia, acute lymphoid leukemia, chronic myeloid leukemia, chronic lymohoid leukemia, multiple meloma, diffuse large B-cell lymphoma, or non-Hodgkin's lymphoma.

In some embodiments of any of the above aspects, the method is used to treat an autoimmune disease, such as by administration of an antibody, antigen-binding fragment thereof, or ADC so as to deplete a population of CD117+ autoimmune cells and/or by administration of an antibody, or antigen-binding fragment thereof, or ADC so as to deplete a population of endogenous hematopoietic stem cells prior to hematopoietic stem cell transplantation. In the latter case, the transplantation may in turn re-constitute, for example, a population of cells depleted during the process of eradicating autoimmune cells. The autoimmune disease may be, for example, scleroderma, multiple sclerosis (MS), human systemic lupus (SLE), rheumatoid arthritis (RA), inflammatory bowel disease (IBD), treating psoriasis, Type 1 diabetes mellitus (Type 1 diabetes), acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, uveitis, vasculitis, vitiligo, vulvodynia ("vulvar vestibulitis"), and Wegener's granulomatosis.

Thus, in some embodiments of any of the above aspects, the invention features a method of treating a hemoglobinopathy disorder, such as sickle cell anemia, thalassemia, Fanconi anemia, aplastic anemia, and Wiskott-Aldrich syndrome. In some embodiments, the invention features a method of treating an immunodeficiency disorder, such as a congenital immunodeficiency disorder or an acquired immunodeficiency disorder (e.g., human immunodeficiency virus or acquired immune deficiency syndrome). In some embodiments, the invention features a method of treating a metabolic disorder, such as glycogen storage diseases, mucopolysaccharidoses, Gaucher's Disease, Hurlers Disease, sphingolipidoses, and metachromatic leukodystrophy. In some embodiments, the invention features a method of treating a disorder selected from the group consisting of adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, and juvenile rheumatoid arthritis In some embodiments, the invention features a method of treating an autoimmune disease, such as scleroderma, multiple sclerosis, ulcerative colitis, Chron's disease, ant Type 1 diabetes. In some embodiments, the invention features a method of treating a cancer or myeloproliferative disease, such as a hematological cancer. In some embodiments, the invention features a method of treating acute myeloid leukemia, acute lymphoid leukemia, chronic myeloid leukemia, chronic lymohoid leukemia, multiple meloma, diffuse large B-cell lymphoma, or non-Hodgkin's lymphoma. In some embodiments, the patient is suffering from a myelodyplastic disease, such as myelodysplastic syndrome. In these embodiments, the method may include the steps of administering an antibody, or antigen-binding fragment thereof, or ADC that binds CD117 (e.g., GNNK+ CD117) and/or a hematopoietic stem cell transplant according to the method of any of the above-described aspects and embodiments of the invention.

Similarly, in some embodiments of any of the above aspects, the invention provides a method of treating cancer directly, such as a cancer characterized by CD117+ cells (e.g., a leukemia characterized by CD117+ cells). In these embodiments, the method includes administering an antibody, antigen-binding fragment thereof, or ADC that binds CD117 (e.g., GNNK+ CD117). The cancer may be a hematological cancer, such as acute myeloid leukemia, acute lymphoid leukemia, chronic myeloid leukemia, chronic lymohoid leukemia, multiple meloma, diffuse large B-cell lymphoma, or non-Hodgkin's lymphoma.

Additionally, in some embodiments of any of the above aspects, the invention provides a method of treating an autoimmune disease, such as multiple sclerosis (MS), human systemic lupus (SLE), rheumatoid arthritis (RA), inflammatory bowel disease (IBD), treating psoriasis, Type 1 diabetes mellitus (Type 1 diabetes) acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, uveitis, vasculitis, vitiligo, vulvodynia ("vulvar vestibulitis"), and Wegener's granulomatosis. In these embodiments, the method includes administering an antibody, or antigen-binding fragment thereof, or ADC that binds CD117 (e.g., GNNK+ CD117).

In another aspect, the invention features a method of depleting a population of CD117+ (e.g., GNNK+ CD117+) cells by contacting the population with an effective amount of a conjugate (or ADC) represented by the formula Ab-Z-L-Am, wherein Ab is an antibody or antigen-binding fragment thereof that binds CD117, Z is a chemical moiety, L is a linker and Am is an amatoxin. Am-L-Z may be represented by formula (IA)

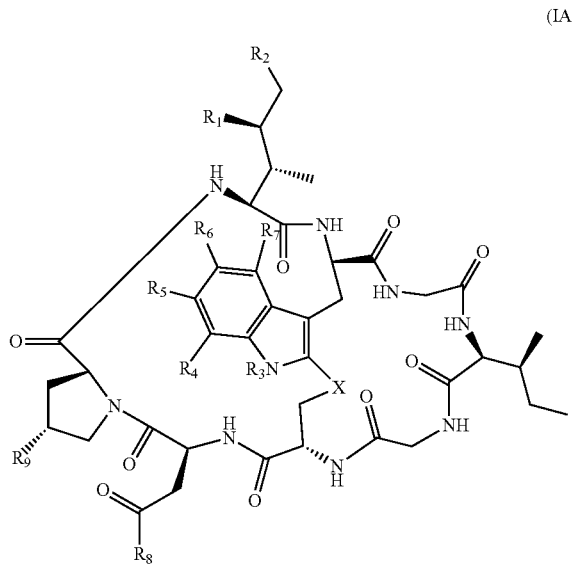

(IA)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;

$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —SO$_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a dipeptide, —(C=O)—, a peptide, or a combination thereof; and Z is a chemical moiety formed from a coupling reaction between a reactive substituent present on L and a reactive substituent present within the antibody or antigen-binding fragment thereof, wherein Am contains exactly one $R_C$ substituent.

In some embodiments, the linker L and the chemical moiety Z, taken together as L-Z, is

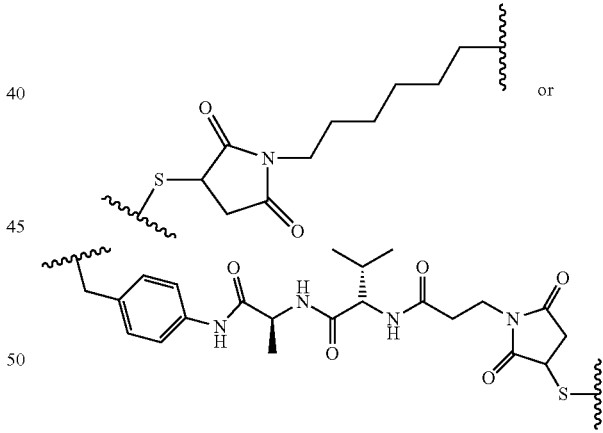

In some embodiments, L-Z is

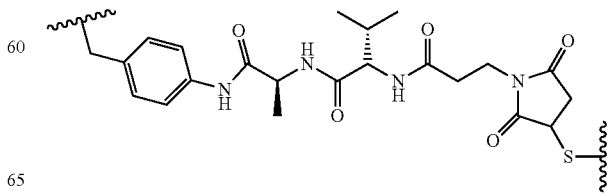

In some embodiments, Am-L-Z is represented by formula (IB)

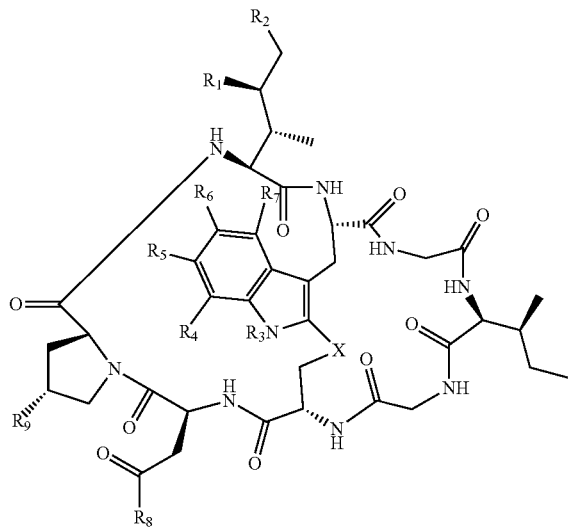

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —SO$_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl; L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a dipeptide, —(C═O)—, a peptide, or a combination thereof;

Z is a chemical moiety formed from a coupling reaction between a reactive substituent present on L and a reactive substituent present within an antibody, or antigen-binding fragment thereof, that binds CD117 (such as GNNK+ CD117); and wherein Am contains exactly one $R_C$ substituent.

In some embodiments, the linker L and the chemical moiety Z, taken together as L-Z, is

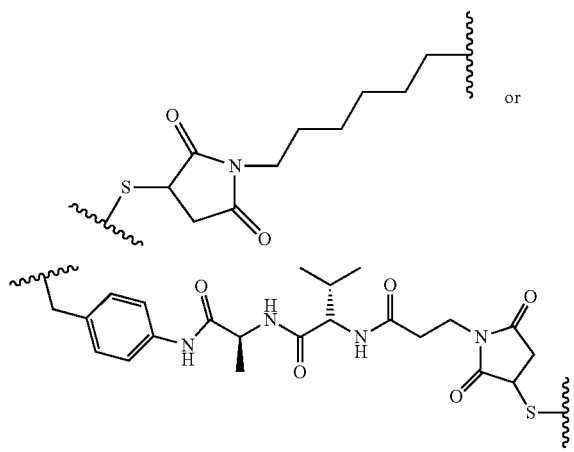

In some embodiments, L-Z is

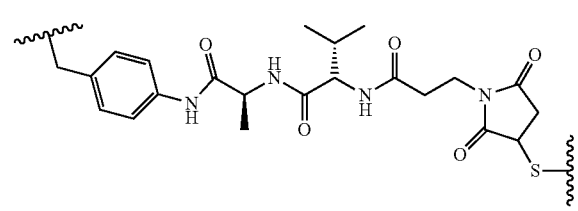

In some embodiments, Am-L-Z-Ab is selected from (IV)

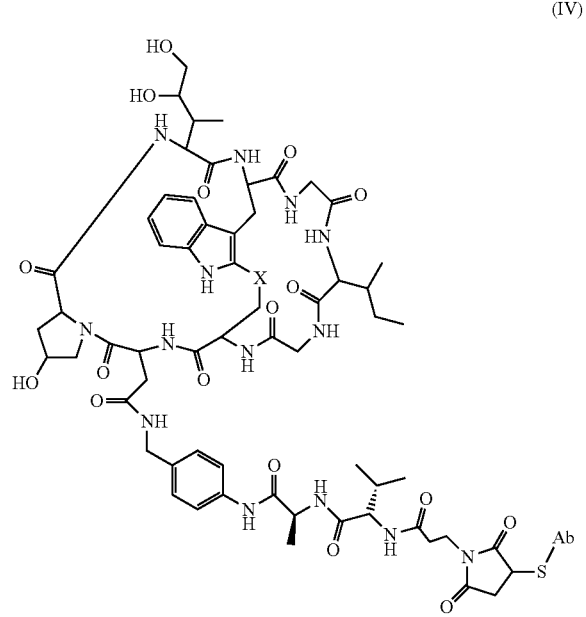

-continued
(IVA)
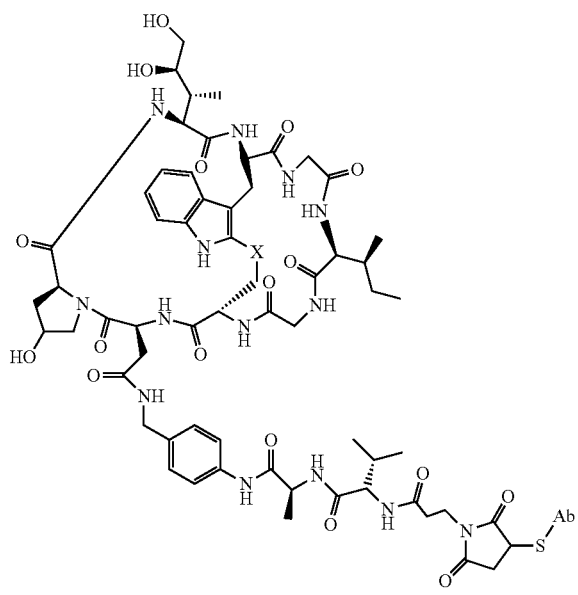
(IVB)
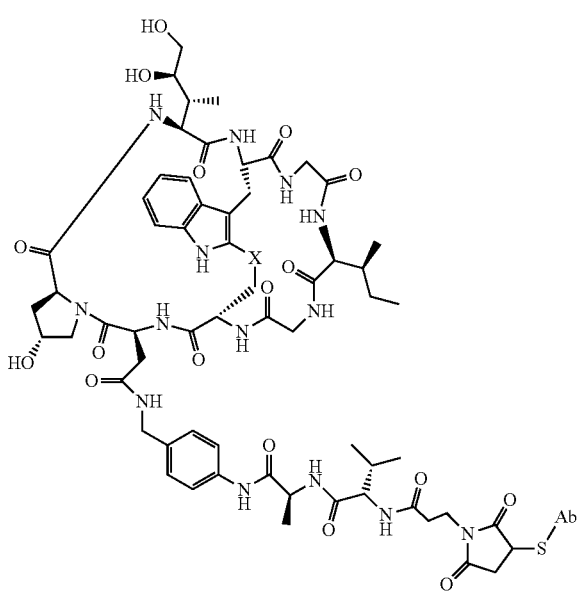
wherein X is —S—, —S(O)—, or —SO$_2$—.
In some embodiments, Am-L-Z-Ab is
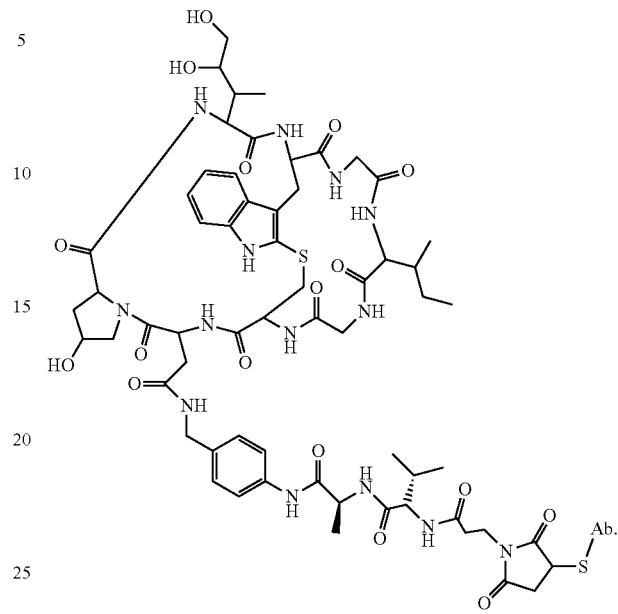
In some embodiments, Am-L-Z-Ab is
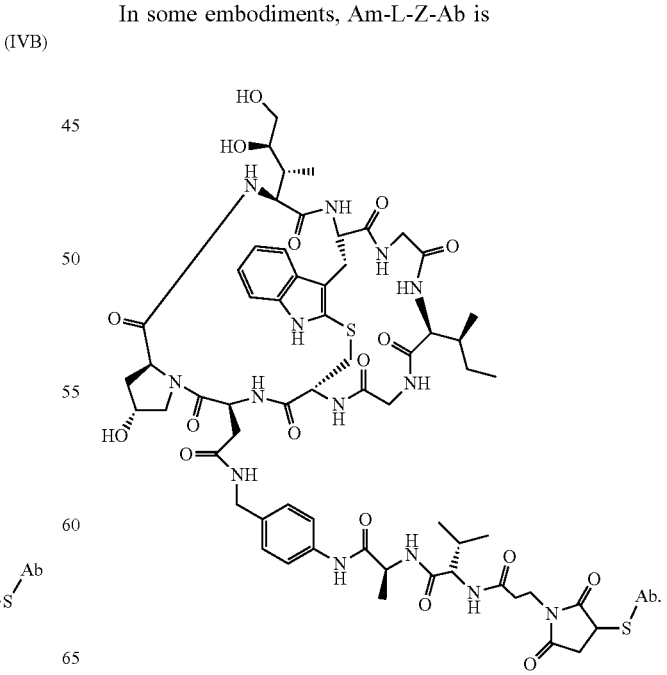

In some embodiments, Am-L-Z-Ab is

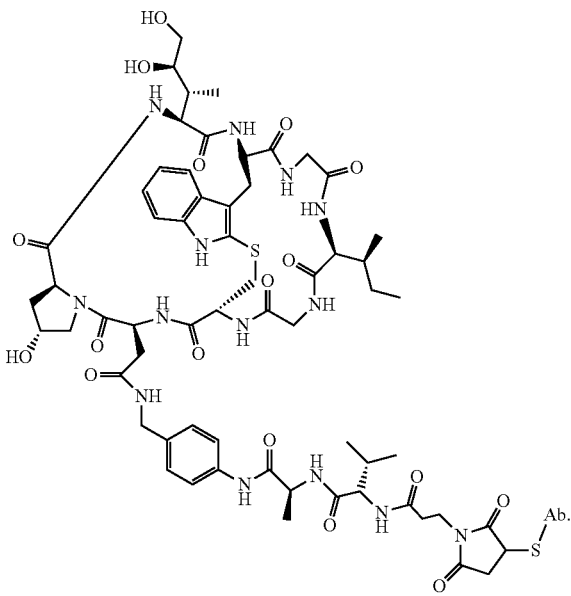

In another aspect, the invention features a conjugate represented by the formula Ab-Z-L-Am, wherein Ab is an antibody or antigen-binding fragment thereof that binds CD117 (e.g., GNNK+CD117) and Am is an amatoxin. In some embodiments, Am-L-Z is represented by formula (I), (IA), (IB), (II), (IIA), (IIB), (IV), (IVA), or (IVB), above.

In some embodiments, the antibody or antigen-binding fragment thereof is conjugated to the amatoxin by way of a cysteine residue in the Fc domain of the antibody or antigen-binding fragment thereof. In some embodiments, the cysteine residue is introduced by way of a mutation in the Fc domain of the antibody or antigen-binding fragment thereof. For instance, the cysteine residue may be selected from the group consisting of Cys118, Cys239, and Cys265.

In some embodiments of these aspects, the cysteine residue is naturally occurring in the Fc domain of the antibody or antigen-binding fragment thereof. For instance, the Fc domain may be an IgG Fc domain, such as a human IgG1 Fc domain, and the cysteine residue may be selected from the group consisting of Cys261, Csy321, Cys367, and Cys425.

In some embodiments of these aspects, $R_1$ is H, OH, or $OR_A$;

$R_2$ is H, OH, or $OR_B$;

$R_A$, and $R_B$, together with the oxygen atoms to which they are bound, combine to form:

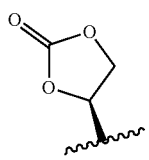 [SMILES: *[C@@H]1COC(=O)O1]

$R_3$, $R_4$, $R_6$, and $R_7$ are each H;
$R_5$ is $OR_C$;
$R_8$ is OH or $NH_2$;
$R_9$ is H or OH; and X is —S—, —S(O)—, or —SO$_2$—. In some embodiments, $R_1$ and $R_2$ are each independently H or OH;
$R_3$ is $R_C$;
$R_4$, $R_6$, and $R_7$ are each H;
$R_5$ is H, OH, or $C_1$-$C_6$ alkyl;
$R_8$ is OH or $NH_2$;
$R_9$ is H or OH; and
X is —S—, —S(O)—, or —SO$_2$—. In some embodiments, $R_1$ and $R_2$ are each independently H or OH;
$R_3$, $R_6$, and $R_7$ are each H;
$R_4$ is $OR_C$, or $R_C$;
$R_5$ is H, OH, or $C_1$-$C_6$ alkyl;
$R_8$ is OH or $NH_2$;
$R_9$ is H or OH; and
X is —S—, —S(O)—, or —SO$_2$—. In some embodiments, $R_1$ and $R_2$ are each independently H or OH;
$R_3$, $R_6$, and $R_7$ are each H;
$R_4$ and $R_5$ are each independently H or OH;
$R_8$ is $OR_C$ or $NHR_C$;
$R_9$ is H or OH; and
X is —S—, —S(O)—, or —SO$_2$—. In some embodiments of these aspects, the antibody or antigen-binding fragment thereof is internalized by a CD117+ cell.

In some embodiments of these aspects, the antibody or antigen-binding fragment thereof binds CD117 with a $K_d$ of less than 1 µM, less than 750 nM, less than 500 nM, less than 250 nM, less than 200 nM, less than 150 nM, less than 100 nM, less than 75 nM, less than 50 nM, less than 10 nM, less than 1 nM, less than 0.1 nM, less than 10 pM, less than 1 pM, or less than 0.1 pM. In some embodiments, the $K_d$ is from about 0.1 pM to about 1 µM.

In some embodiments of these aspects, the antibody or antigen-binding fragment thereof binds CD117 with a $k_{on}$ of from about $9 \times 10^{-2}$ M$^{-1}$ s$^{-1}$ to about $1 \times 10^2$ M$^{-1}$ s$^{-1}$.

In some embodiments of these aspects, the antibody or antigen-binding fragment thereof competitively inhibits the binding of CD117 to a second antibody or antigen binding fragment thereof, or binds the same epitope as a second antibody, wherein the second antibody or antigen-binding fragment thereof has the following complementarity determining regions (CDRs):
a CDR-H1 having the amino acid sequence SYWIG (SEQ ID NO: 1);
a CDR-H2 having the amino acid sequence IIYPGDSDTRYSPSFQG (SEQ ID NO: 2);
a CDR-H3 having the amino acid sequence HGRGYN-GYEGAFDI (SEQ ID NO: 3);
a CDR-L1 having the amino acid sequence RASQGISSALA (SEQ ID NO: 4);
a CDR-L2 having the amino acid sequence DASSLES (SEQ ID NO: 5); and
a CDR-L3 having the amino acid sequence CQQFNSYPLT (SEQ ID NO: 6).

The disclosure further provides isolated anti-CD117 antibodies that may be used in the antibody drug conjugates (ADCs) disclosed herein comprising heavy and light chain CDRs and variable regions described in Table 1, Table 6, or Table 8.

In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 8. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 9. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 10. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 11. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 12. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 13. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 14. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 15. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 16. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 17. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 18. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 19. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 20. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 21. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 22. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 23. In one embodiment, the anti-CD117 antibody, or antigen binding portion thereof, comprises a heavy chain variable region as set forth in the amino acid sequence of SEQ ID NO: 24, and a light chain variable region as set forth in the amino acid sequence of SEQ ID NO: 25. In one embodiment, the anti-CD117 antibody, or antigen binding portion thereof, comprises a heavy chain variable region as set forth in the amino acid sequence of SEQ ID NO: 26, and a light chain variable region as set forth in the amino acid sequence of SEQ ID NO: 27. In one embodiment, the anti-CD117 antibody, or antigen binding portion thereof, comprises a heavy chain variable region as set forth in the amino acid sequence of SEQ ID NO: 28, and a light chain variable region as set forth in the amino acid sequence of SEQ ID NO: 29. In one embodiment, the anti-CD117 antibody, or antigen binding portion thereof, comprises a heavy chain variable region as set forth in the amino acid sequence of SEQ ID NO: 30, and a light chain variable region as set forth in the amino acid sequence of SEQ ID NO: 31. In one embodiment, the anti-CD117 antibody, or antigen binding portion thereof, comprises a heavy chain variable region as set forth in the amino acid sequence of SEQ ID NO: 32, and a light chain variable region as set forth in the amino acid sequence of SEQ ID NO: 33. In one embodiment, the anti-CD117 antibody, or antigen binding portion thereof, comprises a heavy chain variable region as set forth in the amino acid sequence of SEQ ID NO: 34, and a light chain variable region as set forth in the amino acid sequence of SEQ ID NO: 35. In one embodiment, the anti-CD117 antibody, or antigen binding portion thereof, comprises a heavy chain variable region as set forth in the amino acid sequence of SEQ ID NO: 36, and a light chain variable region as set forth in the amino acid sequence of SEQ ID NO: 37. In one embodiment, the anti-CD117 antibody, or antigen binding portion thereof, comprises a heavy chain variable region as set forth in the amino acid sequence of SEQ ID NO: 38, and a light chain variable region as set forth in the amino acid sequence of SEQ ID NO: 39. In one embodiment, the anti-CD117 antibody, or antigen binding portion thereof, comprises a heavy chain variable region as set forth in the amino acid sequence of SEQ ID NO: 40, and a light chain variable region as set forth in the amino acid sequence of SEQ ID NO: 41. In one embodiment, the anti-CD117 antibody, or antigen binding portion thereof, comprises a heavy chain variable region as set forth in the amino acid sequence of SEQ ID NO: 32, and a light chain variable region as set forth in the amino acid sequence of SEQ ID NO: 42. In one embodiment, the anti-CD117 antibody, or antigen binding portion thereof, comprises a heavy chain variable region as set forth in the amino acid sequence of SEQ ID NO: 43, and a light chain variable region as set forth in the amino acid sequence of SEQ ID NO: 44. In one embodiment, the anti-CD117 antibody, or antigen binding portion thereof, comprises a heavy chain variable region as set forth in the amino acid sequence of SEQ ID NO: 45, and a light chain variable region as set forth in the amino acid sequence of SEQ ID NO: 46. In one embodiment, the anti-CD117 antibody, or antigen binding portion thereof, comprises a heavy chain variable region as set forth in the amino acid sequence of SEQ ID NO: 47, and a light chain variable region as set forth in the amino acid sequence of SEQ ID NO: 48. In one embodiment, the anti-CD117 antibody, or antigen binding portion thereof, comprises a heavy chain variable region as set forth in the amino acid sequence of SEQ ID NO: 49, and a light chain variable region as set forth in the amino acid sequence of SEQ ID NO: 50. In one embodiment, the anti-CD117 antibody, or antigen binding portion thereof, comprises a heavy chain variable region as set forth in the amino acid sequence of SEQ ID NO: 51, and a light chain variable region as set forth in the amino acid sequence of SEQ ID NO: 52. In one embodiment, the anti-CD117 antibody, or antigen binding portion thereof, comprises a heavy chain variable region as set forth in the amino acid sequence of SEQ ID NO: 53, and a light chain variable region as set forth in the amino acid sequence of SEQ ID NO: 54. In one embodiment, the anti-CD117 antibody, or antigen binding portion thereof, comprises a heavy chain variable region as set forth in the amino acid sequence of SEQ ID NO: 55, and a light chain variable region as set forth in the amino acid sequence of SEQ ID NO: 56. In one embodiment, the anti-CD117 antibody, or antigen binding portion thereof, comprises a heavy chain variable region as set forth in the amino acid sequence of SEQ ID NO: 57, and a light chain variable region as set forth in the amino acid sequence of SEQ ID NO: 58. In one embodiment, the anti-CD117 antibody, or antigen binding portion thereof, comprises a heavy chain variable region as set forth in the amino acid sequence of SEQ ID NO: 59, and a light chain variable region as set forth in the amino acid sequence of SEQ ID NO: 60. In one embodiment, the anti-CD117 antibody, or antigen binding portion thereof, comprises a heavy chain variable region as set forth in the amino acid sequence of SEQ ID NO: 61, and a light chain variable region as set forth in the amino acid sequence of SEQ ID NO: 50. In one embodiment, the anti-CD117 antibody, or antigen binding portion thereof, comprises a heavy chain variable region as set forth in the amino acid sequence of SEQ ID NO: 62, and a light chain variable region as set forth in the amino acid sequence of SEQ ID NO: 63. In one embodiment, the anti-CD117 antibody, or antigen binding portion thereof, comprises a heavy chain variable region as set forth in the amino acid sequence of SEQ ID NO: 64, and a light chain variable region as set forth in the amino acid sequence of SEQ ID NO: 65. In one embodiment, the anti-CD117 antibody, or antigen binding portion thereof, comprises a heavy chain variable region as set forth in the amino acid sequence of SEQ ID NO: 66, and a light chain variable region as set forth in the amino acid sequence of SEQ ID NO: 67. In one embodiment, the anti-CD117 antibody, or antigen binding portion thereof, comprises a heavy chain variable region as set forth in the amino acid sequence of SEQ ID NO: 68, and a light chain variable region as set forth in the amino acid sequence of SEQ ID NO: 69. In one embodiment, the anti-CD117 antibody, or antigen binding portion thereof, comprises a heavy chain variable region as set forth in the amino acid sequence of SEQ ID NO: 70, and a light chain variable region as set forth in the amino acid sequence of SEQ ID NO: 71. In one embodiment, the anti-CD117 antibody, or antigen binding portion thereof, comprises a heavy chain variable region as set forth in the amino acid sequence of SEQ ID NO: 72, and a light chain variable region as set forth in the amino acid sequence of SEQ ID NO: 73. In one embodiment, the anti-CD117 antibody, or antigen binding portion thereof, comprises a heavy chain variable region as set forth in the amino acid sequence of SEQ ID NO: 74, and a light chain variable region as set forth in the amino acid sequence of SEQ ID NO: 75. In one embodiment, the anti-CD117 antibody, or antigen binding portion thereof, comprises a heavy chain variable region as set forth in the amino acid sequence of SEQ ID NO: 76, and a light chain variable region as set forth in the amino acid sequence of SEQ ID NO: 77. In one embodiment, the anti-CD117 antibody, or antigen binding portion thereof, comprises a heavy chain variable region as set forth in the amino acid sequence of SEQ ID NO: 78, and a light chain variable region as set forth in the amino acid sequence of SEQ ID NO: 79. In one embodiment, the anti-CD117 antibody, or antigen binding portion thereof, comprises a heavy chain variable region as set forth in the amino acid sequence of SEQ ID NO: 80, and a light chain variable region as set forth in the amino acid sequence of SEQ ID NO: 81. In one embodiment, the anti-CD117 antibody, or antigen binding portion thereof, comprises a heavy chain variable region as set forth in the amino acid sequence of SEQ ID NO: 82, and a light chain variable region as set forth in the amino acid sequence of SEQ ID NO: 83. In one embodiment, the anti-CD117 antibody, or antigen binding portion thereof, comprises a heavy chain variable region as set forth in the amino acid sequence of SEQ ID NO: 84, and a light chain variable region as set forth in the amino acid sequence of SEQ ID NO: 85. In one embodiment, the anti-CD117 antibody, or antigen binding portion thereof, comprises a heavy chain variable region as set forth in the amino acid sequence of SEQ ID NO: 86, and a light chain variable region as set forth in the amino acid sequence of SEQ ID NO: 87. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 88. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 89. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 90. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 91. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 92. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 93. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 94. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO:95. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 96. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 97. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 97. In one embodiment, the anti-CD117 antibody, or antigen binding portion thereof, comprises a heavy chain variable region as set forth in the amino acid sequence of SEQ ID NO: 143, and a light chain variable region as set forth in the amino acid sequence of SEQ ID NO: 144. In one embodiment, the anti-CD117 antibody, or antigen binding portion thereof, comprises a heavy chain variable region as set forth in the amino acid sequence of SEQ ID NO: 151, and a light chain variable region as set forth in the amino acid sequence of SEQ ID NO: 152. In one embodiment, the anti-CD117 antibody, or antigen binding portion thereof, comprises a heavy chain variable region as set forth in the amino acid sequence of SEQ ID NO: 143, and a light chain variable region as set forth in the amino acid sequence of SEQ ID NO: 156. In one embodiment, the anti-CD117 antibody, or antigen binding portion thereof, comprises a heavy chain variable region as set forth in the amino acid sequence of SEQ ID NO: 159, and a light chain variable region as set forth in the amino acid sequence of SEQ ID NO: 156. In one embodiment, the anti-CD117 antibody, or antigen binding portion thereof, comprises a heavy chain variable region as set forth in the amino acid sequence of SEQ ID NO: 160, and a light chain variable region as set forth in the amino acid sequence of SEQ ID NO: 152. In one embodiment, the anti-CD117 antibody, or antigen binding portion thereof, comprises a heavy chain variable region as set forth in the amino acid sequence of SEQ ID NO: 98, and a light chain variable region as set forth in the amino acid sequence of SEQ ID NO: 99. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 99. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 100. In one embodiment, the anti-CD117 antibody, or antigen binding portion thereof, comprises a heavy chain variable region as set forth in the amino acid sequence of SEQ ID NO: 98, and a light chain variable region as set forth in the amino acid sequence of SEQ ID NO: 101. In one embodiment, the anti-CD117 antibody, or antigen binding portion thereof, comprises a heavy chain variable region as set forth in the amino acid sequence of SEQ ID NO: 98, and a light chain variable region as set forth in the amino acid sequence of SEQ ID NO: 102.

In some embodiments of these aspects, the antibody, or antigen-binding fragment thereof, is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFV. In one embodiment, the antibody is an intact antibody.

In another aspect, the invention features a conjugate (ADC) represented by the formula Ab-Z-L-Cy, wherein Ab is an antibody or antigen-binding fragment thereof that binds CD117 (e.g., GNNK+CD117) and Cy is a cytotoxin. In some embodiments of this aspect, the cytotoxin is pseudomonas exotoxin A, deBouganin, diphtheria toxin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, or an indolinobenzodiazepine dimer, or a variant of any of the foregoing cytotoxins.

In some embodiments of this aspect, the antibody, antigen-binding fragment thereof, or ADC is internalized by a CD117+ cell.

In some embodiments of this aspect, the antibody, antigen-binding fragment thereof, or ADC binds CD117 with a $K_d$ of less than 1 μM, less than 750 nM, less than 500 nM, less than 250 nM, less than 200 nM, less than 150 nM, less than 100 nM, less than 75 nM, less than 50 nM, less than 10 nM, less than 1 nM, less than 0.1 nM, less than 10 pM, less than 1 pM, or less than 0.1 pM measured by bio-layer interferometry (BLI). In some embodiments, the $K_d$ is from about 0.1 pM to about 1 μM.

In some embodiments of this aspect, the antibody, antigen-binding fragment thereof, or ADC binds CD117 with a $k_{on}$ of from about $9\times10^{-2}$ $M^{-1}$ $s^{-1}$ to about $1\times10^2$ $M^{-1}$ $s^{-1}$ measured by a bio-layer interferometry (BLI) assay.

In certain embodiments, an anti-CD117 antibody, or antigen binding fragment thereof, has a certain dissociation rate which is particularly advantageous when used as a part of a conjugate. For example, an anti-CD117 antibody has, in certain embodiments, an off rate constant (Kdis) for human CD117 of $1\times10^{-2}$ to $1\times10^{-7}$, $1\times10^{-3}$ to $1\times10^{-7}$, $1\times10^{-4}$ to $1\times10^{-7}$, $1\times10^{-5}$ to $1\times10^{-7}$, or $1\times10^{-6}$ to $1\times10^{-7}$ $s^{-1}$, measured by bio-layer interferometry (BLI).

In some embodiments of this aspect, the antibody, antigen-binding fragment thereof, or ADC competitively inhibits the binding of CD117 to a second antibody or antigen binding fragment thereof, wherein the second antibody or antigen-binding fragment thereof has the following CDRs:
a CDR-H1 having the amino acid sequence SYWIG (SEQ ID NO: 1);
a CDR-H2 having the amino acid sequence IIYPGDSDTRYSPSFQG (SEQ ID NO: 2);
a CD-H3 having the amino acid sequence HGRGYNGYEGAFDI (SEQ ID NO: 3);
a CDR-L1 having the amino acid sequence RASQGISSALA (SEQ ID NO: 4);
a CDR-L2 having the amino acid sequence DASSLES (SEQ ID NO: 5); and
a CDR-L3 having the amino acid sequence CQQFNSYPLT (SEQ ID NO: 6).

In some embodiments of this aspect, the antibody or antigen-binding fragment thereof is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv. In some embodiments, the antibody has an isotype selected from the group consisting of IgG, IgA, IgM, IgD, and IgE.

In certain embodiments, the foregoing methods and compositions include an isolated anti-CD117 antibody or antigen-binding fragment thereof comprising the CDRs set forth in the heavy and light chain amino acid sequences set forth in Table 1, Table 6, or Table 8. In certain embodiments, the foregoing methods and compositions include an anti-CD117 antibody or antigen-binding fragment thereof comprising the variable regions set forth in the heavy and light chain amino acid sequences set forth in Table 1. In certain embodiments, the foregoing methods and compositions include an IgG1 anti-CD117 antibody or antigen-binding fragment thereof comprises the variable regions set forth in the heavy and light chain amino acid sequences set forth in Table 1, Table 6, or Table 8.

In another aspect, the invention features a method treating acute myeloid leukemia (AML) in a human patient, the method comprising administering an effective amount of an anti-CD117 ADC to the human patient such that AML is treated, wherein the anti-CD117 ADC comprises an anti-CD117 antibody conjugated to a cytotoxin. In some embodiments, the cytotoxin is an RNA polymerase inhibitor. In another embodiment, the RNA polymerase inhibitor is an amatoxin. In other embodiments, anti-CD117 antibody comprises the CDR sequences set forth in the heavy and light chain amino acid sequences of Table 1. In yet other embodiments, the anti-CD117 antibody is an intact antibody. In another embodiment, the antibody is an IgG1 or an IgG4.

In another aspect, the invention provides a conjugate represented by the formula Ab-Z-L-Am, wherein Ab is an antibody or antigen-binding fragment thereof that binds CD117, L is a linker, Z is a chemical moiety, and Am is an amatoxin, wherein the antibody or antigen-binding fragment thereof comprises the CDRs set forth in the heavy and light chain amino acid sequences of Table 1, Table 6 or Table 8.

In some embodiments, linker-chemical moiety-amatoxin portion (Am-L-Z) of the conjugate is represented by formula (IA)

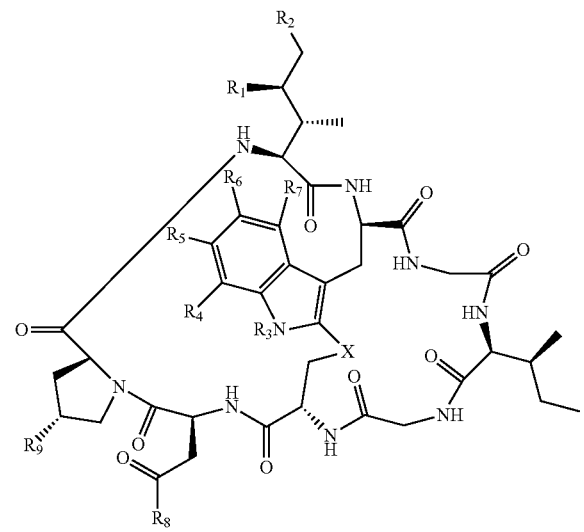

(IA)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;

$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;

L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, optionally substituted heteroarylene, a dipeptide, —(C=O)—, a peptide, or a combination thereof; and Z is a chemical moiety formed from a coupling reaction between a reactive substituent present on L and a reactive substituent present within the antibody or antigen-binding fragment thereof, wherein Am comprises exactly one $R_C$ substituent.

In some embodiments, L-Z is

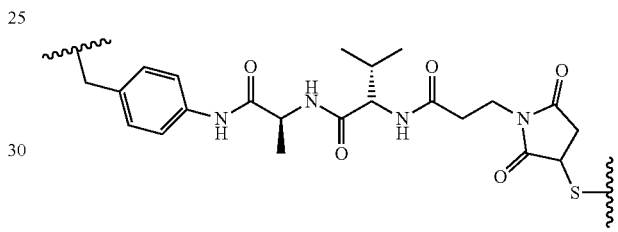

In some embodiments, Am-L-Z is represented by formula (IB)

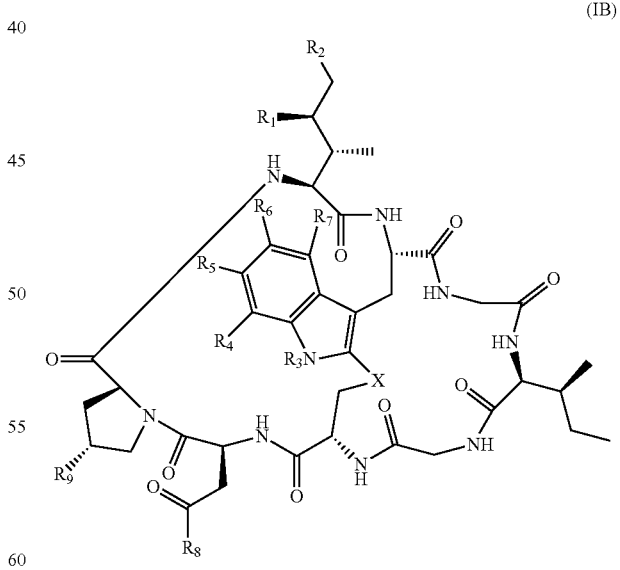

(IB)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;

R$_3$ is H, R$_C$, or R$_D$;

R$_4$, R$_5$, R$_6$, and R$_7$ are each independently H, OH, OR$_C$, OR$_D$, R$_C$, or R$_D$;

R$_8$ is OH, NH$_2$, OR$_C$, OR$_D$, NHR$_C$, or NR$_C$R$_D$;

R$_9$ is H, OH, OR$_C$, or OR$_D$;

X is —S—, —S(O)—, or —SO$_2$—;

R$_C$ is -L-Z;

R$_D$ is optionally substituted C$_1$-C$_6$ alkyl, optionally substituted C$_1$-C$_6$ heteroalkyl, optionally substituted C$_2$-C$_6$ alkenyl, optionally substituted C$_2$-C$_6$ heteroalkenyl, optionally substituted C$_2$-C$_6$ alkynyl, optionally substituted C$_2$-C$_6$ heteroalkynyl, optionally substituted cycloalkyl, optionally substituted heterocycloalkyl, optionally substituted aryl, or optionally substituted heteroaryl;

L is optionally substituted C$_1$-C$_6$ alkylene, optionally substituted C$_1$-C$_6$ heteroalkylene, optionally substituted C$_2$-C$_6$ alkenylene, optionally substituted C$_2$-C$_6$ heteroalkenylene, optionally substituted C$_2$-C$_6$ alkynylene, optionally substituted C$_2$-C$_6$ heteroalkynylene, optionally substituted cycloalkylene, optionally substituted heterocycloalkylene, optionally substituted arylene, optionally substituted heteroarylene, a dipeptide, —(C=O)—, a peptide, or a combination thereof; and Z is a chemical moiety formed from a coupling reaction between a reactive substituent present on L and a reactive substituent present within the antibody or antigen-binding fragment thereof, wherein Am comprises exactly one R$_C$ substituent.

In some embodiments, L-Z is

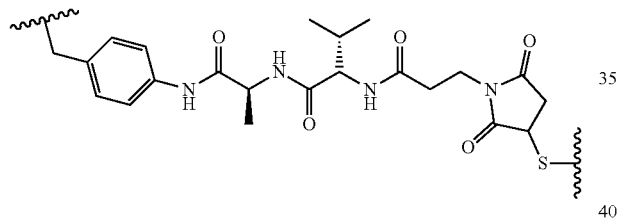

In some embodiments, linker-chemical moiety-amatoxin portion (Am-L-Z) of the conjugate is one of:

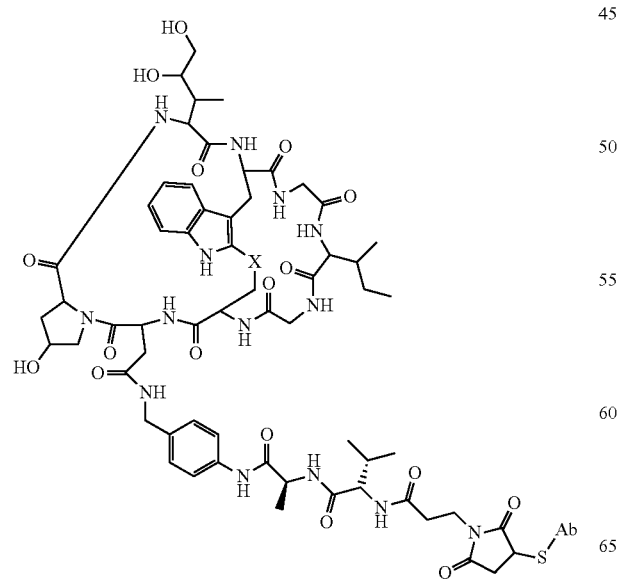

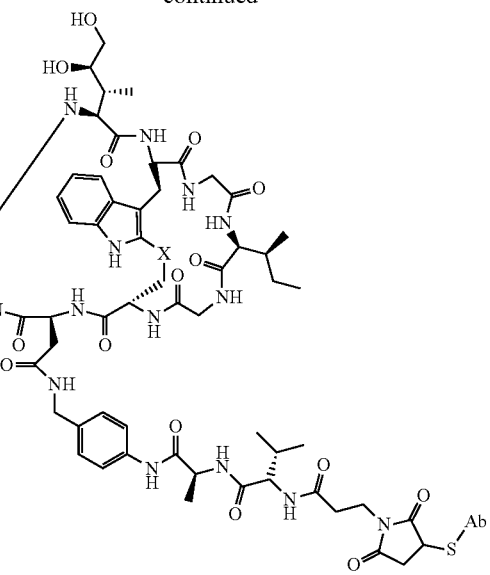

In some embodiments, linker-chemical moiety-amatoxin portion (Am-L-Z) of the conjugate is
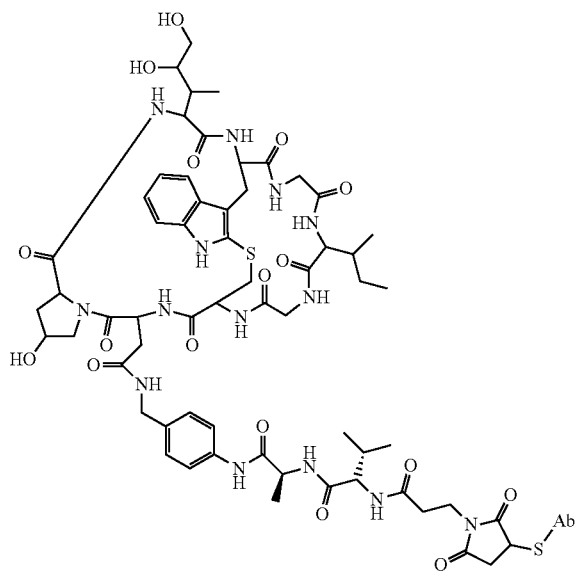

wherein Ab is shown to indicate the point of attachment of the antibody.

In some embodiments, linker-chemical moiety-amatoxin portion (Am-L-Z) of the conjugate is wherein Ab is shown to indicate the point of attachment of the antibody.

In some embodiments, linker-chemical moiety-amatoxin portion (Am-L-Z) of the conjugate is wherein Ab is shown to indicate the point of attachment of the antibody.

In some embodiments, the Am-L-Z precursor is wherein the maleimide reacts with a thiol group found on a cysteine in the antibody.

In some embodiments, the Am-L-Z precursor is

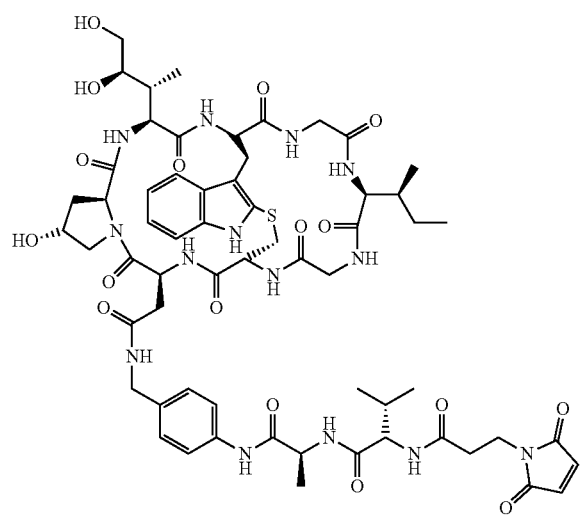

wherein the maleimide reacts with a thiol group found on a cysteine in the antibody.

In some embodiments, Am-L-Z is represented by formula (II), formula (IIA), or formula (IIB)

(II)

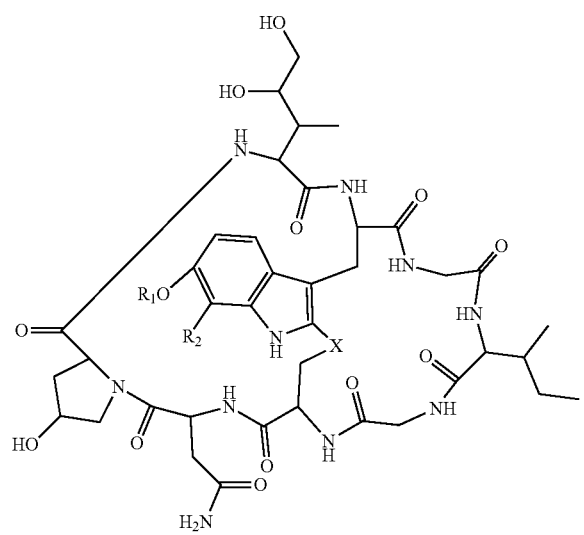

(IIA)

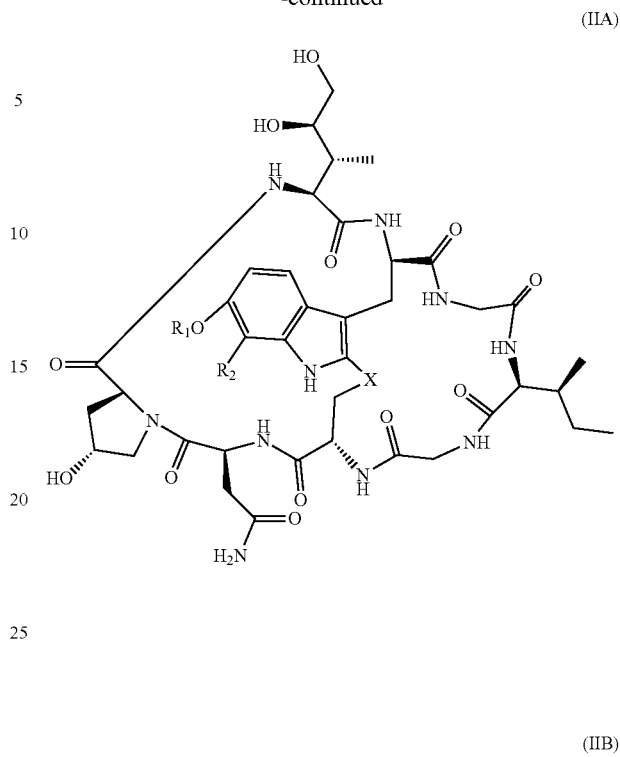

(IIB)

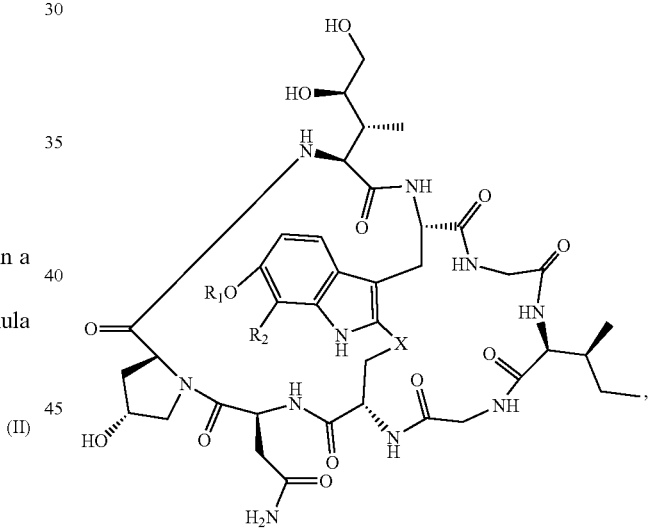

wherein X is S, SO, or $SO_2$;

$R_1$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; and $R_2$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof;

wherein when $R_1$ is H, $R_2$ is the linker, and when $R_2$ is H, $R_1$ is the linker.

In some embodiments, L-Z is

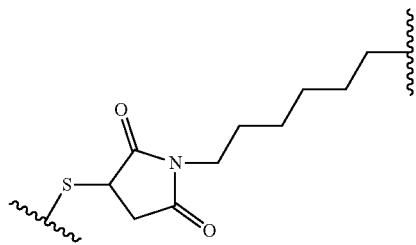 [SMILES: *CCCCCCN1C(=O)CC(S*)C1=O]

In some embodiments, Ab-Z-L-Am is

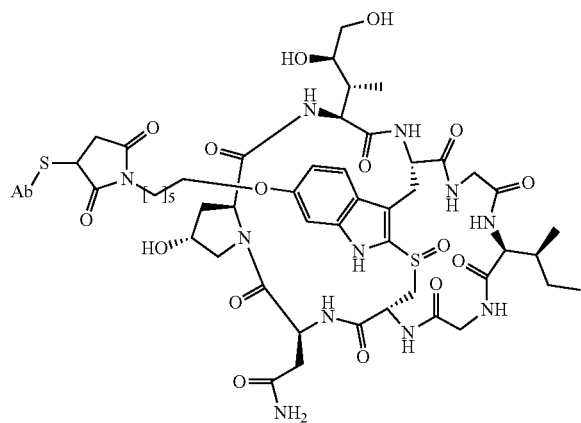

In some embodiments, Ab-Z-L-Am is

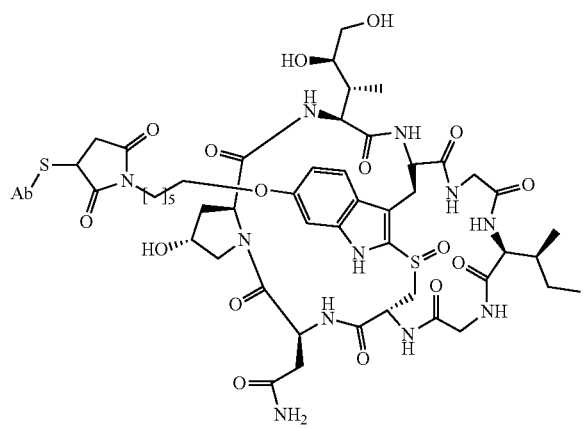

BRIEF DESCRIPTION OF THE FIGURES

FIGS. 3A, 3B, 3C and 3D graphically depict the results of an in vivo cell depletion assay that shows CD117-ADC selectively depletes human HSCs in humanized NSG mice. (A) Schematic of in vivo mouse model. (B) Shows the percent of human myeloid or (C) the percentage of T cells present in the peripheral blood of CD117-ADC or control treated mice, expressed as a percent of that cell population prior to treatment (normalized to baseline). (D) Shows the absolute number of CD34+ cells in the bone marrow of CD117-ADC or control treated mice 21 days after a single administration of the ADC.

FIGS. 4A, 4B, 4C and 4D graphically depict the results of an in vivo tumor study that show CD117-ADC effectively depletes human leukemic cells in NSG mice. (A) Phenotypic analysis of Kasumi-1 cells in culture. (B) Phenotypic analysis of Kasumi-1 cells from bone marrow of tumor bearing mice at time of euthanasia. (C) Survival curve of mice treated 7 days after tumor injection with CD117-ADC or a naked anti-CD117 antibody or untreated controls. (D) Survival curve of mice treated 42 days after tumor injection with CD117-ADC or a naked anti-CD117 antibody or untreated controls.

FIGS. 11A, 11B, 11C, and 11D provide the variable heavy (VH) and variable light (VL) chain region of the amino acid sequences of CK6, Ab85 and Ab249. (A) Depicts the alignment of the variable heavy (VH) chain regions of CK6 (SEQ ID NO: 161) and Ab85 (SEQ ID NO: 143). (B) Depicts the alignment of the variable light (VL) chain regions of CK6 (SEQ ID NO: 162) and Ab85 (SEQ ID NO: 144). (C) Depicts the alignment of the variable heavy (VH) chain regions of CK6 (SEQ ID NO: 161) and Ab249 (SEQ ID NO: 98). (D) Depicts the alignment of the variable light (VL) chain regions of CK6 (SEQ ID NO: 162) and Ab249 (SEQ ID NO: 102).

FIGS. 13A and 13B illustrate the fraction of acidic variants present in the indicated antibody under the indicated incubation conditions (x-axis) for (A) Day 7 (25 QC and 50 QC) and (B) Day 15 (25 QC and 50 QC) compared to $T_0$ as determined by capillary electrophoresis.

FIG. 20 graphically depicts hematopoietic stem and progenitor cell number in bone marrow. The results show that a single dose or a fractionated dose of amanitin conjugated anti-CD117 (HC-85-LC 85) modified with a fast half-life Fc (H435A) eliminates bone marrow HSCs in cynomolgus monkeys. Male cynomolgus monkeys received a single i.v. dose (0.1 or 0.3 mg/kg) or a fractionated i.v. dose (0.3 mg/kg and 0.2 mg/kg Q3D) of anti-CD117 ADC. Bone marrow HSC counts were determined by flow cytometry 7 days post administration.

Figure 22:
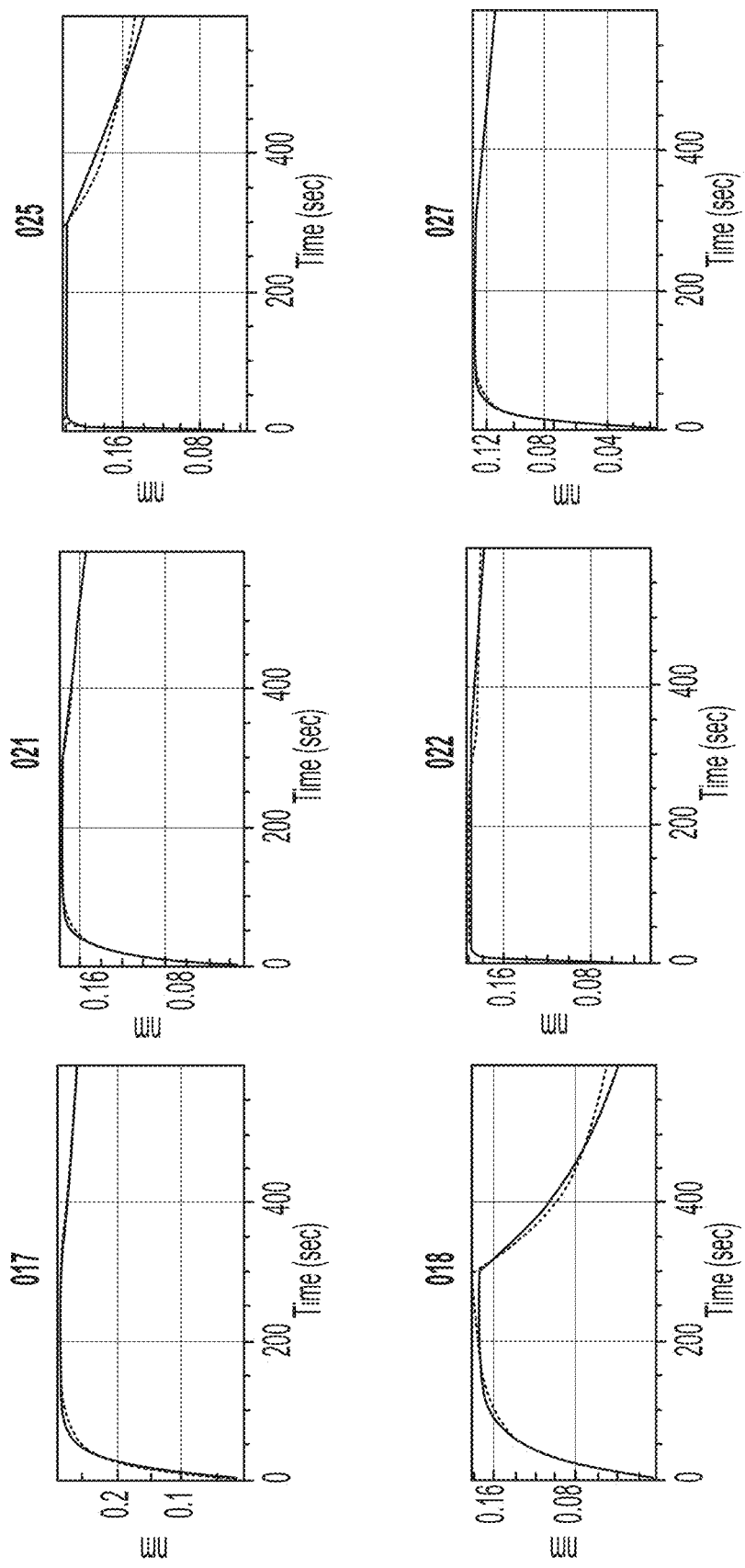
Figure 22:
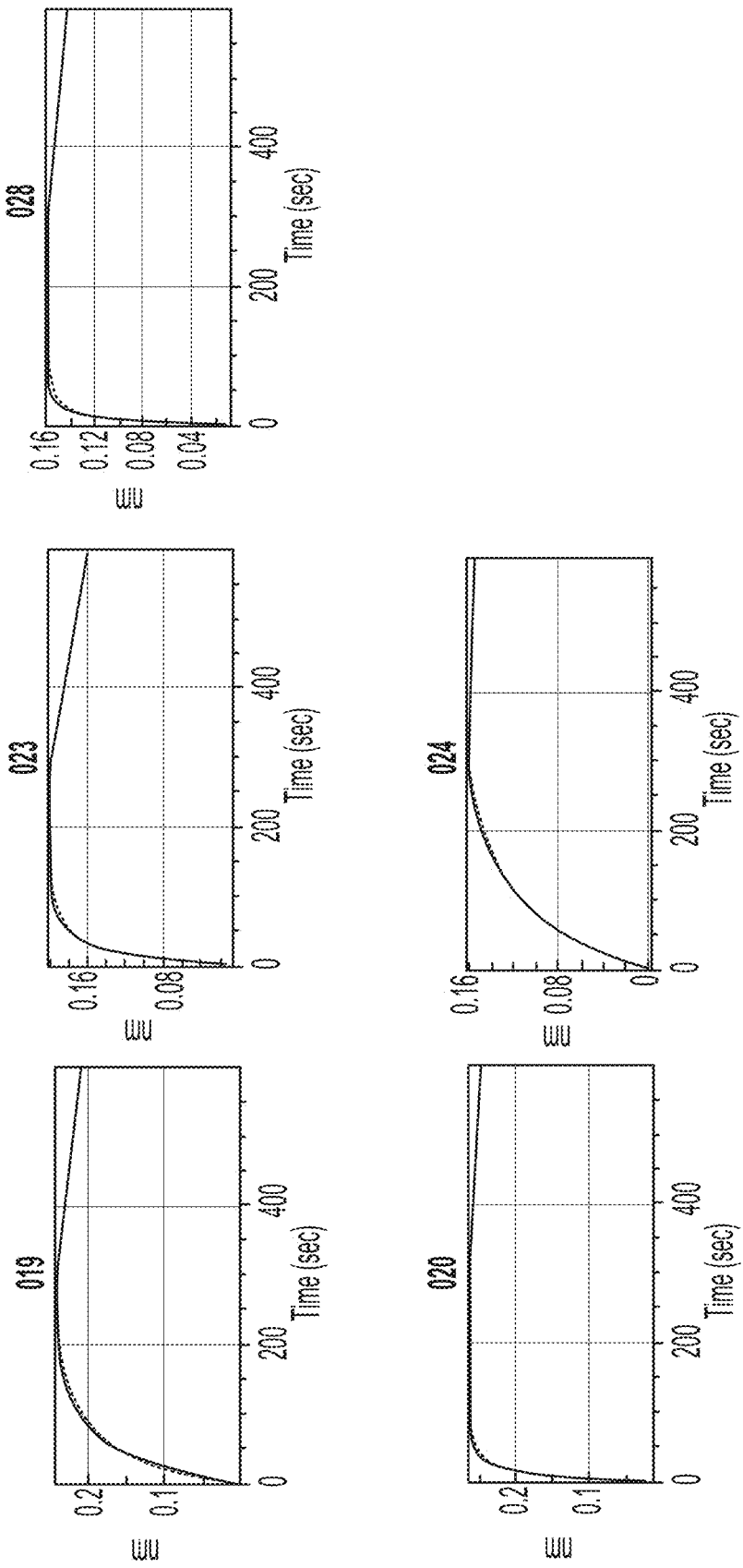

FIG. 22 demonstrates the measurement of binding by Bio-Layer Interferometry (BLI) of the indicated purified IgG (sensor-associated) to 100 nM purified human CD117 ectodomain (R&D Systems #332-SR) as a function of time. The purified IgGs correspond to Ab17 (i.e., 017), Ab18 (i.e., 018), Ab19 (i.e., 019), Ab20 (i.e., 020), Ab21 (i.e., 021), Ab22 (i.e., 022), Ab23 (i.e., 023), Ab24 (i.e., 024), Ab25 (i.e., 025), Ab27 (i.e., 027), and Ab28 (i.e., 028).

Figure 23:
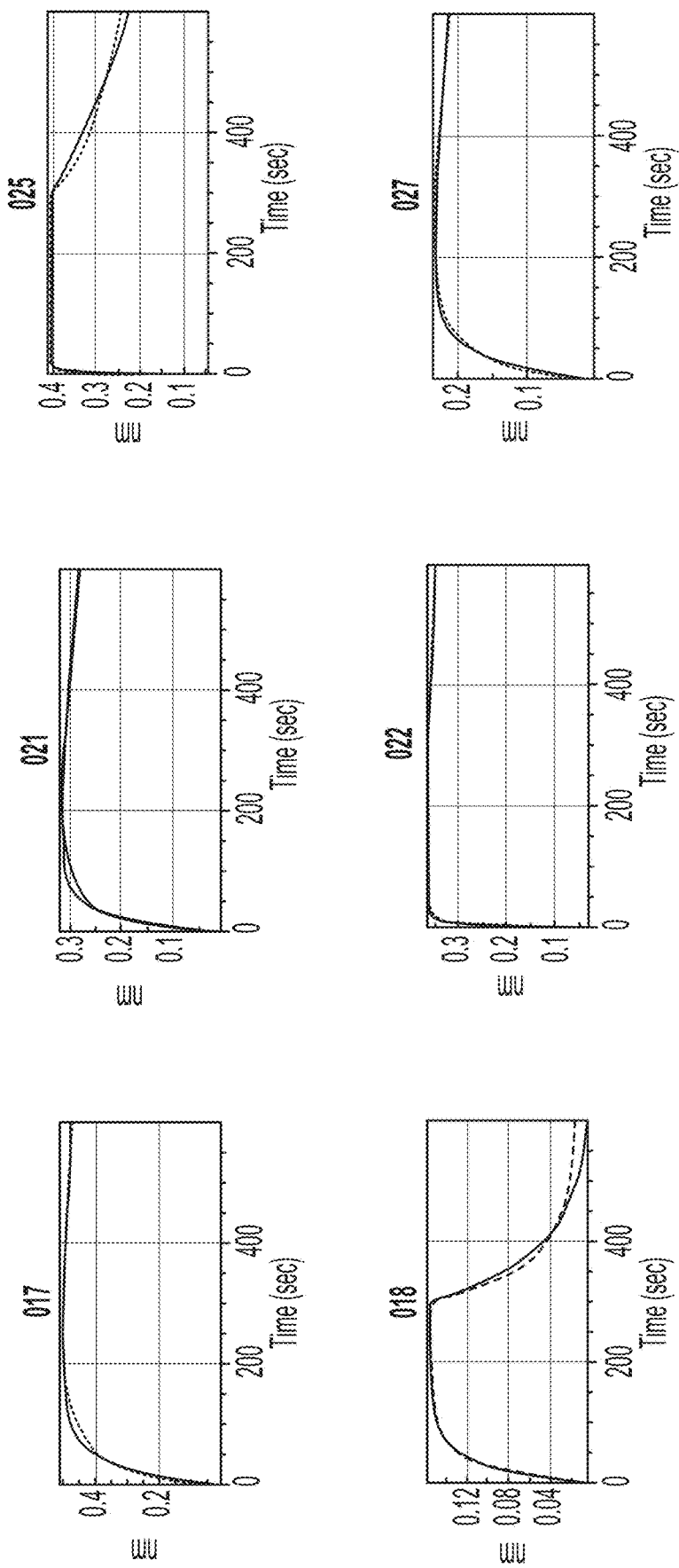
Figure 23:
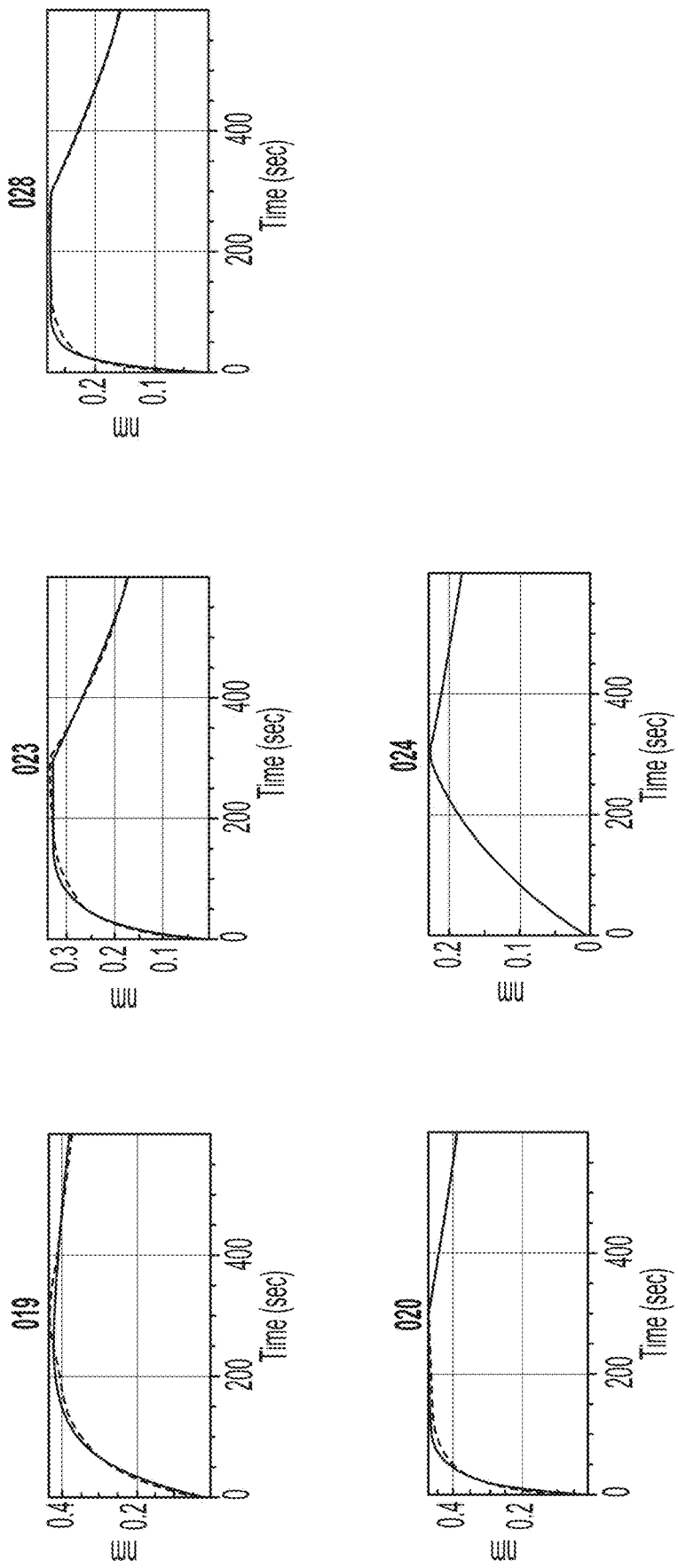

FIG. 23 demonstrates the measurement of binding by Bio-Layer Interferometry (BLI) of the indicated purified IgG (sensor-associated) to 100 nM purified rhesus CD117 ectodomain as a function of time. The purified IgGs correspond to Ab17 (i.e., 017), Ab18 (i.e., 018), Ab19 (i.e., 019), Ab20 (i.e., 020), Ab21 (i.e., 021), Ab22 (i.e., 022), Ab23 (i.e., 023), Ab24 (i.e., 024), Ab25 (i.e., 025), Ab27 (i.e., 027), and Ab28 (i.e., 028).

DETAILED DESCRIPTION

Described herein are isolated anti-CD117 human antibodies that bind to human CD117. The antibodies provided herein have many characteristics making them advantageous for therapy, including methods of conditioning human patients for stem cell transplantation. For example, antibodies disclosed herein, in certain embodiments, have high affinity and a law off rate for human CD117, as well as the ability to internalize in cells expressing CD117. Further, certain of the antibodies presented herein have improved biophysical stability. These features also make the anti-CD117 antibodies disclosed herein advantageous for use in conjugates (antibody drug conjugates (ADCs)) for delivering cytotoxins to CD117 expressing cells.

The invention provides anti-CD117 antibodies, specifically isolated human anti-CD117 antibodies that bind to the ectodomain of human CD117. The binding regions of the isolated anti-CD117 antibodies identified herein are described below and in Table 1, Table 6, and Table 8.

The anti-CD117 antibodies and ADCs described herein can be used in methods of treating a variety of disorders, such as diseases of a cell type in the hematopoietic lineage, cancers, autoimmune diseases, metabolic disorders, and stem cell disorders, among others. The compositions and methods described herein may (i) directly deplete a population of cells that give rise to a pathology, such as a population of cancer cells (e.g., leukemia cells) and autoimmune cells (e.g., autoreactive T-cells), and/or (ii) deplete a population of endogenous hematopoietic stem cells so as to promote the engraftment of transplanted hematopoietic stem cells by providing a niche to which the transplanted cells may home. The foregoing activities can be achieved by administration of an ADC, antibody, or antigen-binding fragment thereof, capable of binding an antigen expressed by an endogenous disease-causing cell or a hematopoietic stem cell. In the case of direct treatment of a disease, this administration can cause a reduction in the quantity of the cells that give rise to the pathology of interest. In the case of preparing a patient for hematopoietic stem cell transplant therapy, this administration can cause the selective depletion of a population of endogenous hematopoietic stem cells, thereby creating a vacancy in the hematopoietic tissue, such as the bone marrow, that can subsequently be filled by transplanted, exogenous hematopoietic stem cells. The invention is based in part on the discovery that ADCs, antibodies, or antigen-binding fragments thereof, capable of binding CD117 (such as GNNK+D117) can be administered to a patient to affect both of the above activities. ADCs, antibodies, or antigen-binding fragments thereof, that bind CD117 can be administered to a patient suffering from a cancer or autoimmune disease to directly deplete a population of cancerous cells or autoimmune cells, and can also be administered to a patient in need of hematopoietic stem cell transplant therapy in order to promote the survival and engraftment potential of transplanted hematopoietic stem cells.

Engraftment of hematopoietic stem cell transplants due to the administration of anti-CD117 ADCs, antibodies, or anti-gen-binding fragments thereof, can manifest in a variety of empirical measurements. For instance, engraftment of transplanted hematopoietic stem cells can be evaluated by assessing the quantity of competitive repopulating units (CRU) present within the bone marrow of a patient following administration of an ADC, antibody or antigen-binding fragment thereof capable of binding CD117 and subsequent administration of a hematopoietic stem cell transplant. Additionally, one can observe engraftment of a hematopoietic stem cell transplant by incorporating a reporter gene, such as an enzyme that catalyzes a chemical reaction yielding a fluorescent, chromophoric, or luminescent product, into a vector with which the donor hematopoietic stem cells have been transfected and subsequently monitoring the corresponding signal in a tissue into which the hematopoietic stem cells have homed, such as the bone marrow. One can also observe hematopoietic stem cell engraftment by evaluation of the quantity and survival of hematopoietic stem and progenitor cells, for instance, as determined by fluorescence activated cell sorting (FACS) analysis methods known in the art. Engraftment can also be determined by measuring white blood cell counts in peripheral blood during a post-transplant period, and/or by measuring recovery of marrow cells by donor cells in a bone marrow aspirate sample.

The sections that follow provide a description of ADCs, antibodies, or antigen-binding fragments thereof, that can be administered to a patient, such as a patient suffering from a cancer (such as acute myelogenous leukemia or myelodysplastic syndrome) or autoimmune disease, or a patient in need of hematopoietic stem cell transplant therapy in order to promote engraftment of hematopoietic stem cell grafts, as well as methods of administering such therapeutics to a patient (e.g., prior to hematopoietic stem cell transplantation).

Definitions

As used herein, the term "about" refers to a value that is within 10% above or below the value being described. For example, the term "about 5 nM" indicates a range of from 4.5 nM to 5.5 nM.

As used herein, the term "amatoxin" refers to a member of the amatoxin family of peptides produced by *Amanita phalloides* mushrooms, or a variant or derivative thereof, such as a variant or derivative thereof capable of inhibiting RNA polymerase II activity. Amatoxins useful in conjunction with the compositions and methods described herein include compounds according to, but are not limited to, formula (III), including α-amanitin, β-amanitin, γ-amanitin, ε-amanitin, amanin, amaninamide, amanullin, amanullinic acid, or proamanullin. As described herein, amatoxins may be conjugated to an antibody, or antigen-binding fragment thereof, for instance, by way of a linker moiety (L) (thus forming an ADC). Exemplary methods of amatoxin conjugation and linkers useful for such processes are described below. Exemplary linker-containing amatoxins useful for conjugation to an antibody, or antigen-binding fragment, in accordance with the compositions and methods are also described herein.

Formula (III) is as follows:

(III)

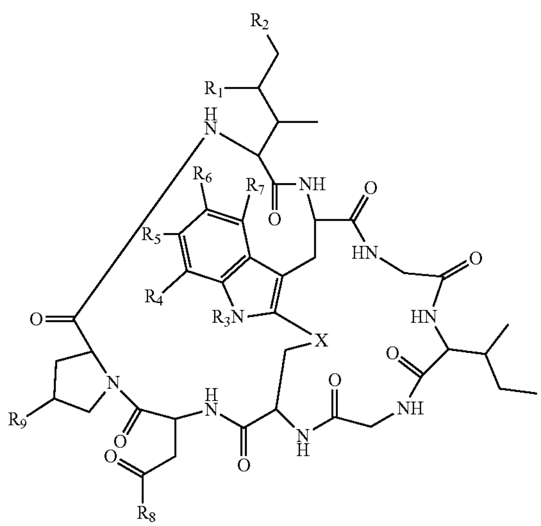

wherein $R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocycloalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

For instance, amatoxins useful in conjunction with the compositions and methods described herein include compounds according to formula (IIIA), below:

(IIIA)

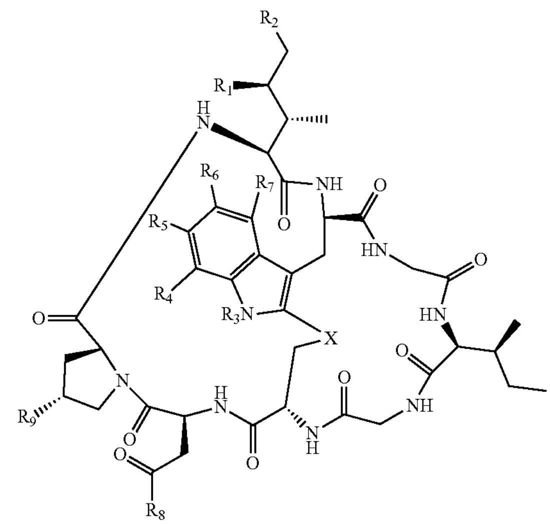

wherein $R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocycloalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

Amatoxins useful in conjunction with the compositions and methods described herein also include compounds according to formula (IIIB), below:

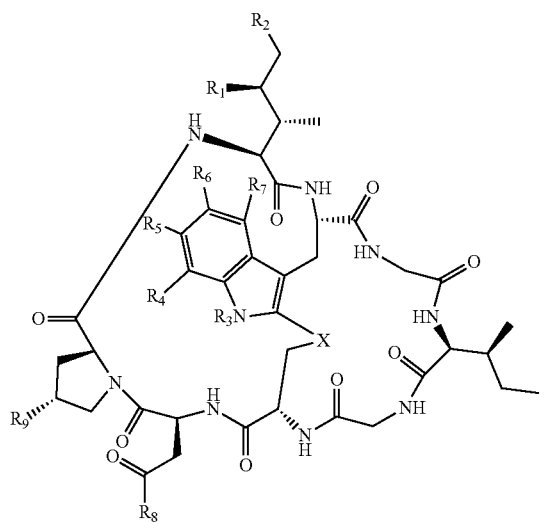

(IIIB)

wherein $R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocycloalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., —$C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

As described herein, amatoxins may be conjugated to an antibody, or antigen-binding fragment thereof, for instance, by way of a linker moiety (L) (thus forming an ADC). Exemplary methods of amatoxin conjugation and linkers useful for such processes are described below, including Table 3. Exemplary linker-containing amatoxins useful for conjugation to an antibody, or antigen-binding fragment, in accordance with the compositions and methods described herein are shown in structural formulas (I), (IA), (IB), (II), (IIA), or (IIB), recited herein.

As used herein, the term "antibody" refers to an immunoglobulin molecule that specifically binds to, or is immunologically reactive with, a particular antigen, and includes monoclonal, genetically engineered, and otherwise modified forms of antibodies, including but not limited to chimeric antibodies, humanized antibodies, heteroconjugate antibodies (e.g., bi- tri- and quad-specific antibodies, diabodies, triabodies, and tetrabodies), and antigen binding fragments of antibodies, including, for example, Fab', F(ab')₂, Fab, Fv, rIgG, and scFv fragments.

The antibodies of the present invention are generally isolated or recombinant. "Isolated," when used herein refers to a polypeptide, e.g., an antibody, that has been identified and separated and/or recovered from a cell or cell culture from which it was expressed. Ordinarily, an isolated antibody will be prepared by at least one purification step. Thus, an "isolated antibody," refers to an antibody which is substantially free of other antibodies having different antigenic specificities. For instance, an isolated antibody that specifically binds to CD117 is substantially free of antibodies that specifically bind antigens other than CD117.

Unless otherwise indicated, the term "monoclonal antibody" (mAb) is meant to include both intact molecules, as well as antibody fragments (including, for example, Fab and F(ab')₂ fragments) that are capable of specifically binding to a target protein. As used herein, the Fab and F(ab')₂ fragments refer to antibody fragments that lack the Fc fragment of an intact antibody. Examples of these antibody fragments are described herein.

Generally, antibodies comprise heavy and light chains containing antigen binding regions. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH, and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

An "intact" or "full length" antibody, as used herein, refers to an antibody having two heavy (H) chain polypeptides and two light (L) chain polypeptides interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH, and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The terms "Fc", "Fc region," and "Fc domain," as used herein refer to the portion of an IgG antibody that correlates to a crystallizable fragment obtained by papain digestion of an IgG molecule. The Fc region comprises the C-terminal half of two heavy chains of an IgG molecule that are linked by disulfide bonds. It has no antigen binding activity but contains the carbohydrate moiety and binding sites for complement and Fc receptors, including the FcRn receptor. An Fc region contains the second constant domain CH2 (e.g., residues at EU positions 231-340 of IgG1) and the third constant domain CH3 (e.g., residues at EU positions 341-447 of human IgG1). As used herein, the Fc region includes the "lower hinge region" (e.g., residues at EU positions 233-239 of IgG1). Fc can refer to this region in isolation, or this region in the context of an antibody, antibody fragment, or Fc fusion protein. Polymorphisms have been observed at a number of positions in Fc domains, including but not limited to EU positions 270, 272, 312, 315, 356, and 358, and thus slight differences between the sequences presented in the instant application and sequences known in the art can exist. Thus, a "wild type IgG Fc domain" or "WT IgG Fc domain" refers to any naturally occurring IgG Fc region (i.e., any allele). The sequences of the heavy chains of human IgG1, IgG2, IgG3 and IgG4 can be found in a number of sequence databases, for example, at the Uniprot database (www.uniprot.org) under accession numbers P01857 (IGHG1_HUMAN), P01859 (IGHG2_HUMAN), P01860 (IGHG3_HUMAN), and P01861 (IGHG1_HUMAN), respectively. An example of a "WT" Fc region is provided in SEQ ID NO: 183 (which provides a heavy chain constant region containing an Fc region).

The terms "modified Fc region" or "variant Fc region" as used herein refers to an IgG Fc domain comprising one or more amino acid substitutions, deletions, insertions or modifications introduced at any position within the Fc region.

The term "antigen-binding fragment," as used herein, refers to one or more fragments of an antibody that retain the ability to specifically bind to a target antigen. The antigen-binding function of an antibody can be performed by fragments of a full-length antibody. The antibody fragments can be, for example, a Fab, F(ab')$_2$, scFv, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the $V_L$, $V_H$, $C_L$, and $C_H 1$ domains; (ii) a F(ab')$_2$ fragment, a bivalent fragment containing two Fab fragments linked by a disulfide bridge at the hinge region; (iii) a Fd fragment consisting of the $V_H$ and $C_H 1$ domains; (iv) a Fv fragment consisting of the $V_L$ and $V_H$ domains of a single arm of an antibody, (v) a dAb including $V_H$ and $V_L$ domains; (vi) a dAb fragment that consists of a $V_H$ domain (see, e.g., Ward et al., Nature 341:544-546, 1989); (vii) a dAb which consists of a $V_H$ or a $V_L$ domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv); see, for example, Bird et al., Science 242:423-426, 1988 and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the term "anti-CD117 antibody" or "an antibody that binds to CD117" refers to an antibody that is capable of binding CD117 with sufficient affinity such that the antibody is useful as a diagnostic and/or therapeutic agent in targeting CD117.

As used herein, the term "bispecific antibody" refers to, for example, a monoclonal, often a human or humanized antibody that is capable of binding at least two different antigens. For instance, one of the binding specificities can be directed towards a hematopoietic stem cell surface antigen, CD117 (e.g., GNNK+ CD117), and the other can specifically bind a different hematopoietic stem cell surface antigen or another cell surface protein, such as a receptor or receptor subunit involved in a signal transduction pathway that potentiates cell growth, among others.

As used herein, the term "complementarity determining region" (CDR) refers to a hypervariable region found both in the light chain and the heavy chain variable domains of an antibody. The more highly conserved portions of variable domains are referred to as framework regions (FRs). The amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The antibodies described herein may contain modifications in these hybrid hypervariable positions. The variable domains of native heavy and light chains each contain four framework regions that primarily adopt a β-sheet configuration, connected by three CDRs, which form loops that connect, and in some cases form part of, the β-sheet structure. The CDRs in each chain are held together in close proximity by the framework regions in the order FR1-CDR1-FR2-CDR2-FR3-CDR3-FR4 and, with the CDRs from the other antibody chains, contribute to the formation of the target binding site of antibodies (see Kabat et al., Sequences of Proteins of Immunological Interest, National Institute of Health, Bethesda, Md., 1987). In certain embodiments, numbering of immunoglobulin amino acid residues is performed according to the immunoglobulin amino acid residue numbering system of Kabat et al., unless otherwise indicated (although any antibody numbering scheme, including, but not limited to IMGT and Chothia, can be utilized).

As used herein, the terms "condition" and "conditioning" refer to processes by which a patient is prepared for receipt of a transplant containing hematopoietic stem cells. Such procedures promote the engraftment of a hematopoietic stem cell transplant (for instance, as inferred from a sustained increase in the quantity of viable hematopoietic stem cells within a blood sample isolated from a patient following a conditioning procedure and subsequent hematopoietic stem cell transplantation. According to the methods described herein, a patient may be conditioned for hematopoietic stem cell transplant therapy by administration to the patient of an ADC, an antibody or antigen-binding fragment thereof capable of binding an antigen expressed by hematopoietic stem cells, such as CD117 (e.g., GNNK+ CD117). As described herein, the antibody may be covalently conjugated to a cytotoxin so as to form an ADC. Administration of an antibody, antigen-binding fragment thereof, or ADC capable of binding one or more of the foregoing antigens to a patient in need of hematopoietic stem cell transplant therapy can promote the engraftment of a hematopoietic stem cell graft, for example, by selectively depleting endogenous hematopoietic stem cells, thereby creating a vacancy filled by an exogenous hematopoietic stem cell transplant.

As used herein, the term "conjugate" refers to a compound formed by the chemical bonding of a reactive functional group of one molecule, such as an antibody or antigen-binding fragment thereof, with an appropriately reactive functional group of another molecule, such as a cytotoxin described herein. Conjugates may include a linker between the two molecules bound to one another. Examples of linkers that can be used for the formation of a conjugate include peptide-containing linkers, such as those that contain naturally occurring or non-naturally occurring amino acids, such as D-amino acids. Linkers can be prepared using a variety of strategies described herein and known in the art. Depending on the reactive components therein, a linker may be cleaved, for example, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012). The foregoing conjugates are also referred to interchangeably herein as a "drug antibody conjugate", an "antibody drug conjugate" and an "ADC".

As used herein, the term "coupling reaction" refers to a chemical reaction in which two or more substituents suitable for reaction with one another react so as to form a chemical moiety that joins (e.g., covalently) the molecular fragments bound to each substituent. Coupling reactions include those in which a reactive substituent bound to a fragment that is a cytotoxin, such as a cytotoxin known in the art or described herein, reacts with a suitably reactive substituent bound to a fragment that is an antibody, or antigen-binding fragment thereof, such as an antibody, or antigen-binding fragment thereof, specific for CD117 (such as GNNK+ CD117) known in the art or described herein. Examples of suitably reactive substituents include a nucleophile/electrophile pair (e.g., a thiol/haloalkyl pair, an amine/carbonyl pair, or a thiol/α,β-unsaturated carbonyl pair, among others), a diene/dienophile pair (e.g., an azide/alkyne pair, among others), and the like. Coupling reactions include, without limitation, thiol alkylation, hydroxyl alkylation, amine alkylation, amine condensation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein.

As used herein, "CRU (competitive repopulating unit)" refers to a unit of measure of long-term engrafting stem cells, which can be detected after in-vivo transplantation.

As used herein, "drug-to-antibody ratio" or "DAR" refers to the number of cytotoxins, e.g., amatoxin, attached to the antibody of an ADC. The DAR of an ADC can range from 1 to 8, although higher loads are also possible depending on the number of linkage sites on an antibody. Thus, in certain embodiments, an ADC described herein has a DAR of 1, 2, 3, 4, 5, 6, 7, or 8.

As used herein, the term "donor" refers to a human or animal from which one or more cells are isolated prior to administration of the cells, or progeny thereof, into a recipient. The one or more cells may be, for example, a population of hematopoietic stem cells.

As used herein, the term "diabody" refers to a bivalent antibody containing two polypeptide chains, in which each polypeptide chain includes $V_H$ and $V_L$ domains joined by a linker that is too short (e.g., a linker composed of five amino acids) to allow for intramolecular association of $V_H$ and $V_L$ domains on the same peptide chain. This configuration forces each domain to pair with a complementary domain on another polypeptide chain so as to form a homodimeric structure. Accordingly, the term "triabody" refers to trivalent antibodies containing three peptide chains, each of which contains one $V_H$ domain and one $V_L$ domain joined by a linker that is exceedingly short (e.g., a linker composed of 1-2 amino acids) to permit intramolecular association of $V_H$ and $V_L$ domains within the same peptide chain. In order to fold into their native structures, peptides configured in this way typically trimerize so as to position the $V_H$ and $V_L$ domains of neighboring peptide chains spatially proximal to one another (see, for example, Holliger et al., Proc. Natl. Acad. Sci. USA 90:6444-48, 1993).

As used herein, a "dual variable domain immunoglobulin" ("DVD-Ig") refers to an antibody that combines the target-binding variable domains of two monoclonal antibodies via linkers to create a tetravalent, dual-targeting single agent (see, for example, Gu et al., Meth. Enzymol., 502:25-41, 2012).

As used herein, the term "endogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is found naturally in a particular organism, such as a human patient.

As used herein, the term "engraftment potential" is used to refer to the ability of hematopoietic stem and progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. Engraftment can also be determined by measuring white blood cell counts in peripheral blood during a post-transplant period. Engraftment can also be assessed by measuring recovery of marrow cells by donor cells in a bone marrow aspirate sample.

As used herein, the term "exogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is not found naturally in a particular organism, such as a human patient. Exogenous substances include those that are provided from an external source to an organism or to cultured matter extracted therefrom.

As used herein, the term "framework region" or "FW region" includes amino acid residues that are adjacent to the CDRs of an antibody or antigen-binding fragment thereof. FW region residues may be present in, for example, human antibodies, humanized antibodies, monoclonal antibodies, antibody fragments, Fab fragments, single chain antibody fragments, scFv fragments, antibody domains, and bispecific antibodies, among others.

As used herein, the term "hematopoietic stem cells" ("HSCs") refers to immature blood cells having the capacity to self-renew and to differentiate into mature blood cells containing diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Such cells may include CD34+ cells. CD34+ cells are immature cells that express the CD34 cell surface marker. In humans, CD34+ cells are believed to include a subpopulation of cells with the stem cell properties defined above, whereas in mice, HSCs are CD34−. In addition, HSCs also refer to long term repopulating HSCs (LT-HSC) and short term repopulating HSCs (ST-HSC). LT-HSCs and ST-HSCs are differentiated, based on functional potential and on cell surface marker expression. For example, human HSCs are CD34+, CD38−, CD45RA−, CD90+, CD49F+, and lin−(negative for mature lineage markers including CD2, CD3, CD4, CD7, CD8, CD10, CD11B, CD19, CD20, CD56, CD235A). In mice, bone marrow LT-HSCs are CD34−, SCA-1+, C-kit+, CD135−, Slamf1/CD150+, CD48−, and lin− (negative for mature lineage markers including Ter119, CD11b, Gr1, CD3, CD4, CD8, B220, IL7ra), whereas ST-HSCs are CD34+, SCA-1+, C-kit+, CD135−, Slamf1/CD150+, and lin− (negative for mature lineage markers including Ter119, CD11b, Gr1, CD3, CD4, CD8, B220, IL7ra). In addition, ST-HSCs are less quiescent and more proliferative than LT-HSCs under homeostatic conditions. However, LT-HSC have greater self renewal potential (i.e., they survive throughout adulthood, and can be serially transplanted through successive recipients), whereas ST-HSCs have limited self renewal (i.e., they survive for only a limited period of time, and do not possess serial transplantation potential). Any of these HSCs can be used in the methods described herein. ST-HSCs are particularly useful because they are highly proliferative and thus, can more quickly give rise to differentiated progeny.

As used herein, the term "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

As used herein, the term "human antibody" is intended to include antibodies having variable and constant regions derived from human germline immunoglobulin sequences. A human antibody may include amino acid residues not encoded by human germline immunoglobulin sequences (e.g., mutations introduced by random or site-specific mutagenesis in vitro or during gene rearrangement or by somatic mutation in vivo). However, the term "human antibody", as used herein, is not intended to include antibodies in which CDR sequences derived from the germline of another mammalian species, such as a mouse, have been grafted onto human framework sequences. A human antibody can be produced in a human cell (for example, by recombinant expression) or by a non-human animal or a prokaryotic or eukaryotic cell that is capable of expressing functionally rearranged human immunoglobulin (such as heavy chain and/or light chain) genes. When a human antibody is a single chain antibody, it can include a linker peptide that is not found in native human antibodies. For example, an Fv can contain a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes (see, for example, PCT Publication Nos. WO 1998/24893; WO 1992/01047; WO 1996/34096; WO 1996/33735; U.S. Pat. Nos. 5,413,923; 5,625,126; 5,633,425; 5,569,825; 5,661,016; 5,545,806; 5,814,318; 5,885,793; 5,916,771; and 5,939,598).

As used herein, patients that are "in need of" a hematopoietic stem cell transplant include patients that exhibit a defect or deficiency in one or more blood cell types, as well as patients having a stem cell disorder, autoimmune disease, cancer, or other pathology described herein. Hematopoietic stem cells generally exhibit 1) multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal, and can thus give rise to daughter cells that have equivalent potential as the mother cell, and 3) the ability to be reintroduced into a transplant recipient whereupon they home to the hematopoietic stem cell niche and re-establish productive and sustained hematopoiesis. Hematopoietic stem cells can thus be administered to a patient defective or deficient in one or more cell types of the hematopoietic lineage in order to re-constitute the defective or deficient population of cells in vivo. For example, the patient may be suffering from cancer, and the deficiency may be caused by administration of a chemotherapeutic agent or other medicament that depletes, either selectively or non-specifically, the cancerous cell population. Additionally or alternatively, the patient may be suffering from a hemoglobinopathy (e.g., a non-malignant hemoglobinopathy), such as sickle cell anemia, thalassemia, Fanconi anemia, aplastic anemia, and Wiskott-Aldrich syndrome. The subject may be one that is suffering from adenosine deaminase severe combined immunodeficiency (ADA SCID), HIV/AIDS, metachromatic leukodystrophy, Diamond-Blackfan anemia, and Schwachman-Diamond syndrome. The subject may have or be affected by an inherited blood disorder (e.g., sickle cell anemia) or an autoimmune disorder. Additionally or alternatively, the subject may have or be affected by a malignancy, such as neuroblastoma or a hematologic cancer. For instance, the subject may have a leukemia, lymphoma, or myeloma. In some embodiments, the subject has acute myeloid leukemia, acute lymphoid leukemia, chronic myeloid leukemia, chronic lymphoid leukemia, multiple myeloma, diffuse large B-cell lymphoma, or non-Hodgkin's lymphoma. In some embodiments, the subject has myelodysplastic syndrome. In some embodiments, the subject has an autoimmune disease, such as scleroderma, multiple sclerosis, ulcerative colitis, Crohn's disease, Type 1 diabetes, or another autoimmune pathology described herein. In some embodiments, the subject is in need of chimeric antigen receptor T-cell (CART) therapy. In some embodiments, the subject has or is otherwise affected by a metabolic storage disorder. The subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy. Additionally or alternatively, a patient "in need of" a hematopoietic stem cell transplant may one that is or is not suffering from one of the foregoing pathologies, but nonetheless exhibits a reduced level (e.g., as compared to that of an otherwise healthy subject) of one or more endogenous cell types within the hematopoietic lineage, such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes. One of skill in the art can readily determine whether one's level of one or more of the foregoing cell types, or other blood cell type, is reduced with respect to an otherwise healthy subject, for instance, by way of flow cytometry and fluorescence activated cell sorting (FACS) methods, among other procedures, known in the art.

As used herein, the term "recipient" refers to a patient that receives a transplant, such as a transplant containing a population of hematopoietic stem cells. The transplanted cells administered to a recipient may be, e.g., autologous, syngeneic, or allogeneic cells.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) taken from a subject.

As used herein, the term "scFv" refers to a single chain Fv antibody in which the variable domains of the heavy chain and the light chain from an antibody have been joined to form one chain. scFv fragments contain a single polypeptide chain that includes the variable region of an antibody light chain ($V_L$) (e.g., CDR-L1, CDR-L2, and/or CDR-L3) and the variable region of an antibody heavy chain ($V_H$) (e.g., CDR-H1, CDR-H2, and/or CDR-H3) separated by a linker. The linker that joins the $V_L$ and $V_H$ regions of a scFv fragment can be a peptide linker composed of proteinogenic amino acids. Alternative linkers can be used to so as to increase the resistance of the scFv fragment to proteolytic degradation (for example, linkers containing D-amino acids), in order to enhance the solubility of the scFv fragment (for example, hydrophilic linkers such as polyethylene glycol-containing linkers or polypeptides containing repeating glycine and serine residues), to improve the biophysical stability of the molecule (for example, a linker containing cysteine residues that form intramolecular or intermolecular disulfide bonds), or to attenuate the immunogenicity of the scFv fragment (for example, linkers containing glycosylation sites). It will also be understood by one of ordinary skill in the art that the variable regions of the scFv molecules described herein can be modified such that they vary in amino acid sequence from the antibody molecule from which they were derived. For example, nucleotide or amino acid substitutions leading to conservative substitutions or changes at amino acid residues can be made (e.g., in CDR and/or framework residues) so as to preserve or enhance the ability of the scFv to bind to the antigen recognized by the corresponding antibody.

As used herein, the terms "subject" and "patient" refer to an organism, such as a human, that receives treatment for a particular disease or condition as described herein. For instance, a patient, such as a human patient, may receive treatment prior to hematopoietic stem cell transplant therapy in order to promote the engraftment of exogenous hematopoietic stem cells.

As used herein, the phrase "substantially cleared from the blood" refers to a point in time following administration of a therapeutic agent (such as an anti-CD117 antibody, or antigen-binding fragment thereof) to a patient when the concentration of the therapeutic agent in a blood sample isolated from the patient is such that the therapeutic agent is not detectable by conventional means (for instance, such that the therapeutic agent is not detectable above the noise threshold of the device or assay used to detect the therapeutic agent). A variety of techniques known in the art can be used to detect antibodies, antibody fragments, and protein ligands, such as ELISA-based detection assays known in the art or described herein. Additional assays that can be used to detect antibodies, or antibody fragments, include immunoprecipitation techniques and immunoblot assays, among others known in the art.

As used herein, the phrase "stem cell disorder" broadly refers to any disease, disorder, or condition that may be treated or cured by conditioning a subject's target tissues, and/or by ablating an endogenous stem cell population in a target tissue (e.g., ablating an endogenous hematopoietic stem or progenitor cell population from a subject's bone marrow tissue) and/or by engrafting or transplanting stem cells in a subject's target tissues. For example, Type I diabetes has been shown to be cured by hematopoietic stem cell transplant and may benefit from conditioning in accordance with the compositions and methods described herein. Additional disorders that can be treated using the compositions and methods described herein include, without limitation, sickle cell anemia, thalassemias, Fanconi anemia, aplastic anemia, Wiskott-Aldrich syndrome, ADA SCID, HIV/AIDS, metachromatic leukodystrophy, Diamond-Blackfan anemia, and Schwachman-Diamond syndrome. Additional diseases that may be treated using the patient conditioning and/or hematopoietic stem cell transplant methods described herein include inherited blood disorders (e.g., sickle cell anemia) and autoimmune disorders, such as scleroderma, multiple sclerosis, ulcerative colitis, and Crohn's disease. Additional diseases that may be treated using the conditioning and/or transplantation methods described herein include a malignancy, such as a neuroblastoma or a hematologic cancer, such as leukemia, lymphoma, and myeloma. For instance, the cancer may be acute myeloid leukemia, acute lymphoid leukemia, chronic myeloid leukemia, chronic lymphoid leukemia, multiple myeloma, diffuse large B-cell lymphoma, or non-Hodgkin's lymphoma. Additional diseases treatable using the conditioning and/or transplantation methods described herein include myelodysplastic syndrome. In some embodiments, the subject has or is otherwise affected by a metabolic storage disorder. For example, the subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy.

As used herein, the term "transfection" refers to any of a wide variety of techniques commonly used for the introduction of exogenous DNA into a prokaryotic or eukaryotic host cell, such as electroporation, lipofection, calcium-phosphate precipitation, DEAE-dextran transfection and the like.

As used herein, the terms "treat" or "treatment" refers to reducing the severity and/or frequency of disease symptoms, eliminating disease symptoms and/or the underlying cause of said symptoms, reducing the frequency or likelihood of disease symptoms and/or their underlying cause, and improving or remediating damage caused, directly or indirectly, by disease. Beneficial or desired clinical results include, but are not limited to, promoting the engraftment of exogenous hematopoietic cells in a patient following antibody conditioning therapy as described herein and subsequent hematopoietic stem cell transplant therapy. Additional beneficial results include an increase in the cell count or relative concentration of hematopoietic stem cells in a patient in need of a hematopoietic stem cell transplant following conditioning therapy and subsequent administration of an exogenous hematopoietic stem cell graft to the patient. Beneficial results of therapy described herein may also include an increase in the cell count or relative concentration of one or more cells of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte, following conditioning therapy and subsequent hematopoietic stem cell transplant therapy. Additional beneficial results may include the reduction in quantity of a disease-causing cell population, such as a population of cancer cells (e.g., CD117+ leukemic cells) or autoimmune cells (e.g., CD117+ autoimmune lymphocytes, such as a CD117+ T-cell that expresses a T-cell receptor that cross-reacts with a self antigen). Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state is completely avoided.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

As used herein, the term "vector" includes a nucleic acid vector, such as a plasmid, a DNA vector, a plasmid, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of antibodies and antibody fragments of the invention include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

The term "acyl" as used herein refers to —C(=O)R, wherein R is hydrogen ("aldehyde"), alkyl, alkenyl, alkynyl, carbocyclyl, aryl, heteroaryl, or heterocyclyl, as defined herein. Non-limiting examples include formyl, acetyl, propanoyl, benzoyl, and acryloyl.

As used herein, the term "alkyl" refers to a straight- or branched-chain alkyl group having, for example, from 1 to 20 carbon atoms in the chain. Examples of alkyl groups include methyl, ethyl, n-propyl, isopropyl, butyl, isobutyl, sec-butyl, tert-butyl, pentyl, isopentyl, tert-pentyl, hexyl, isohexyl, and the like.

As used herein, the term "alkylene" refers to a straight- or branched-chain divalent alkyl group. The divalent positions may be on the same or different atoms within the alkyl chain. Examples of alkylene include methylene, ethylene, propylene, isopropylene, and the like.

As used herein, the term "heteroalkyl" refers to a straight or branched-chain alkyl group having, for example, from 1 to 20 carbon atoms in the chain, and further containing one or more heteroatoms (e.g., oxygen, nitrogen, or sulfur, among others) in the chain.

As used herein, the term "heteroalkylene" refers to a straight- or branched-chain divalent heteroalkyl group. The divalent positions may be on the same or different atoms within the heteroalkyl chain. The divalent positions may be one or more heteroatoms.

As used herein, the term "alkenyl" refers to a straight- or branched-chain alkenyl group having, for example, from 2 to 20 carbon atoms in the chain. Examples of alkenyl groups include vinyl, propenyl, isopropenyl, butenyl, tert-butylenyl, hexenyl, and the like.

As used herein, the term "alkenylene" refers to a straight- or branched-chain divalent alkenyl group. The divalent positions may be on the same or different atoms within the alkenyl chain. Examples of alkenylene include ethenylene, propenylene, isopropenylene, butenylene, and the like.

As used herein, the term "heteroalkenyl" refers to a straight- or branched-chain alkenyl group having, for example, from 2 to 20 carbon atoms in the chain, and further containing one or more heteroatoms (e.g., oxygen, nitrogen, or sulfur, among others) in the chain.

As used herein, the term "heteroalkenylene" refers to a straight- or branched-chain divalent heteroalkenyl group. The divalent positions may be on the same or different atoms within the heteroalkenyl chain. The divalent positions may be one or more heteroatoms.

As used herein, the term "alkynyl" refers to a straight- or branched-chain alkynyl group having, for example, from 2 to 20 carbon atoms in the chain. Examples of alkynyl groups include propargyl, butynyl, pentynyl, hexynyl, and the like.

As used herein, the term "alkynylene" refers to a straight- or branched-chain divalent alkynyl group. The divalent positions may be on the same or different atoms within the alkynyl chain.

As used herein, the term "heteroalkynyl" refers to a straight- or branched-chain alkynyl group having, for example, from 2 to 20 carbon atoms in the chain, and further containing one or more heteroatoms (e.g., oxygen, nitrogen, or sulfur, among others) in the chain.

As used herein, the term "heteroalkynylene" refers to a straight- or branched-chain divalent heteroalkynyl group. The divalent positions may be on the same or different atoms within the heteroalkynyl chain. The divalent positions may be one or more heteroatoms.

As used herein, the term "cycloalkyl" refers to a monocyclic, or fused, bridged, or spiro polycyclic ring structure that is saturated and has, for example, from 3 to 12 carbon ring atoms. Examples of cycloalkyl groups include cyclopropyl, cyclobutyl, cyclopentyl, cyclohexyl, cycloheptyl, cyclooctyl, bicyclo[3.1.0]hexane, and the like.

As used herein, the term "cycloalkylene" refers to a divalent cycloalkyl group. The divalent positions may be on the same or different atoms within the ring structure. Examples of cycloalkylene include cyclopropylene, cyclobutylene, cyclopentylene, cyclohexylene, and the like.

As used herein, the term "heterocyloalkyl" refers to a monocyclic, or fused, bridged, or spiro polycyclic ring structure that is saturated and has, for example, from 3 to 12 ring atoms per ring structure selected from carbon atoms and heteroatoms selected from, e.g., nitrogen, oxygen, and sulfur, among others. The ring structure may contain, for example, one or more oxo groups on carbon, nitrogen, or sulfur ring members. Examples of heterocycloalkyls include by way of example and not limitation dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl.

As used herein, the term "heterocycloalkylene" refers to a divalent heterocyclolalkyl group. The divalent positions may be on the same or different atoms within the ring structure.

As used herein, the term "aryl" refers to a monocyclic or multicyclic aromatic ring system containing, for example, from 6 to 19 carbon atoms. Aryl groups include, but are not limited to, phenyl, fluorenyl, naphthyl, and the like. The divalent positions may be one or more heteroatoms.

As used herein, the term "arylene" refers to a divalent aryl group. The divalent positions may be on the same or different atoms.

As used herein, the term "heteroaryl" refers to a monocyclic heteroaromatic, or a bicyclic or a tricyclic fused-ring heteroaromatic group in which one or more ring atoms is a heteroatom, e.g., nitrogen, oxygen, or sulfur. Heteroaryl groups include pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, and the like.

As used herein, the term "heteroarylene" refers to a divalent heteroaryl group. The divalent positions may be on the same or different atoms. The divalent positions may be one or more heteroatoms.

Unless otherwise constrained by the definition of the individual substituent, the foregoing chemical moieties, such as "alkyl", "alkylene", "heteroalkyl", "heteroalkylene", "alkenyl", "alkenylene", "heteroalkenyl", "heteroalkenylene", "alkynyl", "alkynylene", "heteroalkynyl", "heteroalkynylene", "cycloalkyl", "cycloalkylene", "heterocyclolalkyl", heterocycloalkylene", "aryl," "arylene", "heteroaryl", and "heteroarylene" groups can optionally be substituted with, for example, from 1 to 5 substituents selected from the group consisting of alkyl, alkenyl, alkynyl, cycloalkyl, heterocycloalkyl, alkyl aryl, alkyl heteroaryl, alkyl cycloalkyl, alkyl heterocycloalkyl, amino, ammonium, acyl, acyloxy, acylamino, aminocarbonyl, alkoxycarbonyl, ureido, carbamate, aryl, heteroaryl, sulfinyl, sulfonyl, alkoxy, sulfanyl, halogen, carboxy, trihalomethyl, cyano, hydroxy, mercapto, nitro, and the like. Typical substituents include, but are not limited to, —X, —R, —OH, —OR, —SH, —SR, $NH_2$, —NHR, —$N(R)_2$, —$N^+(R)_3$, —$CX_3$, —CN, —OCN, —SCN, —NCO, —NCS, —NO, —$NO_2$, —$N_3$, —NC(=O)H, —NC(=O)R, —C(=O)H, —C(=O)R, —C(=O)$NH_2$, —C(=O)$N(R)_2$, —$SO_3$, —$SO_3H$, —S(=O)$_2$R, —OS(=O)$_2$OR, —S(=O)$_2$$NH_2$, —S(=O)$_2$$N(R)_2$, —S(=O)R, —OP(=O)(OH)$_2$, —OP(=O)(OR)$_2$, —P(=O)(OR)$_2$, —$PO_3$, —$PO_3H_2$, —C(=O)X, —C(=S)R, —$CO_2H$, —$CO_2R$, —$CO_2^-$, —C(=S)OR, —C(=O)SR, —C(=S)SR, —C(=O)$NH_2$, —C(=O)$N(R)_2$, —C(=S)$NH_2$, —C(=S)$N(R)_2$, —C(=NH)$NH_2$, and —C(=NR)$N(R)_2$; wherein each X is independently selected for each occasion from F, Cl, Br, and I; and each R is independently selected for each occasion from alkyl, aryl, heterocycloalkyl or heteroaryl, protecting group and prodrug moiety. Wherever a group is described as "optionally substituted," that group can be substituted with one or more of the above substituents, independently for each occasion. The substitution may include situations in which neighboring substituents have undergone ring closure, such as ring closure of vicinal functional substituents, to form, for instance, lactams, lactones, cyclic anhydrides, acetals, hemiacetals, thioacetals, aminals, and hemiaminals, formed by ring closure, for example, to furnish a protecting group.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene," "alkenylene," "arylene," "heterocycloalkylene," and the like.

Wherever a substituent is depicted as a di-radical (i.e., has two points of attachment to the rest of the molecule), it is to be understood that the substituent can be attached in any directional configuration unless otherwise indicated Anti-CD117 Antibodies The present invention is based in part on the discovery of novel anti-CD117 antibodies and antigen binding portions thereof that are useful for therapeutic purposes. The present invention is also based in part on the discovery that antibodies, or antigen-binding fragments thereof, capable of binding CD117, such as GNNK+ CD117, can be used as therapeutic agents alone or as ADCs to (i) treat cancers (such as acute myelogenous leukemia or myelodysplastic syndrome) and autoimmune diseases characterized by CD117+ cells and (ii) promote the engraftment of transplanted hematopoietic stem cells in a patient in need of transplant therapy. These therapeutic activities can be caused, for instance, by the binding of anti-CD117 antibodies, or antigen-binding fragments thereof, to CD117 (e.g., GNNK+ CD117) expressed on the surface of a cell, such as a cancer cell, autoimmune cell, or hematopoietic stem cell and subsequently inducing cell death. The depletion of endogenous hematopoietic stem cells can provide a niche toward which transplanted hematopoietic stem cells can home, and subsequently establish productive hematopoiesis. In this way, transplanted hematopoietic stem cells may successfully engraft in a patient, such as human patient suffering from a stem cell disorder described herein.

Antibodies and antigen-binding fragments capable of binding human CD117 (also referred to as c-Kit, mRNA NCBI Reference Sequence: NM_000222.2, Protein NCBI Reference Sequence: NP_000213.1), including those capable of binding GNNK+ CD117, can be used in conjunction with the compositions and methods described herein in order to condition a patient for hematopoietic stem cell transplant therapy. Polymorphisms affecting the coding region or extracellular domain of CD117 in a significant percentage of the population are not currently well-known in non-oncology indications. There are at least four isoforms of CD117 that have been identified, with the potential of additional isoforms expressed in tumor cells. Two of the CD117 isoforms are located on the intracellular domain of the protein, and two are present in the external juxtamembrane region. The two extracellular isoforms, GNNK+ and GNNK−, differ in the presence (GNNK+) or absence (GNNK−) of a 4 amino acid sequence. These isoforms are reported to have the same affinity for the ligand (SCF), but ligand binding to the GNNK− isoform was reported to increase internalization and degradation. The GNNK+ isoform can be used as an immunogen in order to generate antibodies capable of binding CD117, as antibodies generated against this isoform will be inclusive of the GNNK+ and GNNK− proteins.

The disclosure provides novel anti-CD117 antibodies whose heavy and light chain amino acid sequences are provided in Table 1, Table 6, Table 8, and Table 16. Thus, included in the disclosure is anti-CD117 antibody drug conjugates comprising binding regions (heavy and light chain CDRs or variable regions) as set forth in SEQ ID Nos: 7 to 168. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 8. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 9. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 10. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 11. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 12. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 13. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 14. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 15. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 16. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 17. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 18. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 19. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 20. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 21. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 22. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 23. In one embodiment, the anti-CD117 antibody, or antigen binding portion thereof, comprises a heavy chain variable region as set forth in the amino acid sequence of SEQ ID NO: 24, and a light chain variable region as set forth in the amino acid sequence of SEQ ID NO: 25. In one embodiment, the anti-CD117 antibody, or antigen binding portion thereof, comprises a heavy chain variable region as set forth in the amino acid sequence of SEQ ID NO: 26, and a light chain variable region as set forth in the amino acid sequence of SEQ ID NO: 27. In one embodiment, the anti-CD117 antibody, or antigen binding portion thereof, comprises a heavy chain variable region as set forth in the amino acid sequence of SEQ ID NO: 28, and a light chain variable region as set forth in the amino acid sequence of SEQ ID NO: 29. In one embodiment, the anti-CD117 antibody, or antigen binding portion thereof, comprises a heavy chain variable region as set forth in the amino acid sequence of SEQ ID NO: 30, and a light chain variable region as set forth in the amino acid sequence of SEQ ID NO: 31. In one embodiment, the anti-CD117 antibody, or antigen binding portion thereof, comprises a heavy chain variable region as set forth in the amino acid sequence of SEQ ID NO: 32, and a light chain variable region as set forth in the amino acid sequence of SEQ ID NO: 33. In one embodiment, the anti-CD117 antibody, or antigen binding portion thereof, comprises a heavy chain variable region as set forth in the amino acid sequence of SEQ ID NO: 34, and a light chain variable region as set forth in the amino acid sequence of SEQ ID NO:35. In one embodiment, the anti-CD117 antibody, or antigen binding portion thereof, comprises a heavy chain variable region as set forth in the amino acid sequence of SEQ ID NO: 36, and a light chain variable region as set forth in the amino acid sequence of SEQ ID NO: 37. In one embodiment, the anti-CD117 antibody, or antigen binding portion thereof, comprises a heavy chain variable region as set forth in the amino acid sequence of SEQ ID NO: 38, and a light chain variable region as set forth in the amino acid sequence of SEQ ID NO: 39. In one embodiment, the anti-CD117 antibody, or antigen binding portion thereof, comprises a heavy chain variable region as set forth in the amino acid sequence of SEQ ID NO: 40, and a light chain variable region as set forth in the amino acid sequence of SEQ ID NO: 41. In one embodiment, the anti-CD117 antibody, or antigen binding portion thereof, comprises a heavy chain variable region as set forth in the amino acid sequence of SEQ ID NO: 32, and a light chain variable region as set forth in the amino acid sequence of SEQ ID NO: 42. In one embodiment, the anti-CD117 antibody, or antigen binding portion thereof, comprises a heavy chain variable region as set forth in the amino acid sequence of SEQ ID NO: 43, and a light chain variable region as set forth in the amino acid sequence of SEQ ID NO: 44. In one embodiment, the anti-CD117 antibody, or antigen binding portion thereof, comprises a heavy chain variable region as set forth in the amino acid sequence of SEQ ID NO: 45, and a light chain variable region as set forth in the amino acid sequence of SEQ ID NO: 46. In one embodiment, the anti-CD117 antibody, or antigen binding portion thereof, comprises a heavy chain variable region as set forth in the amino acid sequence of SEQ ID NO: 47, and a light chain variable region as set forth in the amino acid sequence of SEQ ID NO: 48. In one embodiment, the anti-CD117 antibody, or antigen binding portion thereof, comprises a heavy chain variable region as set forth in the amino acid sequence of SEQ ID NO: 49, and a light chain variable region as set forth in the amino acid sequence of SEQ ID NO: 50. In one embodiment, the anti-CD117 antibody, or antigen binding portion thereof, comprises a heavy chain variable region as set forth in the amino acid sequence of SEQ ID NO: 51, and a light chain variable region as set forth in the amino acid sequence of SEQ ID NO: 52. In one embodiment, the anti-CD117 antibody, or antigen binding portion thereof, comprises a heavy chain variable region as set forth in the amino acid sequence of SEQ ID NO: 53, and a light chain variable region as set forth in the amino acid sequence of SEQ ID NO: 54. In one embodiment, the anti-CD117 antibody, or antigen binding portion thereof, comprises a heavy chain variable region as set forth in the amino acid sequence of SEQ ID NO: 55, and a light chain variable region as set forth in the amino acid sequence of SEQ ID NO: 56. In one embodiment, the anti-CD117 antibody, or antigen binding portion thereof, comprises a heavy chain variable region as set forth in the amino acid sequence of SEQ ID NO: 57, and a light chain variable region as set forth in the amino acid sequence of SEQ ID NO: 58. In one embodiment, the anti-CD117 antibody, or antigen binding portion thereof, comprises a heavy chain variable region as set forth in the amino acid sequence of SEQ ID NO: 9, and a light chain variable region as set forth in the amino acid sequence of SEQ ID NO: 60. In one embodiment, the anti-CD117 antibody, or antigen binding portion thereof, comprises a heavy chain variable region as set forth in the amino acid sequence of SEQ ID NO: 61, and a light chain variable region as set forth in the amino acid sequence of SEQ ID NO: 50. In one embodiment, the anti-CD117 antibody, or antigen binding portion thereof, comprises a heavy chain variable region as set forth in the amino acid sequence of SEQ ID NO: 62, and a light chain variable region as set forth in the amino acid sequence of SEQ ID NO: 63. In one embodiment, the anti-CD117 antibody, or antigen binding portion thereof, comprises a heavy chain variable region as set forth in the amino acid sequence of SEQ ID NO: 64, and a light chain variable region as set forth in the amino acid sequence of SEQ ID NO: 65. In one embodiment, the anti-CD117 antibody, or antigen binding portion thereof, comprises a heavy chain variable region as set forth in the amino acid sequence of SEQ ID NO: 66, and a light chain variable region as set forth in the amino acid sequence of SEQ ID NO: 67. In one embodiment, the anti-CD117 antibody, or antigen binding portion thereof, comprises a heavy chain variable region as set forth in the amino acid sequence of SEQ ID NO: 68, and a light chain variable region as set forth in the amino acid sequence of SEQ ID NO: 69. In one embodiment, the anti-CD117 antibody, or antigen binding portion thereof, comprises a heavy chain variable region as set forth in the amino acid sequence of SEQ ID NO: 70, and a light chain variable region as set forth in the amino acid sequence of SEQ ID NO: 71. In one embodiment, the anti-CD117 antibody, or antigen binding portion thereof, comprises a heavy chain variable region as set forth in the amino acid sequence of SEQ ID NO: 72, and a light chain variable region as set forth in the amino acid sequence of SEQ ID NO: 73. In one embodiment, the anti-CD117 antibody, or antigen binding portion thereof, comprises a heavy chain variable region as set forth in the amino acid sequence of SEQ ID NO: 74, and a light chain variable region as set forth in the amino acid sequence of SEQ ID NO: 75. In one embodiment, the anti-CD117 antibody, or antigen binding portion thereof, comprises a heavy chain variable region as set forth in the amino acid sequence of SEQ ID NO: 76, and a light chain variable region as set forth in the amino acid sequence of SEQ ID NO: 77. In one embodiment, the anti-CD117 antibody, or antigen binding portion thereof, comprises a heavy chain variable region as set forth in the amino acid sequence of SEQ ID NO: 78, and a light chain variable region as set forth in the amino acid sequence of SEQ ID NO: 79. In one embodiment, the anti-CD117 antibody, or antigen binding portion thereof, comprises a heavy chain variable region as set forth in the amino acid sequence of SEQ ID NO: 80, and a light chain variable region as set forth in the amino acid sequence of SEQ ID NO: 81. In one embodiment, the anti-CD117 antibody, or antigen binding portion thereof, comprises a heavy chain variable region as set forth in the amino acid sequence of SEQ ID NO: 82, and a light chain variable region as set forth in the amino acid sequence of SEQ ID NO: 83. In one embodiment, the anti-CD117 antibody, or antigen binding portion thereof, comprises a heavy chain variable region as set forth in the amino acid sequence of SEQ ID NO: 84, and a light chain variable region as set forth in the amino acid sequence of SEQ ID NO: 85. In one embodiment, the anti-CD117 antibody, or antigen binding portion thereof, comprises a heavy chain variable region as set forth in the amino acid sequence of SEQ ID NO: 86, and a light chain variable region as set forth in the amino acid sequence of SEQ ID NO: 87. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 88. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 89. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 90. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 91. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 92. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 93. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 94. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO:95. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 96.

In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 97. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 97. In one embodiment, the anti-CD117 antibody, or antigen binding portion thereof, comprises a heavy chain variable region as set forth in the amino acid sequence of SEQ ID NO: 143, and a light chain variable region as set forth in the amino acid sequence of SEQ ID NO: 144. In one embodiment, the anti-CD117 antibody, or antigen binding portion thereof, comprises a heavy chain variable region as set forth in the amino acid sequence of SEQ ID NO: 151, and a light chain variable region as set forth in the amino acid sequence of SEQ ID NO: 152. In one embodiment, the anti-CD117 antibody, or antigen binding portion thereof, comprises a heavy chain variable region as set forth in the amino acid sequence of SEQ ID NO: 143, and a light chain variable region as set forth in the amino acid sequence of SEQ ID NO: 156. In one embodiment, the anti-CD117 antibody, or antigen binding portion thereof, comprises a heavy chain variable region as set forth in the amino acid sequence of SEQ ID NO: 158, and a light chain variable region as set forth in the amino acid sequence of SEQ ID NO: 156. In one embodiment, the anti-CD117 antibody, or antigen binding portion thereof, comprises a heavy chain variable region as set forth in the amino acid sequence of SEQ ID NO: 160, and a light chain variable region as set forth in the amino acid sequence of SEQ ID NO: 152. In one embodiment, the anti-CD117 antibody, or antigen binding portion thereof, comprises a heavy chain variable region as set forth in the amino acid sequence of SEQ ID NO: 98, and a light chain variable region as set forth in the amino acid sequence of SEQ ID NO: 99. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 99. In one embodiment, the anti-CD117 antibody, or antigen binding portion thereof, comprises a heavy chain variable region as set forth in the amino acid sequence of SEQ ID NO: 7, and a light chain variable region as set forth in the amino acid sequence of SEQ ID NO: 100. In one embodiment, the anti-CD117 antibody, or antigen binding portion thereof, comprises a heavy chain variable region as set forth in the amino acid sequence of SEQ ID NO: 98, and a light chain variable region as set forth in the amino acid sequence of SEQ ID NO: 101. In one embodiment, the anti-CD117 antibody, or antigen binding portion thereof, comprises a heavy chain variable region as set forth in the amino acid sequence of SEQ ID NO: 98, and a light chain variable region as set forth in the amino acid sequence of SEQ ID NO: 102.

In one embodiment, the antibody is an intact antibody comprising a heavy chain and a light chain variable region as set forth in Table 1. In one embodiment, the anti-CD117 antibody is engineered to have a short half life.

TABLE 1

Antibody heavy and light chain variable region amino acid sequences

| Antibody name | Type of Chain | Amino acid sequence |
| --- | --- | --- |
| HC-1 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-1 | hKappa | AIQLTQSPSSLSASVGDRVTITCRASQGVSSALAWYQQKPGKAP KLLIYDASSLESGVPSRFSGSGSGTDFTLTISSLQPEDFATYYCQ QFNSYPLTFGGGTKVEIK (SEQ ID NO: 8) |
| HC-2 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-2 | hKappa | DIQLTQSPSSLSASVGDRVTITCRASQGIRTDLGWYQQKPGKAP KLLIYDASSLESGVPSRFSGSGSGTDFTLTISSLQPEDFATYYCQ QFNSYPLTFGGGTKVEIK (SEQ ID NO: 9) |
| HC-3 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-3 | hKappa | AIRMTQSPSSLSASVGDRVTITCRASQGIRNDLAWYQQKPGKTP KLLIYDASSLESGVPSRFSGSGSGTDFTLTISSLQPEDFATYYCQ QFNSYPLTFGGGTKVEIK (SEQ ID NO: 10) |
| HC-4 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-4 | hKappa | AIQMTQSPSSLSASVGDRVTITCRASQGIRNDLGWYQQKPGKAP KLLIYDASSLESGVPSRFSGSGSGTDFTLTISSLQPEDFATYYCQ QFNSYPLTFGGGTKVDIK (SEQ ID NO: 11) |
| HC-5 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-5 | hKappa | NIQMTQSPSSLSASVGDRVTITCRASQAISDYLAWFQQKPGKAP KLLIYDASNLETGVPSRFSGSGSGTDFTLTISSLQPEDFATYYCQ QLNSYPLTFGGGTKVEIK (SEQ ID NO: 12) |
| HC-6 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-6 | hKappa | AIRMTQSPSSLSASVGDRVIIACRASQGIGGALAWYQQKPGNAP KVLVYDASTLESGVPSRFSGGGSGTDFTLTISSLQPEDFATYYC QQFNSYPLTFGGGTKLEIK (SEQ ID NO: 13) |
| HC-7 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-7 | hKappa | DIAMTQSPPSLSAFVGDRVTITCRASQGIISSLAWYQQKPGKAPK LLIYDASSLESGVPSRFSGSGSGTDFTLTIRSLQPEDFATYYCQQ FNSYPLTFGGGTKLEIK (SEQ ID NO: 14) |

TABLE 1-continued

Antibody heavy and light chain variable region amino acid sequences

| Antibody name | Type of Chain | Amino acid sequence |
|---|---|---|
| HC-8 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-8 | hKappa | DIQMTQSPSSLSASVGDRVTITCRASQGISSALAWYQQKAGKAP KVLISDASSLESGVPSRFSGSGSGTDFTLSISSLQPEDFATYYCQ QFNGYPLTFGGGTKVDIK (SEQ ID NO: 15) |
| HC-9 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-9 | hKappa | AIRMTQSPSSLSASVGDRVTITCQASQGIRNDLGWYQQKPGKAP KLLIYDASNLETGVPSRFSGSGSGTDFTFTISSLQPEDIATYYCQQ FNSYPLTFGGGTKLEIK (SEQ ID NO: 16) |
| HC-10 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-10 | hKappa | NIQMTQSPSSLSTSVGDRVTITCRASQGIGTSLAWYQQKPGKPP KLLIYDASSLESGVPSRLSGSGSGTDFTLTISSLQPEDFATYYCQ QSNSYPITFGQGTRLEIK (SEQ ID NO: 17) |
| HC-11 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-11 | hKappa | AIQLTQSPSSLSASVGDRVTITCRASQSIGDYLTWYQQKPGKAPK VLIYGASSLQSGVPPRFSGSGSGTDFTLTVSSLQPEDFATYYCQ QLNSYPLTFGGGTKLEIK (SEQ ID NO: 18) |
| HC-12 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-12 | hKappa | DIQLTQSPSSLSASVGDRVTITCRASQGVRSTLAWYQQKPGKAP KLLIYDASILESGVPSRFSGSGSGTDFTLTISSLQPEDFATYYCQQ FNGYPLTFGQGTRLEIK (SEQ ID NO: 19) |
| HC-13 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-13 | hKappa | DIVMTQSPSSLSASVGDRVTITCRASQGIRNDLGWYQQKPGKAP KLLIYDASSLESGVPSRFSGSGSGTDFTLTISSLQPEDFATYYCQ QFNSYPLTFGGGTKLEIK (SEQ ID NO: 20) |
| HC-14 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-14 | hKappa | DIQLTQSPSSLSASVGDRVTITCRASQGISSFLAWYQQKPGKAPK LLIYDASTLQSGVPSRFSGSASGTDFTLTISSLQPEDFATYYCQQ LNGYPLTFGGGTKVEIK (SEQ ID NO: 21) |
| HC-15 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-15 | hKappa | AIQLTQSPSSLSASVGDRVTITCRASQGIGSALAWYQQKPGIGPK LLIYDASTLESGVPARFSGSGSRTDFTLTITSLQPEDFATYYCQQ FNGYPLTFGGGTKLEIK (SEQ ID NO: 22) |

TABLE 1-continued

Antibody heavy and light chain variable region amino acid sequences

| Antibody name | Type of Chain | Amino acid sequence |
|---|---|---|
| HC-16 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-16 | hKappa | AIQLTQSPSSLSASVGDRVTITCRASQGITSALAWYQEKPGKAPN LLIYDASSLESGVPSRFSGSGYGTDFTLTISSLQPEDFATYYCQQ LNSYPLTFGGGTKVDIK (SEQ ID NO: 23) |
| HC-17 | hIgG1 | QIQLVQSGPELRKPGESVKISCKASGYTFTDYAMYWVKQAPGK GLKWMGWINTYTGKPTYADDFKGRFVFSLEASANTANLQISNLK NEDTATYFCARARGLVDDYVMDAWGQGTSVTVSS (SEQ ID NO: 24) |
| LC-17 | hLambda | SYELIQPPSASVTLGNTVSLTCVGDELSKRYAQWYQQKPDKTIV SVIYKDSERPSGISDRFSGSSSGTTATLTIHGTLAEDEADYYCLST YSDDNLPVFGGGTKLTVL (SEQ ID NO: 25) |
| HC-18 | hIgG1 | EVQLQQYGAELGKPGTSVRLSCKVSGYNIRNTYIHWVNQRPGE GLEWIGRIDPTNGNTISAEKFKTKATLTADTSSHTAYLQFSQLKS DDTAIYFCALNYEGYADYWGQGVMVTGSS (SEQ ID NO: 26) |
| LC-18 | hKappa | DIQMTQSPSFLSASVGDRVTINCKASQNINKYLNWYQQKVGEAP KRLIFKTNSLQTGIPSRFSGSGSGTDYTLTISSLQTEDVATYFCFQ YNIGYTFGAGTKVELK (SEQ ID NO: 27) |
| HC-19 | hIgG1 | EVQLQESGPGLVKPSQSLSLTCSVTGYSISSNYRWNWIRKFPGN KVEWMGYINSAGSTNYNPSLKSRISMTRDTSKNQFFLQVNSVTT EDTATYYCARSLRGYITDYSGFFDYWGQGVMVTVSS (SEQ ID NO: 28) |
| LC-19 | hKappa | DIRMTQSPASLSASLGETVNIECLASEDIFSDLAWYQQKPGKSPQ LLIYNANSLQNGVPSRFSGSGSGTRYSLKINSLQSEDVATYFCQ QYKNYPLTFGSGTKLEIK (SEQ ID NO: 29) |
| HC-20 | hIgG1 | EVQLQQYGAELGKPGTSVRLSCKLSGYKIRNTYIHWVNQRPGK GLEWIGRIDPANGNTIYAEKFKSKVTLTADTSSNTAYMQLSQLKS DDTALYFCAMNYEGYEDYWGQGVMVTVSS (SEQ ID NO: 30) |
| LC-20 | hKappa | DIQMTQSPSFLSASVGDSVTINCKASQNINKYLNWYQQKLGEAP KRLIHKTDSLQTGIPSRFSGSGSGTDYTLTISSLQPEDVATYFCFQ YKSGFMFGAGTKLELK (SEQ ID NO: 31) |
| HC-21 | hIgG1 | QIQLVQSGPELKKPGESVKISCKASGYTFTDYAVYWVIQAPGKGL KWMGWINTYTGKPTYADDFKGRFVFSLETSASTANLQISNLKNE DTATYFCARGAGMTKDYVMDAWGRGVLVTVS (SEQ ID NO: 32) |
| LC-21 | hLambda | SYELIQPPSASVTLGNTVSLTCVGDELSKRYAQWYQQKPDKTIV SVIYKDSERPSDISDRFSGSSSGTTATLTIHGTLAEDEADYYCLST YSDDNLPVFGGGTKLTVL (SEQ ID NO: 33) |
| HC-22 | hIgG1 | QVQLKESGPGLVQPSQTLSLTCTVSGFSLTSYLVHWVRQPPGK TLEWVGLMWNDGDTSYNSALKSRLSISRDTSKSQVFLKMHSLQ AEDTATYYCARESNLGFTYWGHGTLVTVSS (SEQ ID NO: 34) |
| LC-22 | hKappa | DIQMTQSPASLSASLEEIVTITCKASQGIDDDLSWYQQKPGKSPQ LLIYDVTRLADGVPSRFSGSRSGTQYSLKISRPQVADSGIYYCLQ SYSTPYTFGAGTKLELK (SEQ ID NO: 35) |
| HC-23 | hIgG1 | EVQLQQYGAELGKPGTSVRLSCKVSGYNIRNTYIHWVHQRPGE GLEWIGRIDPTNGNTISAEKFKSKATLTADTSSNTAYMQFSQLKS DDTAIYFCAMNYEGYADYWGQGVMVTVSS (SEQ ID NO: 36) |
| LC-23 | hKappa | DIQMTQSPSFLSASVGDRLTINCKASQNINKYLNWYQQKLGEAP KRLIFKTNSLQTGIPSRFSGSGSGTDYTLTISSLQPEDVATYFCFQ YNIGFTFGAGTKLELK (SEQ ID NO: 37) |
| HC-24 | hIgG1 | EVQLVESGGGLVQSGRSLKLSCAASGFTVSDYYMAWVRQAPTK GLEWVATINYDGSTTYHRDSVKGRFTISRDNAKSTLYLQMDSLR SEDTATYYCARHGDYGYHYGAYYFDYWGQGVMVTVSS (SEQ ID NO: 38) |

TABLE 1-continued

Antibody heavy and light chain variable region amino acid sequences

| Antibody name | Type of Chain | Amino acid sequence |
|---|---|---|
| LC-24 | hKappa | DIVLTQSPALAVSLGQRATISCRASQTVSLSGYNLIHWYQQRTGQ QPKLLIYRASNLAPGIPARFSGSGSGTDFTLTISPVQSDDIATYYC QQSRESWTFGGGTNLEMK (SEQ ID NO: 39) |
| HC-25 | hIgG1 | QIQLVQSGPELKKPGESVKISCKASGYTFTDYAIHWVKQAPGQG LRWMAWINTETGKPTYADDFKGRFVFSLEASASTAHLQISNLKN EDTATFFCAGGSHWFAYWGQGTLVTVSS (SEQ ID NO: 40) |
| LC-25 | hLambda | SYELIQPPSASVTLENTVSITCSGDELSNKYAHWYQQKPDKTILE VIYNDSERPSGISDRFSGSSSGTTAILTIRDAQAEDEADYYCLSTF SDDDLPIFGGGTKLTVL (SEQ ID NO: 41) |
| HC-26 | hIgG1 | QIQLVQSGPELKKPGESVKISCKASGYTFTDYAVYWVIQAPGKGL KWMGWINTYTGKPTYADDFKGRFVFSLETSASTANLQISNLKNE DTATYFCARGAGMTKDYVMDAWGRGVLVTVS (SEQ ID NO: 32) |
| LC-26 | hLambda | SYELIQPPSTSVTLGNTVSLTCVGNELPKRYAYWFQQKPDQSIV RLIYDDDRRPSGISDRFSGSSSGTTATLTIRDAQAEDEAYYYCHS TYTDDKVPIFGGGTKLTVL (SEQ ID NO: 42) |
| HC-27 | hIgG1 | EVQLVESGGGLVQPGRSMKLSCKASGFTFSNYDMAWVRQAPT RGLEWVASISYDGITAYYRDSVKGRFTISRENAKSTLYLQLVSLR SEDTATYYCTTEGGYVYSGPHYFDYWGQGVMVTVSS (SEQ ID NO: 43) |
| LC-27 | hKappa | DIQMTQSPSSMSVSLGDTVTITCRASQDVGIFVNWFQQKPGRSP RRMIYRATNLADGVPSRFSGSRSGSDYSLTISSLESEDVADYHC LQYDEFPRTFGGGTKLELK (SEQ ID NO: 44) |
| HC-28 | hIgG1 | EVQLQQYGAELGKPGTSVRLSCKVSGYKIRNTYIHWVNQRPGK GLEWIGRIDPANGNTIYAEKFKSKVTLTADTSSNTAYMQLSQLKS DDTALYFCAMNYEGYEDYWGQGVMVTVSS (SEQ ID NO: 45) |
| LC-28 | hKappa | DIQMTQSPSFLSASVGDSVTINCKASQNINKYLNWYQQKLGEAP KRLIHKTNSLQPGFPSRFSGSGSGTDYTLTISSLQPEDVAAYFCF QYNSGFTFGAGTKLELK (SEQ ID NO: 46) |
| HC-29 | hIgG1 | QVQLVQSGAEVKKPGASVKVSCKASGYTFTDYYIHWVRQAPGQ GLEWMGWMNPHSGDTGYAQKFQGRVTMTRDTSTSTVYMELSS LRSEDTAVYYCARHGRGYNGYEGAFDIWGQGTLVTVSSAS (SEQ ID NO: 47) |
| LC-29 | hKappa | DIQMTQSPSSLSASVGDRVTITCRASQGIGNELGWYQQKPGKAP KLLIYAASNLQSGVPSRFSGSGSGTDFTLTISSLQPEDFATYYCQ QYDNLPLTFGQGTKVEIK (SEQ ID NO: 48) |
| HC-30 | hIgG1 | QVQLVQSGAEVKKPGASVKVSCKASGYTFTGYYLHWVRQAPG QGLEWMGWINPNSGDTNYAQNFQGRVTMTRDTSTSTVYMELS SLRSEDTAVYYCARHGRGYNGYEGAFDIWGQGTLVTVSSAS (SEQ ID NO: 49) |
| LC-30 | hKappa | DIQMTQSPSSLSASVGDRVTITCRASQGIRNDLGWYQQKPGKAP KLLIYDASSLESGVPSRFSGSGSGTDFTLTISSLQPEDFATYYCQ QLNGYPLTFGGGTKVEIK (SEQ ID NO: 50) |
| HC-31 | hIgG1 | QVQLVQSGAEVKKPGASVKVSCKASGYTFTGYYLHWVRQAPG QGLEWMGWINPNSGGTNYAQKFQGRVTMTRDTSTSTVYMELS SLRSEDTAVYYCARHGRGYEGYEGAFDIWGQGTLVTVSSAS (SEQ ID NO: 51) |
| LC-31 | hKappa | DIQMTQSPSSLSASVGDRVTITCRASQGIRNDLGWYQQKPGKAP KLLIYDASELETGVPSRFSGSGSGTDFTLTISSLQPEDFATYYCQ QLNGYPITFGQGTKVEIK (SEQ ID NO: 52) |
| HC-32 | hIgG1 | QVQLVQSGAEVKKPGASVKVSCKASGYTFTSYYIHWVRQAPGQ GLEWMGWLNPSGGGTSYAQKFQGRVTMTRDTSTSTVYMELSS LRSEDTAVYYCARHGRGYDGYEGAFDIWGQGTLVTVSSAS (SEQ ID NO: 53) |
| LC-32 | hKappa | DIQMTQSPSSLSASVGDRVTITCRASQGIRNDLGWYQQKPGKAP KLLIYDASNLETGVPSRFSGSGSGTDFTLTISSLQPEDFATYYCQ QLNGYPLTFGGGTKVEIK (SEQ ID NO: 54) |

TABLE 1-continued

Antibody heavy and light chain variable region amino acid sequences

| Antibody name | Type of Chain | Amino acid sequence |
|---|---|---|
| HC-33 | hIgG1 | QVQLVQSGAEVKKPGASVKVSCKASGYTFSTYYMHWVRQAPG QGLEWMGIINPSGGSTSYAQKFQGRVTMTRDTSTSTVYMKLSSL RSEDTAVYYCARHGRGYEGYEGAFDIWGQGTLVTVSSAS (SEQ ID NO: 55) |
| LC-33 | hKappa | DIQMTQSPSSLSASVGDRVTITCRASQGIRDDLGWYQQKPGKAP KLLIYDASNLETGVPSRFSGSGSGTDFTLTISSLQPEDFATYYCQ QANGFPLTFGGGTKVEIK (SEQ ID NO: 56) |
| HC-34 | hIgG1 | QVQLVQSGAEVKKPGASVKVSCKASGYTFTGYYIHWVRQAPGQ GLEWMGIINPSGGNTNYAQNFQGRVTMTRDTSTSTVYMELSSL RSEDTAVYYCARHGRGYNAYEGAFDIWGQGTLVTVSSAS (SEQ ID NO: 57) |
| LC-34 | hKappa | DIQMTQSPSSLSASVGDRVTITCRASQGIRNDLGWYQQKPGKAP KLLIYDASNLETGVPSRFSGSGSGTDFTLTISSLQPEDFATYYCQ QVNGYPLTFGGGTKVEIK (SEQ ID NO: 58) |
| HC-35 | hIgG1 | QVQLVQSGAEVKKPGASVKVSCKASGGTFSSYAISWVRQAPGQ GLEWMGVINPTVGGANYAQKFQGRVTMTRDTSTSTVYMELSSL RSEDTAVYYCARHGRGYNEYEGAFDIWGQGTLVTVSSAS (SEQ ID NO: 59) |
| LC-35 | hKappa | DIQMTQSPSSLSASVGDRVTITCQASQDISDYLNWYQQKPGKAP KLLIYDASNLETGVPSRFSGSGSGTDFTLTISSLQPEDFATYYCQ QGNSFPLTFGGGTKLEIK (SEQ ID NO: 60) |
| HC-36 | hIgG1 | QVQLVQSGAEVKKLGASVKVSCKASGYTFSSYYMHWVRQAPG QGLEWMGVINPNGAGTNFAQKFQGRVTMTRDTSTSTVYMELSS LRSEDTAVYYCARHGRGYEGYEGAFDIWGQGTLVTVSSAS (SEQ ID NO: 61) |
| LC-36 | hKappa | DIQMTQSPSSLSASVGDRVTITCRASQGIRNDLGWYQQKPGKAP KLLIYDASSLESGVPSRFSGSGSGTDFTLTISSLQPEDFATYYCQ QLNGYPLTFGGGTKVEIK (SEQ ID NO: 50) |
| HC-37 | hIgG1 | QVQLVQSGAEVKKPGASVKVSCKASGYTFTTYYMHWVRQAPG QGLEWMGWINPTGGGTNYAQNFQGRVTMTRDTSTSTVYMELS SLRSEDTAVYYCARHGRGYEGYEGAFDIWGQGTLVTVSSAS (SEQ ID NO: 62) |
| LC-37 | hKappa | DIQMTQSPSSLSASVGDRVTITCRASQGIRNDVSWYQQKPGKAP KLLIYDASNLETGVPSRFSGSGSGTDFTLTISSLQPEDFATYYCQ QLSGYPITFGQGTKLEIK (SEQ ID NO: 63) |
| HC-38 | hIgG1 | QVQLVQSGAEVKKPGASVKVSCKASGYTFTSYYIHWVRQAPGQ GLEWMGMINPSGGSTNYAQKFQGRVTMTRDTSTSTVYMELSSL RSEDTAVYYCARHGRGYNDYEGAFDIWGQGTLVTVSSAS (SEQ ID NO: 64) |
| LC-38 | hKappa | DIQMTQSPSSLSASVGDRVTITCRASQSISDWLAWYQQKPGKAP KLLIYEASNLEGGVPSRFSGSGSGTDFTLTISSLQPEDFATYYCQ QANSFPYTFGQGTKVEIK (SEQ ID NO: 65) |
| HC-39 | hIgG1 | QVQLVQSGAEVKKPGASVKVSCKASGYIFSAYYIHWVRQAPGQ GLEWMGIINPSGGSTRYAQKFQGRVTMTRDTSTSTVYMELSSLR SEDTAVYYCARHGRGYGGYEGAFDIWDQGTLVTVSSAS (SEQ ID NO: 66) |
| LC-39 | hKappa | DIQMTQSPSSLSASVGDRVTITCRASQGIGDYVAWYQQKPGKAP KLLIYDASNLETGVPSRFSGSGSGTDFTLTISSLQPEDFATYYCQ QLNGYPITFGQGTRLEIK (SEQ ID NO: 67) |
| HC-40 | hIgG1 | EVQLVQSGAEVKKPGESLKISCKGSGYRFTSYWIGWVRQMPGK GLEWMGIIYPDDSDTRYSPSFQGQVTISVDKSNSTAYLQWSSLK ASDTAMYYCARHGRGYNGYEGAFDIWGQGTLVTVSSAS (SEQ ID NO: 68) |
| LC-40 | hKappa | DIQMTQSPSSLSASVGDRVTITCRASQGISSYLAWYQQKPGKAP KLLIYDASNLETGVPSRFSGSGSGTYFTLTISSLQPEDFATYYCQ QGASFPITFGQGTKVEIK (SEQ ID NO: 69) |

TABLE 1-continued

Antibody heavy and light chain variable region
amino acid sequences

| Antibody name | Type of Chain | Amino acid sequence |
|---|---|---|
| HC-41 | hIgG1 | EVQLVQSGAEVKKPGESLKISCKGSGSSFPNSWIAWVRQMPGK GLEWMGIIYPSDSDTRYSPSFQGQVTISADKSISTAYLQWSSLEA SDTAMYYCARHGRGYNGYEGAFDIWGQGTLVTVSSAS (SEQ ID NO: 70) |
| LC-41 | hKappa | DIQMTQSPSSLSASVGDRVTITCRASQGIRNYLAWYQQKPGKAP KLLIYDASSLQSGVPSRFSGSGSGTDFTLTISSLQPEDFATYYCQ QLNSYPLTFGGGTKVEIK (SEQ ID NO: 71) |
| HC-42 | hIgG1 | EVQLVQSGAEVKKPGESLKISCKGSGYSFDSYWIGWVRQMPGK GLEWMGIMYPGDSDTRYSPSFQGQVTISADKSISTAYLQWSSLK ASDTAMYYCARHGRGYNAYEGAFDIWGQGTLVTVSSAS (SEQ ID NO: 72) |
| LC-42 | hKappa | DIQMTQSPSSLSASVGDRVTITCRASQSINNWLAWYQQKPGKAP KLLIYDAFILQSGVPSRFSGSGSGTDFTLTISSLQPEDFATYYCLQ LNSYPLTFGPGTKVDIK (SEQ ID NO: 73) |
| HC-43 | hIgG1 | EVQLVQSGAEVKKPGESLKISCKGSGYSFTNWIAWVRQMPGKG LEWMGIIYPGDSETRYSPSFQGQVTISADKSISTAYLQWSSLKAS DTAMYYCARHGRGYYGYEGAFDIWGQGTLVTVSSAS (SEQ ID NO: 74) |
| LC-43 | hKappa | DIQMTQSPSSLSASVGDRVTITCRASQGISDNLNWYQQKPGKAP KLLIYDASNLETGVPSRFSGSGSGTDFTLTISSLQPEDFATYYCQ QAISFPPLTFGQGTKVEIK (SEQ ID NO: 75) |
| HC-44 | hIgG1 | EVQLVQSGAEVKKPGESLKISCKGSGYNFTSYWIGWVRQMPGK GLEWMGVIYPDDSETRYSPSFQGQVTISADKSISTAYLQWSSLK ASDTAMYYCARHGRGYNGYEGAFDIWGQGTLVTVSSAS (SEQ ID NO: 76) |
| LC-44 | hKappa | DIQMTQSPSSLSASVGDRVTITCRASRDIRDDLGWYQQKPGKAP KLLIYDASNLETGVPSRFSGSGSGTDFTLTISSLQPEDFATYYCQ QANSFPLTFGGGTKVEIK (SEQ ID NO: 77) |
| HC-45 | hIgG1 | EVQLVQSGAEVKKPGESLKISCKGSGYTFNTYIGWVRQMPGKG LEWMGIIYPGDSGTRYSPSFQGQVTISADKAISTAYLQWSSLKAS DTAMYYCARHSRGYNGYEGAFDIWGQGTLVTVSSAS (SEQ ID NO: 78) |
| LC-45 | hKappa | DIQMTQSPSSLSASVGDRVTITCRASQGISNYLAWYQQKPGKAP KLLIYDASNLETGVPSRFSGSGSGTDFTLTISSLQPEDFATYYCQ QANSFPVTFGQGTKVEIK (SEQ ID NO: 79) |
| HC-46 | hIgG1 | EVQLVQSGAEVKKPGESLKISCKGSGYNFTTYWIGWVRQMPGK GLEWMGIIHPADSDTRYNPSFQGQVTISADKSISTAYLQWSSLKA SDTAMYYCARHGRGYNGYEGAFDIWGQGTLVTVSSAS (SEQ ID NO: 80) |
| LC-46 | hKappa | DIQMTQSPSSLSASVGDRVTITCRVSQGISSYLAWYQQKPGKAP KLLIYDASNLETGVPSRFSGSGSGTDFTLTISSLQPEDFATYYCQ QANSFPLTFGGGTKVEIK (SEQ ID NO: 81) |
| HC-47 | hIgG1 | EVQLVQSGAEVKKPGESLKISCKGSGYRFSNYWIAWVRQMPGK GLEWMGIIYPDNSDTRYSPSFQGQVTISADKSISTAYLQWSSLKA SDTAMYYCARHGRGYDGYEGAFDIWGQGTLVTVSSAS (SEQ ID NO: 82) |
| LC-47 | hKappa | DIQMTQSPSSLSASVGDRVTITCRASQGIRSDLAWYQQKPGKAP KLLIYGASSLQSGVPSRFSGSGSGTDFTLTISSLQPEDFATYYCQ QANSFPLSFGQGTKVEIK (SEQ ID NO: 83) |
| HC-48 | hIgG1 | EVQLVQSGAEVKKPGESLKISCKGSGYRFASYWIGWVRQMPGK GLEWMGITYPGDSETRYNPSQGQVTISADKSISTAYLQWSSLKA SDTAMYYCARHGRGYGGYEGAFDIWGQGTLVTVSSAS (SEQ ID NO: 84) |
| LC-48 | hKappa | DIQMTQSPSSLSASVGDRVTITCRASQGIRNDLGWYQQKPGKAP KLLIYDASNLETGVPSRFSGSGSGTDFTLTISSLQPEDFATYYCQ QANSFPLTFGGGTKVEIK (SEQ ID NO: 85) |

TABLE 1-continued

Antibody heavy and light chain variable region amino acid sequences

| Antibody name | Type of Chain | Amino acid sequence |
|---|---|---|
| HC-49 | hIgG1 | EVQLVQSGAEVKKPGESLKISCKGSGYSFTSYWIGWVRQMPGK<br>GLEWMGIIYPGDSDTRYSPSFQGQVTISADKSISTAYLQWSSLKA<br>SDTAMYYCARHGRGYNGYEGAFDIWGQGTLVTVSSAS (SEQ ID NO: 86) |
| LC-49 | hKappa | DIQMTQSPSSLSASVGDRVTITCRASQSISNWLAWYQQKPGKAP<br>KLLIYDASNLETGVPSRFSGSGSGTDFTLTISSLQPEDFATYYCQ<br>QTNSFPLTFGQGTRLEIK (SEQ ID NO: 87) |
| HC-74 | hIgG1 | QVQLVQSGAAVKKPGESLKISCKGSGYRFTTYWIGWVRQMPGK<br>GLEWMGIIYPGDSDTRYSPSFQGQVTISAGKSISTAYLQWSSLKA<br>SDTAMYYCARHGRGYNGYEGAFDIWGQGTMVTVSS (SEQ ID NO: 7) |
| LC-74 | hKappa | DIQLTQSPSSLSASVGDRVTITCRASQGVISALAWYQQKPGKAP<br>KLLIYDASSLESGVPSRFSGSGSGTDFTLTISSLQPEDFATYYCQ<br>QFNSYPLTFGGGTKVEIK (SEQ ID NO: 88) |
| HC-75 | hIgG1 | QVQLVQSGAAVKKPGESLKISCKGSGYRFTTYWIGWVRQMPGK<br>GLEWMGIIYPGDSDTRYSPSFQGQVTISAGKSISTAYLQWSSLKA<br>SDTAMYYCARHGRGYNGYEGAFDIWGQGTMVTVSS (SEQ ID NO: 7) |
| LC-75 | hKappa | DIQLTQSPSSLSASVGDRVTITCRASQGIRSALAWYQQKPGKAP<br>KLLIYDASSLESGVPSRFSGSGSGTDFTLTISSLQPEDFATYYCQ<br>QFNSYPLTFGGGTKVEIK (SEQ ID NO: 89) |
| HC-76 | hIgG1 | QVQLVQSGAAVKKPGESLKISCKGSGYRFTTYWIGWVRQMPGK<br>GLEWMGIIYPGDSDTRYSPSFQGQVTISAGKSISTAYLQWSSLKA<br>SDTAMYYCARHGRGYNGYEGAFDIWGQGTMVTVSS (SEQ ID NO: 7) |
| LC-76 | hKappa | DIQLTQSPSSLSASVGDRVTITCRASQGVGSALAWYQQKPGKAP<br>KLLIYDASSLESGVPSRFSGSGSGTDFTLTISSLQPEDFATYYCQ<br>QFNSYPLTFGGGTKVEIK (SEQ ID NO: 90) |
| HC-77 | hIgG1 | QVQLVQSGAAVKKPGESLKISCKGSGYRFTTYWIGWVRQMPGK<br>GLEWMGIIYPGDSDTRYSPSFQGQVTISAGKSISTAYLQWSSLKA<br>SDTAMYYCARHGRGYNGYEGAFDIWGQGTMVTVSS (SEQ ID NO: 7) |
| LC-77 | hKappa | DIQLTQSPSSLSASVGDRVTITCRASQGVISALAWYQQKPGKAP<br>KLLIYDASILESGVPSRFSGSGSGTDFTLTISSLQPEDFATYYCQQ<br>FNSYPLTFGGGTKVEIK (SEQ ID NO: 91) |
| HC-78 | hIgG1 | QVQLVQSGAAVKKPGESLKISCKGSGYRFTTYWIGWVRQMPGK<br>GLEWMGIIYPGDSDTRYSPSFQGQVTISAGKSISTAYLQWSSLKA<br>SDTAMYYCARHGRGYNGYEGAFDIWGQGTMVTVSS (SEQ ID NO: 7) |
| LC-78 | hKappa | DIQLTQSPSSLSASVGDRVTITCRASQGIRSALAWYQQKPGKAP<br>KLLIYDASILESGVPSRFSGSGSGTDFTLTISSLQPEDFATYYCQQ<br>FNSYPLTFGGGTKVEIK (SEQ ID NO: 92) |
| HC-79 | hIgG1 | QVQLVQSGAAVKKPGESLKISCKGSGYRFTTYWIGWVRQMPGK<br>GLEWMGIIYPGDSDTRYSPSFQGQVTISAGKSISTAYLQWSSLKA<br>SDTAMYYCARHGRGYNGYEGAFDIWGQGTMVTVSS (SEQ ID NO: 7) |
| LC-79 | hKappa | DIQLTQSPSSLSASVGDRVTITCRASQGVGSALAWYQQKPGKAP<br>KLLIYDASILESGVPSRFSGSGSGTDFTLTISSLQPEDFATYYCQQ<br>FNSYPLTFGGGTKVEIK (SEQ ID NO: 93) |
| HC-80 | hIgG1 | QVQLVQSGAAVKKPGESLKISCKGSGYRFTTYWIGWVRQMPGK<br>GLEWMGIIYPGDSDTRYSPSFQGQVTISAGKSISTAYLQWSSLKA<br>SDTAMYYCARHGRGYNGYEGAFDIWGQGTMVTVSS (SEQ ID NO: 7) |
| LC-80 | hKappa | DIQLTQSPSSLSASVGDRVTITCRASQGISSALAWYQQKPGKAP<br>KLLIYDASILESGVPSRFSGSGSGTDFTLTISSLQPEDFATYYCQQ<br>FNSYPLTFGGGTKVEIK (SEQ ID NO: 94) |

TABLE 1-continued

Antibody heavy and light chain variable region amino acid sequences

| Antibody name | Type of Chain | Amino acid sequence |
|---|---|---|
| HC-81 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-81 | hKappa | DIQLTQSPSSLSASVGDRVTITCRASQGVISALAWYQQKPGKAP KLLIYDASTLESGVPSRFSGSGSGTDFTLTISSLQPEDFATYYCQ QFNSYPLTFGGGTKVEIK (SEQ ID NO: 95) |
| HC-82 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-82 | hKappa | DIQLTQSPSSLSASVGDRVTITCRASQGIRSALAWYQQKPGKAP KLLIYDASTLESGVPSRFSGSGSGTDFTLTISSLQPEDFATYYCQ QFNSYPLTFGGGTKVEIK (SEQ ID NO: 96) |
| HC-83 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-83 | hKappa | DIQLTQSPSSLSASVGDRVTITCRASQGVGSALAWYQQKPGKAP KLLIYDASTLESGVPSRFSGSGSGTDFTLTISSLQPEDFATYYCQ QFNSYPLTFGGGTKVEIK (SEQ ID NO: 97) |
| HC-84 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-84 | hKappa | DIQLTQSPSSLSASVGDRVTITCRASQGVGSALAWYQQKPGKAP KLLIYDASTLESGVPSRFSGSGSGTDFTLTISSLQPEDFATYYCQ QFNSYPLTFGGGTKVEIK (SEQ ID NO: 97) |
| HC-245 | hIaG1 | EVQLVQSGAEVKKPGESLKISCKGSGYRFTTSWIGWVRQMPGK GLEWMGIIYPGDSDTRYSPSFQGQVTISADKSISTAYLQWSSLKA SDTAMYYCARHGLGYNGYEGAFDIWGQGTLVTVSS (SEQ ID NO: 98) |
| LC-245 | hKappa | DIQMTQSPSSLSASVGDRVTITCRASQGIGSALAWYQQKPGKAP KLLIYDASTLESGVPSRFSGSGSGTDFTLTISSLQPEDFATYYCQ QFNGYPLTFGQGTRLEIK (SEQ ID NO: 99) |
| HC-246 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-246 | hKappa | DIQMTQSPSSLSASVGDRVTITCRASQGIGSALAWYQQKPGKAP KLLIYDASTLESGVPSRFSGSGSGTDFTLTISSLQPEDFATYYCQ QFNGYPLTFGQGTRLEIK (SEQ ID NO: 99) |
| HC-247 | hIgG1 | QVQLVQSGAAVKKPGESLKISCKGSGYRFTTYWIGWVRQMPGK GLEWMGIIYPGDSDTRYSPSFQGQVTISAGKSISTAYLQWSSLKA SDTAMYYCARHGRGYNGYEGAFDIWGQGTMVTVSS (SEQ ID NO: 7) |
| LC-247 | hKappa | DIQMTQSPSSLSASVGDRVTITCRASRGISDYLAWYQQKPGKAP KLLIYDASNLETGVPSRFSGSGSGTDFTLTISSLQPEDFATYYCQ QANSFPITFGQGTRLEIK (SEQ ID NO: 100) |
| HC-248 | hIgG1 | EVQLVQSGAEVKKPGESLKISCKGSGYRFTTSWIGWVRQMPGK GLEWMGIIYPGDSDTRYSPSFQGQVTISADKSISTAYLQWSSLKA SDTAMYYCARHGLGYNGYEGAFDIWGQGTLVTVSS (SEQ ID NO: 98) |
| LC-248 | hKappa | DIQMTQSPSSLSASVGDRVTITCRASQGIGSALAWYQQKPGKAP KLLIYDASTLESGVPSRFSGSGSGTDFTLTISSLQPEDFATYYCQ QLNGYPLTFGQGTRLEIK (SEQ ID NO: 101) |

TABLE 1-continued

Antibody heavy and light chain variable region
amino acid sequences

| Antibody name | Type of Chain | Amino acid sequence |
|---|---|---|
| HC-249 | hIgG1 | EVQLVQSGAEVKKPGESLKISCKGSGYRFTTSWIGWVRQMPGK GLEWMGIIYPGDSDTRYSPSFQGQVTISADKSISTAYLQWSSLKA SDTAMYYCARHGLGYNGYEGAFDIWGQGTLVTVSS (SEQ ID NO: 98) |
| LC-249 | hKappa | DIQMTQSPSSLSASVGDRVTITCRASQGIGSALAWYQQKPGKAP KLLIYDASNLETGVPSRFSGSGSGTDFTLTISSLQPEDFATYYCQ QLNGYPLTFGQGTRLEIK (SEQ ID NO: 102) |

The nucleic acid sequences corresponding to the heavy and light chain regions of certain sequences described above are provided in Table 2.

TABLE 2

Heavy and light chain anitbody variable region nucleic acid sequences

| HC-1 | hIgG1 | CAGGTGCAGCTGGTGCAGAGCGGTGCGGCGGTGAAAAAACCTGGCGAAAGC CTGAAAATTAGCTGCAAAGGCAGCGGCTATCGTTTTACCACCTATTGGATTGG CTGGGTGCGTCAGATGCCGGGCAAAGGACTGGAATGGATGGGCATTATCTAT CCGGGCGATAGCGATACCCGTTACAGCCCTAGCTTTCAGGGGCAGGTGACCA TTAGCGCGGGAAAAAGCATTAGCACCGCGTATCTGCAGTGGAGCAGCTTAAA AGCGAGCGACACCGCGATGTATTATTGCGCGCGTCATGGCCGTGGCTATAAT GGCTATGAAGGCGCGTTTGATATTTGGGGCCAGGGGACTATGGTTACCGTGA GCAGCGCTAGCACCAAGGGCCCCAGCGTGTTCCTCTGGCCCCAGCAGCAA GAGCACCAGCGGCGGAACCGCCGCCCTGGGCTGCCTGGTGAAGGACTACTTC CCCGAGCCCGTGACCGTGTCCTGGAACAGCGGCGCTCTGACCAGCGGAGTGC ACACCTTCCCTGCCGTGCTGCAGAGCAGCGGCCTGTACTCCCTGAGCAGCGTG GTGACCGTGCCCAGCAGCAGCCTGGGCACCCAGACCTACATCTGCAACGTGA ACCACAAGCCCTCCAACACCAAGGTGGACAAGAAGGTGGAGCCTAAGAGCTG CGACAAGACCCACACCTGCCCTCCCTGCCCCGCCCCCGAGCTGCTGGGCGGAC CCAGCGTGTTCCTGTTCCCTCCCAAGCCCAAGGACACCCTGATGATCAGCCGC ACCCCCGAGGTGACCTGCGTGGTGGTGGACGTGAGCCACGAGGACCCCGAG GTGAAGTTCAACTGGTACGTGGACGGCGTGGAGGTGCACAACGCCAAGACCA AGCCTCGGGAGGAGCAGTACAACTCCACCTACCGCGTGGTGAGCGTGCTGAC CGTGCTGCACCAGGACTGGCTGAACGGCAAGGAGTACAAGTGCAAGGTGAG CAACAAGGCCCTGCCCGCTCCCATCGAGAAGACCATCAGCAAGGCCAAGGGC CAGCCCCGGGAGCCTCAGGTGTACACCCTGCCCCCCAGCCGCGACGAGCTGA CCAAGAACCAGGTGAGCCTGACCTGCCTGGTGAAGGGCTTCTACCCCTCCGAC ATCGCCGTGGAGTGGGAGAGCAACGGCCAGCCTGAGAACAACTACAAGACC ACCCCTCCCGTGCTGGACAGCGACGGCAGCTTCTTCCTGTACAGCAAGCTGAC CGTGGACAAGTCCCGGTGGCAGCAGGGCAACGTGTTCAGCTGCAGCGTGATG CACGAGGCCCTGCACAACCACTACACCCAGAAGAGCCTGAGCCTGAGCCCCG GATAGTAA (SEQ ID NO: 103) |
|---|---|---|
| LC-1 | hKappa | GCCATTCAACTTACACAAAGTCCGAGTAGTCTCAGCGCGAGCGTCGGGGACC GGGTAACCATAACTTGCCGAGCCAGCCAGGGCGTCTCTAGCGCATTGGCATG GTATCAACAAAAACCTGGAAAGGCTCCCAAGCTCCTCATTTACGATGCTAGCT CCCTTGAATCTGGCGTACCATCCCGCTTTAGTGGCAGTGGGTCTGGAACAGAC TTTACTCTTACAATATCATCCCTGCAACCAGAAGATTTTGCTACCTACTACTGTC AACAGTTTAATAGTTACCCACTCACATTCGGCGGGGGTACGAAAGTAGAAATA AAGCGAACCGTGGCTGCGCCTAGCGTCTTTATCTTTCCCCCGAGCGATGAACA GTTGAAATCAGGAACTGCTTCTGTGGTATGTTGCTTAATAATTTTTACCCACG GGAAGCAAAAGTGCAGTGGAAAGTAGACAATGCGCTCCAGTCCGGCAATTCT CAAGAGAGTGTGACTGAACAGGATTCTAAGGATAGCACTTATTCACTGTCAAG TACCTTGACATTGTCAAAGGCGGACTATGAGAAACATAAGGTTTACGCCTGTG AGGTAACACACCAAGGGCTCAGCTCACCTGTTACGAAATCCTTCAATAGGGGC GAGTGT (SEQ ID NO: 104) |
| HC-2 | hIgG1 | CAGGTGCAGCTGGTGCAGAGCGGTGCGGCGGTGAAAAAACCTGGCGAAAGC CTGAAAATTAGCTGCAAAGGCAGCGGCTATCGTTTTACCACCTATTGGATTGG CTGGGTGCGTCAGATGCCGGGCAAAGGACTGGAATGGATGGGCATTATCTAT CCGGGCGATAGCGATACCCGTTACAGCCCTAGCTTTCAGGGGCAGGTGACCA TTAGCGCGGGAAAAAGCATTAGCACCGCGTATCTGCAGTGGAGCAGCTTAAA AGCGAGCGACACCGCGATGTATTATTGCGCGCGTCATGGCCGTGGCTATAAT GGCTATGAAGGCGCGTTTGATATTTGGGGCCAGGGGACTATGGTTACCGTGA GCAGCGCTAGCACCAAGGGCCCCAGCGTGTTCCTCTGGCCCCAGCAGCAA GAGCACCAGCGGCGGAACCGCCGCCCTGGGCTGCCTGGTGAAGGACTACTTC CCCGAGCCCGTGACCGTGTCCTGGAACAGCGGCGCTCTGACCAGCGGAGTGC ACACCTTCCCTGCCGTGCTGCAGAGCAGCGGCCTGTACTCCCTGAGCAGCGTG |

TABLE 2-continued

Heavy and light chain anitbody variable region nucleic acid sequences

|  |  | |
|---|---|---|
|  |  | GTGACCGTGCCCAGCAGCAGCCTGGGCACCCAGACCTACATCTGCAACGTGA<br>ACCACAAGCCCTCCAACACCAAGGTGGACAAGAAGGTGGAGCCTAAGAGCTG<br>CGACAAGACCCACACCTGCCCTCCCTGCCCCGCCCCCGAGCTGCTGGGCGGAC<br>CCAGCGTGTTCCTGTTCCCTCCCAAGCCCAAGGACACCCTGATGATCAGCCGC<br>ACCCCCGAGGTGACCTGCGTGGTGGTGGACGTGAGCCACGAGGACCCCGAG<br>GTGAAGTTCAACTGGTACGTGGACGGCGTGGAGGTGCACAACGCCAAGACCA<br>AGCCTCGGGAGGAGCAGTACAACTCCACCTACCGCGTGGTGAGCGTGCTGAC<br>CGTGCTGCACCAGGACTGGCTGAACGGCAAGGAGTACAAGTGCAAGGTGAG<br>CAACAAGGCCCTGCCCGCTCCCATCGAGAAGACCATCAGCAAGGCCAAGGGC<br>CAGCCCCGGGAGCCTCAGGTGTACACCCTGCCCCCCAGCCGCGACGAGCTGA<br>CCAAGAACCAGGTGAGCCTGACCTGCCTGGTGAAGGGCTTCTACCCCTCCGAC<br>ATCGCCGTGGAGTGGGAGAGCAACGGCCAGCTGGAGAACAACTACAAGACC<br>ACCCCTCCCGTGCTGGACAGCGACGGCAGCTTCTTCCTGTACAGCAAGCTGAC<br>CGTGGACAAGTCCCGGTGGCAGCAGGGCAACGTGTTCAGCTGCAGCGTGATG<br>CACGAGGCCCTGCACAACCACTACACCCAGAAGAGCCTGAGCCTGAGCCCCG<br>GATAGTAA (SEQ ID NO: 103) |
| LC-2 | hKappa | GACATCCAGTTGACCCAGTCTCCATCCTCCCTGTCTGCATCTGTGGGAGACAG<br>AGTCACCATCACTTGCCGGGCAAGTCAGGGCATTAGAACTGATTTAGGCTGG<br>ATCAGCAGAAACCAGGGAAAGCTCCTAAGCTCCTGATCTATGATGCCTCCAGT<br>TTGGAAAGTGGGGTCCCATCAAGGTTCAGCGGCAGTGGATCTGGGACAGATT<br>TCACTCTCACCATCAGCAGCCTGCAGCCTGAAGATTTTGCAACTTATTACTGTC<br>AACAGTTTAATAGTTACCCTCTCACTTTCGGCGGAGGGACCAAGGTGGAAATC<br>AAACGGACCGTGGCCGCCCCCAGCGTGTTCATCTTCCCTCCCAGCGACGAGCA<br>GCTGAAGTCTGGCACCGCCAGCGTGGTGTGCCTGCTGAACAACTTCTACCCCC<br>GCGAGGCCAAGGTGCAGTGGAAGGTGGACAACGCCCTGCAGAGCGGCAACA<br>GCCAGGAGAGCGTGACCGAGCAGGACTCCAAGGACAGCACCTACAGCCTGA<br>GCAGCACCCTGACCCTGAGCAAGGCCGACTACGAGAAGCACAAGGTGTACGC<br>CTGCGAGGTGACCCACCAGGGACTGTCTAGCCCCGTGACCAAGAGCTTCAAC<br>CGGGGCGAGTGCTAA (SEQ ID NO: 105) |
| HC-3 | hIgG1 | CAGGTGCAGCTGGTGCAGAGCGGTGCGGCGGTGAAAAAACCTGGCGAAAGC<br>CTGAAAATTAGCTGCAAAGGCAGCGGCTATCGTTTTACCACCTATTGGATTGG<br>CTGGGTGCGTCAGATGCCGGGCAAAGGACTGGAATGGATGGGCATTATCTAT<br>CCGGGCGATAGCGATACCCGTTACAGCCCTAGCTTTCAGGGGCAGGTGACCA<br>TTAGCGCGGAAAAAGCATTAGCACCGCGTATCTGCAGTGGAGCAGCTTAAA<br>AGCGAGCGACACCGCGATGTATTATTGCGCGCGTCATGGCCGTGGCTATAAT<br>GGCTATGAAGGCGCGTTTGATATTTGGGGCCAGGGGACTATGGTTACCGTGA<br>GCAGCGCTAGCACCAAGGGCCCCAGCGTGTTCCCTCTGGCCCCCAGCAGCAA<br>GAGCACCAGCGGCGGAACCGCCGCCCTGGGCTGCCTGGTGAAGGACTACTTC<br>CCCGAGCCCGTGACCGTGTCCTGGAACAGCGGCGCTCTGACCAGCGGAGTGC<br>ACACCTTCCCTGCCGTGCTGCAGAGCAGCGGCCTGTACTCCCTGAGCAGCGTG<br>GTGACCGTGCCCAGCAGCAGCCTGGGCACCCAGACCTACATCTGCAACGTGA<br>ACCACAAGCCCTCCAACACCAAGGTGGACAAGAAGGTGGAGCCTAAGAGCTG<br>CGACAAGACCCACACCTGCCCTCCCTGCCCCGCCCCCGAGCTGCTGGGCGGAC<br>CCAGCGTGTTCCTGTTCCCTCCCAAGCCCAAGGACACCCTGATGATCAGCCGC<br>ACCCCCGAGGTGACCTGCGTGGTGGTGGACGTGAGCCACGAGGACCCCGAG<br>GTGAAGTTCAACTGGTACGTGGACGGCGTGGAGGTGCACAACGCCAAGACCA<br>AGCCTCGGGAGGAGCAGTACAACTCCACCTACCGCGTGGTGAGCGTGCTGAC<br>CGTGCTGCACCAGGACTGGCTGAACGGCAAGGAGTACAAGTGCAAGGTGAG<br>CAACAAGGCCCTGCCCGCTCCCATCGAGAAGACCATCAGCAAGGCCAAGGGC<br>CAGCCCCGGGAGCCTCAGGTGTACACCCTGCCCCCCAGCCGCGACGAGCTGA<br>CCAAGAACCAGGTGAGCCTGACCTGCCTGGTGAAGGGCTTCTACCCCTCCGAC<br>ATCGCCGTGGAGTGGGAGAGCAACGGCCAGCTGGAGAACAACTACAAGACC<br>ACCCCTCCCGTGCTGGACAGCGACGGCAGCTTCTTCCTGTACAGCAAGCTGAC<br>CGTGGACAAGTCCCGGTGGCAGCAGGGCAACGTGTTCAGCTGCAGCGTGATG<br>CACGAGGCCCTGCACAACCACTACACCCAGAAGAGCCTGAGCCTGAGCCCCG<br>GATAGTAA (SEQ ID NO: 103) |
| LC-3 | hKappa | GCCATCCGGATGACCCAGTCTCCATCCTCCCTGTCTGCATCTGTAGGAGACAG<br>AGTCACCATCACTTGCCGGGCAAGTCAGGGCATTAGAAATGATTTAGCCTGGT<br>ATCAGCAGAAACCAGGGAAAACTCCTAAGCTCCTGATCTATGATGCCTCCAGT<br>TTGGAAAGTGGGGTCCCATCAAGGTTCAGCGGCAGTGGATCTGGGACAGATT<br>TCACTCTCACCATCAGCAGCCTGCAGCCTGAAGATTTTGCAACTTATTACTGTC<br>AACAGTTTAATAGTTACCCGCTCACTTTCGGCGGAGGGACCAAGGTGGAGAT<br>CAAACGGACCGTGGCCGCCCCCAGCGTGTTCATCTTCCCTCCCAGCGACGAGC<br>AGCTGAAGTCTGGCACCGCCAGCGTGGTGTGCCTGCTGAACAACTTCTACCCC<br>CGCGAGGCCAAGGTGCAGTGGAAGGTGGACAACGCCCTGCAGAGCGGCAAC<br>AGCCAGGAGAGCGTGACCGAGCAGGACTCCAAGGACAGCACCTACAGCCTG<br>AGCAGCACCCTGACCCTGAGCAAGGCCGACTACGAGAAGCACAAGGTGTACG<br>CCTGCGAGGTGACCCACCAGGGACTGTCTAGCCCCGTGACCAAGAGCTTCAA<br>CCGGGGCGAGTGCTAA (SEQ ID NO: 106) |
| HC-4 | hIgG1 | CAGGTGCAGCTGGTGCAGAGCGGTGCGGCGGTGAAAAAACCTGGCGAAAGC<br>CTGAAAATTAGCTGCAAAGGCAGCGGCTATCGTTTTACCACCTATTGGATTGG<br>CTGGGTGCGTCAGATGCCGGGCAAAGGACTGGAATGGATGGGCATTATCTAT<br>CCGGGCGATAGCGATACCCGTTACAGCCCTAGCTTTCAGGGGCAGGTGACCA<br>TTAGCGCGGGAAAAAGCATTAGCACCGCGTATCTGCAGTGGAGCAGCTTAAA |

TABLE 2-continued

Heavy and light chain antibody variable region nucleic acid sequences

|  |  |  |
|---|---|---|
|  |  | AGCGAGCGACACCGCGATGTATTATTGCGCGCGTCATGGCCGTGGCTATAAT<br>GGCTATGAAGGCGCGTTTGATATTTGGGGCCAGGGGACTATGGTTACCGTGA<br>GCAGCGCTAGCACCAAGGGCCCCAGCGTGTTCCCTCTGGCCCCCAGCAGCAA<br>GAGCACCAGCGGCGGAACCGCCGCCCTGGGCTGCCTGGTGAAGGACTACTTC<br>CCCGAGCCCGTGACCGTGTCCTGGAACAGCGGCGCTCTGACCAGCGGAGTGC<br>ACACCTTCCCTGCCGTGCTGCAGAGCAGCGGCCTGTACTCCCTGAGCAGCGTG<br>GTGACCGTGCCCAGCAGCAGCCTGGGCACCCAGACCTACATCTGCAACGTGA<br>ACCACAAGCCCTCCAACACCAAGGTGGACAAGAAGGTGGAGCCTAAGAGCTG<br>CGACAAGACCCACACCTGCCCTCCCTGCCCCGCCCCCGAGCTGCTGGGCGGAC<br>CCAGCGTGTTCCTGTTCCCTCCCAAGCCCAAGGACACCCTGATGATCAGCCGC<br>ACCCCCGAGGTGACCTGCGTGGTGGTGGACGTGAGCCACGAGGACCCCGAG<br>GTGAAGTTCAACTGGTACGTGGACGGCGTGGAGGTGCACAACGCCAAGACCA<br>AGCCTCGGGAGGAGCAGTACAACTCCACCTACCGCGTGGTGAGCGTGCTGAC<br>CGTGCTGCACCAGGACTGGCTGAACGGCAAGGAGTACAAGTGCAAGGTGAG<br>CAACAAGGCCCTGCCCGCTCCCATCGAGAAGACCATCAGCAAGGCCAAGGGC<br>CAGCCCCGGGAGCCTCAGGTGTACACCCTGCCCCCCAGCCGCGACGAGCTGA<br>CCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACC<br>ACCCCTCCCGTGCTGGACAGCGACGGCAGCTTCTTCCTGTACAGCAAGCTGAC<br>CGTGGACAAGTCCCGGTGGCAGCAGGGCAACGTGTTCAGCTGCAGCGTGATG<br>CACGAGGCCCTGCACAACCACTACACCCAGAAGAGCCTGAGCCTGAGCCCCG<br>GATAGTAA (SEQ ID NO: 103) |
| LC-4 | hKappa | GCCATCCAGATGACCCAGTCTCCATCCTCCCTGTCTGCATCTGTAGGAGACAG<br>AGTCACCATCACTTGCCGGGCAAGTCAGGGCATTAGAAATGATTTAGGCTGGT<br>ATCAACAGAAACCAGGGAAAGCCCCTAAGCTCCTGATCTATGATGCCTCCAGT<br>TTGGAAAGTGGGGTCCCATCAAGGTTCAGCGGCAGTGGATCTGGGACAGATT<br>TCACTCTCACCATCAGCAGCCTGCAGCCTGAAGATTTTGCAACTTATTACTGTC<br>AACAGTTTAATAGTTACCCTCTGACTTTCGGCGGAGGGACCAAAGTGGATATC<br>AAACGGACCGTGGCCGCCCCCAGCGTGTTCATCTTCCCTCCCAGCGACGAGCA<br>GCTGAAGTCTGGCACCGCCAGCGTGGTGTGCCTGCTGAACAACTTCTACCCCC<br>GCGAGGCCAAGGTGCAGTGGAAGGTGGACAACGCCCTGCAGAGCGGCAACA<br>GCCAGGAGAGCGTGACCGAGCAGGACTCCAAGGACAGCACCTACAGCCTGA<br>GCAGCACCCTGACCCTGAGCAAGGCCGACTACGAGAAGCACAAGGTGTACGC<br>CTGCGAGGTGACCCACCAGGGACTGTCTAGCCCCGTGACCAAGAGCTTCAAC<br>CGGGGCGAGTGCTAA (SEQ ID NO: 107) |
| HC-5 | hIgG1 | CAGGTGCAGCTGGTGCAGAGCGGTGCGGCGGTGAAAAAACCTGGCGAAAGC<br>CTGAAAATTAGCTGCAAAGGCAGCGGCTATCGTTTTACCACCTATTGGATTGG<br>CTGGGTGCGTCAGATGCCGGGCAAAGGACTGGAATGGATGGGCATTATCTAT<br>CCGGGCGATAGCGATACCCGTTACAGCCCAGCTTTCAGGGGCAGGTGACCA<br>TTAGCGCGGGAAAAAGCATTAGCACCGCGTATCTGCAGTGGAGCAGCTTAAA<br>AGCGAGCGACACCGCGATGTATTATTGCGCGCGTCATGGCCGTGGCTATAAT<br>GGCTATGAAGGCGCGTTTGATATTTGGGGCCAGGGGACTATGGTTACCGTGA<br>GCAGCGCTAGCACCAAGGGCCCCAGCGTGTTCCCTCTGGCCCCCAGCAGCAA<br>GAGCACCAGCGGCGGAACCGCCGCCCTGGGCTGCCTGGTGAAGGACTACTTC<br>CCCGAGCCCGTGACCGTGTCCTGGAACAGCGGCGCTCTGACCAGCGGAGTGC<br>ACACCTTCCCTGCCGTGCTGCAGAGCAGCGGCCTGTACTCCCTGAGCAGCGTG<br>GTGACCGTGCCCAGCAGCAGCCTGGGCACCCAGACCTACATCTGCAACGTGA<br>ACCACAAGCCCTCCAACACCAAGGTGGACAAGAAGGTGGAGCCTAAGAGCTG<br>CGACAAGACCCACACCTGCCCTCCCTGCCCCGCCCCCGAGCTGCTGGGCGGAC<br>CCAGCGTGTTCCTGTTCCCTCCCAAGCCCAAGGACACCCTGATGATCAGCCGC<br>ACCCCCGAGGTGACCTGCGTGGTGGTGGACGTGAGCCACGAGGACCCCGAG<br>GTGAAGTTCAACTGGTACGTGGACGGCGTGGAGGTGCACAACGCCAAGACCA<br>AGCCTCGGGAGGAGCAGTACAACTCCACCTACCGCGTGGTGAGCGTGCTGAC<br>CGTGCTGCACCAGGACTGGCTGAACGGCAAGGAGTACAAGTGCAAGGTGAG<br>CAACAAGGCCCTGCCCGCTCCCATCGAGAAGACCATCAGCAAGGCCAAGGGC<br>CAGCCCCGGGAGCCTCAGGTGTACACCCTGCCCCCCAGCCGCGACGAGCTGA<br>CCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACC<br>ACCCCTCCCGTGCTGGACAGCGACGGCAGCTTCTTCCTGTACAGCAAGCTGAC<br>CGTGGACAAGTCCCGGTGGCAGCAGGGCAACGTGTTCAGCTGCAGCGTGATG<br>CACGAGGCCCTGCACAACCACTACACCCAGAAGAGCCTGAGCCTGAGCCCCG<br>GATAGTAA (SEQ ID NO: 103) |
| LC-5 | hKappa | AACATCCAGATGACCCAGTCTCCATCCTCACTGTCTGCATCTGTGGGAGACAG<br>AGTCACCATCACTTGTCGGGCGAGTCAGGCCATTAGCGATTATTTAGCCTGGT<br>TTCAGCAGAAACCAGGGAAAGCCCCTAAGCTCCTGATCTACGATGCATCCAAT<br>TTGGAAACAGGGGTCCCATCAAGGTTCAGTGGAAGTGGATCTGGGACAGATT<br>TCACTCTCACCATCAGCAGCCTGCAGCCTGAAGATTTTGCAACTTATTACTGTC<br>AACAGCTTAATAGTTACCCCCTCACTTTCGGCGGAGGGACCAAGGTGGAGATC<br>AAACGGACCGTGGCCGCCCCCAGCGTGTTCATCTTCCCTCCCAGCGACGAGCA<br>GCTGAAGTCTGGCACCGCCAGCGTGGTGTGCCTGCTGAACAACTTCTACCCCC<br>GCGAGGCCAAGGTGCAGTGGAAGGTGGACAACGCCCTGCAGAGCGGCAACA<br>GCCAGGAGAGCGTGACCGAGCAGGACTCCAAGGACAGCACCTACAGCCTGA<br>GCAGCACCCTGACCCTGAGCAAGGCCGACTACGAGAAGCACAAGGTGTACGC<br>CTGCGAGGTGACCCACCAGGGACTGTCTAGCCCCGTGACCAAGAGCTTCAAC<br>CGGGGCGAGTGCTAA (SEQ ID NO: 108) |

TABLE 2-continued

Heavy and light chain anitbody variable region nucleic acid sequences

HC-6  hIgG1  CAGGTGCAGCTGGTGCAGAGCGGTGCGGCGGTGAAAAAACCTGGCGAAAGC
CTGAAAATTAGCTGCAAAGGCAGCGGCTATCGTTTTACCACCTATTGGATTGG
CTGGGTGCGTCAGATGCCGGGCAAAGGACTGGAATGGATGGGCATTATCTAT
CCGGGCGATAGCGATACCCGTTACAGCCCTAGCTTTCAGGGGCAGGTGACCA
TTAGCGCGGGAAAAAGCATTAGCACCGCGTATCTGCAGTGGAGCAGCTTAAA
AGCGAGCGACACCGCGATGTATTATTGCGCGCGTCATGGCCGTGGCTATAAT
GGCTATGAAGGCGCGTTTGATATTTGGGGCCAGGGGACTATGGTTACCGTGA
GCAGCGCTAGCACCAAGGGCCCCAGCGTGTTCCCTCTGGCCCCCAGCAGCAA
GAGCACCAGCGGCGGAACCGCCGCCCTGGGCTGCCTGGTGAAGGACTACTTC
CCCGAGCCCGTGACCGTGTCCTGGAACAGCGGCGCTCTGACCAGCGGAGTGC
ACACCTTCCCTGCCGTGCTGCAGAGCAGCGGCCTGTACTCCCTGAGCAGCGTG
GTGACCGTGCCCAGCAGCAGCCTGGGCACCCAGACCTACATCTGCAACGTGA
ACCACAAGCCCTCCAACACCAAGGTGGACAAGAAGGTGGAGCCTAAGAGCTG
CGACAAGACCCACACCTGCCCTCCCTGCCCCGCCCCCGAGCTGCTGGGCGGAC
CCAGCGTGTTCCTGTTCCCTCCCAAGCCCAAGGACACCCTGATGATCAGCCGC
ACCCCCGAGGTGACCTGCGTGGTGGTGGACGTGAGCCACGAGGACCCCGAG
GTGAAGTTCAACTGGTACGTGGACGGCGTGGAGGTGCACAACGCCAAGACCA
AGCCTCGGGAGGAGCAGTACAACTCCACCTACCGCGTGGTGAGCGTGCTGAC
CGTGCTGCACCAGGACTGGCTGAACGGCAAGGAGTACAAGTGCAAGGTGAG
CAACAAGGCCCTGCCCGCTCCCATCGAGAAGACCATCAGCAAGGCCAAGGGC
CAGCCCCGGGAGCCTCAGGTGTACACCCTGCCCCCCAGCCGCGACGAGCTGA
CCAAGAACCAGGTGAGCCTGACCTGCCTGGTGAAGGGCTTCTACCCCTCCGAC
ATCGCCGTGGAGTGGGAGAGCAACGGCCAGCCTGAGAACAACTACAAGACC
ACCCCTCCCGTGCTGGACAGCGACGGCAGCTTCTTCCTGTACAGCAAGCTGAC
CGTGGACAAGTCCCGGTGGCAGCAGGGCAACGTGTTCAGCTGCAGCGTGATG
CACGAGGCCCTGCACAACCACTACACCCAGAAGAGCCTGAGCCTGAGCCCCG
GATAGTAA (SEQ ID NO: 103)

LC-6  hKappa  GCCATCCGGATGACCCAGTCTCCATCCTCCCTGTCTGCATCTGTGGGGGACAG
AGTCATTATCGCTTGCCGGGCAAGTCAGGGCATCGGCGGTGCTTTAGCCTGGT
ATCAGCAGAAACCAGGGAATGCTCCTAAGGTCCTGGTCTATGATGCCTCCACT
TTGGAAAGTGGGGTCCCATCACGGTTCAGCGGCGGTGGATCTGGGACAGATT
TCACTCTCACCATCAGCAGCCTGCAGCCTGAAGATTTTGCAACTTACTACTGTC
AACAGTTTAATAGTTACCCTCTCACTTTCGGCGGAGGGACCAAGCTGGAGATC
AAACGGACCGTGGCCGCCCCCAGCGTGTTCATCTTCCCTCCCAGCGACGAGCA
GCTGAAGTCTGGCACCGCCAGCGTGGTGTGCCTGCTGAACAACTTCTACCCCC
GCGAGGCCAAGGTGCAGTGGAAGGTGGACAACGCCCTGCAGAGCGGCAACA
GCCAGGAGAGCGTGACCGAGCAGGACTCCAAGGACAGCACCTACAGCCTGA
GCAGCACCCTGACCCTGAGCAAGGCCGACTACGAGAAGCACAAGGTGTACGC
CTGCGAGGTGACCCACCAGGGACTGTCTAGCCCCGTGACCAAGAGCTTCAAC
CGGGGCGAGTGCTAA (SEQ ID NO: 109)

HC-7  hIgG1  CAGGTGCAGCTGGTGCAGAGCGGTGCGGCGGTGAAAAAACCTGGCGAAAGC
CTGAAAATTAGCTGCAAAGGCAGCGGCTATCGTTTTACCACCTATTGGATTGG
CTGGGTGCGTCAGATGCCGGGCAAAGGACTGGAATGGATGGGCATTATCTAT
CCGGGCGATAGCGATACCCGTTACAGCCCTAGCTTTCAGGGGCAGGTGACCA
TTAGCGCGGGAAAAAGCATTAGCACCGCGTATCTGCAGTGGAGCAGCTTAAA
AGCGAGCGACACCGCGATGTATTATTGCGCGCGTCATGGCCGTGGCTATAAT
GGCTATGAAGGCGCGTTTGATATTTGGGGCCAGGGGACTATGGTTACCGTGA
GCAGCGCTAGCACCAAGGGCCCCAGCGTGTTCCCTCTGGCCCCCAGCAGCAA
GAGCACCAGCGGCGGAACCGCCGCCCTGGGCTGCCTGGTGAAGGACTACTTC
CCCGAGCCCGTGACCGTGTCCTGGAACAGCGGCGCTCTGACCAGCGGAGTGC
ACACCTTCCCTGCCGTGCTGCAGAGCAGCGGCCTGTACTCCCTGAGCAGCGTG
GTGACCGTGCCCAGCAGCAGCCTGGGCACCCAGACCTACATCTGCAACGTGA
ACCACAAGCCCTCCAACACCAAGGTGGACAAGAAGGTGGAGCCTAAGAGCTG
CGACAAGACCCACACCTGCCCTCCCTGCCCCGCCCCCGAGCTGCTGGGCGGAC
CCAGCGTGTTCCTGTTCCCTCCCAAGCCCAAGGACACCCTGATGATCAGCCGC
ACCCCCGAGGTGACCTGCGTGGTGGTGGACGTGAGCCACGAGGACCCCGAG
GTGAAGTTCAACTGGTACGTGGACGGCGTGGAGGTGCACAACGCCAAGACCA
AGCCTCGGGAGGAGCAGTACAACTCCACCTACCGCGTGGTGAGCGTGCTGAC
CGTGCTGCACCAGGACTGGCTGAACGGCAAGGAGTACAAGTGCAAGGTGAG
CAACAAGGCCCTGCCCGCTCCCATCGAGAAGACCATCAGCAAGGCCAAGGGC
CAGCCCCGGGAGCCTCAGGTGTACACCCTGCCCCCCAGCCGCGACGAGCTGA
CCAAGAACCAGGTGAGCCTGACCTGCCTGGTGAAGGGCTTCTACCCCTCCGAC
ATCGCCGTGGAGTGGGAGAGCAACGGCCAGCCTGAGAACAACTACAAGACC
ACCCCTCCCGTGCTGGACAGCGACGGCAGCTTCTTCCTGTACAGCAAGCTGAC
CGTGGACAAGTCCCGGTGGCAGCAGGGCAACGTGTTCAGCTGCAGCGTGATG
CACGAGGCCCTGCACAACCACTACACCCAGAAGAGCCTGAGCCTGAGCCCCG
GATAGTAA (SEQ ID NO: 103)

LC-7  hKappa  GACATCGCGATGACCCAGTCTCCACCCTCCCTGTCTGCATTTGTAGGGGACAG
AGTCACCATCACTTGCCGGGCAAGTCAGGGCATTAGTCTTCTTTAGCCTGGT
ATCAGCAGAAACCAGGGAAAGCTCCTAAGCTCCTGATCTATGATGCCTCCAGT
TTGGAAAGTGGGGTCCCATCAAGGTTCAGTGGCAGTGGATCTGGGACAGATT
TCACTCTCACCATCCGCAGCCTGCAGCCTGAAGATTTTGCCACTTATTACTGTC
AACAGTTTAATAGTTACCCTCTCACTTTCGGCGGAGGGACCAAGCTGGAGATC
AAACGGACCGTGGCCGCCCCCAGCGTGTTCATCTTCCCTCCCAGCGACGAGCA

TABLE 2-continued

Heavy and light chain anitbody variable region nucleic acid sequences

|  |  |  |
|---|---|---|
|  |  | GCTGAAGTCTGGCACCGCCAGCGTGGTGTGCCTGCTGAACAACTTCTACCCCC<br>GCGAGGCCAAGGTGCAGTGGAAGGTGGACAACGCCCTGCAGAGCGGCAACA<br>GCCAGGAGAGCGTGACCGAGCAGGACTCCAAGGACAGCACCTACAGCCTGA<br>GCAGCACCCTGACCCTGAGCAAGGCCGACTACGAGAAGCACAAGGTGTACGC<br>CTGCGAGGTGACCCACCAGGGACTGTCTAGCCCCGTGACCAAGAGCTTCAAC<br>CGGGGCGAGTGCTAA (SEQ ID NO: 110) |
| HC-8 | hIgG1 | CAGGTGCAGCTGGTGCAGAGCGGTGCGGCGGTGAAAAAACCTGGCGAAAGC<br>CTGAAAATTAGCTGCAAAGGCAGCGGCTATCGTTTTACCACCTATTGGATTGG<br>CTGGGTGCGTCAGATGCCGGGCAAAGGACTGGAATGGATGGGCATTATCTAT<br>CCGGGCGATAGCGATACCCGTTACAGCCCTAGCTTTCAGGGGCAGGTGACCA<br>TTAGCGCGGGAAAAAGCATTAGCACCGCGTATCTGCAGTGGAGCAGCTTAAA<br>AGCGAGCGACACCGCGATGTATTATTGCGCGCGTCATGGCCGTGGCTATAAT<br>GGCTATGAAGGCGCGTTTGATATTTGGGGCCAGGGGACTATGGTTACCGTGA<br>GCAGCGCTAGCACCAAGGGCCCCAGCGTGTTCCCTCTGGCCCCCAGCAGCAA<br>GAGCACCAGCGGCGGAACCGCCGCCCTGGGCTGCCTGGTGAAGGACTACTTC<br>CCCGAGCCCGTGACCGTGTCCTGGAACAGCGGCGCTCTGACCAGCGGAGTGC<br>ACACCTTCCCTGCCGTGCTGCAGAGCAGCGGCCTGTACTCCCTGAGCAGCGTG<br>GTGACCGTGCCCAGCAGCAGCCTGGGCACCCAGACCTACATCTGCAACGTGA<br>ACCACAAGCCCTCCAACACCAAGGTGGACAAGAAGGTGGAGCCTAAGAGCTG<br>CGACAAGACCCACACCTGCCCTCCCTGCCCCGCCCCCGAGCTGCTGGGCGGAC<br>CCAGCGTGTTCCTGTTCCCTCCCAAGCCCAAGGACACCCTGATGATCAGCCGC<br>ACCCCCGAGGTGACCTGCGTGGTGGTGGACGTGAGCCACGAGGACCCCGAG<br>GTGAAGTTCAACTGGTACGTGGACGGCGTGGAGGTGCACAACGCCAAGACCA<br>AGCCTCGGGAGGAGCAGTACAACTCCACCTACCGCGTGGTGAGCGTGCTGAC<br>CGTGCTGCACCAGGACTGGCTGAACGGCAAGGAGTACAAGTGCAAGGTGAG<br>CAACAAGGCCCTGCCCGCTCCCATCGAGAAGACCATCAGCAAGGCCAAGGGC<br>CAGCCCCGGGAGCCTCAGGTGTACACCCTGCCCCCCAGCCGCGACGAGCTGA<br>CCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACC<br>ACCCCTCCCGTGCTGGACAGCGACGGCAGCTTCTTCCTGTACAGCAAGCTGAC<br>CGTGGACAAGTCCCGGTGGCAGCAGGGCAACGTGTTCAGCTGCAGCGTGATG<br>CACGAGGCCCTGCACAACCACTACACCCAGAAGAGCCTGAGCCTGAGCCCCG<br>GATAGTAA (SEQ ID NO: 103) |
| LC-8 | hKappa | GACATCCAGATGACCCAGTCTCCATCCTCCCTGTCTGCGTCTGTTGGAGACAG<br>AGTCACCATCACTTGCCGGGCAAGTCAGGGCATTAGCAGTGCTTTAGCCTGGT<br>ATCAGCAGAAAGCAGGGAAAGCTCCTAAAGTCCTGATCTCTGATGCCTCCAGT<br>TTGGAAAGTGGGGTCCCATCAAGGTTCAGCGGCAGTGGATCTGGGACAGATT<br>TCACTCTCAGCATCAGCAGCCTGCAGCCTGAAGATTTTGCAACTTATTACTGTC<br>AACAGTTTAATGGTTACCCGCTCACTTTCGGCGGAGGGACCAAAGTGGATATC<br>AAACGGACCGTGGCCGCCCCCAGCGTGTTCATCTTCCCTCCCAGCGACGAGCA<br>GCTGAAGTCTGGCACCGCCAGCGTGGTGTGCCTGCTGAACAACTTCTACCCCC<br>GCGAGGCCAAGGTGCAGTGGAAGGTGGACAACGCCCTGCAGAGCGGCAACA<br>GCCAGGAGAGCGTGACCGAGCAGGACTCCAAGGACAGCACCTACAGCCTGA<br>GCAGCACCCTGACCCTGAGCAAGGCCGACTACGAGAAGCACAAGGTGTACGC<br>CTGCGAGGTGACCCACCAGGGACTGTCTAGCCCCGTGACCAAGAGCTTCAAC<br>CGGGGCGAGTGCTAA (SEQ ID NO: 111) |
| HC-9 | hIgG1 | CAGGTGCAGCTGGTGCAGAGCGGTGCGGCGGTGAAAAAACCTGGCGAAAGC<br>CTGAAAATTAGCTGCAAAGGCAGCGGCTATCGTTTTACCACCTATTGGATTGG<br>CTGGGTGCGTCAGATGCCGGGCAAAGGACTGGAATGGATGGGCATTATCTAT<br>CCGGGCGATAGCGATACCCGTTACAGCCCTAGCTTTCAGGGGCAGGTGACCA<br>TTAGCGCGGGAAAAAGCATTAGCACCGCGTATCTGCAGTGGAGCAGCTTAAA<br>AGCGAGCGACACCGCGATGTATTATTGCGCGCGTCATGGCCGTGGCTATAAT<br>GGCTATGAAGGCGCGTTTGATATTTGGGGCCAGGGGACTATGGTTACCGTGA<br>GCAGCGCTAGCACCAAGGGCCCCAGCGTGTTCCCTCTGGCCCCCAGCAGCAA<br>GAGCACCAGCGGCGGAACCGCCGCCCTGGGCTGCCTGGTGAAGGACTACTTC<br>CCCGAGCCCGTGACCGTGTCCTGGAACAGCGGCGCTCTGACCAGCGGAGTGC<br>ACACCTTCCCTGCCGTGCTGCAGAGCAGCGGCCTGTACTCCCTGAGCAGCGTG<br>GTGACCGTGCCCAGCAGCAGCCTGGGCACCCAGACCTACATCTGCAACGTGA<br>ACCACAAGCCCTCCAACACCAAGGTGGACAAGAAGGTGGAGCCTAAGAGCTG<br>CGACAAGACCCACACCTGCCCTCCCTGCCCCGCCCCCGAGCTGCTGGGCGGAC<br>CCAGCGTGTTCCTGTTCCCTCCCAAGCCCAAGGACACCCTGATGATCAGCCGC<br>ACCCCCGAGGTGACCTGCGTGGTGGTGGACGTGAGCCACGAGGACCCCGAG<br>GTGAAGTTCAACTGGTACGTGGACGGCGTGGAGGTGCACAACGCCAAGACCA<br>AGCCTCGGGAGGAGCAGTACAACTCCACCTACCGCGTGGTGAGCGTGCTGAC<br>CGTGCTGCACCAGGACTGGCTGAACGGCAAGGAGTACAAGTGCAAGGTGAG<br>CAACAAGGCCCTGCCCGCTCCCATCGAGAAGACCATCAGCAAGGCCAAGGGC<br>CAGCCCCGGGAGCCTCAGGTGTACACCCTGCCCCCCAGCCGCGACGAGCTGA<br>CCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACC<br>ACCCCTCCCGTGCTGGACAGCGACGGCAGCTTCTTCCTGTACAGCAAGCTGAC<br>CGTGGACAAGTCCCGGTGGCAGCAGGGCAACGTGTTCAGCTGCAGCGTGATG<br>CACGAGGCCCTGCACAACCACTACACCCAGAAGAGCCTGAGCCTGAGCCCCG<br>GATAGTAA (SEQ ID NO: 103) |

TABLE 2-continued

Heavy and light chain anitbody variable region nucleic acid sequences

LC-9  hKappa  GCCATCCGGATGACCCAGTCTCCATCCTCCCTGTCTGCATCTGTAGGAGACAG
AGTCACCATCACTTGCCAGGCGAGTCAGGGCATTAGAAATGATTTAGGCTGGT
ATCAGCAGAAACCAGGGAAAGCCCCTAAGCTCCTGATCTACGATGCATCCAAT
TTGGAAACAGGGGTCCCATCAAGGTTCAGTGGAAGTGGATCTGGGACAGATT
TTACTTTCACCATCAGCAGCCTGCAGCCTGAAGATATTGCAACATATTACTGTC
AACAGTTTAATAGTTACCCGCTCACTTTCGGCGGAGGGACCAAGCTGGAGATC
AAACGGACCGTGGCCGCCCCCAGCGTGTTCATCTTCCCTCCCAGCGACGAGCA
GCTGAAGTCTGGCACCGCCAGCGTGGTGTGCCTGCTGAACAACTTCTACCCCC
GCGAGGCCAAGGTGCAGTGGAAGGTGGACAACGCCCTGCAGAGCGGCAACA
GCCAGGAGAGCGTGACCGAGCAGGACTCCAAGGACAGCACCTACAGCCTGA
GCAGCACCCTGACCCTGAGCAAGGCCGACTACGAGAAGCACAAGGTGTACGC
CTGCGAGGTGACCCACCAGGGACTGTCTAGCCCCGTGACCAAGAGCTTCAAC
CGGGGCGAGTGCTAA (SEQ ID NO: 112)

HC-10  hIgG1  CAGGTGCAGCTGGTGCAGAGCGGTGCGGCGGTGAAAAAACCTGGCGAAAGC
CTGAAAATTAGCTGCAAAGGCAGCGGCTATCGTTTTACCACCTATTGGATTGG
CTGGGTGCGTCAGATGCCGGGCAAAGGACTGGAATGGATGGGCATTATCTAT
CCGGGCGATAGCGATACCCGTTACAGCCCTAGCTTTCAGGGGCAGGTGACCA
TTAGCGCGGGAAAAAGCATTAGCACCGCGTATCTGCAGTGGAGCAGCTTAAA
AGCGAGCGACACCGCGATGTATTATTGCGCGCGTCATGGCCGTGGCTATAAT
GGCTATGAAGGCGCGTTTGATATTTGGGGCCAGGGGACTATGGTTACCGTGA
GCAGCGCTAGCACCAAGGGCCCCAGCGTGTTCCCTCTGGCCCCCAGCAGCAA
GAGCACCAGCGGCGGAACCGCCGCCCTGGGCTGCCTGGTGAAGGACTACTTC
CCCGAGCCCGTGACCGTGTCCTGGAACAGCGGCGCTCTGACCAGCGGAGTGC
ACACCTTCCCTGCCGTGCTGCAGAGCAGCGGCCTGTACTCCCTGAGCAGCGTG
GTGACCGTGCCCAGCAGCAGCCTGGGCACCCAGACCTACATCTGCAACGTGA
ACCACAAGCCCTCCAACACCAAGGTGGACAAGAAGGTGGAGCCTAAGAGCTG
CGACAAGACCCACACCTGCCCTCCCTGCCCCGCCCCCGAGCTGCTGGGCGGAC
CCAGCGTGTTCCTGTTCCCTCCCAAGCCCAAGGACACCCTGATGATCAGCCGC
ACCCCCGAGGTGACCTGCGTGGTGGTGGACGTGAGCCACGAGGACCCCGAG
GTGAAGTTCAACTGGTACGTGGACGGCGTGGAGGTGCACAACGCCAAGACCA
AGCCTCGGGAGGAGCAGTACAACTCCACCTACCGCGTGGTGAGCGTGCTGAC
CGTGCTGCACCAGGACTGGCTGAACGGCAAGGAGTACAAGTGCAAGGTGAG
CAACAAGGCCCTGCCCGCTCCCATCGAGAAGACCATCAGCAAGGCCAAGGGC
CAGCCCCGGGAGCCTCAGGTGTACACCCTGCCCCCCAGCCGCGACGAGCTGA
CCAAGAACCAGGTGAGCCTGACCTGCCTGGTGAAGGGCTTCTACCCCTCCGAC
ATCGCCGTGGAGTGGGAGAGCAACGGCCAGCCTGAGAACAACTACAAGACC
ACCCCTCCCGTGCTGGACAGCGACGGCAGCTTCTTCCTGTACAGCAAGCTGAC
CGTGGACAAGTCCCGGTGGCAGCAGGGCAACGTGTTCAGCTGCAGCGTGATG
CACGAGGCCCTGCACAACCACTACACCCAGAAGAGCCTGAGCCTGAGCCCCG
GATAGTAA (SEQ ID NO: 103)

LC-10  hKappa  AACATCCAGATGACCCAGTCTCCATCCTCCCTGTCTACATCCGTAGGAGACAG
AGTCACCATCACTTGCCGGGCAAGTCAGGGCATTGGCACTTCTTTAGCCTGGT
ATCAGCAGAAGCCAGGGAAGCCTCCTAAGTTACTGATCTATGATGCCTCCAGT
TTGGAAAGTGGGGTCCCATCAAGGCTCAGCGGCAGTGGATCTGGGACAGATT
TCACTCTCACCATCAGCAGCCTGCAGCCTGAAGATTTTGCAACTTATTACTGTC
AACAGTCTAATAGTTATCCGATCACCTTCGGCCAAGGGACACGACTGGAGATT
AAACGGACCGTGGCCGCCCCCAGCGTGTTCATCTTCCCTCCCAGCGACGAGCA
GCTGAAGTCTGGCACCGCCAGCGTGGTGTGCCTGCTGAACAACTTCTACCCCC
GCGAGGCCAAGGTGCAGTGGAAGGTGGACAACGCCCTGCAGAGCGGCAACA
GCCAGGAGAGCGTGACCGAGCAGGACTCCAAGGACAGCACCTACAGCCTGA
GCAGCACCCTGACCCTGAGCAAGGCCGACTACGAGAAGCACAAGGTGTACGC
CTGCGAGGTGACCCACCAGGGACTGTCTAGCCCCGTGACCAAGAGCTTCAAC
CGGGGCGAGTGCTAA (SEQ ID NO: 113)

HC-11  hIgG1  CAGGTGCAGCTGGTGCAGAGCGGTGCGGCGGTGAAAAAACCTGGCGAAAGC
CTGAAAATTAGCTGCAAAGGCAGCGGCTATCGTTTTACCACCTATTGGATTGG
CTGGGTGCGTCAGATGCCGGGCAAAGGACTGGAATGGATGGGCATTATCTAT
CCGGGCGATAGCGATACCCGTTACAGCCCTAGCTTTCAGGGGCAGGTGACCA
TTAGCGCGGGAAAAAGCATTAGCACCGCGTATCTGCAGTGGAGCAGCTTAAA
AGCGAGCGACACCGCGATGTATTATTGCGCGCGTCATGGCCGTGGCTATAAT
GGCTATGAAGGCGCGTTTGATATTTGGGGCCAGGGGACTATGGTTACCGTGA
GCAGCGCTAGCACCAAGGGCCCCAGCGTGTTCCCTCTGGCCCCCAGCAGCAA
GAGCACCAGCGGCGGAACCGCCGCCCTGGGCTGCCTGGTGAAGGACTACTTC
CCCGAGCCCGTGACCGTGTCCTGGAACAGCGGCGCTCTGACCAGCGGAGTGC
ACACCTTCCCTGCCGTGCTGCAGAGCAGCGGCCTGTACTCCCTGAGCAGCGTG
GTGACCGTGCCCAGCAGCAGCCTGGGCACCCAGACCTACATCTGCAACGTGA
ACCACAAGCCCTCCAACACCAAGGTGGACAAGAAGGTGGAGCCTAAGAGCTG
CGACAAGACCCACACCTGCCCTCCCTGCCCCGCCCCCGAGCTGCTGGGCGGAC
CCAGCGTGTTCCTGTTCCCTCCCAAGCCCAAGGACACCCTGATGATCAGCCGC
ACCCCCGAGGTGACCTGCGTGGTGGTGGACGTGAGCCACGAGGACCCCGAG
GTGAAGTTCAACTGGTACGTGGACGGCGTGGAGGTGCACAACGCCAAGACCA
AGCCTCGGGAGGAGCAGTACAACTCCACCTACCGCGTGGTGAGCGTGCTGAC
CGTGCTGCACCAGGACTGGCTGAACGGCAAGGAGTACAAGTGCAAGGTGAG
CAACAAGGCCCTGCCCGCTCCCATCGAGAAGACCATCAGCAAGGCCAAGGGC
CAGCCCCGGGAGCCTCAGGTGTACACCCTGCCCCCCAGCCGCGACGAGCTGA

TABLE 2-continued

Heavy and light chain anitbody variable region nucleic acid sequences

```
                CCAAGAACCAGGTGAGCCTGACCTGCCTGGTGAAGGGCTTCTACCCCTCCGAC
                ATCGCCGTGGAGTGGGAGAGCAACGGCCAGCCTGAGAACAACTACAAGACC
                ACCCCTCCCGTGCTGGACAGCGACGGCAGCTTCTTCCTGTACAGCAAGCTGAC
                CGTGGACAAGTCCCGGTGGCAGCAGGGCAACGTGTTCAGCTGCAGCGTGATG
                CACGAGGCCCTGCACAACCACTACACCCAGAAGAGCCTGAGCCTGAGCCCCG
                GATAGTAA (SEQ ID NO: 103)

LC-11  hKappa   GCCATCCAGTTGACCCAGTCTCCATCCTCCCTGTCTGCATCTGTAGGAGACAGA
                GTCACCATCACTTGCCGGGCAAGTCAGAGCATTGGCGACTATTTGACTTGGTA
                TCAGCAGAAACCAGGCAAAGCCCCTAAGGTCCTGATCTATGGTGCATCCAGTT
                TGCAAAGTGGGGTCCCACCAAGGTTCAGTGGCAGTGGTTCTGGGACAGATTT
                CACTCTCACCGTCAGCAGTCTGCAACCTGAAGATTTTGCAACTTATTACTGTCA
                ACAGCTTAATAGTTACCCCCTCACTTTCGGCGGAGGGACCAAGCTGGAGATCA
                AACGGACCGTGGCCGCCCCAGCGTGTTCATCTTCCCTCCCAGCGACGAGCAG
                CTGAAGTCTGGCACCGCCAGCGTGGTGTGCCTGCTGAACAACTTCTACCCCCG
                CGAGGCCAAGGTGCAGTGGAAGGTGGACAACGCCCTGCAGAGCGGCAACAG
                CCAGGAGAGCGTGACCGAGCAGGACTCCAAGGACAGCACCTACAGCCTGAG
                CAGCACCCTGACCCTGAGCAAGGCCGACTACGAGAAGCACAAGGTGTACGCC
                TGCGAGGTGACCCACCAGGGACTGTCTAGCCCCGTGACCAAGAGCTTCAACC
                GGGGCGAGTGCTAA (SEQ ID NO: 114)

HC-12  hIgG1    CAGGTGCAGCTGGTGCAGAGCGGTGCGGCGGTGAAAAAACCTGGCGAAAGC
                CTGAAAATTAGCTGCAAAGGCAGCGGCTATCGTTTTACCACCTATTGGATTGG
                CTGGGTGCGTCAGATGCCGGGCAAAGGACTGGAATGGATGGGCATTATCTAT
                CCGGGCGATAGCGATACCCGTTACAGCCCTAGCTTTCAGGGGCAGGTGACCA
                TTAGCGCGGGAAAAAGCATTAGCACCGCGTATCTGCAGTGGAGCAGCTTAAA
                AGCGAGCGACACCGCGATGTATTATTGCGCGCGTCATGGCCGTGGCTATAAT
                GGCTATGAAGGCGCGTTTGATATTTGGGGCCAGGGGACTATGGTTACCGTGA
                GCAGCGCTAGCACCAAGGGCCCCAGCGTGTTCCCTCTGGCCCCCAGCAGCAA
                GAGCACCAGCGGCGGAACCGCCGCCCTGGGCTGCCTGGTGAAGGACTACTTC
                CCCGAGCCCGTGACCGTGTCCTGGAACAGCGGCGCTCTGACCAGCGGAGTGC
                ACACCTTCCCTGCCGTGCTGCAGAGCAGCGGCCTGTACTCCCTGAGCAGCGTG
                GTGACCGTGCCCAGCAGCAGCCTGGGCACCCAGACCTACATCTGCAACGTGA
                ACCACAAGCCCTCCAACACCAAGGTGGACAAGAAGGTGGAGCCTAAGAGCTG
                CGACAAGACCCACACCTGCCCTCCCTGCCCCGCCCCCGAGCTGCTGGGCGGAC
                CCAGCGTGTTCCTGTTCCCTCCCAAGCCCAAGGACACCCTGATGATCAGCCGC
                ACCCCCGAGGTGACCTGCGTGGTGGTGGACGTGAGCCACGAGGACCCCGAG
                GTGAAGTTCAACTGGTACGTGGACGGCGTGGAGGTGCACAACGCCAAGACCA
                AGCCTCGGGAGGAGCAGTACAACTCCACCTACCGCGTGGTGAGCGTGCTGAC
                CGTGCTGCACCAGGACTGGCTGAACGGCAAGGAGTACAAGTGCAAGGTGAG
                CAACAAGGCCCTGCCCGCTCCCATCGAGAAGACCATCAGCAAGGCCAAGGGC
                CAGCCCCGGGAGCCTCAGGTGTACACCCTGCCCCCCAGCCGCGACGAGCTGA
                CCAAGAACCAGGTGAGCCTGACCTGCCTGGTGAAGGGCTTCTACCCCTCCGAC
                ATCGCCGTGGAGTGGGAGAGCAACGGCCAGCCTGAGAACAACTACAAGACC
                ACCCCTCCCGTGCTGGACAGCGACGGCAGCTTCTTCCTGTACAGCAAGCTGAC
                CGTGGACAAGTCCCGGTGGCAGCAGGGCAACGTGTTCAGCTGCAGCGTGATG
                CACGAGGCCCTGCACAACCACTACACCCAGAAGAGCCTGAGCCTGAGCCCCG
                GATAGTAA (SEQ ID NO: 103)

LC-12  hKappa   GACATCCAGTTGACCCAGTCTCCATCCTCCCTGTCTGCATCTGTAGGAGACAG
                AGTCACCATCACGTGCCGGGCAAGTCAGGGCGTTAGGAGTACTTTAGCCTGG
                TATCAGCAGAAACCAGGGAAAGCTCCTAAGCTCCTGATCTATGATGCCTCCAT
                TTTGGAAAGTGGGGTCCCATCAAGGTTCAGCGGCAGTGGATCTGGGACAGAT
                TTCACTCTCACCATCAGCAGCCTGCAGCCTGAAGATTTTGCAACTTATTACTGT
                CAACAGTTTAATGGTTACCCTCTCACCTTCGGCCAAGGGACACGACTGGAGAT
                TAAACGGACCGTGGCCGCCCCCAGCGTGTTCATCTTCCCTCCCAGCGACGAGC
                AGCTGAAGTCTGGCACCGCCAGCGTGGTGTGCCTGCTGAACAACTTCTACCCC
                CGCGAGGCCAAGGTGCAGTGGAAGGTGGACAACGCCCTGCAGAGCGGCAAC
                AGCCAGGAGAGCGTGACCGAGCAGGACTCCAAGGACAGCACCTACAGCCTG
                AGCAGCACCCTGACCCTGAGCAAGGCCGACTACGAGAAGCACAAGGTGTACG
                CCTGCGAGGTGACCCACCAGGGACTGTCTAGCCCCGTGACCAAGAGCTTCAA
                CCGGGGCGAGTGCTAA (SEQ ID NO: 115)

HC-13  hIgG1    CAGGTGCAGCTGGTGCAGAGCGGTGCGGCGGTGAAAAAACCTGGCGAAAGC
                CTGAAAATTAGCTGCAAAGGCAGCGGCTATCGTITTACCACCTATTGGATTGG
                CTGGGTGCGTCAGATGCCGGGCAAAGGACTGGAATGGATGGGCATTATCTAT
                CCGGGCGATAGCGATACCCGTTACAGCCCTAGCTTTCAGGGGCAGGTGACCA
                TTAGCGCGGGAAAAAGCATTAGCACCGCGTATCTGCAGTGGAGCAGCTTAAA
                AGCGAGCGACACCGCGATGTATTATTGCGCGCGTCATGGCCGTGGCTATAAT
                GGCTATGAAGGCGCGTTTGATATTTGGGGCCAGGGGACTATGGTTACCGTGA
                GCAGCGCTAGCACCAAGGGCCCCAGCGTGTTCCCTCTGGCCCCCAGCAGCAA
                GAGCACCAGCGGCGGAACCGCCGCCCTGGGCTGCCTGGTGAAGGACTACTTC
                CCCGAGCCCGTGACCGTGTCCTGGAACAGCGGCGCTCTGACCAGCGGAGTGC
                ACACCTTCCCTGCCGTGCTGCAGAGCAGCGGCCTGTACTCCCTGAGCAGCGTG
                GTGACCGTGCCCAGCAGCAGCCTGGGCACCCAGACCTACATCTGCAACGTGA
                ACCACAAGCCCTCCAACACCAAGGTGGACAAGAAGGTGGAGCCTAAGAGCTG
                CGACAAGACCCACACCTGCCCTCCCTGCCCCGCCCCCGAGCTGCTGGGCGGAC
                CCAGCGTGTTCCTGTTCCCTCCCAAGCCCAAGGACACCCTGATGATCAGCCGC
```

TABLE 2-continued

Heavy and light chain antibody variable region nucleic acid sequences

|  |  |  |
|---|---|---|
|  |  | ACCCCCGAGGTGACCTGCGTGGTGGTGGACGTGAGCCACGAGGACCCCGAG<br>GTGAAGTTCAACTGGTACGTGGACGGCGTGGAGGTGCACAACGCCAAGACCA<br>AGCCTCGGGAGGAGCAGTACAACTCCACCTACCGCGTGGTGAGCGTGCTGAC<br>CGTGCTGCACCAGGACTGGCTGAACGGCAAGGAGTACAAGTGCAAGGTGAG<br>CAACAAGGCCCTGCCCGCTCCCATCGAGAAGACCATCAGCAAGGCCAAGGGC<br>CAGCCCCGGGAGCCTCAGGTGTACACCCTGCCCCCCAGCCGCGACGAGCTGA<br>CCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACC<br>ACCCCTCCCGTGCTGGACAGCGACGGCAGCTTCTTCCTGTACAGCAAGCTGAC<br>CGTGGACAAGTCCCGGTGGCAGCAGGGCAACGTGTTCAGCTGCAGCGTGATG<br>CACGAGGCCCTGCACAACCACTACACCCAGAAGAGCCTGAGCCTGAGCCCCG<br>GATAGTAA (SEQ ID NO: 103) |
| LC-13 | hKappa | GATATTGTGATGACTCAGTCTCCATCCTCCCTGTCTGCATCTGTAGGAGACAGA<br>GTCACCATCACTTGCCGGGCAAGTCAGGGCATTAGAAATGATTTAGGCTGGTA<br>TCAGCAGAAACCAGGGAAAGCCCCTAAGCTCCTGATCTATGATGCCTCCAGTT<br>TGGAAAGTGGGGTCCCATCAAGGTTCAGCGGCAGTGGATCTGGGACAGATTT<br>CACTCTCACCATCAGCAGCCTGCAGCCTGAAGATTTTGCAACTTATTACTGTCA<br>ACAGTTTAATAGTTACCCTCTCACTTTCGGCGGAGGGACCAAGCTGGAGATCA<br>AACGGACCGTGGCCGCCCCAGCGTGTTCATCTTCCCTCCCAGCGACGAGCAG<br>CTGAAGTCTGGCACCGCCAGCGTGGTGTGCCTGCTGAACAACTTCTACCCCCG<br>CGAGGCCAAGGTGCAGTGGAAGGTGGACAACGCCCTGCAGAGCGGCAACAG<br>CCAGGAGAGCGTGACCGAGCAGGACTCCAAGGACAGCACCTACAGCCTGAG<br>CAGCACCCTGACCCTGAGCAAGGCCGACTACGAGAAGCACAAGGTGTACGCC<br>TGCGAGGTGACCCACCAGGGACTGTCTAGCCCCGTGACCAAGAGCTTCAACC<br>GGGGCGAGTGCTAA (SEQ ID NO: 116) |
| HC-14 | hIgG1 | CAGGTGCAGCTGGTGCAGAGCGGTGCGGCGGTGAAAAAACCTGGCGAAAGC<br>CTGAAAATTAGCTGCAAAGGCAGCGGCTATCGTTTTACCACCTATTGGATTGG<br>CTGGGTGCGTCAGATGCCGGGCAAAGGACTGGAATGGATGGGCATTATCTAT<br>CCGGGCGATAGCGATACCCGTTACAGCCCTAGCTTTCAGGGGCAGGTGACCA<br>TTAGCGCGGGAAAAAGCATTAGCACCGCGTATCTGCAGTGGAGCAGCTTAAA<br>AGCGAGCGACACCGCGATGTATTATTGCGCGCGTCATGGCCGTGGCTATAAT<br>GGCTATGAAGGCGCGTTTGATATTTGGGGCCAGGGGACTATGGTTACCGTGA<br>GCAGCGCTAGCACCAAGGGCCCCAGCGTGTTCCCTCTGGCCCCCAGCAGCAA<br>GAGCACCAGCGGCGGAACCGCCGCCCTGGGCTGCCTGGTGAAGGACTACTTC<br>CCCGAGCCCGTGACCGTGTCCTGGAACAGCGGCGCTCTGACCAGCGGAGTGC<br>ACACCTTCCCTGCCGTGCTGCAGAGCAGCGGCCTGTACTCCCTGAGCAGCGTG<br>GTGACCGTGCCCAGCAGCAGCCTGGGCACCCAGACCTACATCTGCAACGTGA<br>ACCACAAGCCCTCCAACACCAAGGTGGACAAGAAGGTGGAGCCTAAGAGCTG<br>CGACAAGACCCACACCTGCCCTCCCTGCCCCGCCCCCGAGCTGCTGGGCGGAC<br>CCAGCGTGTTCCTGTTCCCTCCCAAGCCCAAGGACACCCTGATGATCAGCCGC<br>ACCCCCGAGGTGACCTGCGTGGTGGTGGACGTGAGCCACGAGGACCCCGAG<br>GTGAAGTTCAACTGGTACGTGGACGGCGTGGAGGTGCACAACGCCAAGACCA<br>AGCCTCGGGAGGAGCAGTACAACTCCACCTACCGCGTGGTGAGCGTGCTGAC<br>CGTGCTGCACCAGGACTGGCTGAACGGCAAGGAGTACAAGTGCAAGGTGAG<br>CAACAAGGCCCTGCCCGCTCCCATCGAGAAGACCATCAGCAAGGCCAAGGGC<br>CAGCCCCGGGAGCCTCAGGTGTACACCCTGCCCCCCAGCCGCGACGAGCTGA<br>CCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACC<br>ACCCCTCCCGTGCTGGACAGCGACGGCAGCTTCTTCCTGTACAGCAAGCTGAC<br>CGTGGACAAGTCCCGGTGGCAGCAGGGCAACGTGTTCAGCTGCAGCGTGATG<br>CACGAGGCCCTGCACAACCACTACACCCAGAAGAGCCTGAGCCTGAGCCCCG<br>GATAGTAA (SEQ ID NO: 103) |
| LC-14 | hKappa | GACATCCAGTTGACCCAGTCTCCATCCTCCCTGTCTGCATCTGTAGGAGACAG<br>AGTCACCATCACTTGCCGGGCCAGTCAGGGCATTAGCAGTTTTTTAGCCTGGT<br>ATCAGCAAAAACCAGGGAAAGCCCCTAAGCTCCTGATCTATGATGCATCCACT<br>TTGCAAAGTGGGGTCCCATCAAGGTTCAGCGGCAGTGCATCTGGGACAGATT<br>TCACTCTCACCATCAGCAGCCTGCAGCCTGAAGATTTTGCAACTTATTACTGTC<br>AACAGCTTAATGGTTACCCTCTCACTTTCGGCGGAGGGACCAAGGTGGAGATC<br>AAACGGACCGTGGCCGCCCCCAGCGTGTTCATCTTCCCTCCCAGCGACGAGCA<br>GCTGAAGTCTGGCACCGCCAGCGTGGTGTGCCTGCTGAACAACTTCTACCCCC<br>GCGAGGCCAAGGTGCAGTGGAAGGTGGACAACGCCCTGCAGAGCGGCAACA<br>GCCAGGAGAGCGTGACCGAGCAGGACTCCAAGGACAGCACCTACAGCCTGA<br>GCAGCACCCTGACCCTGAGCAAGGCCGACTACGAGAAGCACAAGGTGTACGC<br>CTGCGAGGTGACCCACCAGGGACTGTCTAGCCCCGTGACCAAGAGCTTCAAC<br>CGGGGCGAGTGCTAA (SEQ ID NO: 117) |
| HC-15 | hIgG1 | CAGGTGCAGCTGGTGCAGAGCGGTGCGGCGGTGAAAAAACCTGGCGAAAGC<br>CTGAAAATTAGCTGCAAAGGCAGCGGCTATCGTTTTACCACCTATTGGATTGG<br>CTGGGTGCGTCAGATGCCGGGCAAAGGACTGGAATGGATGGGCATTATCTAT<br>CCGGGCGATAGCGATACCCGTTACAGCCCTAGCTTTCAGGGGCAGGTGACCA<br>TTAGCGCGGGAAAAAGCATTAGCACCGCGTATCTGCAGTGGAGCAGCTTAAA<br>AGCGAGCGACACCGCGATGTATTATTGCGCGCGTCATGGCCGTGGCTATAAT<br>GGCTATGAAGGCGCGTTTGATATTTGGGGCCAGGGGACTATGGTTACCGTGA<br>GCAGCGCTAGCACCAAGGGCCCCAGCGTGTTCCCTCTGGCCCCCAGCAGCAA<br>GAGCACCAGCGGCGGAACCGCCGCCCTGGGCTGCCTGGTGAAGGACTACTTC |

TABLE 2-continued

Heavy and light chain anitbody variable region nucleic acid sequences

|  |  |  |
| --- | --- | --- |
|  |  | CCCGAGCCCGTGACCGTGTCCTGGAACAGCGGCGCTCTGACCAGCGGAGTGC<br>ACACCTTCCCTGCCGTGCTGCAGAGCAGCGGCCTGTACTCCCTGAGCAGCGTG<br>GTGACCGTGCCCAGCAGCAGCCTGGGCACCCAGACCTACATCTGCAACGTGA<br>ACCACAAGCCCTCCAACACCAAGGTGGACAAGAAGGTGGAGCCTAAGAGCTG<br>CGACAAGACCCACACCTGCCCTCCCTGCCCCGCCCCCGAGCTGCTGGGCGGAC<br>CCAGCGTGTTCCTGTTCCCTCCCAAGCCCAAGGACACCCTGATGATCAGCCGC<br>ACCCCCGAGGTGACCTGCGTGGTGGTGGACGTGAGCCACGAGGACCCCGAG<br>GTGAAGTTCAACTGGTACGTGGACGGCGTGGAGGTGCACAACGCCAAGACCA<br>AGCCTCGGGAGGAGCAGTACAACTCCACCTACCGCGTGGTGAGCGTGCTGAC<br>CGTGCTGCACCAGGACTGGCTGAACGGCAAGGAGTACAAGTGCAAGGTGAG<br>CAACAAGGCCCTGCCCGCTCCCATCGAGAAGACCATCAGCAAGGCCAAGGGC<br>CAGCCCCGGGAGCCTCAGGTGTACACCCTGCCCCCCAGCCGCGACGAGCTGA<br>CCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACC<br>ACCCCTCCCGTGCTGGACAGCGACGGCAGCTTCTTCCTGTACAGCAAGCTGAC<br>CGTGGACAAGTCCCGGTGGCAGCAGGGCAACGTGTTCAGCTGCAGCGTGATG<br>CACGAGGCCCTGCACAACCACTACACCCAGAAGAGCCTGAGCCTGAGCCCCG<br>GATAGTAA (SEQ ID NO: 103) |
| LC-15 | hKappa | GCCATCCAGTTGACCCAGTCTCCATCCTCCCTGTCTGCATCTGTAGGAGACAGA<br>GTCACCATCACTTGCCGGGCAAGTCAGGGCATTGGCAGTGCTTTAGCCTGGTA<br>TCAGCAGAAACCAGGGATAGGTCCTAAGCTCCTGATCTATGATGCCTCAACTT<br>TGGAAAGTGGGGTCCCAGCAAGGTTCAGCGGCAGTGGATCTAGGACAGATTT<br>CACTCTCACCATCACCAGCCTGCAGCCTGAAGATTTTGCAACTTATTACTGTCA<br>ACAGTTTAATGGTTACCCTCTCACTTTCGGCGGAGGGACCAAGCTGGAGATCA<br>AACGGACCGTGGCCGCCCCAGCGTGTTCATCTTCCCTCCAGCGACGAGCAG<br>CTGAAGTCTGGCACCGCCAGCGTGGTGTGCCTGCTGAACAACTTCTACCCCCG<br>CGAGGCCAAGGTGCAGTGGAAGGTGGACAACGCCCTGCAGAGCGGCAACAG<br>CCAGGAGAGCGTGACCGAGCAGGACTCCAAGGACAGCACCTACAGCCTGAG<br>CAGCACCCTGACCCTGAGCAAGGCCGACTACGAGAAGCACAAGGTGTACGCC<br>TGCGAGGTGACCCACCAGGGACTGTCTAGCCCCGTGACCAAGAGCTTCAACC<br>GGGGCGAGTGCTAA (SEQ ID NO: 118) |
| HC-16 | hIgG1 | CAGGTGCAGCTGGTGCAGAGCGGTGCGGCGGTGAAAAAACCTGGCGAAAGC<br>CTGAAAATTAGCTGCAAAGGCAGCGGCTATCGTTTTACCACCTATTGGATTGG<br>CTGGGTGCGTCAGATGCCGGGCAAAGGACTGGAATGGATGGGCATTATCTAT<br>CCGGGCGATAGCGATACCCGTTACAGCCCTAGCTTTCAGGGGCAGGTGACCA<br>TTAGCGCGGGAAAAAGCATTAGCACCGCGTATCTGCAGTGGAGCAGCTTAAA<br>AGCGAGCGACACCGCGATGTATTATTGCGCGCGTCATGGCCGTGGCTATAAT<br>GGCTATGAAGGCGCGTTTGATATTTGGGGCCAGGGGACTATGGTTACCGTGA<br>GCAGCGCTAGCACCAAGGGCCCCAGCGTGTTCCCTCTGGCCCCCAGCAGCAA<br>GAGCACCAGCGGCGGAACCGCCGCCCTGGGCTGCCTGGTGAAGGACTACTTC<br>CCCGAGCCCGTGACCGTGTCCTGGAACAGCGGCGCTCTGACCAGCGGAGTGC<br>ACACCTTCCCTGCCGTGCTGCAGAGCAGCGGCCTGTACTCCCTGAGCAGCGTG<br>GTGACCGTGCCCAGCAGCAGCCTGGGCACCCAGACCTACATCTGCAACGTGA<br>ACCACAAGCCCTCCAACACCAAGGTGGACAAGAAGGTGGAGCCTAAGAGCTG<br>CGACAAGACCCACACCTGCCCTCCCTGCCCCGCCCCCGAGCTGCTGGGCGGAC<br>CCAGCGTGTTCCTGTTCCCTCCCAAGCCCAAGGACACCCTGATGATCAGCCGC<br>ACCCCCGAGGTGACCTGCGTGGTGGTGGACGTGAGCCACGAGGACCCCGAG<br>GTGAAGTTCAACTGGTACGTGGACGGCGTGGAGGTGCACAACGCCAAGACCA<br>AGCCTCGGGAGGAGCAGTACAACTCCACCTACCGCGTGGTGAGCGTGCTGAC<br>CGTGCTGCACCAGGACTGGCTGAACGGCAAGGAGTACAAGTGCAAGGTGAG<br>CAACAAGGCCCTGCCCGCTCCCATCGAGAAGACCATCAGCAAGGCCAAGGGC<br>CAGCCCCGGGAGCCTCAGGTGTACACCCTGCCCCCCAGCCGCGACGAGCTGA<br>CCAAGAACCAGGTGAGCCTGACCTGCCTGGTGAAGGGCTTCTACCCCTCCGAC<br>ATCGCCGTGGAGTGGGAGAGCAACGGCCAGCCTGAGAACAACTACAAGACC<br>ACCCCTCCCGTGCTGGACAGCGACGGCAGCTTCTTCCTGTACAGCAAGCTGAC<br>CGTGGACAAGTCCCGGTGGCAGCAGGGCAACGTGTTCAGCTGCAGCGTGATG<br>CACGAGGCCCTGCACAACCACTACACCCAGAAGAGCCTGAGCCTGAGCCCCG<br>GATAGTAA (SEQ ID NO: 103) |
| LC-16 | hKappa | GCCATCCAGTTGACCCAGTCTCCATCCTCCCTGTCTGCATCTGTAGGAGACAGA<br>GTCACCATCACTTGCCGGGCAAGTCAGGGCATTACCAGTGCTTTAGCCTGGTA<br>TCAGGAGAAACCAGGGAAAGCTCCTAACCTCCTGATCTATGATGCCTCCAGTT<br>TGGAAAGTGGGGTCCCATCAAGGTTCAGCGGCAGTGGATATGGACAGATTT<br>CACTCTCACCATCAGCAGCCTGCAGCCTGAAGATTTTGCAACTTATTACTGTCA<br>ACAGCTTAATAGTTACCCTCTCACTTTCGGCGGAGGGACCAAAGTGGATATCA<br>AACGGACCGTGGCCGCCCCAGCGTGTTCATCTTCCCTCCAGCGACGAGCAG<br>CTGAAGTCTGGCACCGCCAGCGTGGTGTGCCTGCTGAACAACTTCTACCCCCG<br>CGAGGCCAAGGTGCAGTGGAAGGTGGACAACGCCCTGCAGAGCGGCAACAG<br>CCAGGAGAGCGTGACCGAGCAGGACTCCAAGGACAGCACCTACAGCCTGAG<br>CAGCACCCTGACCCTGAGCAAGGCCGACTACGAGAAGCACAAGGTGTACGCC<br>TGCGAGGTGACCCACCAGGGACTGTCTAGCCCCGTGACCAAGAGCTTCAACC<br>GGGGCGAGTGCTAA (SEQ ID NO: 119) |
| HC-17 | hIgG1 | cagatccagttggtacagtctggacctgagctgaggaagcctggcgagtcagtgaagatctcctgcaa<br>ggcttctggatataccttcacagactatgcaatgtattgggtgaaacaggctccaggaaagggcttgaa<br>gtggatgggctggatcaacacctatactgggaagccaacatatgctgatgacttcaaaggacgatttgt |

TABLE 2-continued

Heavy and light chain anitbody variable region nucleic acid sequences

|         |         |                                                                                                                                                                                                                                                                                                                                                                                                                                                                                       |
|---------|---------|---------------------------------------------------------------------------------------------------------------------------------------------------------------------------------------------------------------------------------------------------------------------------------------------------------------------------------------------------------------------------------------------------------------------------------------------------------------------------------------|
|         |         | cttctctttggaagcctctgccaacactgcaaatttgcagatcagcaacctcaaaaatgaggacacggc<br>tacatatttctgtgcaagagcccgcggattagtcgatgactatgttatggatgcctggggtcaagggact<br>tcagtcactgtctcctct (SEQ ID NO: 120)                                                                                                                                                                                                                                                                                                 |
| LC-17   | hLambda | agctatgagctgatccaaccaccttcggcatcagtcactctgggaaatactgtctcactccacttgtgtcg<br>gagatgaattatcaaaaagatatgctcagtggtatcaacaaaagccagacaagaccattgtgtccgtg<br>atatacaaagatagtgagcggccctcaggcatctctgaccgattctctggttccagctccgggacaaca<br>gccactctgacaatccatggcaccctggctgaggatgaggctgattattactgtttgtcaacatatagtg<br>atgataatctccctgttttcggtggtggaaccaagctcactgtccta (SEQ ID NO: 121)                                                                                                                   |
| HC-18   | hIgG1   | gaagtccagctgcagcagtatggggctgagcttgggaaacctggggacctcagtcaggttgtcttgcaa<br>ggtttctggctataacattaggaatacctacattcactgggtgaatcagaggcctggagagggcctgga<br>atggataggaaggattgatcctacaaacggaaatactatatctgctgagaaattcaaaaccaaggcca<br>cactgactgcagatacatcgtcccacacagcctacttgcagttcagccaactgaaatctgacgacaca<br>gcaatctattttgtgctctgaactatgagggatatgcggattattggggccaggggagtcatggtcacag<br>gctcctcc (SEQ ID NO: 122)                                                                                    |
| LC-18   | hKappa  | gacatccagatgacccagtctccttcattcctgtctgcatctgtgggagacagagtcactatcaactgca<br>aagcaagtcagaatattaacaagtacttaaactggtatcagcaaaaggttggagaagctcccaaacg<br>cctgatatttaagacaaacagtttgcaaacgggcatcccatcaaggttcagtggcagtggatctggaac<br>agattatacacactccaccatcagcagcctgcagactgaagatgttgccacatatttctgctttcagtataac<br>attgggtacacgtttggagctgggaccaaggtggagctgaaa (SEQ ID NO: 123)                                                                                                                       |
| HC-19   | hIgG1   | gaggtgcagcttcaggagtcaggacctggcccttgtgaaaccctcacagtcactctcccctcacctgttcg<br>gtcactggatactccatttccagtaattatagatggaactggatccggaagttcccaggaaataaagtg<br>gagtggatgggatatatatataaacagtgcaggcagtactaactacaatccgtctctcaaaagtcgaatctcc<br>atgactagagacacatccaagaatcagttcttcctgcaggtgaactctgtaacaactgaggacacagc<br>cacttattactgtgcgagatcccctaagagggtatattacggattattcaggcttctttgattactggggcc<br>aaggagtcatggtcacagtctcctca (SEQ ID NO: 124)                                                          |
| LC-19   | hKappa  | gatatccggatgacacagtctccagcttccctgtctgcatctctgggagagactgtcaacatcgaatgtc<br>tagcaagtgaggacatttttcagtgatttagcatggtatcagcaagccagggaaatctcctcaactcc<br>tgatctataatgcaaatagcttgcaaaatggggtcccttcacggtttagtggcagtggatctggcacac<br>ggtattctctcaaaataaacagcctgcaatctgaagatgtcgcgacttatttctgtcaacaatataagaa<br>ttatccgctcacgttcggttctgggaccaagctggagatcaaa (SEQ ID NO: 125)                                                                                                                        |
| HC-20   | hIgG1   | gaagtccagctgcagcagtatggggctgagcttgggaaacctggggacctcagtcaggttgtcttgcaa<br>gctttctggctataagattaggaatacctacatacactgggtgaatcagaggcctggaaagggcctgg<br>aatggattgggaggattgatcctgcaaatggaaatactatctatgctgagaagttcaaaagcaaggtt<br>acactgactgcagatacatcgtccaacacagcctacatgcaactcagccaactgaaatctgacgacac<br>agcactctatttttgtgctatgaactacgaagggtatgaggattactggggccaaggagtcatggtcac<br>agtctccctca (SEQ ID NO: 126)                                                                                   |
| LC-20   | hKappa  | gacatccagatgacccagtctccttcattcctgtctgcatctgtgggagacagcgtcactatcaactgca<br>aagcaagtcagaatattaacaagtacttaaattggtatcagcaaaagcttggagaagctcccaaacgc<br>ctgatacataaaacagacagtctgcaaacgggcatcccatcaaggttcagtggcagtggatctggtac<br>agattacacactccaccatcagcagcctgcagcctgaagatgttgccacatacttctgctttcagtataag<br>agtggggttcatgtttggagctgggaccaaggctggaactgaaa (SEQ ID NO: 127)                                                                                                                       |
| HC-21   | hIgG1   | cagatccagttggtacagtctggacctgagctgaagaagcctggagagtcagtgaagatctcctgcaa<br>ggcctctgggtataccttcacagactatgcagtgtactgggtgatacaggctccaggaaagggcttgaa<br>gtggatgggctggatcaacacctatactgggagccaacatatgccagtgacttcaaaggacggtttg<br>tcttctctttggaaacctctgccagcactgcaaatttgcagatcagcaacctcaaaaatgaggacacgg<br>ctacatatttctgtgcaagaggagcgggcatgactaaggactatgttatggatgcctggggtcgaggg<br>gttttagtcactgtctcctca (SEQ ID NO: 128)                                                                          |
| LC-21   | hLambda | agctatgagctgatccaaccaccttcggcgtcagtcactctgggaaatactgtctcactccacttgtgtcg<br>gagatgaattatcaaaaagatatgctcagtggtatcaacaaaagccagacaagaccattgtgtccgtg<br>atatacaaagatagtgagcggccctcagacatctctgaccgattctctggttccagctccgggacaaca<br>gccactctgacaatccatggcaccctggctgaggatgaggctgattattactgtttgtcaacatatagtg<br>atgataatctccctgttttcggtggtggaaccaagctcactgtccta (SEQ ID NO: 129)                                                                                                                   |
| HC-22   | hIgG1   | caggtgcagctgaaggagtcaggacctggcctggtgcagccctcacagaccctgtctctcacctgcact<br>gtctctggattctcattaaccagctatcttgttcactgggttcgacagcctccaggaaaaactctggagt<br>gggtggattaatgtggaatgatggagacacatcatataattcagctctcaaatcccgactgagcatca<br>gcagggacacctccaagagccaagttttcttaaagatgcacagtcttcaagctgaggacacagccact<br>tactactgtgccagagagagcaactgggatttacttactggggccacggcactctggtcactgtctcctt<br>ca (SEQ ID NO: 130)                                                                                         |
| LC-22   | hKappa  | gacatccagatgacacagtctcctgcctcccctgtctgcttctctggaagaaattgtcaccatcacctgca<br>aggcaagccagggcattgatgatgacttatcatggtatcagcagaaaccagggaaatctcctcagctc<br>ctgatctatgatgtaaccagattggcagatggggtcccatcacggttcagcggcagtagatctggcaca<br>cagtattctcttaagatcagcagaccacaggtgctgattctgaatctattactgtctgcagagttaca<br>gtactccgtacacgtttggagctgggaccaagctggaactgaaa (SEQ ID NO: 131)                                                                                                                        |
| HC-23   | hIgG1   | gaagtccagctgcagcagtatggggctgagcttgggaaacctggggacctcagtcaggttgtcttgcaa<br>ggtttctggctataacattaggaatacctacattcactgggtgcatcagaggcctggagagggcctgga<br>atggataggaaggattgatcctacaaacggaaatactatatctgctgagaagttcaaaagcaaggcc                                                                                                                                                                                                                                                                   |

TABLE 2-continued

Heavy and light chain anitbody variable region nucleic acid sequences

|   |   |   |
|---|---|---|
|   |   | acactgactgcagatacatcgtccaatacagcctacatgcagttcagccaactgaaatctgacgacac<br>agcaatctattttgtgctatgaactacgaagggtatgcggattattggggccaaggagtcatggtcac<br>agtctcctcc (SEQ ID NO: 132) |
| LC-23 | hKappa | gacatccagatgacccagtctccttcattcctgtctgcatctgtgggagacagactcactatcaactgca<br>aagcaagtcagaatattaacaagtacttaaactggtatcagcaaaagcttggagaagctcccaaacg<br>cctgatatttaagacaaacagtttgcaaacgggcatcccatcaaggttcagtggcagtggatctggaac<br>agattacacactcaccatcagcagcctgcagcctgaagatgttgccacatatttctgctttcagtataac<br>attgggttcacgtttggagctgggaccaagctggagctgaaa (SEQ ID NO: 133) |
| HC-24 | hIgG1 | gaggtgcagctggtggagtctggtggaggcttagtgcagtctggaaggtccctaaaactctcctgtgca<br>gcctcaggattcactgtcagtgactattacatggcctgggtccgccaggctccaacgaaggggctgga<br>gtgggtcgcaaccattaattatgatggtagtaccacttaccatcgagactccgtgaagggccgattcac<br>tatctccagggataatgcaaaaagcacctatacctgcaaatggacagtctgcggtctgaggacacgg<br>ccacttattactgtgcaagacatgggactatgggtatcactacggggcctattattttgattactgggg<br>ccaaggagtcatggtcacagtctcctca (SEQ ID NO: 134) |
| LC-24 | hKappa | gacattgtcttgacccagtctcctgctttggctgtgtctctggggcagagggccactatctcctgtagggc<br>cagccagactgtcagtttatctggatataatcttatacactggtaccaacagagaacaggacagcaac<br>ccaaactcctcatctatcgtgcatccaatctagcacctgggatccctgccaggttcagtggcagtgggtc<br>tgggacagacttcaccctcaccatcagccctgtgcagtctgatgatattgcaacctattactgtcagcag<br>agtagggagtcgtgacgttcggtggaggcaccaacttggaaatgaag (SEQ ID NO: 135) |
| HC-25 | hIgG1 | cagatccagttggtacagtctggacctgagctgaagaagcctggagagtcagtgaagatctcctgcaa<br>ggcttctgggtataccttcacagactatgcaatacactgggtgaaacaggctccaggacagggcttga<br>ggtggatggcctggatcaacaccgaaactgggaagcctacatatgctgatgacttcaaaggacggttt<br>gtcttctctttggaggcctctgccagcactgcacatttgcagatcagcaacctcaaaaatgaggacacg<br>gctacattttctgtgcaggcgggtcccattggttgcttactggggccaaggcactctggtcactgtctc<br>ttca (SEQ ID NO: 136) |
| LC-25 | hLambda | agctatgagctgatccaaccaccttcagcatctgtcactctggaaaatactgtctcaatcacttgttctgg<br>agatgaattatcaaacaaatatgctcattggtatcaacaaaagccagacaagaccatttggaagtga<br>tctacaacgatagtgagcggccctcaggcatctctgaccgattctctgggtccagctcagggacaacag<br>ccattctcacaatccgtgatgcccaggctgaggatgaggctgattattactgtttgtcaacatttagtgat<br>gatgatctccctattttcggtggtggcaccaagctcactgtccta (SEQ ID NO: 137) |
| HC-26 | hIgG1 | cagatccagttggtacagtctggacctgagctgaagaagcctggagagtcagtgaagatctcctgcaa<br>ggcctctgggtataccttcacagactatgcagtgtactgggtgatacaggctccaggaaagggcttgaa<br>gtggatgggctggatcaacacctatactgggaagccaacatatgccgatgacttcaaaggacggttg<br>tcttctctttggaaacctctgccagcactgcaaatttgcagatcagcaacctcaaaaatgaggacacgg<br>ctacatatttctgtgcaagaggagcgggcatgactaaggactatgttatggatgcctgggtcgagggg<br>ttttagtcactgtctcctca (SEQ ID NO: 128) |
| LC-26 | hLambda | agctatgagctgatccaaccaccttcaacatcagtcactctgggaaatactgtctcactcacctgtgttg<br>gaaatgaattaccaaaaagatatgcttattggtttcaacaaaagccagaccagtccattgtgagactg<br>atatatgacgatgacaggcgggccctcaggcatctctgaccgattctctgggtccagctctgggacaaca<br>gccactctgacaatccgtgacgcccaggctgaggatgaggcttattattactgtcactcaacatatactg<br>atgataaagtccctattttcggtggtggaaccaagctcactgtccta (SEQ ID NO: 138) |
| HC-27 | hIgG1 | gaggtgcagctggtggagtctgggggaggcttagtgcagcctggaaggtccatgaaactctcctgtaa<br>ggcctcaggattcacttcagtaactatgacatggcctgggtccgccaggctccaacgagggtctgga<br>gtgggtcgcatccattagttatgatggtattaccgcttactatcgagactccgtgaagggccgattcact<br>atctccagagagaatgcaaaaagcacctatacctgcaattggtcagtctgagatctgaggacacggc<br>cacttattactgtacaacagagggggttatgtgtactccggaccacactactttgattactggggccaa<br>ggagtcatggtcacagtctcctca (SEQ ID NO: 139) |
| LC-27 | hKappa | gacattcagatgacccagtctccatcctccatgtctgtgtctctgggagacacagtcactattacttgccg<br>ggcaagtcaggacgttgggattttgtaaattggttccagcagaaaccagggagatctcctaggcgtat<br>gattatcgtgcaacgaacttggcagatggggtcccatcaaggttcagcggcagtaggtctggatcaga<br>ttattctctcaccatcagcagcctggagtctgaagatgtggcagactatcactgtctacagtatgatgag<br>tttcctcggacgttcggtggaggcaccaagctggaattgaaa (SEQ ID NO: 140) |
| HC-28 | hIgG1 | gaagtccagctgcagcagtatggggctgagcttgggaaacctggggacctcagtcaggttgtcttgcaa<br>ggtttctggctataagattaggaatacctacatacactgggtgaatcagaggcctggaaagggcctgg<br>aatggatagggaggattgatcctgcaaatgaaatactatatgctgagaagttcaaaagcaaggtt<br>acactgactgcagatacatcgtccaacacagcctacatgcaactcagccaactgaaatctgacgacac<br>agcactctattttgtgctatgaactacgaagggtatgaggattactggggccaaggagtcatggtcac<br>agtctcctca (SEQ ID NO: 141) |
| LC-28 | hKappa | gacatccagatgacccagtctccttcattcctgtctgcatctgtgggagacagcgtcactatcaactgca<br>aagcaagtcagaatattaataagtatttaaactggtatcagcaaaagcttggagaagctcccaaacgc<br>ctgatacataaaacaaacagtttgcaaccgggcttcccatcaaggttcagtggcagtggatctggtaca<br>gattacacactcaccatcagcagcctgcagcctgaagatgttgccgcatatttctgctttcagtataaca<br>gtgggttcacgtttggagctgggaccaagctggaactgaaa (SEQ ID NO: 142) |

As described below, an scFV phage display library screen of human antibodies was performed to identify novel anti-CD117 antibodies, and fragments thereof, having therapeutic use. Antibodies 85 (Ab85), 86 (Ab86), 87 (Ab87), 88 (Ab88), and 89 (Ab89), among others, were identified in this screen.

The heavy chain variable region (VH) amino acid sequence of Ab85 is provided below as SEQ ID NO: 143. The VH CDR amino acid sequences of Ab85 are underlined below and are as follows:

```
                                  (VH CDR1; SEQ ID NO: 145)
NYWIG;

(VH CDR2; SEQ ID NO: 146)
IINPRDSDTRYRPSFQG;
and (VH CDR3; SEQ ID NO: 147)
HGRGYEGYEGAFDI.

Ab85 VH sequence
                                            (SEQ ID NO: 143)
EVQLVQSGAEVKKPGESLKISCKGSGYSFTNYWIGWVRQMPGKGLEWMA

IINPRDSDTRYRPSFQGQVTISADKSISTAYLQWSSLKASDTAMYYCAR

HGRGYEGYEGAFDIWGQGTLVTVSS
```

The light chain variable region (VL) amino acid sequence of Ab85 is provided below as SEQ ID NO 144. The VL CDR amino acid sequences of Ab85 are underlined below and are as follows:

```
                                  (VL CDR1; SEQ ID NO: 148)
RSSQGIRSDLG;

(VL CDR2; SEQ ID NO: 149)
DASNLET;
and (VL CDR3; SEQ ID NO: 150)
QQANGFPLT.

Ab85 VL sequence
                                            (SEQ ID NO: 144)
DIQMTQSPSSLSASVGDRVTITCRSSQGIRSDLGWYQQKPGKAPKLLIY

DASNLETGVPSRFSGSGSGTDFTLTISSLQPEDFATYYCQQANGFPLTF

GGGTKVEIK
```

Antibody HC-86/LC-86 (Ab86)

The heavy chain variable region (VH) amino acid sequence of Ab86 is provided below as SEQ ID NO: 151. The VH CDR amino acid sequences Ab86 are underlined below and are as follows:

```
                                  (VH CDR1; SEQ ID NO: 145)
NYWIG;

(VH CDR2; SEQ ID NO: 153)
IIYPGDSDIRYSPSLQG;
and (VH CDR3; SEQ ID NO: 3)
HGRGYNGYEGAFDI.

Ab86 VH sequence
                                            (SEQ ID NO: 151)
EVQLVQSGAEVKKPGESLKISCKGSGYSFTNYWIGWVRQMPGKGLEWMG

IIYPGDSDIRYSPSLQGQVTISVDTSTSTAYLQWNSLKPSDTAMYYCAR

HGRGYNGYEGAFDIWGQGTLVTVSS
```

The light chain variable region (VL) amino acid sequence of Ab86 is provided below as SEQ ID NO 152. The VL CDR amino acid sequences of Ab86 are underlined below and are as follows:

```
                                  (VL CDR1; SEQ ID NO: 154)
RASQGIGDSLA;

(VL CDR2; SEQ ID NO: 149)
DASNLET;
and (VL CDR3; SEQ ID NO: 155)
QQLNGYPIT.

Ab86 VL sequence
                                            (SEQ ID NO: 152)
DIQMTQSPSSLSASVGDRVTITCRASQGIGDSLAWYQQKPGKAPKLLIY

DASNLETGVPSRFSGSGSGTDFTLTISSLQPEDFATYYCQQLNGYPITF

GQGTKVEIK
```

Antibody HC-87/LC-87 (Ab87)

The heavy chain variable region (VH) amino acid sequence of Ab87 is provided below as SEQ ID NO: 143. The VH CDR amino acid sequences of Ab87 are underlined below and are as follows:

```
                                  (VH CDR1; SEQ ID NO: 145)
NYWIG;

(VH CDR2; SEQ ID NO: 146)
IINPRDSDTRYRPSFQG;
and (VH CDR3; SEQ ID NO: 147)
HGRGYEGYEGAFDI.

Ab87 VH sequence
                                            (SEQ ID NO: 143)
EVQLVQSGAEVKKPGESLKISCKGSGYSFTNYWIGWVRQMPGKGLEWMA

IINPRDSDTRYRPSFQGQVTISADKSISTAYLQWSSLKASDTAMYYCAR

HGRGYEGYEGAFDIWGQGTLVTVSS
```

The light chain variable region (VL) amino acid sequence of Ab87 is provided below as SEQ ID NO 156. The VL CDR amino acid sequences of Ab87 are underlined below and are as follows:

```
                                  (VL CDR1; SEQ ID NO: 157)
RASQGIRNDLG;

(VL CDR2; SEQ ID NO: 5)
DASSLES;
and (VL CDR3; SEQ ID NO: 155)
QQLNGYPIT.

Ab87 VL sequence
                                            (SEQ ID NO: 156)
DIQMTQSPSSLSASVGDRVTITCRASQGIRNDLGWYQQKPGKAPKLLIY

DASSLESGVPSRFSGSGSGTDFTLTISSLQPEDFATYYCQQLNGYPITF

GQGTKVEIK
```

Antibody HC-88/LC-88 (Ab88)

The heavy chain variable region (VH) amino acid sequence of Ab88 is provided below as SEQ ID NO: 158. The VH CDR amino acid sequences of Ab88 are underlined below and are as follows:

NYWIG; (VH CDR1; SEQ ID NO: 145)

IIYPGDSLTRYSPSFQG; (VH CDR2; SEQ ID NO: 159)
and

HGRGYNGYEGAFDI. (VH CDR3; SEQ ID NO: 3)

Ab88 VH sequence
(SEQ ID NO: 158)
EVQLVQSGAEVKKPGESLKISCKGSGYSFT<u>NYWIG</u>WVRQMPGKGLEWMG <u>IIYPGDSLTRYSPSFQG</u>QVTISADKSISTAYLQWSSLKASDTAMYYCAR <u>HGRGYNGYEGAFDI</u>WGQGTLVTVSS The light chain variable region (VL) amino acid sequence of Ab88 is provided below as SEQ ID NO: 156. The VL CDR amino acid sequences of Ab88 are underlined below and are as follows:

RASQGIRNDLG; (VL CDR1; SEQ ID NO: 157)

DASSLES; (VL CDR2; SEQ ID NO: 5)
and

QQLNGYPIT. (VL CDR3; SEQ ID NO: 155)

Ab88 VL sequence
(SEQ ID NO: 156)
DIQMTQSPSSLSASVGDRVTITC<u>RASQGIRNDLG</u>WYQQKPGKAPKLLIY <u>DASSLES</u>GVPSRFSGSGSGTDFTLTISSLQPEDFATYYC<u>QQLNGYPIT</u>F

GQGTKVEIK

Antibody HC-89/LC-89 (Ab89)

The heavy chain variable region (VH) amino acid sequence of Ab89 is provided below as SEQ ID NO: 160. The VH CDR amino acid sequences of Ab89 are underlined below and are as follows:

NYWIG; (VH CDR1; SEQ ID NO: 145)

IIYPGDSDTRYSPSFQG; (VH CDR2; SEQ ID NO: 2)
and

HGRGYNGYEGAFDI. (VH CDR3; SEQ ID NO: 3)

Ab89 VH sequence
(SEQ ID NO: 160)
EVQLVQSGAEVKKPGESLKISCKGSGYSFT<u>NYWIG</u>WVRQMPGKGLEWMG <u>IIYPGDSDTRYSPSFQG</u>QVTISADKSISTAYLQWSSLKASDTAMYYCAR <u>HGRGYNGYEGAFDI</u>WGQGTLVTVSS The light chain variable region (VL) amino acid sequence of Ab89 is provided below as SEQ ID NO: 152. The VL CDR amino acid sequences of Ab89 are underlined below and are as follows:

RASQGIGDSLA; (VL CDR1; SEQ ID NO: 154)

DASNLET; (VL CDR2; SEQ ID NO: 149)
and

QQLNGYPIT. (VL CDR3; SEQ ID NO: 155)

Ab89 VL sequence
(SEQ ID NO: 152)
DIQMTQSPSSLSASVGDRVTITC<u>RASQGIGDSLA</u>WYQQKPGKAPKLLIY <u>DASNLET</u>GVPSRFSGSGSGTDFTLTISSLQPEDFATYYC<u>QQLNGYPIT</u>F

GQGTKVEIK

Antibody HC-249/LC-249 (Ab249)

The heavy chain variable region (VH) amino acid sequence of Ab249 is provided below as SEQ ID NO: 98. The VH CDR amino acid sequences of Ab249 are underlined below and are as follows: TSWIG (VH CDR1; SEQ ID NO: 186); IIYPGDSDTRYSPSFQG (VH CDR2; SEQ ID NO: 2); and HGLGYNGYEGAFDI (VH CDR3; SEQ ID NO: 187).

Ab249 VH sequence
(SEQ ID NO: 98)
EVQLVQSGAEVKKPGESLKISCKGSGYRFT<u>TSWIG</u>WVRQMPGKGLEWMG <u>IIYPGDSDTRYSPSFQG</u>QVTISADKSISTAYLQWSSLKASDTAMYYCAR <u>HGLGYNGYEGAFDI</u>WGQGTLVTVSS The light chain variable region (VL) amino acid sequence of Ab249 is provided below as SEQ ID NO: 102. The VL CDR amino acid sequences of Ab249 are underlined below and are as follows:

RASQGIGSALA; (VL CDR1; SEQ ID NO: 188)

DASNLET; (VL CDR2; SEQ ID NO: 149)
and

QQLNGYPLT. (VL CDR3; SEQ ID NO: 189)

Ab249 VL sequence
(SEQ ID NO: 102)
DIQMTQSPSSLSASVGDRVTITC<u>RASQGIGSALA</u>WYQQKPGKAPKLLIY <u>DASNLET</u>GVPSRFSGSGSGTDFTLTISSLQPEDFATYYC<u>QQLNGYPLT</u>F

GQGTRLEIK

Human antibodies Ab85 and Ab249 were both derived from antibody CK6, which is an antagonist anti-CD117 antibody. A comparison of the amino acid sequences of the variable regions of Ab85 and Ab249 versus CK6 is shown in FIGS. 11A to 11D (where the CDRs are also designated). Both antibodies have improved properties, e.g., improved binding characteristics, over CK6.

CK6 includes a potential deamidation site in the CDR3 domain of the heavy chain variable region. While advantageous to remove for future production of the antibody, the position of the asparagine presents a significant challenge. The potential deamidation site was successfully removed, however, in the Ab85 heavy chain CDR3 such that the antibody (having Ab85 heavy and light chain CDRs) was able to maintain a high affinity level specificity for human CD117 and the ability to internalize. Further, Ab85 has an improved off rate relative to its parent.

Thus, in certain embodiments, an anti-CD117 antibody comprises a heavy chain comprising a CDR set (CDR1, CDR2, and CDR3) as set forth in SEQ ID Nos: 145, 146, and 147, and a light chain comprising a CDR set as set forth in SEQ ID Nos: 148, 149, and 150, internalizes in cells expressing CD117, and has a $k_{off}$ rate of $5 \times 10^{-4}$ $s^{-1}$ or less as measured by BLI.

As described in Jain et al. (2017) PNAS 114 (5) 944-949, while the activity of an antibody is key for developing it as a therapeutic, what is often overlooked is the "developability" of an antibody for manufacturing. Identifying an antibody that can achieve both therapeutic and superior biophysical characteristics is challenging. Indeed, biophysical properties of an antibody are essential for antibodies being used for therapeutic purposes. Biophysical testing of Ab 85 indicated that it is a particularly stable antibody. For example, a population of Ab85 antibodies maintains a low level of acid variants even at higher temperatures over time (see FIGS. 13A and 13B). This was true even in relation to other CK6-derived antibodies. Thus, in certain embodiments, included in the invention is a composition comprising less than 20% acidic variants as determined by capillary electrophoresis following storage at 25 degrees Celsius for seven days, wherein the antibody is an IgG antibody that specifically binds to CD117 and comprises a heavy chain comprising a CDR set (CDR1, CDR2, and CDR3) as set forth in SEQ ID Nos: 145, 146, and 147, and a light chain comprising a CDR set as set forth in SEQ ID Nos: 148, 149, and 150.

The anti-CD117 antibodies or binding fragments described herein may also include modifications and/or mutations that alter the properties of the antibodies and/or fragments, such as those that increase half-life, increase or decrease ADCC, etc., as is known in the art.

In one embodiment, the anti-CD117 antibody, or binding fragment thereof, comprises a variant Fc region, wherein said variant Fc region comprises at least one amino acid modification relative to a wild-type Fc region, such that said molecule has an altered affinity for an FcgammaR. Certain amino acid positions within the Fc region are known through crystallography studies to make a direct contact with FcγR. Specifically amino acids 234-239 (hinge region), amino acids 265-269 (B/C loop), amino acids 297-299 (C'/E loop), and amino acids 327-332 (F/G) loop. (see Sondermann et al., 2000 Nature, 406: 267-273). For example, amino acid substitutions at amino acid positions 234 and 235 of the Fc region have been identified as decreasing affinity of an IgG antibody for binding to an Fc receptor, particularly an Fc gamma receptor (FcγR). In one embodiment, an anti-CD117 antibody described herein comprises an Fc region comprising an amino acid substitution at L234 and/or L235, e.g., L234A and L235A (EU index). Thus, the anti-CD117 antibodies described herein may comprise variant Fc regions comprising modification of at least one residue that makes a direct contact with an FcγR based on structural and crystallographic analysis. In one embodiment, the Fc region of the anti-CD117 antibody (or Fc containing fragment thereof) comprises an amino acid substitution at amino acid 265 according to the EU index as in Kabat et al., Sequences of Proteins of Immunological Interest, 5th Ed. Public Health Service, NH1, MD (1991), expressly incorporated herein by references. The "EU index as in Kabat" or "EU index" refers to the numbering of the human IgG1 EU antibody and is used herein in reference to Fc amino acid positions unless otherwise indicated.

In one embodiment, the Fc region comprises a D265A mutation. In one embodiment, the Fc region comprises a D265C mutation.

In some embodiments, the Fc region of the anti-CD117 antibody (or fragment thereof) comprises an amino acid substitution at amino acid 234 according to the EU index as in Kabat. In one embodiment, the Fc region comprises a L234A mutation. In some embodiments, the Fc region of the anti-CD117 antibody (or fragment thereof) comprises an amino acid substitution at amino acid 235 according to the EU index as in Kabat. In one embodiment, the Fc region comprises a L235A mutation. In yet another embodiment, the Fc region comprises a L234A and L235A mutation. In a further embodiment, the Fc region comprises a D265C, L234A, and L235A mutation.

In certain aspects a variant IgG Fc domain comprises one or more amino acid substitutions resulting in decreased or ablated binding affinity for an FcgammaR and/or C1q as compared to the wild type Fc domain not comprising the one or more amino acid substitutions. Fc binding interactions are essential for a variety of effector functions and downstream signaling events including, but not limited to, antibody dependent cell-mediated cytotoxicity (ADCC) and complement dependent cytotoxicity (CDC). Accordingly, in certain aspects, an antibody comprising a modified Fc region (e.g., comprising a L234A, L235A, and a D265C mutation) has substantially reduced or abolished effector functions.

Affinity to an Fc region can be determined using a variety of techniques known in the art, for example but not limited to, equilibrium methods (e.g., enzyme-linked immunoabsorbent assay (ELISA); KinExA, Rathanaswami et al. Analytical Biochemistry, Vol. 373:52-60, 2008; or radioimmunoassay (RIA)), or by a surface plasmon resonance assay or other mechanism of kinetics-based assay (e.g., BIACORE™ analysis or Octet™ analysis (forteBIO)), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmunoassay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound in the presence of increasing amounts of an unlabeled second antibody.

In one embodiment, an anti-CD117 antibody described herein comprises an Fc region comprising L235A, L235A, and D265C (EU index). The antibodies of the invention may be further engineered to further modulate antibody half-life by introducing additional Fc mutations, such as those described for example in (Dall'Acqua et al. (2006) J Biol Chem 281: 23514-24), (Zalevsky et al. (2010) Nat Biotechnol 28: 157-9), (Hinton et al. (2004) J Biol Chem 279: 6213-6), (Hinton et al. (2006) J Immunol 176: 346-56), (Shields et al. (2001) J Biol Chem 276: 6591-604), (Petkova et al. (2006) Int Immunol 18: 1759-69), (Datta-Mannan et al. (2007) Drug Metab Dispos 35: 86-94), (Vaccaro et al. (2005) Nat Biotechnol 23: 1283-8), (Yeung et al. (2010) Cancer Res 70: 3269-77) and (Kim et al. (1999) Eur J Immunol 29: 2819-25), and include positions 250, 252, 253, 254, 256, 257, 307, 376, 380, 428, 434 and 435. Exemplary mutations that may be made singularly or in combination are T250Q, M252Y, 1253A, S254T, T256E, P2571, T307A, D376V, E380A, M428L, H433K, N434S, N434A, N434H, N434F, H435A and H435R mutations.

Thus, in one embodiment, the Fc region comprises a mutation resulting in a decrease in half life. An antibody having a short half life may be advantageous in certain instances where the antibody is expected to function as a short-lived therapeutic, e.g., the conditioning step described herein where the antibody is administered followed by HSCs. Ideally, the antibody would be substantially cleared prior to delivery of the HSCs, which also generally express CD117 but are not the target of the anti-CD117 antibody, unlike the endogenous stem cells. In one embodiment, the Fc region comprises a mutation at position 435 (EU index according to Kabat). In one embodiment, the mutation is an H435A mutation.

In one embodiment, the anti-CD117 antibody described herein has a half life of equal to or less than 24 hours, equal to or less than 22 hours, equal to or less than 20 hours, equal to or less than 18 hours, equal to or less than 16 hours, equal to or less than 14 hours, equal to or less than 13 hours, equal to or less than 12 hours, or equal to or less than 11 hours. In one embodiment, the half life of the antibody is 11 hours to 24 hours; 12 hours to 22 hours; 10 hours to 20 hours; 8 hours to 18 hours; or 14 hours to 24 hours Anti-CD117 antibodies that can be used in conjunction with the patient conditioning methods described herein include, for instance, antibodies produced and released from ATCC Accession No. 10716 (deposited as BA7.3C.9), such as the SR-1 antibody, which is described, for example, in U.S. Pat. No. 5,489,516, the disclosure of which is incorporated herein by reference as it pertains to anti-CD117 antibodies.

In one embodiment, an anti-CD117 antibody described herein comprises an Fc region comprising L235A, L235A, D265C, and H435A (EU index).

Additional anti-CD117 antibodies that can be used in conjunction with the patient conditioning methods described herein include those described in U.S. Pat. No. 7,915,391, which describes, e.g., humanized SR-1 antibodies; U.S. Pat. No. 5,808,002, which describes, e.g., the anti-CD117 A3C6E2 antibody, as well as those described in, for example, WO 2015/050959, which describes anti-CD117 antibodies that bind epitopes containing Pro317, Asn320, Glu329, Va1331, Asp332, Lus358, Glue360, Glue376, His378, and/or Thr380 of human CD117; and US 2012/0288506 (also published as U.S. Pat. No. 8,552,157), which describes, e.g., the anti-CD117 antibody CK6, having the CDR sequences of:

a CDR-H1 having the amino acid sequence SYWIG (SEQ ID NO: 1);
a CDR-H2 having the amino acid sequence IIYPGDSDTRYSPSFQG (SEQ ID NO: 2);
a CDR-H3 having the amino acid sequence HGRGYN-GYEGAFDI (SEQ ID NO: 3);
a CDR-L1 having the amino acid sequence RASQGISSALA (SEQ ID NO: 4);
a CDR-L2 having the amino acid sequence DASSLES (SEQ ID NO: 5); and
a CDR-L3 having the amino acid sequence CQQFNSYPLT (SEQ ID NO: 6)

The heavy chain variable region amino acid sequence of CK6 is provided in SEQ ID NO: 161):

```
QVQLVQSGAAVKKPGESLKISCKGSGYRFTSYWIGWVRQMPGKGLEWMG

IIYPGDSDTRYSPSFQGQVTI SAGKSISTAYLQWSSLKASDTAMYYCA

RHGRGYNGYEGAFDIWGQGTMVTVSS
(SEQ ID NO: 161; CDRs are underlined are in bold).
```

The light chain amino acid variable sequence of CK6 is provided in SEQ ID NO: 162:

```
AIQLTQSPSSLSASVGDRVTITCRASQGISSALAWYQQKPGKAPKLLIY

DASSLESGVPSRFSGSGSGTD FTLTISSLQPEDFATYYCQQFNSYPLT

FGGGTKVEIK
(SEQ ID NO: 162; CDRs are underlinedand in bold).
```

Additional anti-CD117 antibodies and antigen-binding fragments thereof that may be used in conjunction with the compositions and methods described herein include those described in US 2015/0320880, such as the clones 9P3, NEG024, NEG027, NEG085, NEG086, and 20376.

The disclosures of each of the foregoing publications are incorporated herein by reference as they pertain to anti-CD117 antibodies. Antibodies and antigen-binding fragments that may be used in conjunction with the compositions and methods described herein include the above-described antibodies and antigen-binding fragments thereof, as well as humanized variants of those non-human antibodies and antigen-binding fragments described above and antibodies or antigen-binding fragments that bind the same epitope as those described above, as assessed, for instance, by way of a competitive CD117 binding assay.

Exemplary antigen-binding fragments of the foregoing antibodies include a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv, among others.

Antibodies may be produced using recombinant methods and compositions, e.g., as described in U.S. Pat. No. 4,816,567. In one embodiment, isolated nucleic acid encoding an anti-CD117 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CLL-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD117 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli.*) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In one embodiment, the anti-CD117 antibody, or antigen binding fragment thereof, comprises variable regions having an amino acid sequence that is at least 95%, 96%, 97% or 99% identical to the SEQ ID Nos disclosed herein. Alternatively, the anti-CD117 antibody, or antigen binding fragment thereof, comprises CDRs comprising the SEQ ID Nos disclosed herein with framework regions of the variable regions described herein having an amino acid sequence that is at least 95%, 96%, 97% or 99% identical to the SEQ ID Nos disclosed herein.

In one embodiment, the anti-CD117 antibody, or antigen binding fragment thereof, comprises a heavy chain variable region and a heavy chain constant region having an amino acid sequence that is disclosed herein. In another embodiment, the anti-CD117 antibody, or antigen binding fragment thereof, comprises a light chain variable region and a light chain constant region having an amino acid sequence that is disclosed herein. In yet another embodiment, the anti-CD117 antibody, or antigen binding fragment thereof, comprises a heavy chain variable region, a light chain variable region, a heavy chain constant region and a light chain constant region having an amino acid sequence that is disclosed herein.

Methods of Identifying Anti-CD117 Antibodies

Methods for high throughput screening of antibody, or antibody fragment, libraries for molecules capable of binding CD117 (e.g., GNNK+ CD117) can be used to identify and affinity mature antibodies useful for treating cancers, autoimmune diseases, and conditioning a patient (e.g., a human patient) in need of hematopoietic stem cell therapy as described herein. Such methods include in vitro display techniques known in the art, such as phage display, bacterial display, yeast display, mammalian cell display, ribosome display, mRNA display, and cDNA display, among others. The use of phage display to isolate ligands that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules). In addition, functional antibody fragments, such as Fab and scFv fragments, have been expressed in in vitro display formats (see, for example, McCafferty et al., Nature 348: 552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules). These techniques, among others, can be used to identify and improve the affinity of antibodies that bind CD117 (e.g., GNNK+ CD117) that can in turn be used to deplete endogenous hematopoietic stem cells in a patient (e.g., a human patient) in need of hematopoietic stem cell transplant therapy.

In addition to in vitro display techniques, computational modeling techniques can be used to design and identify antibodies, or antibody fragments, in silico that bind CD117 (e.g., GNNK+ CD117). For example, using computational modeling techniques, one of skill in the art can screen libraries of antibodies, or antibody fragments, in silico for molecules capable of binding specific epitopes, such as extracellular epitopes of this antigen. The antibodies, or antigen-binding fragments thereof, identified by these computational techniques can be used in conjunction with the therapeutic methods described herein, such as the cancer and autoimmune disease treatment methods described herein and the patient conditioning procedures described herein.

Additional techniques can be used to identify antibodies, or antigen-binding fragments thereof, that bind CD117 (e.g., GNNK+ CD117) on the surface of a cell (e.g., a cancer cell, autoimmune cell, or hematopoietic stem cell) and that are internalized by the cell, for instance, by receptor-mediated endocytosis. For example, the in vitro display techniques described above can be adapted to screen for antibodies, or antigen-binding fragments thereof, that bind CD117 (e.g., GNNK+ CD117) on the surface of a cancer cell, autoimmune cell, or hematopoietic stem cell and that are subsequently internalized. Phage display represents one such technique that can be used in conjunction with this screening paradigm. To identify antibodies, or fragments thereof, that bind CD117 (e.g., GNNK+CD117) and are subsequently internalized by cancer cells, autoimmune cells, or hematopoietic stem cells, one of skill in the art can adapt the phage display techniques described, for example, in Williams et al., Leukemia 19:1432-1438, 2005, the disclosure of which is incorporated herein by reference in its entirety. For example, using mutagenesis methods known in the art, recombinant phage libraries can be produced that encode antibodies, antibody fragments, such as scFv fragments, Fab fragments, diabodies, triabodies, and $^{10}$Fn3 domains, among others, that contain randomized amino acid cassettes (e.g., in one or more, or all, of the CDRs or equivalent regions thereof or an antibody or antibody fragment). The framework regions, hinge, Fc domain, and other regions of the antibodies or antibody fragments may be designed such that they are non-immunogenic in humans, for instance, by virtue of having human germline antibody sequences or sequences that exhibit only minor variations relative to human germline antibodies.

Using phage display techniques described herein or known in the art, phage libraries containing randomized antibodies, or antibody fragments, covalently bound to the phage particles can be incubated with CD117 (e.g., GNNK+ CD117) antigen, for instance, by first incubating the phage library with blocking agents (such as, for instance, milk protein, bovine serum albumin, and/or IgG so as to remove phage encoding antibodies, or fragments thereof, that exhibit non-specific protein binding and phage that encode antibodies or fragments thereof that bind Fc domains, and then incubating the phage library with a population of hematopoietic stem cells. The phage library can be incubated with the target cells, such as cancer cells, autoimmune cells, or hematopoietic stem cells for a time sufficient to allow CD117-specific antibodies, or antigen-binding fragments thereof, (e.g., GNNK+ CD117-specific antibodies, or antigen-binding fragments thereof) to bind cell-surface CD117 (e.g., sell-surface GNNK+ CD117) antigen and to subsequently be internalized by the cancer cells, autoimmune cells, or hematopoietic stem cells (e.g., from 30 minutes to 6 hours at 4° C., such as 1 hour at 4° C.). Phage containing antibodies, or fragments thereof, that do not exhibit sufficient affinity for one or more of these antigens so as to permit binding to, and internalization by, cancer cells, autoimmune cells, or hematopoietic stem cells can subsequently be removed by washing the cells, for instance, with cold (4° C.) 0.1 M glycine buffer at pH 2.8. Phage bound to antibodies, or fragments thereof, or that have been internalized by the cancer cells, autoimmune cells, or hematopoietic stem cells can be identified, for instance, by lysing the cells and recovering internalized phage from the cell culture medium. The phage can then be amplified in bacterial cells, for example, by incubating bacterial cells with recovered phage in 2×YT medium using methods known in the art. Phage recovered from this medium can then be characterized, for instance, by determining the nucleic acid sequence of the gene(s) encoding the antibodies, or fragments thereof, inserted within the phage genome. The encoded antibodies, or fragments thereof, can subsequently be prepared de novo by chemical synthesis (for instance, of antibody fragments, such as scFv fragments) or by recombinant expression (for instance, of full-length antibodies).

The internalizing capacity of the prepared antibodies, or fragments thereof, can be assessed, for instance, using radionuclide internalization assays known in the art. For example, antibodies, or fragments thereof, identified using in vitro display techniques described herein or known in the art can be functionalized by incorporation of a radioactive isotope, such as $^{18}$F, $^{75}$Br, $^{77}$Br, $^{122}$I, $^{123}$I, $^{124}$I, $^{125}$I, $^{129}$I, $^{131}$I, $^{211}$At, $^{67}$Ga, $^{111}$In, $^{99}$Tc, $^{169}$Yb, $^{186}$Re, $^{64}$Cu, $^{67}$Cu, $^{177}$Lu, $^{77}$As, $^{72}$As, $^{86}$Y, $^{90}$Y, $^{89}$Zr, $^{212}$Bi, $^{213}$Bi, or $^{225}$Ac. For instance, radioactive halogens, such as $^{18}$F, $^{75}$Br, $^{77}$Br, $^{122}$I, $^{123}$I, $^{124}$I, $^{125}$I, $^{129}$I, $^{131}$I, $^{211}$At, can be incorporated into antibodies, or fragments thereof, using beads, such as polystyrene beads, containing electrophilic halogen reagents (e.g., Iodination Beads, Thermo Fisher Scientific, Inc., Cambridge, Mass.). Radiolabeled antibodies, or fragments thereof, can be incubated with cancer cells, autoimmune cells, or hematopoietic stem cells for a time sufficient to permit internalization (e.g., from 30 minutes to 6 hours at 4° C., such as 1 hour at 4° C.). The cells can then be washed to remove non-internalized antibodies, or fragments thereof, (e.g., using cold (4° C.) 0.1 M glycine buffer at pH 2.8). Internalized antibodies, or fragments thereof, can be identified by detecting the emitted radiation (e.g., γ-radiation) of the resulting cancer cells, autoimmune cells, or hematopoietic stem cells in comparison with the emitted radiation (e.g., γ-radiation) of the recovered wash buffer.

Antibody Drug Conjugates (ADCs)
Cytotoxins

Anti-CD117 antibodies, and antigen-binding fragments thereof, described herein can be conjugated (linked) to a cytotoxin. In some embodiments, the cytotoxic molecule is conjugated to a cell internalizing antibody, or antigen-binding fragment thereof as disclosed herein such that following the cellular uptake of the antibody, or fragment thereof, the cytotoxin may access its intracellular target and mediate hematopoietic cell death. Any number of cytotoxins can be conjugated to the anti-CD117 antibody, e.g., 1, 2, 3, 4, 5, 6, 7, or 8.

Cytotoxins suitable for use with the compositions and methods described herein include DNA-intercalating agents, (e.g., anthracyclines), agents capable of disrupting the mitotic spindle apparatus (e.g., vinca alkaloids, maytansine, maytansinoids, and derivatives thereof), RNA polymerase inhibitors (e.g., an amatoxin, such as α-amanitin, and derivatives thereof), and agents capable of disrupting protein biosynthesis (e.g., agents that exhibit rRNA N-glycosidase activity, such as saporin and ricin A-chain), among others known in the art.

In some embodiments, the cytotoxin is a microtubule-binding agent (for instance, maytansine or a maytansinoid), an amatoxin, pseudomonas exotoxin A, deBouganin, diphtheria toxin, saporin, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, or a variant thereof, or another cytotoxic compound described herein or known in the art.

Additional cytotoxins suitable for use with the compositions and methods described herein include, without limitation, 5-ethynyluracil, abiraterone, acylfulvene, adecypenol, adozelesin, aldesleukin, altretamine, ambamustine, amidox, amifostine, aminolevulinic acid, amrubicin, amsacrine, anagrelide, anastrozole, andrographolide, angiogenesis inhibitors, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitors, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), capecitabine, carboxamide-amino-triazole, carboxyamidotriazole, carzelesin, casein kinase inhibitors, castanospermine, cecropin B, cetrorelix, chlorins, chloroquinoxaline sulfonamide, cicaprost, cis-porphyrin, cladribine, clomifene and analogues thereof, clotrimazole, collismycin A, collismycin B, combretastatin A4, combretastatin analogues, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, epithilones, epristeride, estramustine and analogues thereof, etoposide, etoposide 4'-phosphate (also referred to as etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, homoharringtonine (HHT), hypericin, ibandronic acid, idoxifene, idramantone, ilmofosine, ilomastat, imidazoacridones, imiquimod, immunostimulant peptides, iobenguane, iododoxorubicin, ipomeanol, irinotecan, iroplact, irsogladine, isobengazole, jasplakinolide, kahalalide F, lamellarin-N triacetate, lanreotide, leinamycin, lenograstim, lentinan sulfate, leptolstatin, letrozole, lipophilic platinum compounds, lissoclinamide 7, lobaplatin, lometrexol, lonidamine, losoxantrone, loxoribine, lurtotecan, lutetium texaphyrin, lysofylline, masoprocol, maspin, matrix metalloproteinase inhibitors, menogaril, merbarone, meterelin, methioninase, metoclopramide, MIF inhibitor, ifepristone, miltefosine, mirimostim, mithracin, mitoguazone, mitolactol, mitomycin and analogues thereof, mitonafide, mitoxantrone, mofarotene, molgramostim, mycaperoxide B, myriaporone, N-acetyldinaline, N-substituted benzamides, nafarelin, nagrestip, napavin, naphterpin, nartograstim, nedaplatin, nemorubicin, neridronic acid, nilutamide, nisamycin, nitrullyn, octreotide, okicenone, onapristone, ondansetron, oracin, ormaplatin, oxaliplatin, oxaunomycin, paclitaxel and analogues thereof, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, phenazinomycin, picibanil, pirarubicin, piritrexim, podophyllotoxin, porfiromycin, purine nucleoside phosphorylase inhibitors, raltitrexed, rhizoxin, rogletimide, rohitukine, rubiginone B1, ruboxyl, safingol, saintopin, sarcophytol A, sargramostim, sobuzoxane, sonermin, sparfosic acid, spicamycin D, spiromustine, stipiamide, sulfinosine, tallimustine, tegafur, temozolomide, teniposide, thaliblastine, thiocoraline, tirapazamine, topotecan, topsentin, triciribine, trimetrexate, veramine, vinorelbine, vinxaltine, vorozole, zeniplatin, and zilascorb, among others.

Anti-CD117 antibodies, and antigen-binding fragments thereof, described herein can be conjugated to a cytotoxin that is a microtubule binding agent. As used herein, the term "microtubule-binding agent" refers to a compound which acts by disrupting the microtubular network that is essential for mitotic and interphase cellular function in a cell. Examples of microtubule-binding agents include, but are not limited to, maytasine, maytansinoids, and derivatives thereof, such as those described herein or known in the art, vinca alkaloids, such as vinblastine, vinblastine sulfate, vincristine, vincristine sulfate, vindesine, and vinorelbine, taxanes, such as docetaxel and paclitaxel, macrolides, such as discodermolides, cochicine, and epothilones, and derivatives thereof, such as epothilone B or a derivative thereof.

Maytansinoids

In some embodiments, the microtubule binding agent is a maytansine, a maytansinoid or a maytansinoid analog. Maytansinoids are mitototic inhibitors which bind microtubules and act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Examples of suitable maytansinoids include esters of maytansinol, synthetic maytansinol, and maytansinol analogs and derivatives. Included herein are any cytotoxins that inhibit microtubule formation and that are highly toxic to mammalian cells, as are maytansinoids, maytansinol, and maytansinol analogs, and derivatives.

Examples of suitable maytansinol esters include those having a modified aromatic ring and those having modifications at other positions. Such suitable maytansinoids are disclosed in U.S. Pat. Nos. 4,137,230; 4,151,042; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,362,663; 4,364,866; 4,424,219; 4,450,254; 4,322,348; 4,362,663; 4,371,533; 5,208,020; 5,416,064; 5,475,092; 5,585,499; 5,846,545; 6,333,410; 7,276,497; and 7,473,796, the disclosures of each of which are incorporated herein by reference as they pertain to maytansinoids and derivatives thereof.

In some embodiments, the immunoconjugates of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the structural formula (VII):

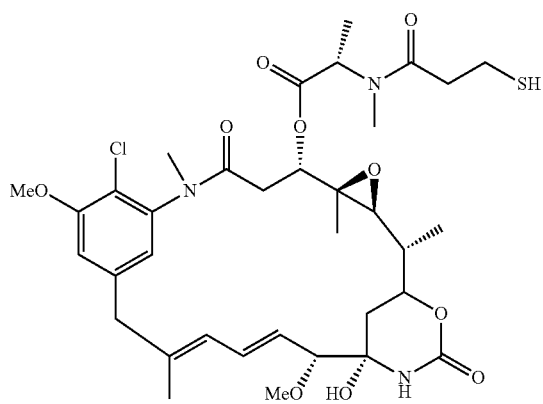

(VII)

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the structural formula (V):

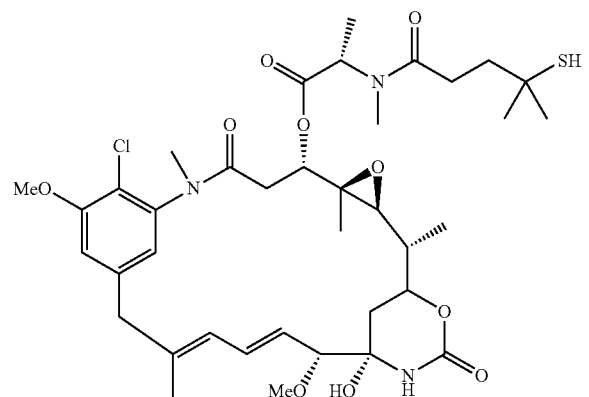

(V)

Another maytansinoid comprising a side chain that contains a sterically hindered thiol bond is $N^{2'}$-deacetyl-$N^{2'}$(4-mercapto-1-oxopentyl)-maytansine (termed DM3), represented by the structural formula (VI):

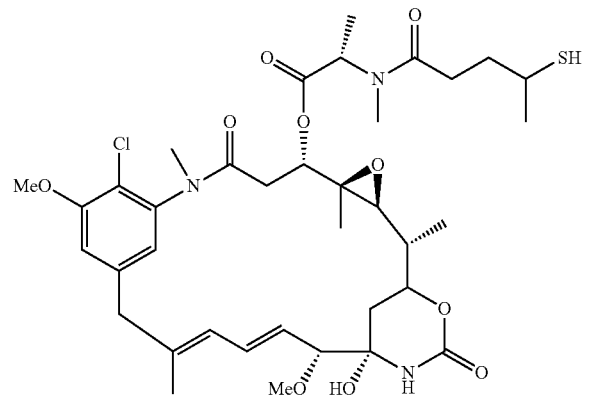

(VI)

Each of the maytansinoids taught in U.S. Pat. Nos. 5,208,020 and 7,276,497, can also be used in the conjugate of the present invention. In this regard, the entire disclosure of U.S. Pat. Nos. 5,208,020 and 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to chemically link the linking moiety, and in some particular embodiments, the C-3 position of maytansinol serves as the position to chemically link the linking moiety. There are many linking groups known in the art for making antibody-maytansinoid conjugates, including, for example, those disclosed in U.S. Pat. Nos. 5,208,020, 6,441,163, and EP Patent No. 0425235 B1; Chari et al., Cancer Research 52:127-131 (1992); and U.S. 2005/0169933 A1, the disclosures of which are hereby expressly incorporated by reference. Additional linking groups are described and exemplified herein. The present disclosure also includes various isomers and mixtures of maytansinoids and conjugates. Certain compounds and conjugates of the present invention may exist in various stereoisomeric, enantiomeric, and diastereomeric forms. Several descriptions for producing such antibody-maytansinoid conjugates are provided in U.S. Pat. Nos. 5,208,020, 5,416,064 6,333,410, 6,441,163, 6,716,821, and 7,368,565, each of which is incorporated herein in its entirety.

A therapeutically effective number of maytansinoid molecules bound per antibody molecule can be determined by measuring spectrophotometrically the ratio of the absorbance at 252 nm and 280 nm. An average of 3 to 4 maytansinoid molecules conjugated per antibody molecule can enhancing cytotoxicity of target cells without negatively affecting the function or solubility of the antibody, although one molecule of toxin/antibody can enhance cytotoxicity over antibody alone. The average number of maytansinoid molecules/antibody or antigen binding fragment thereof can be, for example, 1-10 or 2-5.

Anthracyclines

In other embodiments, the antibodies and antigen-binding fragments thereof described herein can be conjugated to a cytotoxin that is an anthracycline molecule. Anthracyclines are antibiotic compounds that exhibit cytotoxic activity. Studies have indicated that anthracyclines may operate to kill cells by a number of different mechanisms including: 1) intercalation of the drug molecules into the DNA of the cell thereby inhibiting DNA-dependent nucleic acid synthesis; 2) production by the drug of free radicals which then react with cellular macromolecules to cause damage to the cells or 3) interactions of the drug molecules with the cell membrane [see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102]. Because of their cytotoxic potential anthracyclines have been used in the treatment of numerous cancers such as leukemia, breast carcinoma, lung carcinoma, ovarian adenocarcinoma and sarcomas [see e.g., P. H-Wiernik, in *Anthracycline: Current Status And New Developments* p 11]. Commonly used anthracyclines include doxorubicin, epirubicin, idarubicin and daunomycin.

The anthracycline analog, doxorubicin (ADRIAMYCINO) is thought to interact with DNA by intercalation and inhibition of the progression of the enzyme topoisomerase II, which unwinds DNA for transcription. Doxorubicin stabilizes the topoisomerase II complex after it has broken the DNA chain for replication, preventing the DNA double helix from being resealed and thereby stopping the process of replication. Doxorubicin and daunorubicin (DAUNOMYCIN) are prototype cytotoxic natural product anthracycline chemotherapeutics (Sessa et al., (2007) Cardiovasc. Toxicol. 7:75-79).

Pyrrolobenzodiazepines (PBDs)

In other embodiments, the anti-CD117 antibodies or antigen-binding fragments thereof described herein can be conjugated to a cytotoxin that is a pyrrolobenzodiazepine (PBD) or a cytotoxin that comprises a PBD. PBDs are natural products produced by certain actinomycetes and have been shown to be sequence selective DNA alkylating compounds. PBD cytotoxins include, but are not limited to, anthramycin, dimeric PBDs, and those disclosed in, for example, Hartley, J. A. (2011). "The development of pyrrolobenzodiazepines as antitumour agents." Expert Opin. Inv. Drug, 20(6), 733-744; and Antonow, D.; Thurston, D. E. (2011) "Synthesis of DNA-interactive pyrrolo[2,1-c][1,4]benzodiazepines (PBDs)." Chem. Rev. 111: 2815-2864.

Calicheamicin

In other embodiments, the antibodies and antigen-binding fragments thereof described herein can be conjugated to a cytotoxin that is a calicheamicin molecule. The calicheamicin family of antibiotics are capable of producing double-stranded DNA breaks at sub-picomolar concentrations. For the preparation of conjugates of the calicheamicin family, see U.S. Pat. Nos. 5,712,374; 5,714,586; 5,739,116; 5,767,285; 5,770,701; 5,770,710; 5,773,001; and 5,877,296 (all to American Cyanamid Company). Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents to American Cyanamid.

Auristatins

Anti-CD117 antibodies, and antigen-binding fragments thereof, described herein can be conjugated to a cytotoxin that is an auristatin (U.S. Pat. Nos. 5,635,483; 5,780,588). Auristatins are anti-mitotic agents that interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). (U.S. Pat. Nos. 5,635,483; 5,780,588). The auristatin drug moiety may be attached to the antibody through the N-(amino) terminus or the C-(carboxyl) terminus of the peptidic drug moiety (WO 02/088172).

Exemplary auristatin embodiments include the N-terminus linked monomethylauristatin drug moieties DE and DF, disclosed in Senter et al, Proceedings of the American Association for Cancer Research, Volume 45, Abstract Number 623, presented Mar. 28, 2004, the disclosure of which is expressly incorporated by reference in its entirety.

An exemplary auristatin embodiment is MMAE, wherein the wavy line indicates the point of covalent attachment to the linker of an antibody-linker conjugate (-L-Z-Ab, as described herein).

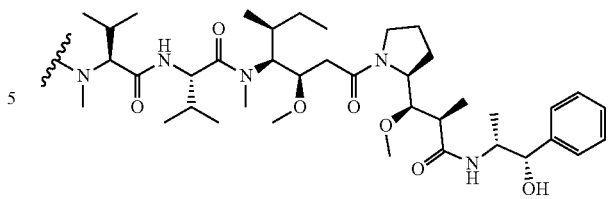

Another exemplary auristatin embodiment is MMAF, wherein the wavy line indicates the point of covalent attachment to the linker of an antibody-linker conjugate (-L-Z-Ab, as described herein), as disclosed in US 2005/0238649:

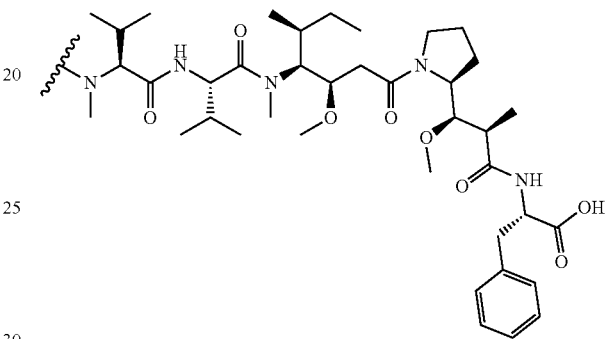

Auristatins may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 15:859-863; and Doronina (2003) Nat. Biotechnol. 21(7):778-784.

Amatoxins

In some embodiments, the cytotoxin of the antibody-drug conjugate is an RNA polymerase inhibitor. In some embodiments, the RNA polymerase inhibitor is an amatoxin or derivative thereof.

In some embodiments, the cytotoxin is an amatoxin or derivative thereof, such as α-amanitin, β-amanitin, γ-amanitin, ε-amanitin, amanin, amaninamide, amanullin, amanullinic acid, and proamanullin. Structures of the various naturally occurring amatoxins are represented by formula III, and are disclosed in, e.g., Zanotti et al., Int. J. Peptide Protein Res. 30, 1987, 450-459.

In one embodiment, the cytotoxin is an amanitin. For instance, the antibodies, or antigen-binding fragments, described herein may be bound to an amatoxin so as to form a conjugate represented by the formula Ab-Z-L-Am, wherein Ab is the antibody, or antigen-binding fragment thereof, L is a linker, Z is a chemical moiety and Am is an amatoxin. Many positions on amatoxins or derivatives thereof can serve as the position to covalently bond the linking moiety L, and, hence the antibodies or antigen-binding fragments thereof. In some embodiments, Am-L-Z is represented by formula (I)

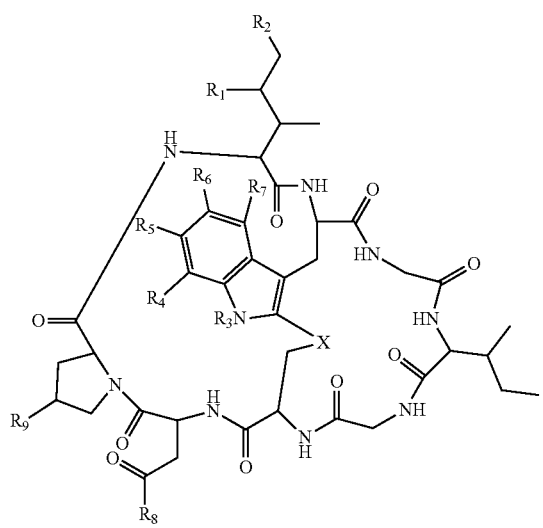

(I)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene,
a dipeptide, —(C=O)—, a peptide, or a combination thereof; and
Z is a chemical moiety formed from a coupling reaction between a reactive substituent present on L and a reactive substituent present within an antibody, or antigen-binding fragment thereof, that binds CD117 (such as GNNK+ CD117).

In some embodiments, Am contains exactly one $R_C$ substituent.

In some embodiments, the linker comprises a —$(CH_2)_{2n}$— unit, where n is an integer from 2-6. In some embodiments, the linker includes —$((CH_2)_n$ where n is 6. In some embodiments, L-Z is

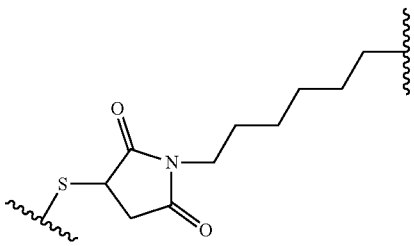

where S is a sulfur atom which represents the reactive substituent present within an antibody, or antigen-binding fragment thereof, that binds CD117 (e.g., from the —SH group of a cysteine residue).

In some embodiments, L-Z is

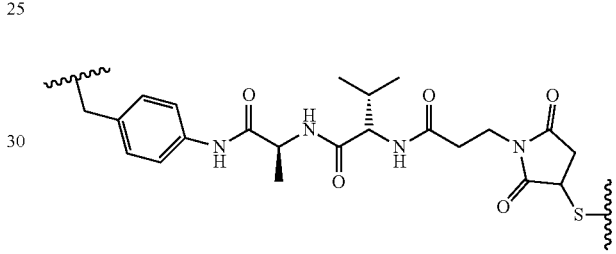

In some embodiments, Am-L-Z-Ab is one of:

(IV)

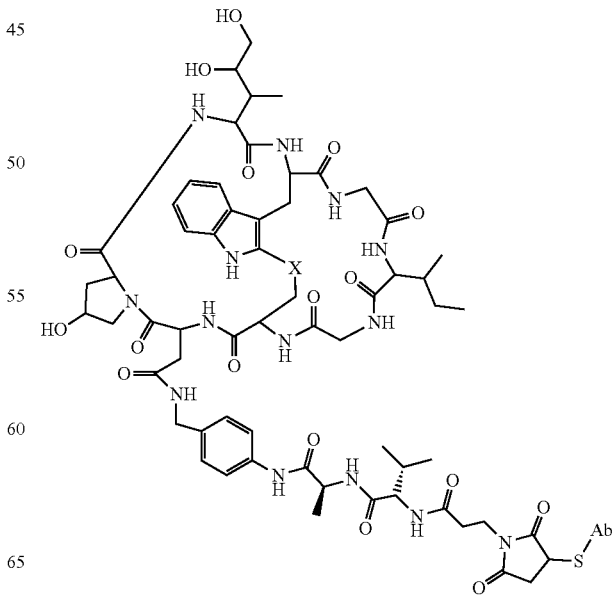

127
-continued
(IVA)
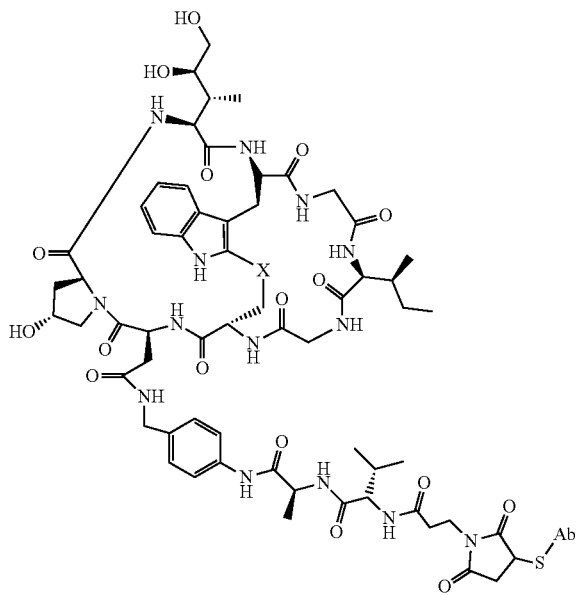
(IVB)
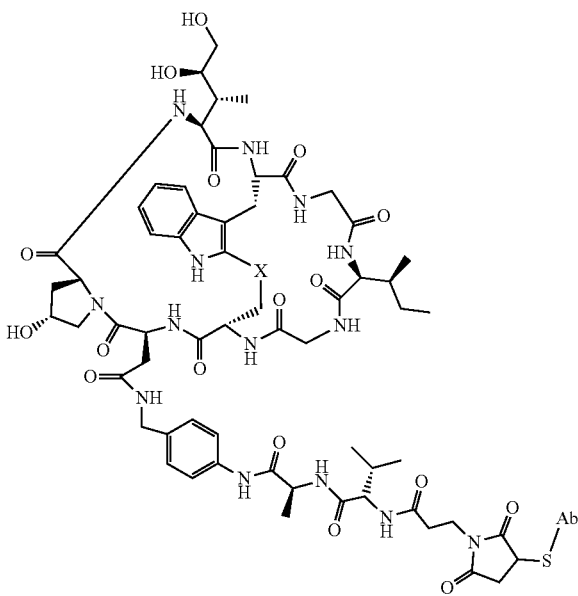
wherein X is —S—, —S(O)—, or —SO$_2$—.
128
In some embodiments, Am-L-Z-Ab is
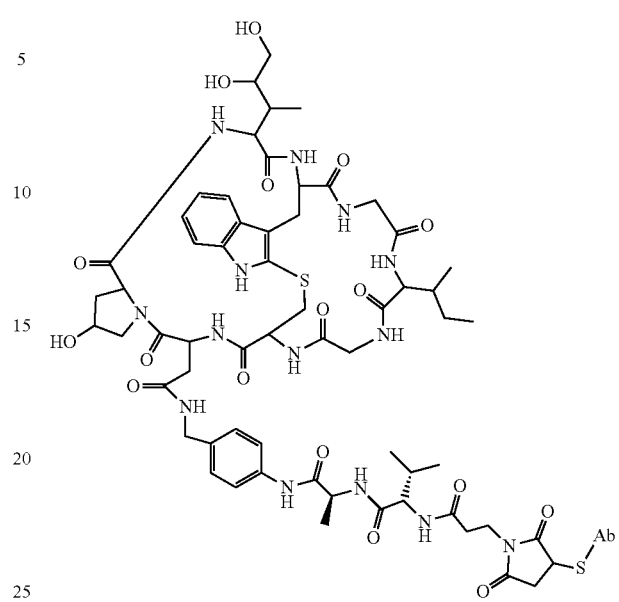
In some embodiments, Am-L-Z-Ab is
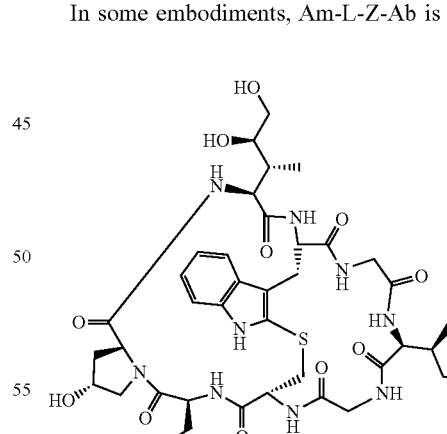

In some embodiments, Am-L-Z-Ab is

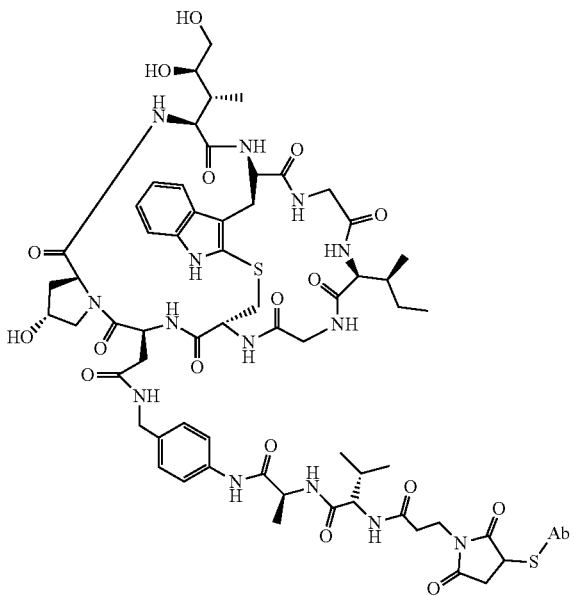

In some embodiments, Am is represented by formula (IA)

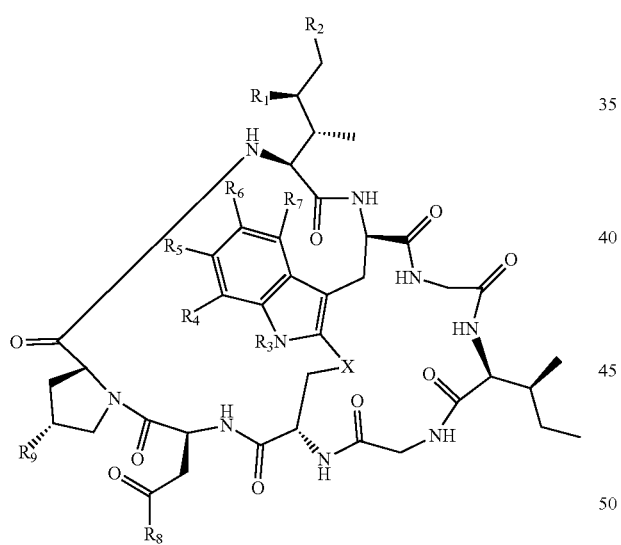

(IA)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —SO$_2$—;
$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a dipeptide, —(C=O)—, a peptide, or a combination thereof;

Z is a chemical moiety formed from a coupling reaction between a reactive substituent present on L and a reactive substituent present within an antibody, or antigen-binding fragment thereof, that binds CD117 (such as GNNK+ CD117); and wherein Am contains exactly one $R_C$ substituent. In some embodiments, the linker includes —((CH$_2$)$_n$ where n is 6. In some embodiments, L-Z is

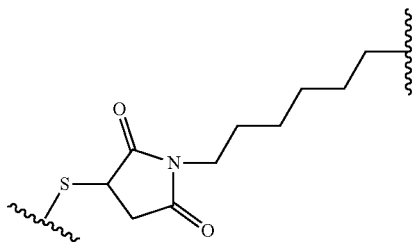

In some embodiments, L-Z is

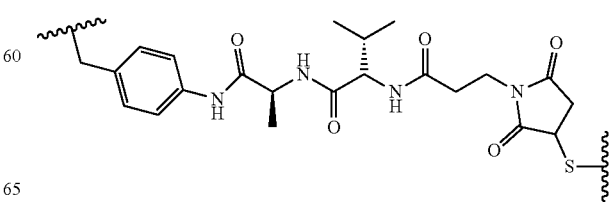

In some embodiments, Am-L-Z is represented by formula (IB)

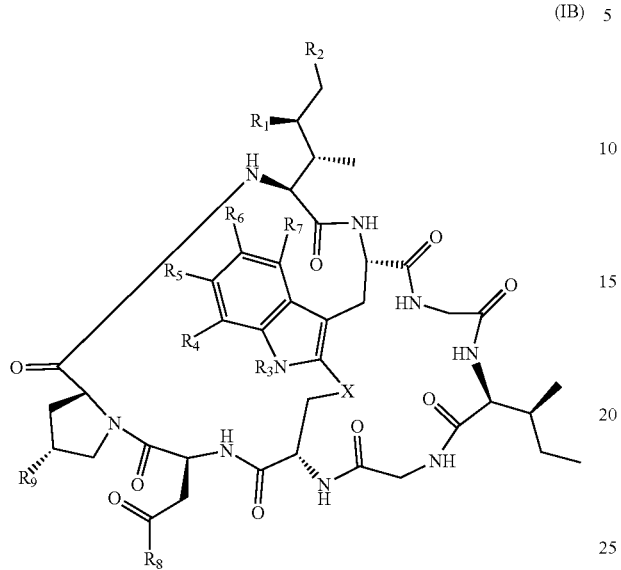

(IB)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene,
a dipeptide, —(C=O)—, a peptide, or a combination thereof;
Z is a chemical moiety formed from a coupling reaction between a reactive substituent present on L and a reactive substituent present within an antibody, or antigen-binding fragment thereof, that binds CD117 (such as GNNK+ CD117); and
wherein Am contains exactly one $R_C$ substituent.

In some embodiments, the linker L and the chemical moiety Z, taken together as L-Z, is

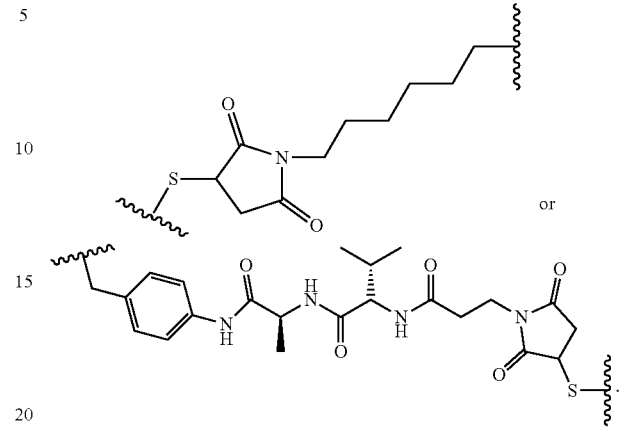

or

In some embodiments, L-Z is

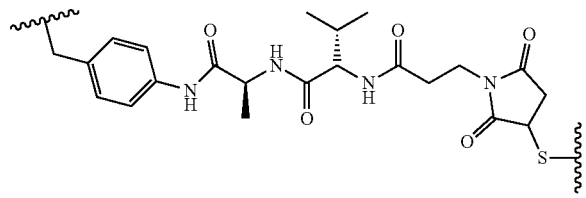

In some embodiments, $R_A$ and $R_B$, together with the oxygen atoms to which they are bound, combine to form to form a 5-membered heterocycloalkyl group of formula:

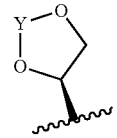

wherein Y is —(C=O)—, —(C=S)—, —(C=$NR_E$)—, or —($CR_ER_{E'}$)—; and $R_E$ and $R_{E'}$ are each independently optionally substituted $C_1$-$C_6$ alkylene-$R_C$, optionally substituted $C_1$-$C_6$ heteroalkylene-$R_C$, optionally substituted $C_2$-$C_6$ alkenylene-$R_C$, optionally substituted $C_2$-$C_6$ heteroalkenylene-$R_C$, optionally substituted $C_2$-$C_6$ alkynylene-$R_C$, optionally substituted $C_2$-$C_6$ heteroalkynylene-$R_C$, optionally substituted cycloalkylene-$R_C$, optionally substituted heterocycloalkylene-$R_C$, optionally substituted arylene-$R_C$, or optionally substituted heteroarylene-$R_C$.

In some embodiments, Am-L-Z is represented by formula (IA) or formula (IB),
wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form:

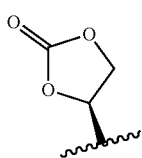 [SMILES: *[C@@H]1COC(=O)O1]

$R_3$ is H or $R_C$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, or $NHR_C$;
$R_9$ is H or OH;
X is —S—, —S(O)—, or —SO$_2$—; and
wherein $R_C$ and $R_D$ are each as defined above.

In some embodiments, Am-L-Z is represented by formula (IA) or formula (IB), wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form:

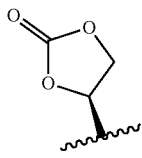 [SMILES: *[C@@H]1COC(=O)O1]

$R_3$ is H or $R_C$;
$R_4$ and $R_5$ are each independently H, OH, $OR_C$, $R_C$, or $OR_D$;
$R_6$ and $R_7$ are each H;
$R_8$ is OH, $NH_2$, $OR_C$, or $NHR_C$;
$R_9$ is H or OH;
X is —S—, —S(O)—, or —SO$_2$—; and
wherein $R_C$ is as defined above.

In some embodiments, Am-L-Z is represented by formula (IA) or formula (IB),
wherein $R_1$ is H, OH, or $OR_A$;
$R_2$ is H, OH, or $OR_B$;
$R_A$ and $R_B$, when present, together with the oxygen atoms to which they are bound, combine to form:

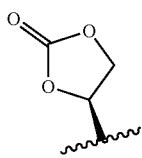 [SMILES: *[C@@H]1COC(=O)O1]

$R_3$, $R_4$, $R_6$, and $R_7$ are each H;
$R_5$ is $OR_C$;
$R_8$ is OH or $NH_2$;
$R_9$ is H or OH;
X is —S—, —S(O)—, or —SO$_2$—; and
wherein $R_C$ is as defined above. Such amatoxin conjugates are described, for example, in US Patent Application Publication No. 2016/0002298, the disclosure of which is incorporated herein by reference in its entirety.

In some embodiments, Am-L-Z is represented by formula (IA) or formula (IB),
wherein $R_1$ and $R_2$ are each independently H or OH;
$R_3$ is $R_C$;
$R_4$, $R_6$, and $R_7$ are each H;
$R_5$ is H, OH, or $C_1$-$C_6$ alkyl;
$R_8$ is OH or $NH_2$;
$R_9$ is H or OH; and
wherein $R_C$ is as defined above. Such amatoxin conjugates are described, for example, in US Patent Application Publication No. 2014/0294865, the disclosure of which is incorporated herein by reference in its entirety.

In some embodiments, Am-L-Z is represented by formula (IA) or formula (IB),
wherein $R_1$ and $R_2$ are each independently H or OH;
$R_3$, $R_6$, and $R_7$ are each H;
$R_4$ and $R_5$ are each independently H, OH, $OR_C$, or $R_C$;
$R_8$ is OH or $NH_2$;
$R_9$ is H or OH; and
wherein $R_C$ is as defined above. Such amatoxin conjugates are described, for example, in US Patent Application Publication No. 2015/0218220, the disclosure of which is incorporated herein by reference in its entirety.

In some embodiments, Am-L-Z is represented by formula (IA) or formula (IB),
wherein $R_1$ and $R_2$ are each independently H or OH;
$R_3$, $R_6$, and $R_7$ are each H;
$R_4$ and $R_5$ are each independently H or OH;
$R_8$ is OH, $NH_2$, $OR_C$, or $NHR_C$;
$R_9$ is H or OH; and
wherein $R_C$ is as defined above. Such amatoxin conjugates are described, for example, in U.S. Pat. Nos. 9,233,173 and 9,399,681, as well as in US 2016/0089450, the disclosures of each of which are incorporated herein by reference in their entirety.

Additional amatoxins that may be used for conjugation to an antibody, or antigen-binding fragment thereof, in accordance with the compositions and methods described herein are described, for example, in WO 2016/142049; WO 2016/071856; WO 2017/046658; and WO2018/115466, the disclosures of each of which are incorporated herein by reference in their entirety.

In some embodiments, Am-L-Z is represented by formula (II), formula IIA, or formula IIB

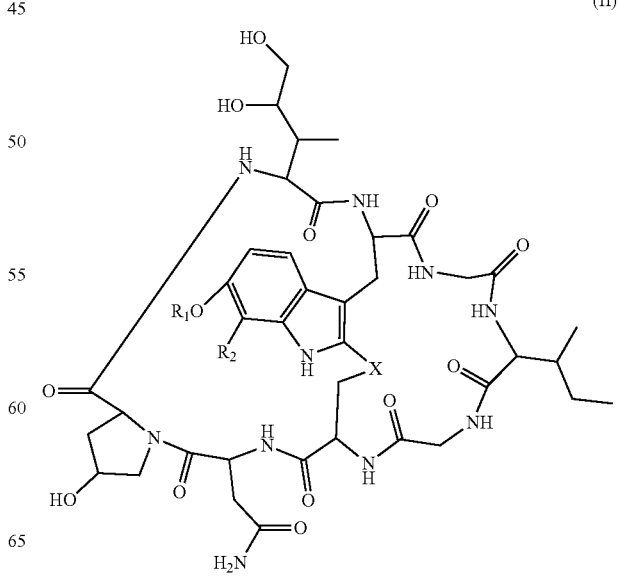

(II)

-continued

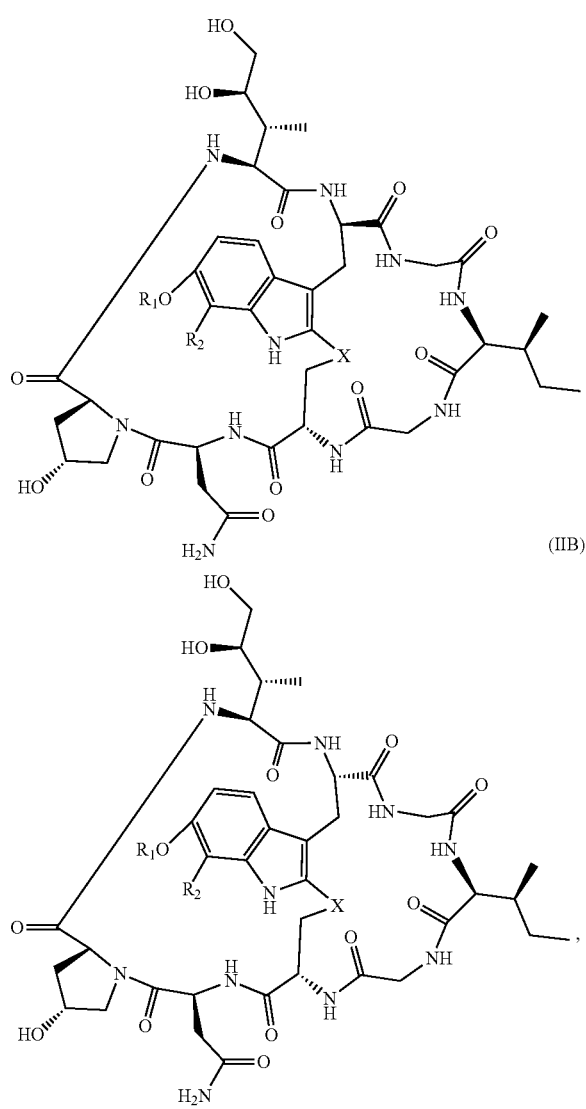

(IIA)

(IIB)

wherein X is S, SO, or $SO_2$; $R_1$ is H or a linker covalently bound to the antibody or antigen-binding fragment thereof through a chemical moeity Z, formed from a coupling reaction between a reactive substituent present on the linker and a reactive substituent present within an antibody, or antigen-binding fragment thereof; and $R_2$ is H or a linker covalently bound to the antibody or antigen-binding fragment thereof through a chemical moeity Z, formed from a coupling reaction between a reactive substituent present on the linker and a reactive substituent present within an antibody, or antigen-binding fragment thereof; wherein when $R_1$ is H, $R_2$ is the linker, and when $R_2$ is H, $R_1$ is the linker.

In some embodiments, the linker includes a $-(CH_2)_n-$ unit, where n is an integer from 2-6. In some embodiments, $R_1$ is the linker and $R_2$ is H, and the linker and chemical moiety, together as L-Z, is

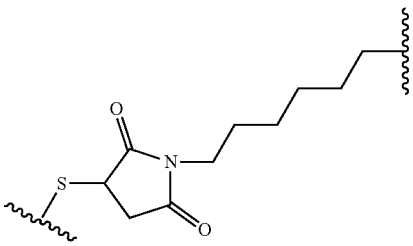

In some embodiments, Am-L-Z-Ab is:

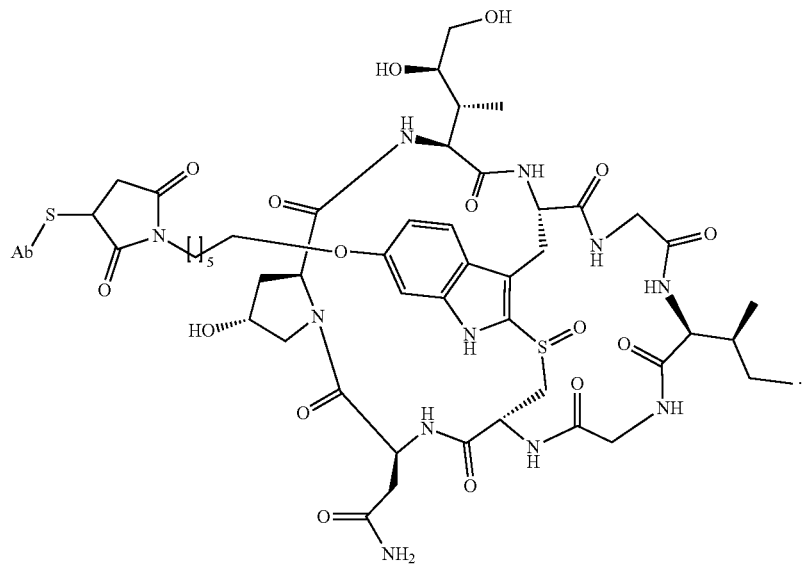

In some embodiments, Am-L-Z-Ab is:

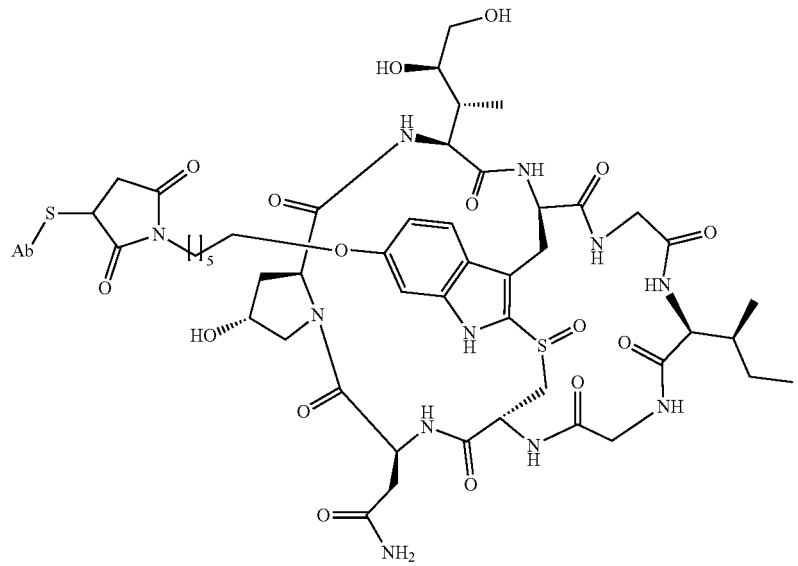

In some embodiments, the cytotoxin is an α-amanitin. In some embodiments, the α-amanitin is a compound of formula III. In some embodiments, the α-amanitin of formula III is attached to an anti-CD117 antibody via a linker L. The linker L may be attached to the α-amanitin of formula III at any one of several possible positions (e.g., any of $R^1$-$R^9$) to provide an α-amanitin-linker conjugate of formula I, IA, IB, II, IIA, IIB, IV, IVA or IVB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C═O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C═O)(CH$_2$)$_n$—. In some embodiments, the linker is -PAB-Ala-Val-((C═O)(CH$_2$)$_n$—. In some embodiments, the linker L and the chemical moiety Z, taken together as L-Z, is

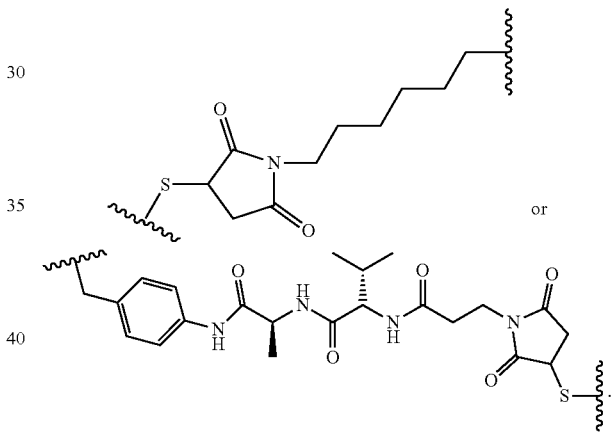

In some embodiments, the cytotoxin is a β-amanitin. In some embodiments, the β-amanitin is a compound of formula I. In some embodiments, the α-amanitin is a compound of formula III. In some embodiments, the β-amanitin of formula III is attached to an anti-CD117 antibody via a linker L. The linker L may be attached to the β-amanitin of formula III at any one of several possible positions (e.g., any of $R^1$-$R^9$) to provide an β-amanitin-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a ((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

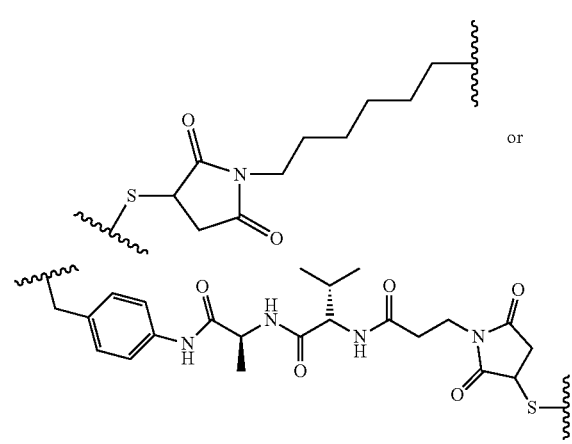

or

In some embodiments, the cytotoxin is a γ-amanitin. In some embodiments, the γ-amanitin is a compound of formula III. In some embodiments, the γ-amanitin of formula III is attached to an anti-CD117 antibody via a linker L. The linker L may be attached to the γ-amanitin of formula III at any one of several possible positions (e.g., any of $R^1$—$R^9$) to provide an γ-amanitin-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

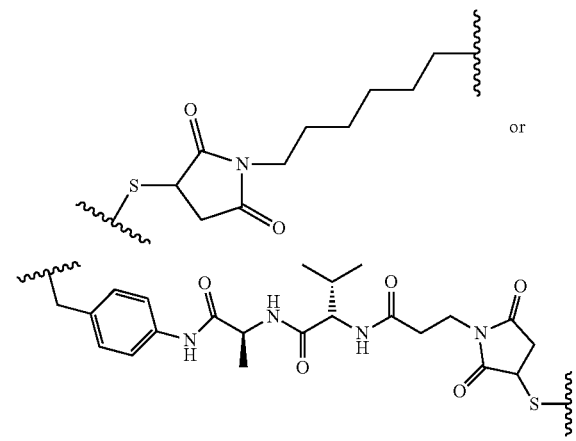

or

In some embodiments, the cytotoxin is a ε-amanitin. In some embodiments, the ε-amanitin is a compound of formula III. In some embodiments, the ε-amanitin of formula III is attached to an anti-CD117 antibody via a linker L. The linker L may be attached to the ε-amanitin of formula III at any one of several possible positions (e.g., any of $R^1$-$R^9$) to provide an ε-amanitin-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

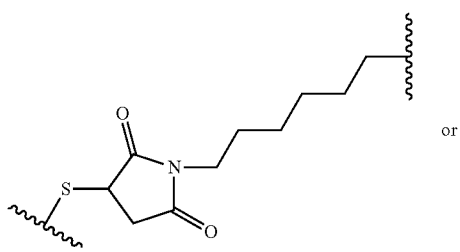

or

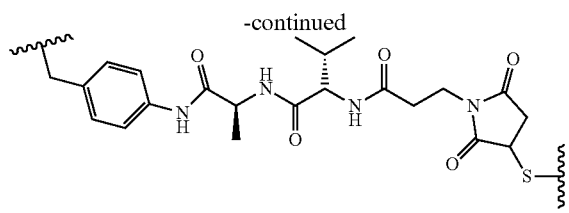

In some embodiments, the cytotoxin is an amanin. In some embodiments, the amanin is a compound of formula III. In some embodiments, the amanin of formula III is attached to an anti-CD117 antibody via a linker L. The linker L may be attached to the amanin of formula III at any one of several possible positions (e.g., any of $R^1$-$R^9$) to provide an amanin-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a $((C=O)(CH_2)_n$— unit, wherein n is an integer from 1-6.

In some embodiments, the linker includes a —$(CH_2)_n$— unit, where n is an integer from 2-6. In some embodiments, the linker is -PAB-Cit-Val-$((C=O)(CH_2)_n$—. In some embodiments, the linker is -PAB-Ala-Val-$((C=O)(CH_2)_n$—. In some embodiments, the linker L and the chemical moiety Z, taken together as L-Z, is

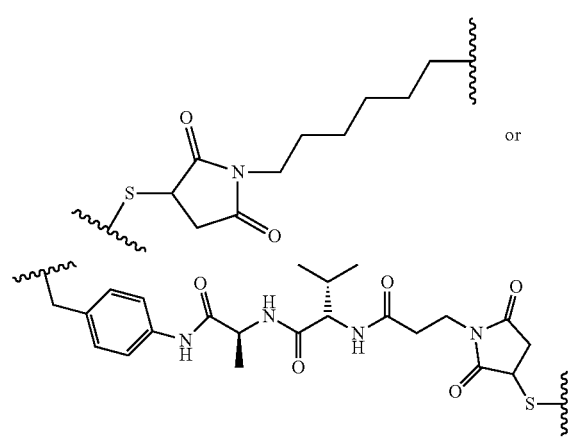

In some embodiments, the cytotoxin is an amaninamide. In some embodiments, the amaninamide is a compound of formula III. In some embodiments, the amaninamide of formula III is attached to an anti-CD117 antibody via a linker L. The linker L may be attached to the amaninamide of formula III at any one of several possible positions (e.g., any of $R^1$-$R^9$) to provide an amaninamide-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —$((C=O)(CH_2)_n$— unit, wherein n is an integer from 1-6.

In some embodiments, the linker includes a —$(CH_2)_n$— unit, where n is an integer from 2-6. In some embodiments, the linker is -PAB-Cit-Val-$((C=O)(CH_2)_n$—. In some embodiments, the linker is -PAB-Ala-Val-$((C=O)(CH_2)_n$—. In some embodiments, the linker L and the chemical moiety Z, taken together as L-Z, is

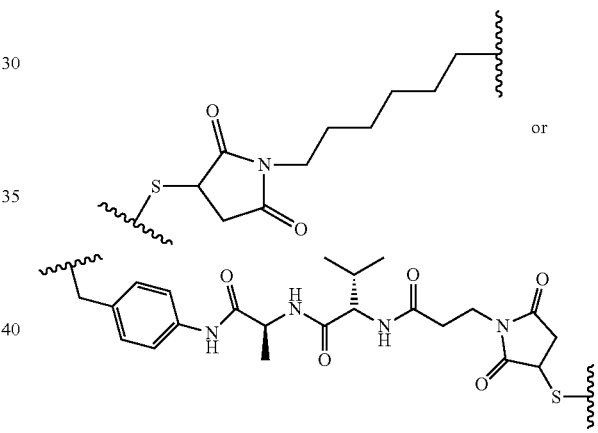

In some embodiments, the cytotoxin is an amanullin. In some embodiments, the amanullin is a compound of formula III. In some embodiments, the amanullin of formula III is attached to an anti-CD117 antibody via a linker L. The linker L may be attached to the amanullin of formula III at any one of several possible positions (e.g., any of $R^1$-$R^9$) to provide an amanullin-linker conjugate of formula I, IA, IB, II, IIA, or IIB. In some embodiments, the linker is attached at position $R^1$. In some embodiments, the linker is attached at position $R^2$. In some embodiments, the linker is attached at position $R^3$. In some embodiments, the linker is attached at position $R^4$. In some embodiments, the linker is attached at position $R^5$. In some embodiments, the linker is attached at position $R^6$. In some embodiments, the linker is attached at position $R^7$. In some embodiments, the linker is attached at position $R^8$. In some embodiments, the linker is attached at position $R^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6. I In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

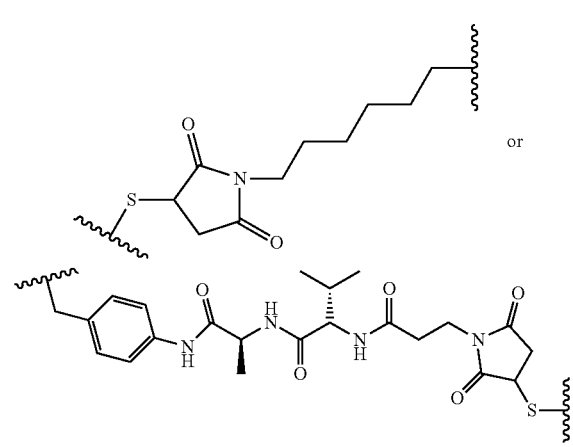

In some embodiments, the cytotoxin is an amanullinic acid. In some embodiments, the amanullinic acid is a compound of formula III. In some embodiments, the amanullinic acid of formula III is attached to an anti-CD117 antibody via a linker L. The linker L may be attached to the amanullinic acid of formula III at any one of several possible positions (e.g., any of R$^1$-R$^9$) to provide an amanullinic acid-linker conjugate of formula I, IA, IB, II, IIA, or IIB. In some embodiments, the linker is attached at position R$^1$. In some embodiments, the linker is attached at position R$^2$. In some embodiments, the linker is attached at position R$^3$. In some embodiments, the linker is attached at position R$^4$. In some embodiments, the linker is attached at position R$^5$. In some embodiments, the linker is attached at position R$^6$. In some embodiments, the linker is attached at position R$^7$. In some embodiments, the linker is attached at position R$^8$. In some embodiments, the linker is attached at position R$^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

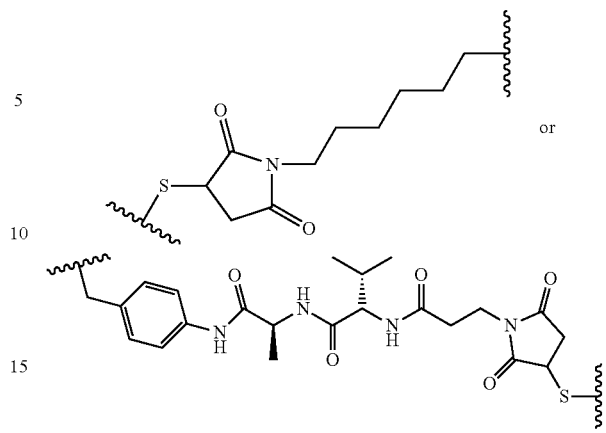

In some embodiments, the cytotoxin is a proamanullin. In some embodiments, the proamanullin is a compound of formula III. In some embodiments, the proamanullin of formula III is attached to an anti-CD117 antibody via a linker L. The linker L may be attached to the proamanullin of formula III at any one of several possible positions (e.g., any of R$^1$-R$^9$) to provide an proamanullin-linker conjugate of formula I, IA, IB, II, IIA, or IIB. In some embodiments, the linker is attached at position R$^1$. In some embodiments, the linker is attached at position R$^2$. In some embodiments, the linker is attached at position R$^3$. In some embodiments, the linker is attached at position R$^4$. In some embodiments, the linker is attached at position R$^5$. In some embodiments, the linker is attached at position R$^6$. In some embodiments, the linker is attached at position R$^7$. In some embodiments, the linker is attached at position R$^8$. In some embodiments, the linker is attached at position R$^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

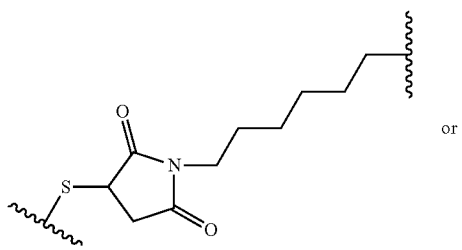

-continued

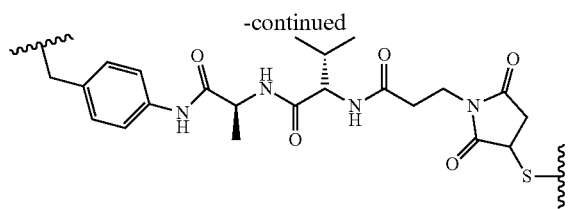
Synthetic methods of making amatoxin are described in U.S. Pat. No. 9,676,702, which is incorporated by reference herein.

Antibodies, or antigen-binding fragments, for use with the compositions and methods described herein can be conjugated to an amatoxin, such as α-amanitin or a variant thereof, using conjugation techniques known in the art or described herein. For instance, antibodies, or antigen-binding fragments thereof, that recognize and bind CD117 (such as GNNK+ CD117) can be conjugated to an amatoxin, such as α-amanitin or a variant thereof, as described in US 2015/0218220, the disclosure of which is incorporated herein by reference as it pertains, for example, to amatoxins, such as α-amanitin and variants thereof, as well as covalent linkers that can be used for covalent conjugation.

Exemplary antibody-drug conjugates useful in conjunction with the methods described herein may be formed by the reaction of an antibody, or antigen-binding fragment thereof, with an amatoxin that is conjugated to a linker containing a substituent suitable for reaction with a reactive residue on the antibody, or antigen-binding fragment thereof. Amatoxins that are conjugated to a linker containing a substituent suitable for reaction with a reactive residue on the antibody, or antigen-binding fragment thereof, described herein include, without limitation, 7'C-(4-(6-(maleimido)hexanoyl)piperazin-1-yl)-amatoxin; 7'C-(4-(6-(maleimido)hexanamido)piperidin-1-yl)-amatoxin; 7'C-(4-(6-(6-(maleimido)hexanamido)hexanoyl)piperazin-1-yl)-amatoxin; 7'C-(4-(4-((maleimido)methyl)cyclohexanecarbonyl)piperazin-1-yl)-amatoxin; 7'C-(4-(6-(4-((maleimido)methyl)cyclohexanecarboxamido)hexanoyl)piperazin-1-yl)-amatoxin; 7'C-(4-(2-(6-(maleimido)hexanamido)ethyl)piperidin-1-yl)-amatoxin; 7'C-(4-(2-(6-(6-(maleimido)hexanamido)hexanamido)ethyl)piperidin-1-yl)-amatoxin; 7'C-(4-(2-(4-((maleimido)methyl)cyclohexanecarboxamido)ethyl)piperidin-1-yl)-amatoxin; 7'C-(4-(2-(6-(4-((maleimido)methyl)cyclohexanecarboxamido)hexanamido)ethyl)piperidin-1-yl)-amatoxin; 7'C-(4-(2-(3-carboxypropanamido)ethyl)piperidin-1-yl)-amatoxin; 7'C-(4-(2-(2-bromoacetamido)ethyl)piperidin-1-yl)-amatoxin; 7'C-(4-(2-(3-(pyridin-2-yldisulfanyl)propanamido)ethyl)piperidin-1-yl)-amatoxin; 7'C-(4-(2-(4-(maleimido)butanamido)ethyl)piperidin-1-yl)-amatoxin; 7'C-(4-(2-(maleimido)acetyl)piperazin-1-yl)-amatoxin; 7'C-(4-(3-(maleimido)propanoyl)piperazin-1-yl)-amatoxin; 7'C-(4-(4-(maleimido)butanoyl)piperazin-1-yl)-amatoxin; 7'C-(4-(2-(6-(4-((maleimido)methyl)cyclohexanecarboxamido)hexanamido)ethyl)piperidin-1-yl)-amatoxin; 7'C-(3-((6-(maleimido)hexanamido)methyl)pyrrolidin-1-yl)-amatoxin; 7'C-(3-((6-(6-(maleimido)hexanamido)hexanamido)methyl)pyrrolidin-1-yl)-amatoxin; 7'C-(3-((4-((maleimido)methyl)cyclohexanecarboxamido)methyl)pyrrolidin-1-yl)-amatoxin; 7'C-(3-((6-((4-(maleimido)methyl)cyclohexanecarboxamido)hexanamido)methyl)pyrrolidin-1-yl)-amatoxin; 7'C-(4-(2-(6-(2-(aminooxy)acetamido)hexanamido)ethyl)piperidin-1-yl)-amatoxin; 7'C-(4-(2-(4-(2-(aminooxy)acetamido)butanamido)ethyl)piperidin-1-yl)-amatoxin; 7'C-(4-(4-(2-(aminooxy)acetamido)butanoyl)piperazin-1-yl)-amatoxin; 7'C-(4-(6-(2-(aminooxy)acetamido)hexanoyl)piperazin-1-yl)-amatoxin; 7'C-((4-(6-(maleimido)hexanamido)piperidin-1-yl)methyl)-amatoxin; 7'C-((4-(2-(6-(maleimido)hexanamido)ethyl)piperidin-1-yl)methyl)-amatoxin; 7'C-((4-(6-(maleimido)hexanoyl)piperazin-1-yl)methyl)-amatoxin; (R)-7'C-((3-((6-(maleimido)hexanamido)methyl)pyrrolidin-1-yl)methyl)-amatoxin; (S)-7'C-((3-((6-(maleimido)hexanamido)methyl)pyrrolidin-1-yl)methyl)-amatoxin; 7'C-((4-(2-(6-(6-(maleimido)hexanamido)hexanamido)ethyl)piperidin-1-yl)methyl)-amatoxin; 7'C-((4-(2-(4-((maleimido)methyl)cyclohexanecarboxamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((4-(2-(6-(maleimido)hexanamido)ethyl)piperazin-1-yl)methyl)-amatoxin; 7'C-((4-(2-(6-(6-(maleimido)hexanamido)hexanamido)ethyl)piperazin-1-yl)methyl)-amatoxin; 7'C-((4-(2-(4-((maleimido)methyl)cyclohexanecarboxamido)ethyl)piperazin-1-yl)methyl)-amatoxin; 7'C-((4-(2-(6-(4-((maleimido)methyl)cyclohexanecarboxamido)hexanamido)ethyl)piperazin-1-yl)methyl)-amatoxin; 7'C-((3-((6-(6-(maleimido)hexanamido)hexanamido)-S-methyl)pyrrolidin-1-yl)methyl)-amatoxin; 7'C-((3-((6-(6-(maleimido)hexanamido)hexanamido)-R-methyl)pyrrolidin-1-yl)methyl)-amatoxin; 7'C-((3-((4-((maleimido)methyl)cyclohexanecarboxamido)-S-methyl)pyrrolidin-1-yl)methyl)-amatoxin; 7'C-((3-((4-((maleimido)methyl)cyclohexanecarboxamido)-R-methyl)pyrrolidin-1-yl)methyl)-amatoxin; 7'C-((3-((6-(4-((maleimido)methyl)cyclohexanecarboxamido)hexanamido)methyl)pyrrolidin-1-yl)methyl)-amatoxin; 7'C-((4-(2-(3-carboxypropanamido)ethyl)piperazin-1-yl)methyl)-amatoxin; 7'C-((4-(6-(6-(maleimido)hexanamido)hexanoyl)piperazin-1-yl)methyl)-amatoxin; 7'C-((4-(6-(4-((maleimido)methyl)cyclohexanecarboxamido)hexanoyl)piperazin-1-yl)methyl)-amatoxin; 7'C-((4-(2-(maleimido)acetyl)piperazin-1-yl)methyl)-amatoxin; 7'C-((4-(3-(maleimido)propanoyl)piperazin-1-yl)methyl)-amatoxin; 7'C-((4-(4-(maleimido)butanoyl)piperazin-1-yl)methyl)-amatoxin; 7'C-((4-(2-(2-(maleimido)acetamido)ethyl)piperidin-1-yl)methyl)-amatoxin; 7'C-((4-(2-(4-(maleimido)butanamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((3-((6-(maleimido)hexanamido)methyl)azetidin-1-yl)methyl)-amatoxin; 7'C-((3-(2-(6-(maleimido)hexanamido)ethyl)azetidin-1-yl)methyl)-amatoxin; 7'C-((3-((4-((maleimido)methyl)cyclohexanecarboxamido)methyl)azetidin-1-yl)methyl)-amatoxin; 7'C-((3-(2-(4-((maleimido)methyl)cyclohexanecarboxamido)ethyl)azetidin-1-yl)methyl)-amatoxin; 7'C-((3-(2-(6-(4-((maleimido)methyl)cyclohexanecarboxamido)hexanamido)ethyl)azetidin-1-yl)methyl)-amatoxin; 7'C-(((2-(6-(maleimido)-N-methylhexanamido)ethyl)(methyl)amino)methyl)-amatoxin; 7'C-(((4-(6-(maleimido)-N-methylhexanamido)butyl(methyl)amino)methyl)-amatoxin; 7'C-((2-(2-(6-(maleimido)hexanamido)ethyl)aziridin-1-yl)methyl)-amatoxin; 7'C-((2-(2-(6-(4-((maleimido)methyl)cyclohexanecarboxamido)hexanamido)ethyl)aziridin-1-yl)methyl)-amatoxin; 7'C-((4-(6-(6-(2-(aminooxy)acetamido)hexanamido)hexanoyl)piperazin-1-yl)methyl)-amatoxin; 7'C-((4-(1-(aminooxy)-2-oxo-6,9,12,15-tetraoxa-3-azaheptadecan-17-oyl)piperazin-1-yl)methyl)-amatoxin; 7'C-((4-(2-(2-(aminooxy)acetamido)acetyl)piperazin-1-yl)methyl)-amatoxin; 7'C-((4-(3-(2-(aminooxy)acetamido)propanoyl)piperazin-1-yl)methyl)-amatoxin; 7'C-((4-(4-(2-(aminooxy)acetamido)butanoyl)piperazin-1-yl)methyl)-amatoxin; 7'C-((4-(2-(6-(2-(aminooxy)acetamido)hexanamido)ethyl)piperidin-1-yl)

methyl)-amatoxin; 7'C-((4-(2-(2-(2-(aminooxy)acetamido) acetamido)ethyl)piperidin-1-yl)methyl)-amatoxin; 7'C-((4-(2-(4-(2-(aminooxy)acetamido)butanamido)ethyl)piperidin-1-yl)methyl)-amatoxin; 7'C-((4-(20-(aminooxy)-4,19-dioxo-6,9,12,15-tetraoxa-3,18-diazaicosyl)piperidin-1-yl) methyl)-amatoxin; 7'C-(((2-(6-(2-(aminooxy)acetamido)-N-methylhexanamido)ethyl)(methyl)amino)methyl)-amatoxin; 7'C-(((4-(6-(2-(aminooxy)acetamido)-N-methylhexanamido)butyl)(methyl)amino)methyl)-amatoxin; 7'C-((3-((6-(4-((maleimido)methyl)cyclohexanecarboxamido) hexanamido)methyl)pyrrolidin-1-yl)-S-methyl)-amatoxin; 7'C-((3-((6-(4-((maleimido)methyl)cyclohexanecarboxamido)hexanamido)-R-methyl)pyrrolidin-1-yl)methyl)-amatoxin; 7'C-((4-(2-(2-bromoacetamido)ethyl)piperazin-1-yl)methyl)-amatoxin; 7'C-((4-(2-(2-bromoacetamido)ethyl) piperidin-1-yl)methyl)-amatoxin; 7'C-((4-(2-(3-(pyridine-2-yldisulfanyl)propanamido)ethyl)piperidin-1-yl)methyl)-amatoxin; 6'O-(6-(6-(maleimido)hexanamido)hexyl)-amatoxin; 6'O-(5-(4-((maleimido)methyl)cyclohexanecarboxamido)pentyl)-amatoxin; 6'O-(2-((6-(maleimido) hexyl)oxy)-2-oxoethyl)-amatoxin; 6'O-((6-(maleimido) hexyl)carbamoyl)-amatoxin; 6'O-((6-(4-((maleimido) methyl)cyclohexanecarboxamido)hexyl)carbamoyl)-amatoxin; 6'O-(6-(2-bromoacetamido)hexyl)-amatoxin; 7'C-(4-(6-(azido)hexanamido)piperidin-1-yl)-amatoxin; 7'C-(4-(hex-5-ynoylamino)piperidin-1-yl)-amatoxin; 7'C-(4-(2-(6-(maleimido)hexanamido)ethyl)piperazin-1-yl)-amatoxin; 7'C-(4-(2-(6-(6-(maleimido)hexanamido)hexanamido) ethyl)piperazin-1-yl)-amatoxin; 6'O-(6-(6-(11,12-didehydro-5,6-dihydro-dibenz[b,f]azocin-5-yl)-6-oxohexanamido)hexyl)-amatoxin; 6'O-(6-(hex-5-ynoylamino)hexyl)-amatoxin; 6'O-(6-(2-(aminooxy)acetylamido)hexyl)-amatoxin; 6'O-((6-aminooxy)hexyl)-amatoxin; and 6'O-(6-(2-iodoacetamido)hexyl)-amatoxin. The foregoing linkers, among others useful in conjunction with the compositions and methods described herein, are described, for example, in US Patent Application Publication No. 2015/0218220, the disclosure of which is incorporated herein by reference in its entirety.

Additional cytotoxins that can be conjugated to antibodies, or antigen-binding fragments thereof, that recognize and bind CD117 (such as GNNK+ CD117 for use in directly treating a cancer, autommine condition, or for conditioning a patient (e.g., a human patient) in preparation for hematopoietic stem cell transplant therapy include, without limitation, 5-ethynyluracil, abiraterone, acylfulvene, adecypenol, adozelesin, aldesleukin, altretamine, ambamustine, amidox, amifostine, aminolevulinic acid, amrubicin, amsacrine, anagrelide, anastrozole, andrographolide, angiogenesis inhibitors, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitors, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), capecitabine, carboxamide-amino-triazole, carboxyamidotriazole, carzelesin, casein kinase inhibitors, castanospermine, cecropin B, cetrorelix, chlorins, chloroquinoxaline sulfonamide, cicaprost, cis-porphyrin, cladribine, clomifene and analogues thereof, clotrimazole, collismycin A, collismycin B, combretastatin A4, combretastatin analogues, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, epithilones, epristeride, estramustine and analogues thereof, etoposide, etoposide 4'-phosphate (also referred to as etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, homoharringtonine (HHT), hypericin, ibandronic acid, idoxifene, idramantone, ilmofosine, ilomastat, imidazoacridones, imiquimod, immunostimulant peptides, iobenguane, iododoxorubicin, ipomeanol, irinotecan, iroplact, irsogladine, isobengazole, jasplakinolide, kahalalide F, lamellarin-N triacetate, lanreotide, leinamycin, lenograstim, lentinan sulfate, leptolstatin, letrozole, lipophilic platinum compounds, lissoclinamide 7, lobaplatin, lometrexol, lonidamine, losoxantrone, loxoribine, lurtotecan, lutetium texaphyrin, lysofylline, masoprocol, maspin, matrix metalloproteinase inhibitors, menogaril, rnerbarone, meterelin, methioninase, metoclopramide, MIF inhibitor, ifepristone, miltefosine, mirimostim, mithracin, mitoguazone, mitolactol, mitomycin and analogues thereof, mitonafide, mitoxantrone, mofarotene, molgramostim, mycaperoxide B, myriaporone, N-acetyldinaline, N-substituted benzamides, nafarelin, nagrestip, napavin, naphterpin, nartograstim, nedaplatin, nemorubicin, neridronic acid, nilutamide, nisamycin, nitrullyn, octreotide, okicenone, onapristone, ondansetron, oracin, ormaplatin, oxaliplatin, oxaunomycin, paclitaxel and analogues thereof, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, phenazinomycin, picibanil, pirarubicin, piritrexim, podophyllotoxin, porfiromycin, purine nucleoside phosphorylase inhibitors, raltitrexed, rhizoxin, rogletimide, rohitukine, rubiginone B1, ruboxyl, safingol, saintopin, sarcophytol A, sargramostim, sobuzoxane, sonermin, sparfosic acid, spicamycin D, spiromustine, stipiamide, sulfinosine, tallimustine, tegafur, temozolomide, teniposide, thaliblastine, thiocoraline, tirapazamine, topotecan, topsentin, triciribine, trimetrexate, veramine, vinorelbine, vinxaltine, vorozole, zeniplatin, and zilascorb, among others.

Linkers for Chemical Conjugation

A variety of linkers can be used to conjugate antibodies, or antigen-binding fragments, as described herein (e.g., antibodies, or antigen-binding fragments thereof, that recognize and bind CD117 (such as GNNK+ CD117) with a cytotoxic molecule.

The term "Linker" as used herein means a divalent chemical moiety comprising a covalent bond or a chain of atoms that covalently attaches an antibody or fragment thereof (Ab) to a drug moiety (D) to form antibody-drug conjugates of the present disclosure (ADCs; Ab-Z-L-D, where D is a cytotoxin). Suitable linkers have two reactive termini, one for conjugation to an antibody and the other for conjugation to a cytotoxin. The antibody conjugation reactive terminus of the linker (reactive moiety, Z) is typically a site that is capable of conjugation to the antibody through a cysteine thiol or lysine amine group on the antibody, and so is typically a thiol-reactive group such as a double bond (as in maleimide) or a leaving group such as a chloro, bromo, iodo, or an R-sulfanyl group, or an amine-reactive group such as a carboxyl group; while the antibody conjugation reactive terminus of the linker is typically a site that is capable of conjugation to the cytotoxin through formation of an amide bond with a basic amine or carboxyl group on the cytotoxin, and so is typically a carboxyl or basic amine group. When the term "linker" is used in describing the linker in conjugated form, one or both of the reactive termini will be absent (such as reactive moiety Z, having been converted to chemical moiety Z) or incomplete (such as being only the carbonyl of the carboxylic acid) because of the formation of the bonds between the linker and/or the cytotoxin, and between the linker and/or the antibody or antigen-binding fragment thereof. Such conjugation reactions are described further herein below.

In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation. The linkers useful for the present ADCs are preferably stable extracellularly, prevent aggregation of ADC molecules and keep the ADC freely soluble in aqueous media and in a monomeric state. Before transport or delivery into a cell, the ADC is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the cytotoxic moiety. Stability of the ADC may be measured by standard analytical techniques such as mass spectroscopy, HPLC, and the separation/analysis technique LC/MS. Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p. 234-242).

Linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for covalent conjugation).

Linkers hydrolyzable under acidic conditions include, for example, hydrazones, semicarbazones, thiosemicarbazones, cis-aconitic amides, orthoesters, acetals, ketals, or the like. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661, the disclosure of each of which is incorporated herein by reference in its entirety as it pertains to linkers suitable for covalent conjugation. Such linkers are relatively stable under neutral pH conditions, such as those in the blood, but are unstable at below pH 5.5 or 5.0, the approximate pH of the lysosome.

Linkers cleavable under reducing conditions include, for example, a disulfide. A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935, the disclosure of each of which is incorporated herein by reference in its entirety as it pertains to linkers suitable for covalent conjugation.

Additional linkers suitable for the synthesis of drug-antibody conjugates conjugates as described herein include those capable of releasing a cytotoxin by a 1,6-elimination process (a "self-immolative" group), such as p-aminobenzyl alcohol (PABC), p-aminobenzyl (PAB), 6-maleimidohexanoic acid, pH-sensitive carbonates, and other reagents described in Jain et al., Pharm. Res. 32:3526-3540, 2015, the disclosure of which is incorporated herein by reference in its entirety.

In some embodiments, the linker includes a self-immolative group such as the aforementioned PAB or PABC (para-aminobenzyloxycarbonyl), which are disclosed in, for example, Carl et al., J. Med. Chem. (1981) 24:479-480; Chakravarty et al (1983) J. Med. Chem. 26:638-644; U.S. Pat. No. 6,214,345; US20030130189; US20030096743; U.S. Pat. No. 6,759,509; US20040052793; U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). Other such chemical moieties capable of this process ("self-immolative linkers") include methylene carbamates and heteroaryl groups such as aminothiazoles, aminoimidazoles, aminopyrimidines, and the like. Linkers containing such heterocyclic self-immolative groups are disclosed in, for example, U.S. Patent Publication Nos. 20160303254 and 20150079114, and U.S. Pat. No. 7,754,681; Hay et al. (1999) Bioorg. Med. Chem. Lett. 9:2237; US 2005/0256030; de Groot et al (2001) J. Org. Chem. 66:8815-8830; and U.S. Pat. No. 7,223,837.

Linkers susceptible to enzymatic hydrolysis can be, e.g., a peptide-containing linker that is cleaved by an intracellular peptidase or protease enzyme, including, but not limited to, a lysosomal or endosomal protease. One advantage of using intracellular proteolytic release of the therapeutic agent is that the agent is typically attenuated when conjugated and the serum stabilities of the conjugates are typically high. In some embodiments, the peptidyl linker is at least two amino acids long or at least three amino acids long. Exemplary amino acid linkers include a dipeptide, a tripeptide, a tetrapeptide or a pentapeptide. Examples of suitable peptides include those containing amino acids such as Valine, Alanine, Citrulline (Cit), Phenylalanine, Lysine, Leucine, and Glycine. Amino acid residues which comprise an amino acid linker component include those occurring naturally, as well as minor amino acids and non-naturally occurring amino acid analogs, such as citrulline. Exemplary dipeptides include valine-citrulline (vc or val-cit) and alanine-phenylalanine (af or ala-phe). Exemplary tripeptides include glycine-valine-citrulline (gly-val-cit) and glycine-glycine-glycine (gly-gly-gly). In some embodiments, the linker includes a dipeptide such as Val-Cit, Ala-Val, or Phe-Lys, Val-Lys, Ala-Lys, Phe-Cit, Leu-Cit, Ile-Cit, Phe-Arg, or Trp-Cit. Linkers containing dipeptides such as Val-Cit or Phe-Lys are disclosed in, for example, U.S. Pat. No. 6,214,345, the disclosure of which is incorporated herein by reference in its entirety as it pertains to linkers suitable for covalent conjugation. In some embodiments, the linker includes a dipeptide selected from Val-Ala and Val-Cit. In some embodiments, a dipeptide is used in combination with a self-immolative linker.

Linkers suitable for use herein further may include one or more groups selected from $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, heteroarylene, and combinations thereof, each of which may be optionally substituted. Non-limiting examples of such groups include $(CH_2)_n$, $(CH_2CH_2O)_n$, and $-(C=O)(CH_2)_n-$ units, wherein n is an integer from 1-6, independently selected for each occasion.

In some embodiments, the linker may include one or more of a hydrazine, a disulfide, a thioether, a dipeptide, a p-aminobenzyl (PAB) group, a heterocyclic self-immolative group, an optionally substituted $C_1$-$C_6$ alkyl, an optionally substituted $C_1$-$C_6$ heteroalkyl, an optionally substituted $C_2$-$C_6$ alkenyl, an optionally substituted 02-06 heteroalkenyl, an optionally substituted 02-06 alkynyl, an optionally substituted $C_2$-$C_6$ heteroalkynyl, an optionally substituted $C_3$-$C_6$ cycloalkyl, an optionally substituted heterocycloalkyl, an optionally substituted aryl, an optionally substituted heteroaryl, acyl, $-(C=O)-$, or $-(CH_2CH_2O)_n-$ group, wherein n is an integer from 1-6. One of skill in the art will recognize that one or more of the groups listed may be present in the form of a bivalent (diradical) species, e.g., $C_1$-$C_6$ alkylene and the like.

In some embodiments, the linker includes a p-aminobenzyl group (PAB). In one embodiment, the p-aminobenzyl group is disposed between the cytotoxic drug and a protease cleavage site in the linker. In one embodiment, the p-aminobenzyl group is part of a p-aminobenzyloxycarbonyl unit. In one embodiment, the p-aminobenzyl group is part of a p-aminobenzylamido unit.

In some embodiments, the linker comprises PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a combination of one or more of a peptide, oligosaccharide, $-(CH_2)_n-$, $-(CH_2CH_2O)_n-$, PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a $-(C=O)(CH_2)_n-$ unit, wherein n is an integer from 1-6.

In some embodiments, the linker comprises a $-(CH_2)_n-$ unit, wherein n is an integer from 2 to 6.

Linkers that can be used to conjugate an antibody, or antigen-binding fragment thereof, to a cytotoxic agent include those that are covalently bound to the cytotoxic agent on one end of the linker and, on the other end of the linker, contain a chemical moiety formed from a coupling reaction between a reactive substituent present on the linker and a reactive substituent present within the antibody, or antigen-binding fragment thereof, that binds CD117 (such as GNNK+ CD117). Reactive substituents that may be present within an antibody, or antigen-binding fragment thereof, that binds CD117 (such as GNNK+ CD117) include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids.

Examples of linkers useful for the synthesis of drug-antibody conjugates conjugates include those that contain electrophiles, such as Michael acceptors (e.g., maleimides), activated esters, electron-deficient carbonyl compounds, and aldehydes, among others, suitable for reaction with nucleophilic substituents present within antibodies or antigen-binding fragments, such as amine and thiol moieties. For instance, linkers suitable for the synthesis of drug-antibody conjugates include, without limitation, succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, for instance, Liu et al., 18:690-697, 1979, the disclosure of which is incorporated herein by reference as it pertains to linkers for chemical conjugation. Additional linkers include the non-cleavable maleimidocaproyl linkers, which are particularly useful for the conjugation of microtubule-disrupting agents such as auristatins, are described by Doronina et al., Bioconjugate Chem. 17:14-24, 2006, the disclosure of which is incorporated herein by reference as it pertains to linkers for chemical conjugation.

It will be recognized by one of skill in the art that any one or more of the chemical groups, moieties and features disclosed herein may be combined in multiple ways to form linkers useful for conjugation of the antibodies and cytotoxins as disclosed herein. Further linkers useful in conjunction with the compositions and methods described herein, are described, for example, in U.S. Patent Application Publication No. 2015/0218220, the disclosure of which is incorporated herein by reference in its entirety.

Linkers useful in conjunction with the antibody-drug described herein include, without limitation, linkers containing chemical moieties formed by coupling reactions as depicted in Table 3, below. Curved lines designate points of attachment to the antibody, or antigen-binding fragment, and the cytotoxic molecule, respectively.

TABLE 3
Exemplary chemical moieties Z formed by coupling reactions in the formation of antibody-drug
| Exemplary Coupling Reactions | Chemical Moiety Z Formed by Coupling Reactions |
|---|---|
| [3 + 2] Cycloaddition | 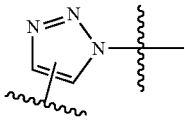 |
| [3 + 2] Cycloaddition | 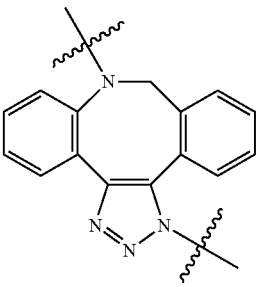 [SMILES: *N1Cc2ccccc2-c2c(nnn2*)-c2ccccc21] |
| [3 + 2] Cycloaddition, Esterification | 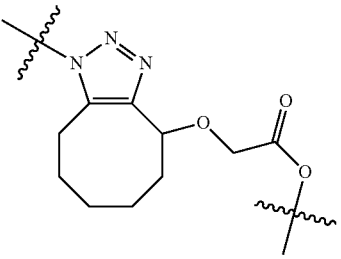 [SMILES: *OC(=O)COC1CCCCCc2c1nnn2*] |
| [3 + 2] Cycloaddition, Esterification | 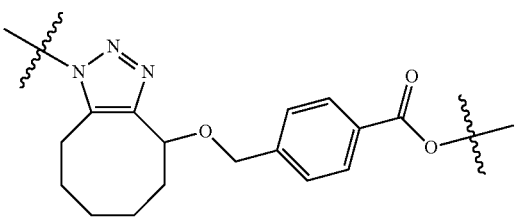 [SMILES: *OC(=O)c1ccc(COC2CCCCCc3c2nnn3*)cc1] |
| [3 + 2] Cycloaddition, Esterification | 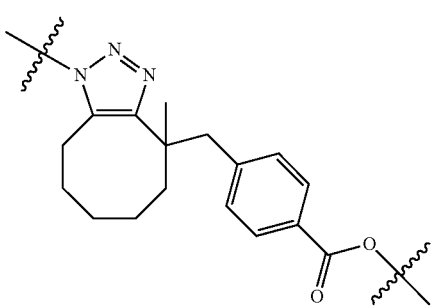 [SMILES: *OC(=O)c1ccc(CC2(C)CCCCCc3c2nnn3*)cc1] |

TABLE 3-continued
Exemplary chemical moieties Z formed by coupling reactions in the formation of antibody-drug
| Exemplary Coupling Reactions | Chemical Moiety Z Formed by Coupling Reactions |
|---|---|
| [3 + 2] Cycloaddition, Esterification | 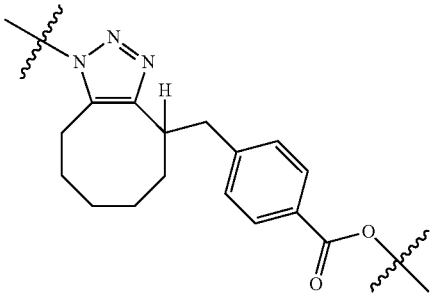 [SMILES: *OC(=O)c1ccc(CC2CCCCCc3c2nnn3*)cc1] |
| [3 + 2] Cycloaddition, Esterification | 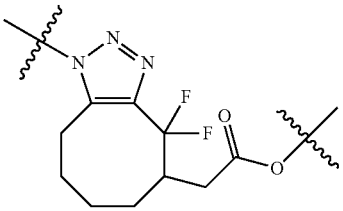 [SMILES: *OC(=O)CC1CCCCc2c(nnn2*)C1(F)F] |
| [3 + 2] Cycloaddition, Esterification | 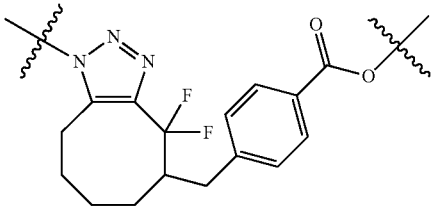 [SMILES: *OC(=O)c1ccc(CC2CCCCc3c(nnn3*)C2(F)F)cc1] |
| [3 + 2] Cycloaddition, Esterification | 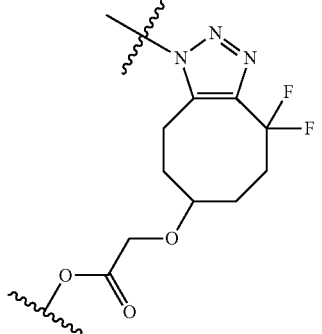 [SMILES: *OC(=O)COC1CCc2c(nnn2*)C(F)(F)CC1] |
| [3 + 2] Cycloaddition, Esterification | 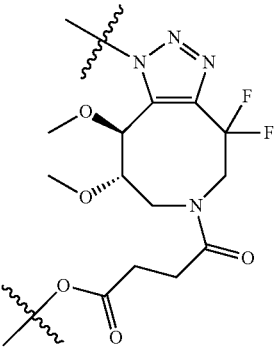 [SMILES: *OC(=O)CCC(=O)N1C[C@H](OC)[C@@H](OC)c2c(nnn2*)C(F)(F)C1] |

TABLE 3-continued
Exemplary chemical moieties Z formed by coupling reactions in the formation of antibody-drug
| Exemplary Coupling Reactions | Chemical Moiety Z Formed by Coupling Reactions |
|---|---|
| [3 + 2] Cycloaddition, Esterification | 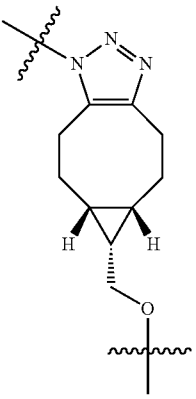 [SMILES: *OC[C@@H]1[C@@H]2CCc3c(nnn3*)CC[C@@H]21] |
| [3 + 2] Cycloaddition, Esterification | 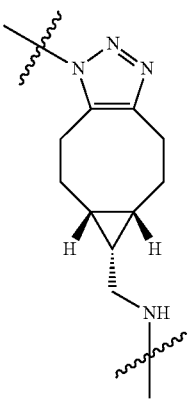 [SMILES: *NC[C@@H]1[C@@H]2CCc3c(nnn3*)CC[C@@H]21] |
| [3 + 2] Cycloaddition, Esterification | 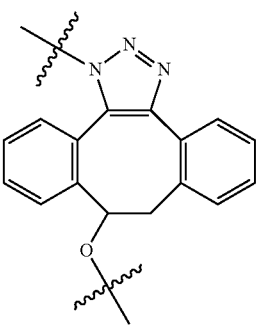 [SMILES: *OC1Cc2ccccc2-c2nnn(*)c2-c2ccccc21] |
| [3 + 2] Cycloaddition, Etherification | 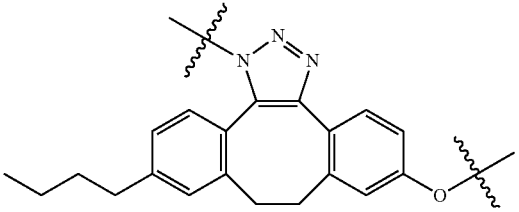 [SMILES: *Oc1ccc2c(c1)CCc1cc(CCCC)ccc1-c1c-2nnn1*] |

TABLE 3-continued

Exemplary chemical moieties Z formed by coupling reactions in the formation of antibody-drug

| Exemplary Coupling Reactions | Chemical Moiety Z Formed by Coupling Reactions |
|---|---|
| [3 + 2] Cycloaddition | |
| Michael addition | |
| Michael addition | |
| Imine condensation, Amidation | |
| Imine condensation | |
| Disulfide formation | |
| Thiol alkylation | |
| Condensation, Michael addition | |

One of skill in the art will recognize that a reactive substituent Z attached to the linker and a reactive substituent on the antibody or antigen-binding fragment thereof, are engaged in the covalent coupling reaction to produce the chemical moiety Z, and will recognize the reactive substituent Z. Therefore, antibody-drug conjugates useful in conjunction with the methods described herein may be formed by the reaction of an antibody, or antigen-binding fragment thereof, with a linker or cytotoxin-linker conjugate, as described herein, the linker or cytotoxin-linker conjugate including a reactive substituent Z, suitable for reaction with a reactive substituent on the antibody, or antigen-binding fragment thereof, to form the chemical moiety Z.

As depicted in Table 3, examples of suitably reactive substituents on the linker and antibody or antigen-binding fragment thereof include a nucleophile/electrophile pair (e.g., a thiol/haloalkyl pair, an amine/carbonyl pair, or a thiol/α,β-unsaturated carbonyl pair, and the like), a diene/dienophile pair (e.g., an azide/alkyne pair, or a diene/α,β-unsaturated carbonyl pair, among others), and the like. Coupling reactions between the reactive substitutents to form the chemical moiety Z include, without limitation, thiol alkylation, hydroxyl alkylation, amine alkylation, amine or hydroxylamine condensation, hydrazine formation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein. Preferably, the linker contains an electrophilic functional group for reaction with a nucleophilic functional group on the antibody, or antigen-binding fragment thereof.

Reactive substituents that may be present within an antibody, or antigen-binding fragment thereof, as disclosed herein include, without limitation, nucleophilic groups such as (i) N-terminal amine groups, (ii) side chain amine groups, e.g. lysine, (iii) side chain thiol groups, e.g. cysteine, and (iv) sugar hydroxyl or amino groups where the antibody is glycosylated. Reactive substituents that may be present within an antibody, or antigen-binding fragment thereof, as disclosed herein include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. In some embodiments, the reactive substituents present within an antibody, or antigen-binding fragment thereof as disclosed herein include, are amine or thiol moieties. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In some embodiments, the reactive moiety Z attached to the linker is a nucleophilic group which is reactive with an electrophilic group present on an antibody. Useful electrophilic groups on an antibody include, but are not limited to, aldehyde and ketone carbonyl groups. The heteroatom of a nucleophilic group can react with an electrophilic group on an antibody and form a covalent bond to the antibody. Useful nucleophilic groups include, but are not limited to, hydrazide, oxime, amino, hydroxyl, hydrazine, thiosemicarbazone, hydrazine carboxylate, and arylhydrazide.

In some embodiments, Z is the product of a reaction between reactive nucleophilic substituents present within the antibodies, or antigen-binding fragments thereof, such as amine and thiol moieties, and a reactive electrophilic substituent Z. For instance, Z may be a Michael acceptor (e.g., maleimide), activated ester, electron-deficient carbonyl compound, or an aldehyde, among others.

In some embodiments, the ADC comprises an anti-CD117 antibody conjugated to an amatoxin of any of formulae I, IA, IB, II, IIA, or IIB as disclosed herein via a linker and a chemical moiety Z. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val.

In some embodiments, the linker includes a —((C=O)(CH$_2$)$_n$— unit, wherein n is an integer from 1-6. In some embodiments, the linker is -PAB-Cit-Val-((C=O)(CH$_2$)$_n$—.

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker is —(CH$_2$)$_n$—. In some embodiments, the linker is —((CH$_2$)$_n$—, wherein n is 6.

In some embodiments, the chemical moiety Z is selected from Table 3. In some embodiments, the chemical moiety Z is

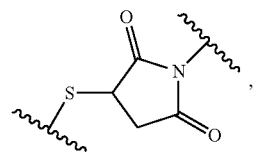

where S is a sulfur atom which represents the reactive substituent present within an antibody, or antigen-binding fragment thereof, that binds CD117 (e.g., from the —SH group of a cysteine residue).

In some embodiments, the linker L and the chemical moiety Z, taken together as L-Z, is

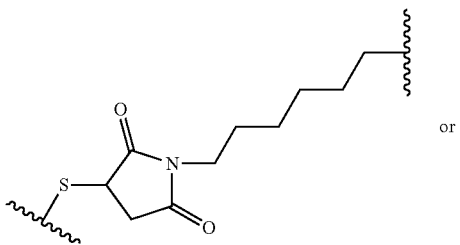

or

-continued

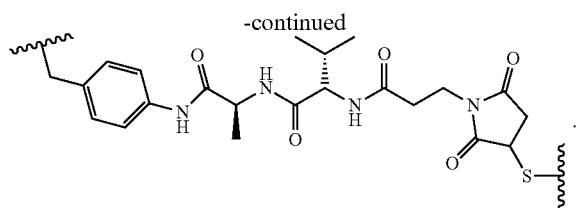

One of skill in the art will recognize the linker-reactive substituent group structure, prior to conjugation with the antibody or antigen binding fragment thereof, includes a maleimide as the group Z. The foregoing linker moieties and amatoxin-linker conjugates, among others useful in conjunction with the compositions and methods described herein, are described, for example, in U.S. Patent Application Publication No. 2015/0218220 and Patent Application Publication No. WO2017/149077, the disclosure of each of which is incorporated herein by reference in its entirety.

Preparation of Antibody-Drug Conjugates

In the ADCs of formula I as disclosed herein, an antibody or antigen binding fragment thereof is conjugated to one or more cytotoxic drug moieties (D), e.g. about 1 to about 20 drug moieties per antibody, through a linker L and a chemical moiety Z as disclosed herein. The ADCs of the present disclosure may be prepared by several routes, employing organic chemistry reactions, conditions, and reagents known to those skilled in the art, including: (1) reaction of a reactive substituent of an antibody or antigen binding fragment thereof with a bivalent linker reagent to form Ab-Z-L as described herein above, followed by reaction with a drug moiety D; or (2) reaction of a reactive substituent of a drug moiety with a bivalent linker reagent to form D-L-Z, followed by reaction with a reactive substituent of an antibody or antigen binding fragment thereof as described herein above to form an ADC of formula D-L-Z-Ab, such as Am-Z-L-Ab. Additional methods for preparing ADC are described herein.

In another aspect, the antibody or antigen binding fragment thereof has one or more lysine residues that can be chemically modified to introduce one or more sulfhydryl groups. The ADC is then formed by conjugation through the sulfhydryl group's sulfur atom as described herein above. The reagents that can be used to modify lysine include, but are not limited to, N-succinimidyl S-acetylthioacetate (SATA) and 2-Iminothiolane hydrochloride (Traut's Reagent).

In another aspect, the antibody or antigen binding fragment thereof can have one or more carbohydrate groups that can be chemically modified to have one or more sulfhydryl groups. The ADC is then formed by conjugation through the sulfhydryl group's sulfur atom as described herein above.

In yet another aspect, the antibody can have one or more carbohydrate groups that can be oxidized to provide an aldehyde (—CHO) group (see, for e.g., Laguzza, et al., J. Med. Chem. 1989, 32(3), 548-55). The ADC is then formed by conjugation through the corresponding aldehyde as described herein above. Other protocols for the modification of proteins for the attachment or association of cytotoxins are described in Coligan et al., Current Protocols in Protein Science, vol. 2, John Wiley & Sons (2002), incorporated herein by reference.

Methods for the conjugation of linker-drug moieties to cell-targeted proteins such as antibodies, immunoglobulins or fragments thereof are found, for example, in U.S. Pat. Nos. 5,208,020; 6,441,163; WO2005037992; WO2005081711; and WO2006/034488, all of which are hereby expressly incorporated by reference in their entirety.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

Methods of Treatment

As described herein, hematopoietic stem cell transplant therapy can be administered to a subject in need of treatment so as to populate or re-populate one or more blood cell types. Hematopoietic stem cells generally exhibit multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Hematopoietic stem cells are additionally capable of self-renewal, and can thus give rise to daughter cells that have equivalent potential as the mother cell, and also feature the capacity to be reintroduced into a transplant recipient whereupon they home to the hematopoietic stem cell niche and re-establish productive and sustained hematopoiesis.

Hematopoietic stem cells can thus be administered to a patient defective or deficient in one or more cell types of the hematopoietic lineage in order to re-constitute the defective or deficient population of cells in vivo, thereby treating the pathology associated with the defect or depletion in the endogenous blood cell population. The compositions and methods described herein can thus be used to treat a non-malignant hemoglobinopathy (e.g., a hemoglobinopathy selected from the group consisting of sickle cell anemia, thalassemia, Fanconi anemia, aplastic anemia, and Wiskott-Aldrich syndrome). Additionally or alternatively, the compositions and methods described herein can be used to treat an immunodeficiency, such as a congenital immunodeficiency. Additionally or alternatively, the compositions and methods described herein can be used to treat an acquired immunodeficiency (e.g., an acquired immunodeficiency selected from the group consisting of HIV and AIDS). The compositions and methods described herein can be used to treat a metabolic disorder (e.g., a metabolic disorder selected from the group consisting of glycogen storage diseases, mucopolysaccharidoses, Gaucher's Disease, Hurlers Disease, sphingolipidoses, and metachromatic leukodystrophy).

Additionally or alternatively, the compositions and methods described herein can be used to treat a malignancy or proliferative disorder, such as a hematologic cancer, myeloproliferative disease. In the case of cancer treatment, the compositions and methods described herein may be administered to a patient so as to deplete a population of endogenous hematopoietic stem cells prior to hematopoietic stem cell transplantation therapy, in which case the transplanted cells can home to a niche created by the endogenous cell depletion step and establish productive hematopoiesis. This, in turn, can re-constitute a population of cells depleted during cancer cell eradication, such as during systemic chemotherapy. Exemplary hematological cancers that can be treated using the compositions and methods described herein include, without limitation, acute myeloid leukemia, acute lymphoid leukemia, chronic myeloid leukemia, chronic lymphoid leukemia, multiple myeloma, diffuse large B-cell lymphoma, and non-Hodgkin's lymphoma, as well as other cancerous conditions, including neuroblastoma.

Additional diseases that can be treated with the compositions and methods described herein include, without limitation, adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

The antibodies, antigen-binding fragments thereof, and conjugates described herein may be used to induce solid organ transplant tolerance. For instance, the compositions and methods described herein may be used to deplete or ablate a population of cells from a target tissue (e.g., to deplete hematopoietic stem cells from the bone marrow stem cell niche). Following such depletion of cells from the target tissues, a population of stem or progenitor cells from an organ donor (e.g., hematopoietic stem cells from the organ donor) may be administered to the transplant recipient, and following the engraftment of such stem or progenitor cells, a temporary or stable mixed chimerism may be achieved, thereby enabling long-term transplant organ tolerance without the need for further immunosuppressive agents. For example, the compositions and methods described herein may be used to induce transplant tolerance in a solid organ transplant recipient (e.g., a kidney transplant, lung transplant, liver transplant, and heart transplant, among others). The compositions and methods described herein are well-suited for use in connection the induction of solid organ transplant tolerance, for instance, because a low percentage temporary or stable donor engraftment is sufficient to induce long-term tolerance of the transplanted organ.

In addition, the compositions and methods described herein can be used to treat cancers directly, such as cancers characterized by cells that are CD117+. For instance, the compositions and methods described herein can be used to treat leukemia, particularly in patients that exhibit CD117+ leukemic cells. By depleting CD117+ cancerous cells, such as leukemic cells, the compositions and methods described herein can be used to treat various cancers directly. Exemplary cancers that may be treated in this fashion include hematological cancers, such as acute myeloid leukemia, acute lymphoid leukemia, chronic myeloid leukemia, chronic lymphoid leukemia, multiple myeloma, diffuse large B-cell lymphoma, and non-Hodgkin's lymphoma.

Acute myeloid leukemia (AML) is a cancer of the myeloid line of blood cells, characterized by the rapid growth of abnormal white blood cells that build up in the bone marrow and interfere with the production of normal blood cells. AML is the most common acute leukemia affecting adults, and its incidence increases with age. The symptoms of AML are caused by replacement of normal bone marrow with leukemic cells, which causes a drop in red blood cells, platelets, and normal white blood cells. As an acute leukemia, AML progresses rapidly and may be fatal within weeks or months if left untreated. In one embodiment, the anti-CD117 ADCs described herein are used to treat AML in a human patient in need thereof. In certain embodiments the anti-CD117 ADC treatment depletes AML cells in the treated subjects. In some embodiments 50% or more of the AML cells are depleted. In other embodiments, 60% or more of the AML cells are depleted, or 70% or more of the AML cells are depleted, or 80% of more or 90% or more, or 95% or more of the AML cells are depleted. In certain embodiments the anti-CD117 ADC treatments is a single dose treatment. In certain embodiments the single dose anti-CD117 ADC treatment depletes 60%, 70%, 80%, 90% or 95% or more of the AML cells.

In addition, the compositions and methods described herein can be used to treat autoimmune disorders. For instance, an antibody, or antigen-binding fragment thereof, can be administered to a subject, such as a human patient suffering from an autoimmune disorder, so as to kill a CD117+ immune cell. The CD117+ immune cell may be an autoreactive lymphocyte, such as a T-cell that expresses a T-cell receptor that specifically binds, and mounts an immune response against, a self antigen. By depleting self-reactive, CD117+ cells, the compositions and methods described herein can be used to treat autoimmune pathologies, such as those described below. Additionally or alternatively, the compositions and methods described herein can be used to treat an autoimmune disease by depleting a population of endogenous hematopoietic stem cells prior to hematopoietic stem cell transplantation therapy, in which case the transplanted cells can home to a niche created by the endogenous cell depletion step and establish productive hematopoiesis. This, in turn, can re-constitute a population of cells depleted during autoimmune cell eradication.

Autoimmune diseases that can be treated using the compositions and methods described herein include, without limitation, psoriasis, psoriatic arthritis, Type 1 diabetes mellitus (Type 1 diabetes), rheumatoid arthritis (RA), human systemic lupus (SLE), multiple sclerosis (MS), inflammatory bowel disease (IBD), lymphocytic colitis, acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, collagenous colitis, uveitis, vasculitis, vitiligo, vulvodynia ("vulvar vestibulitis"), and Wegener's granulomatosis.

Routes of Administration and Dosing

ADCs, antibodies, or antigen-binding fragments thereof, or described herein can be administered to a patient (e.g., a human patient suffering from cancer, an autoimmune disease, or in need of hematopoietic stem cell transplant therapy) in a variety of dosage forms. For instance, antibodies, or antigen-binding fragments thereof, described herein can be administered to a patient suffering from cancer, an autoimmune disease, or in need of hematopoietic stem cell transplant therapy in the form of an aqueous solution, such as an aqueous solution containing one or more pharmaceutically acceptable excipients. Pharmaceutically acceptable excipients for use with the compositions and methods described herein include viscosity-modifying agents. The aqueous solution may be sterilized using techniques known in the art.

Pharmaceutical formulations comprising anti-CD117 ADCs or antibodies as described herein are prepared by mixing such ADC or anti-CD117 antibody with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

The ADCs, antibodies, or antigen-binding fragments, described herein may be administered by a variety of routes, such as orally, transdermally, subcutaneously, intranasally, intravenously, intramuscularly, intraocularly, or parenterally. The most suitable route for administration in any given case will depend on the particular antibody, or antigen-binding fragment, administered, the patient, pharmaceutical formulation methods, administration methods (e.g., administration time and administration route), the patient's age, body weight, sex, severity of the diseases being treated, the patient's diet, and the patient's excretion rate.

The effective dose of an ADC, antibody, or antigen-binding fragment thereof, described herein can range, for example from about 0.001 to about 100 mg/kg of body weight per single (e.g., bolus) administration, multiple administrations, or continuous administration, or to achieve an optimal serum concentration (e.g., a serum concentration of 0.0001-5000 µg/mL) of the antibody, antigen-binding fragment thereof. The dose may be administered one or more times (e.g., 2-10 times) per day, week, or month to a subject (e.g., a human) suffering from cancer, an autoimmune disease, or undergoing conditioning therapy in preparation for receipt of a hematopoietic stem cell transplant. In the case of a conditioning procedure prior to hematopoietic stem cell transplantation, the ADC, antibody, or antigen-binding fragment thereof, can be administered to the patient at a time that optimally promotes engraftment of the exogenous hematopoietic stem cells, for instance, from 1 hour to 1 week (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) or more prior to administration of the exogenous hematopoietic stem cell transplant.

EXAMPLES

Figure 1:
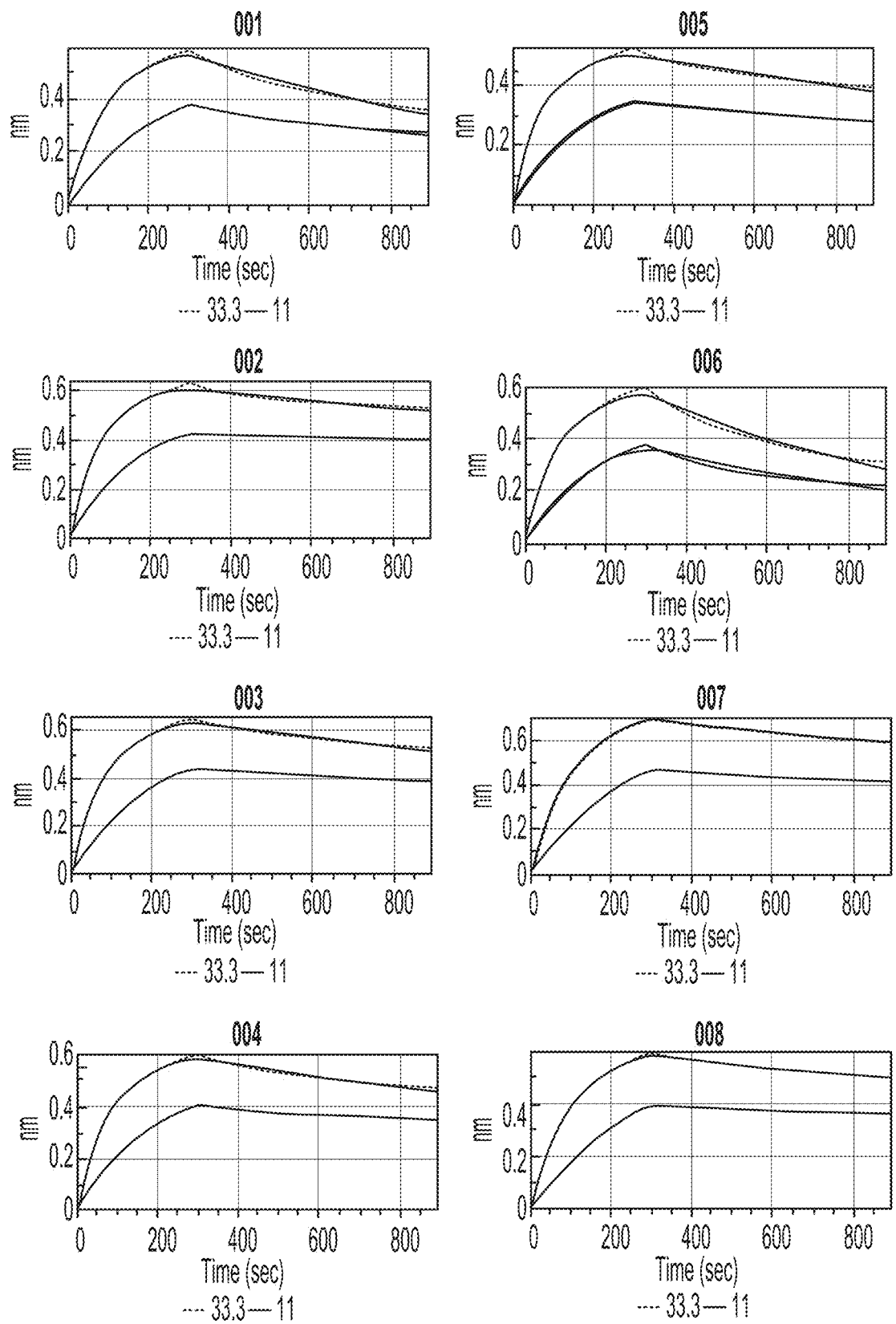
FIG. 1 demonstrates the measurement of binding by Bio-Layer Interferometry (BLI) of the indicated purified IgG (sensor-associated) to purified human CD117 ectodomain (R&D Systems #332-SR) at concentrations of 33.3 nM (top traces) and 11 nM (bottom traces) as a function of time. The purified IgGs correspond to Ab1 (i.e., 001), Ab2 (i.e., 002), Ab3 (i.e., 003), Ab4 (i.e., 004), Ab5 (i.e., 005), Ab6 (i.e., 006), Ab7 (i.e., 007), Ab8 (i.e., 008), Ab9 (i.e., 009), Ab10 (i.e., 010), Ab11 (i.e., 011), Ab12 (i.e., 012), Ab13 (i.e., 013), Ab14 (i.e., 014), Ab15 (i.e., 015), and Ab16 (i.e., 016).

The data provided in FIGS. 1, 22, and 23 disclosed herein represent data based on the compositions and methods described herein, including the sequences disclosed in Tables 1 and 2, and are intended to be purely exemplary of the invention and are not intended to limit the scope of what the inventors regard as their invention.

In Examples 1 through 3 (including the data provided in FIGS. 2-4), CD117-ADC is a CK6, a fully human antagonistic antibody specific for CD117 that is conjugated to a toxin capable of depleting cycling and non-cycling cells. The isotype control ADC is a non-targeted monoclonal human IgG antibody conjugated to the same toxin as CD117-ADC. In the experiments described in Examples 1 to 3, the control naked CD117 antibody is the same CK6 antibody used in the CD117-ADC.

Example 1. In Vitro Analysis of an Anti-CD117-ADC Using an In Vitro Cell Killing Assay The anti-CD117 antibody used in the ADC in the following Example is anti-CD117 antibody CK6 conjugated to amatoxin. For in vitro killing assays using Kasumi-1 cells, Kasumi-1 cells were grown according to ATCC guidelines. More specifically, Kasumi-1 cells were cultured for three days in the presence of CD117-ADC or the controls. Cell viability was measured by Celltiter Glo. For in vitro killing assays using Human HSCs (i.e., isolated primary human CD34+ selected Bone Marrow Cells (BMCs)), human CD34+ BMCs were cultured for five days with CD117-ADC or the controls in the presence of IL-6, TPO, and FLT-3 ligand, with or without SCF. Live cell counts were determined by flow cytometry. Killing of total nucleated cells in culture mirrored the results shown in FIG. 4.

Figure 2A:
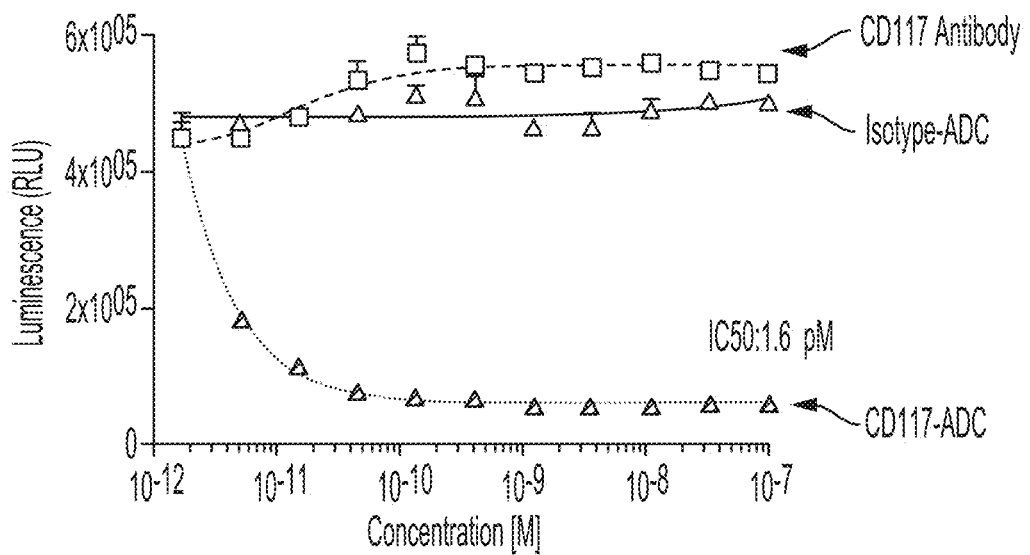
FIGS. 2A and 2B graphically depict the results of in vitro cell killing assays that show Kasumi-1 cell viability as measured in luminescene (RLU) by Celltiter Glo (FIG. 2A) or viable CD34+CD90+ cell count (FIG. 2B) in the presence of CD117-ADC or controls (y-axis) as a function of CD117-ADC or controls concentration (x-axis).
Figure 2B:
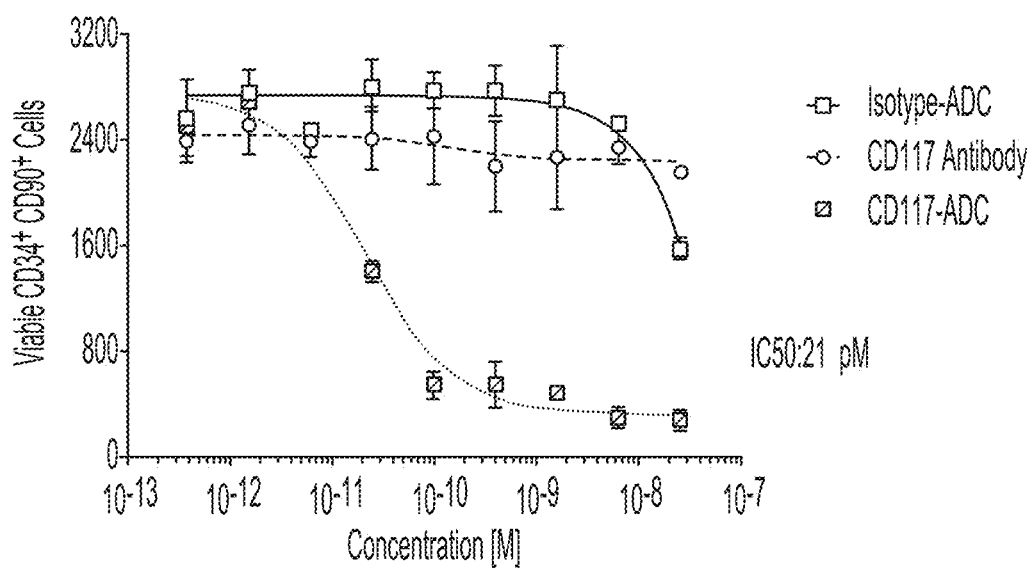

The results in FIGS. 2A and 2B indicate that CD117-ADC is highly effective at killing CD117 expressing cell lines (e.g., Kasumi-1 cells) or primary human CD34+ cells in vitro, demonstrating greater than 90% killing of the leukemia cell line Kasumi-1 (FIG. 2A; $IC_{50}$=1.6 pM), and equally effective killing of primary human CD34+ bone marrow cells during in vitro culture (FIG. 26; $IC_{50}$=21 pM). Thus, CD117-ADC is highly effective at killing CD117 expressing cell lines and primary human CD34+ cells.

Example 2. In Vivo HSC Depletion Assay Using an Anti-CD117-ADC

Figure 3A:
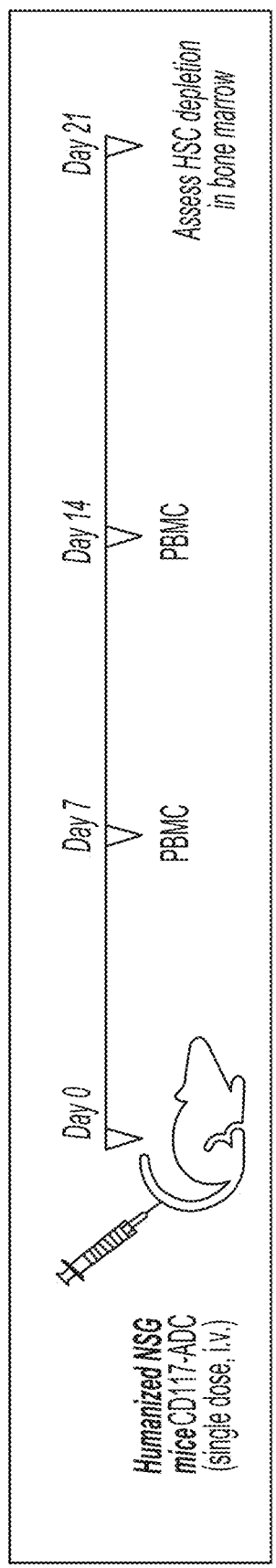
Figure 3B:
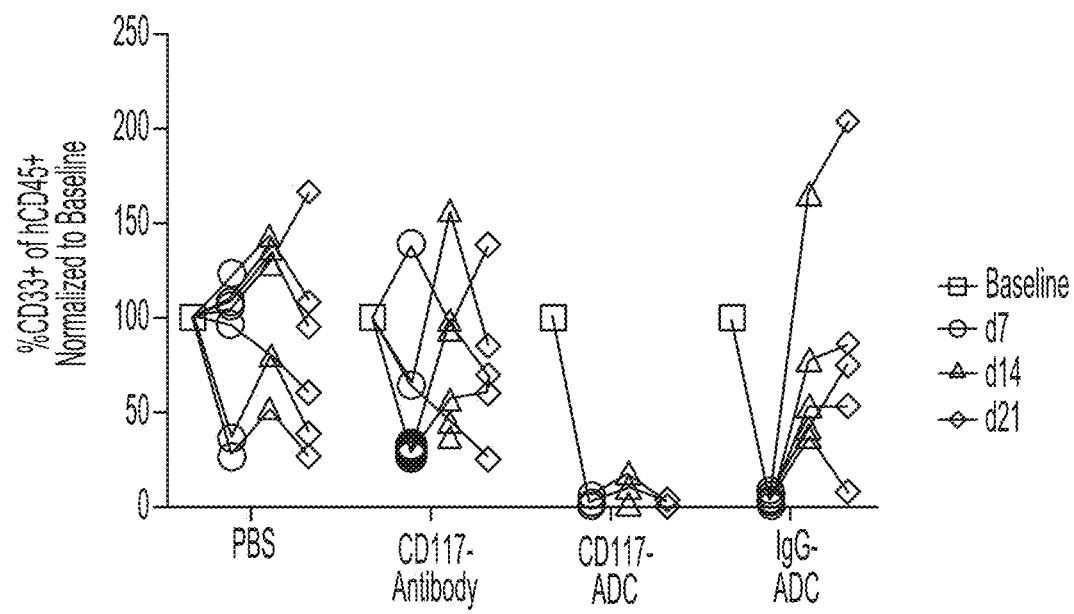
Figure 3C:
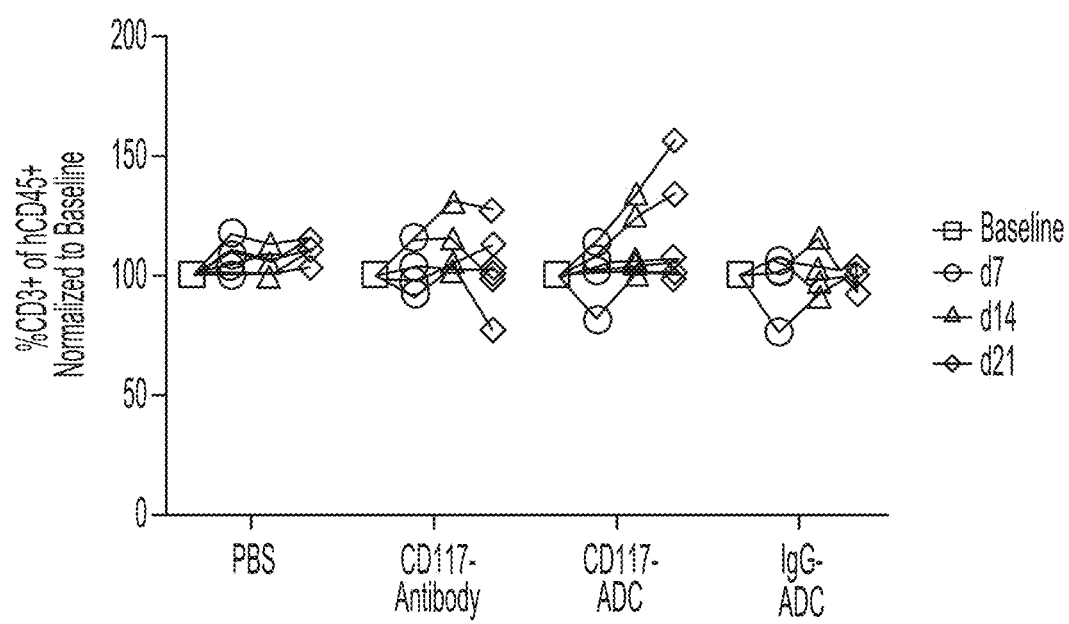

The anti-CD117 antibody used in the ADC in the following Example is antibody CK6 conjugated to an amatoxin. In vivo HSC depletion assays were conducted using humanized mice (purchased from Jackson Laboratories). As schematically shown in FIG. 3A, CD117-ADC (single injection of 0.3 mg/kg CD117-ADC) or controls were administered in a single dose on day 0 to the humanized NSG mice. PBMCs were collected on days 7, 14, and 21 and examined by flow cytometry. On day 21 (post injection), the presence or absence human CD34+ cells in the bone marrow was quantitated. The percent of human myeloid (FIG. 3B) or the percentage of T cells (FIG. 3C) present in the peripheral blood of CD117-ADC or control treated mice (non-CD117 binding isotype matched antibody), were determined and expressed as a percent of that cell population prior to treatment (normalized to baseline). The absolute number of CD34+ cells in the bone marrow of CD117-ADC or control treated mice 21 days after a single administration of the antibody drug conjugate are shown in FIG. 3D.

The results indicate that humanized NSG mice treated with CD117-ADC had greater than 90% depletion of human HSPCs in the bone marrow, 21 days following a single administration of the ADC. Similar results were obtained for CD34+ CD90+ and CD34+, CD90+, CD117+ cells (data not shown). The specificity of CD117-ADC for HSPCs was confirmed by the presence of stable peripheral human lymphocyte populations, and the absence of human myeloid cells, indicating a lack of stem and progenitor cells capable of replenishing these short-lived cells. Accordingly, these data indicate that the CD117-ADC depletes human CD34+ cells in the bone marrow of humanized NSG mice.

Example 3. In Vivo Tumor Study Using an Anti-CD117-ADC

Figures 4A, 4B:
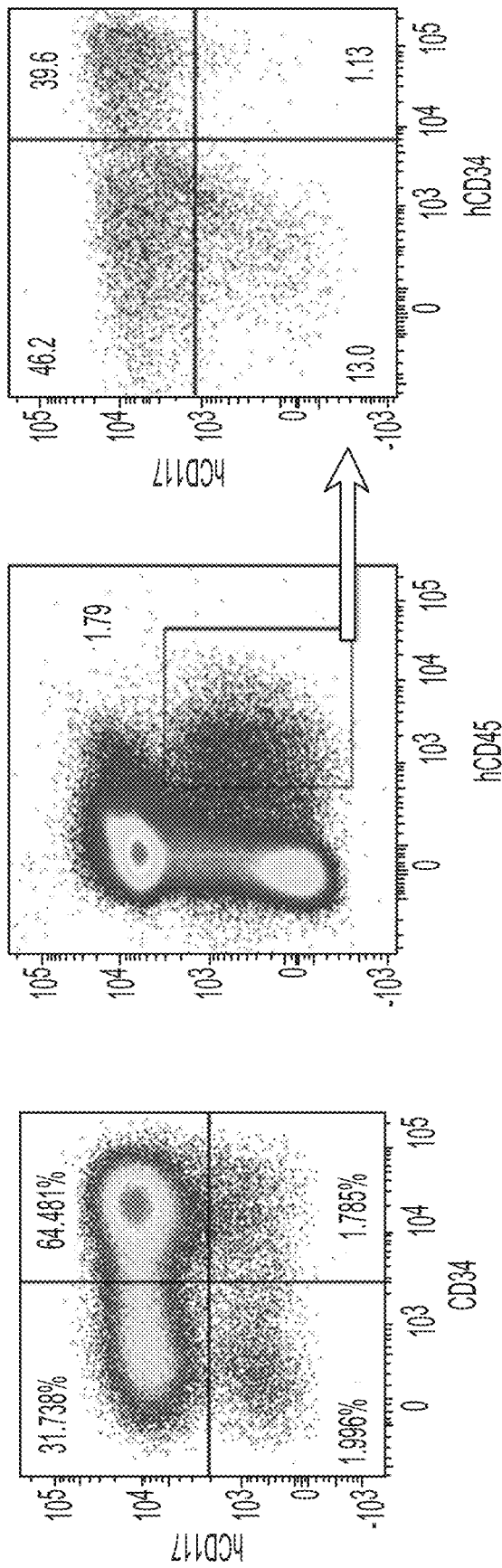

The anti-CD117 antibody used in the ADC and in the naked antibody used in the following Example is CK6. The drug conjugated to the CK6 antibody in this Example is an amatoxin. 5 million Kasumi-1 cells were IV injected into naïve NSG mice. On day 7 (FIG. 4C) or on day 42 (FIG. 4D) mice were treated with CD117-ADC (0.3 mg/kg) or controls (either 0.3 mg/kg or 1.0 mg/kg for CD117-antibody group). The bone marrow of mice was analyzed for the presence of Kasumi-1 cells following euthanasia. FIG. 4A depicts the phenotypic analysis of Kasumi-1 cells in culture. FIG. 4B depicts the phenotypic analysis of Kasumi-1 cells from bone marrow of tumor bearing mice at time of euthanasia. FIG. 4C graphically depicts the survival curve of mice treated with CD117-ADC or controls. FIG. 4D graphically depicts the survival curve of mice (with a greater tumor burden than those treated in FIG. 4C) treated with CD117-ADC or controls. There were at least 5 mice in the untreated, CD117-antibody, and CD117-ADC groups.

As demonstrated in FIG. 4C, the animals treated with a single dose of the anti-CD117-ADC show 100% survival, even at 150 days post-injection, while the animals administered the controls show significant decreases in percent survival at 110 days post-injection. As demonstrated in FIG. 4D, the animals treated with a single dose of the anti-CD117-ADC show 100% survival, even at 130 days post-injection, while the animals administered the controls show significant decreases in percent survival at 100 days post-injection. These results also indicate that the CD117-ADC was well tolerated at the doses given and enabled complete survival of the treated mice.

Example 4. In Vivo HSC Depletion/Engraftment Assays Using an Anti-CD117-ADC

The anti-CD117 antibody used in the ADC in the following example is 2B8.

Figure 5A:
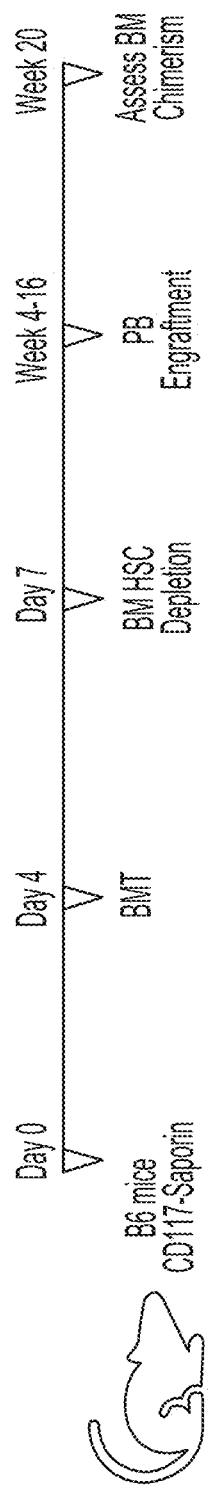
FIGS. 5A, 5B and 5C graphically depict the results of an in vivo cell depletion assay that shows CD117-ADC selectively depletes HSCs in B6 mice. (A) Schematic of an in vivo depletion assay in a B6 mouse model. (B) Shows the results of a mouse HSC depletion assay after the administration of a single dose of an anti-CD117-ADC (i.e., "CD117-Saporin") in comparison to controls (i.e., "control" and "isotype-Saporin"), expressed as the kit+SCA+CD150+ CD48− cell number (y-axis) as a function of a single injection of anti-CD117-ADC (i.e., "CD117-Saporin") or the controls (x-axis). (C) Shows the results of an engraftment assay, expressed as the percent donor chimerism (y-axis) as a function of treatment mode (i.e., "control," "isotype-Saporin" and "CD117-Saporin").
Figure 5C:
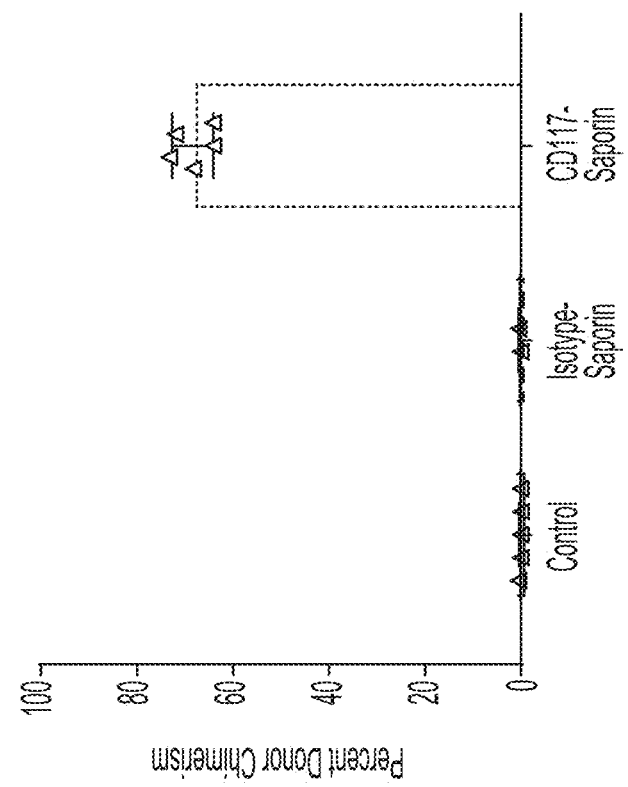
Figure 5B:
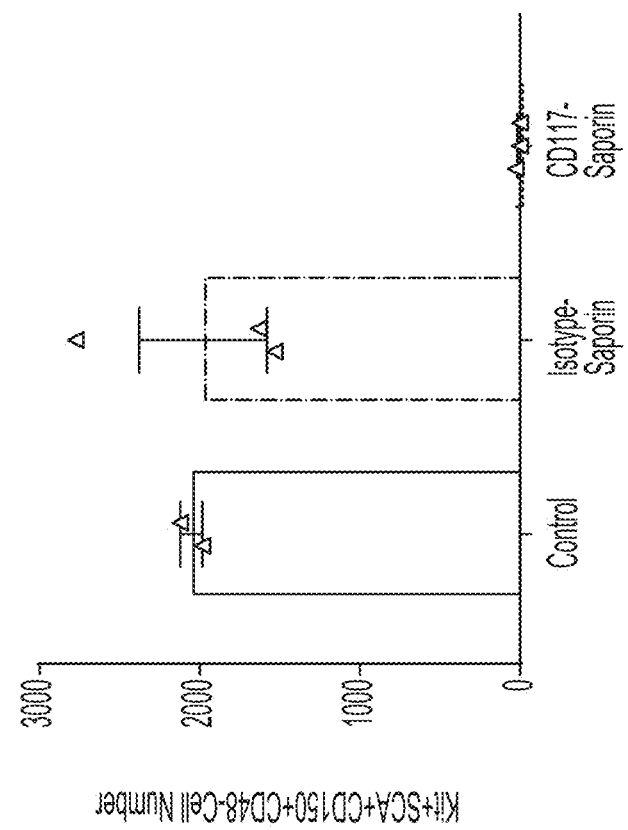

In vivo HSC depletion assays were conducted using B6 mice (purchased from Jackson Laboratories). As schematically shown in FIG. 5A, anti-CD117-ADC (single injection of 1.0 mg/kg i.v. anti-CD117-ADC) or controls were administered in a single dose on day 0 to the B6 mice. 4 days following the single administration of the anti-CD117 ADC, $1 \times 10^7$ donor CD45.1+ donor cells were infused. Blood was collected on weeks 4, 8, 16, 20 and bone marrow was collected on week 20 and examined by flow cytometry. Post-transplant, the presence or absence Kit+SCA+CD150+ CD48+ cells in the bone marrow was quantitated from the B6 mice treated with anti-CD117-ADC or a control (FIG. 5B). The percentage of donor chimerism in the B6 mice treated with anti-CD117-ADC or a control are shown in FIG. 5C.

The results indicate that B6 mice treated with anti-CD117-ADC (i.e., CD117-Saporin) had greater than 95% depletion of Kit+SCA+CD150+CD48+ cells, following a single administration of the ADC. Further, the results indicate that B6 mice treated with anti-CD117-ADC (i.e., CD117-Saporin) had greater than 70% donor chimerism post treatment, indicating that treatment with an anti-CD117-ADC (i.e., CD117-Saporin) enables robust donor engraftment.

Example 5. Analysis of Non-Human Primate Pharmacokinetics

Figure 6:
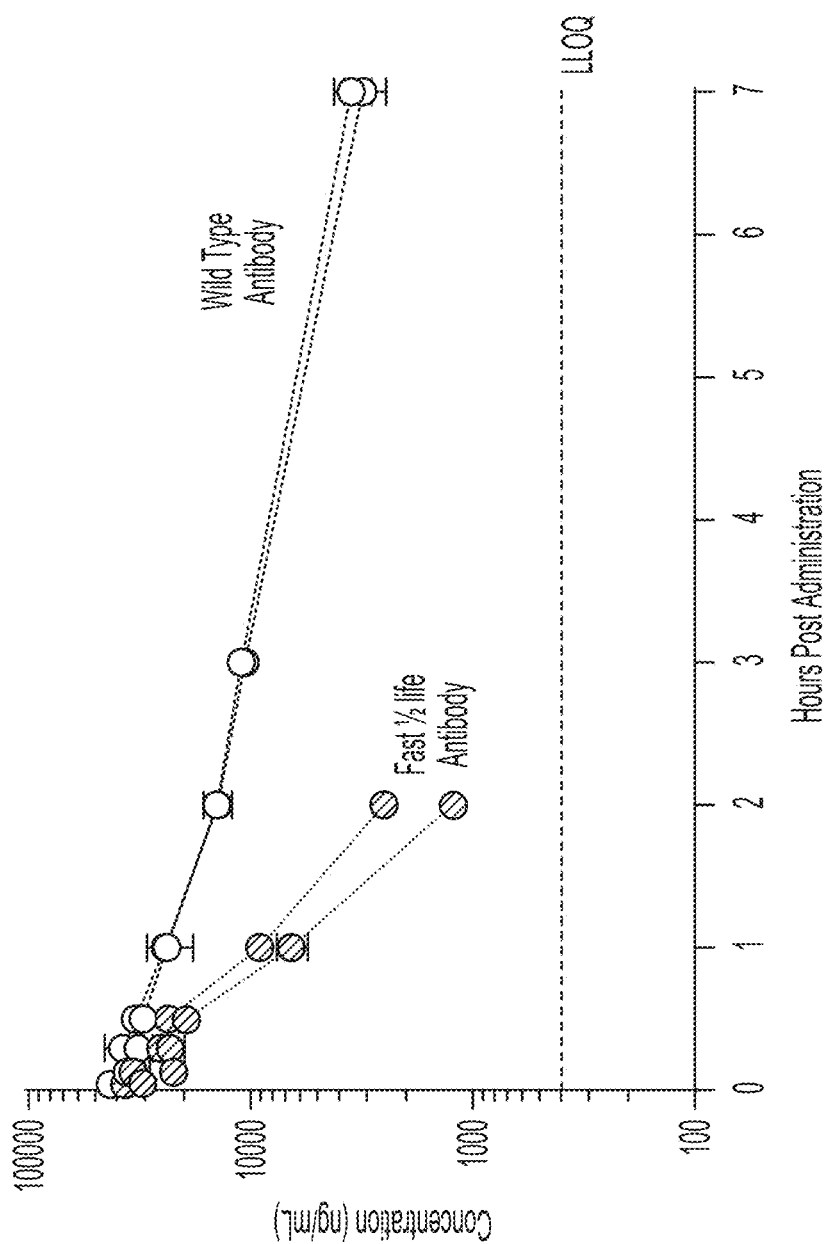
FIG. 6 graphically depicts the results of a non-human primate pharmacokinetic assay expressed as the concentration (ng/mL) of an isotype control antibody (i.e., "wild type antibody") in comparison to an CK6 variant antibody with a shorter half life as a function time (i.e., hours post-administration; x-axis).

A non-human primate pharmacokinetic assay was performed to determine the change in the concentration (ng/mL) of a isotype control antibody (i.e., "wild type antibody") compared to an Fc-modified CK6 variant antibody (i.e., an H435A Fc mutation; variant refers to the Fc modification) to possess a shorter half life as a function time (post-administration). The results in FIG. 6 demonstrate that the CK6 variant antibody is characterized by a significantly shorter half-life in a non-human primate.

Example 6. In Vivo HSC Depletion Assay Using an Anti-CD117-ADC

Figure 7A:
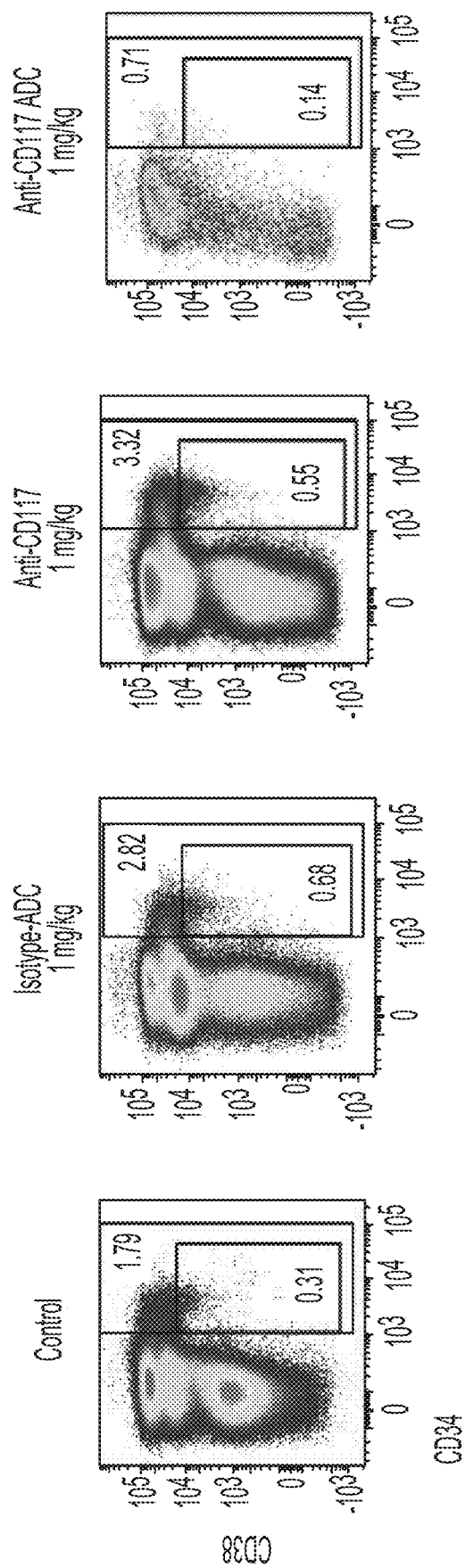
FIGS. 7A and 7B graphically depict the results of an in vivo depletion assay showing that CD117-ADC effectively depletes human CD34+ cells in humanized NSG mice. (A) Phenotypic analysis of human cells in NSG bone marrow at day 21 when treated with a single dose of (i) wild type anti-CD117-ADC, (ii) a CK6 variant anti-CD117-ADC with a shorter half life or (iii) a control. (B) Shows the results of a humanized NSG mouse depletion assay after the administration of a single dose of a wild type anti-CD117-ADC (mg/kg) in comparison to a CK6 variant anti-CD117-ADC with a shorter half life (mg/kg) and various controls (i.e., "control," "isotype-ADC (1 mg/kg)" and "Anti-CD117 (1 mg/kg)"), expressed as the CD34+ cell number per femur (y-axis) as a function of a single injection of (i) wild type anti-CD117-ADC, (ii) "short half life" variant anti-CD117-ADC or (iii) the controls (x-axis).

An experiment was performed to compare the Fc-modified CK6 variant antibody (i.e., an H435A Fc mutation; variant in this example refers to the Fc modification) from Example 5 to a wild-type anti-CD117 ADC (containing the CK6 antibody conjugated to an amatoxin). In vivo HSC depletion assays were conducted using humanized mice (purchased from Jackson Laboratories). The Fc-modified CK6 variant antibody (i.e., an H435A Fc mutation) from Example 5 was administered as a single injection of 1 mg/kg CD117-ADC, 0.3 mg/kg CD117-ADC, 0.1 mg/kg CD117-ADC, or 0.03 mg/kg CD117-ADC) to the humanized mouse model. In addition, a wild-type anti-CD117 ADC was similarly administered as a single injection of 1 mg/kg, 0.3 mg/kg, 0.1 mg/kg, or 0.03 mg/kg) to the humanized mice on day 0. Bone marrow was collected on day 21 and examined by flow cytometry (FIG. 7A). The absolute number of CD34+ cells in the bone marrow of treated or control treated mice on day 21 after a single administration of the treatment regimen are shown in FIG. 7B.

Figure 7B:
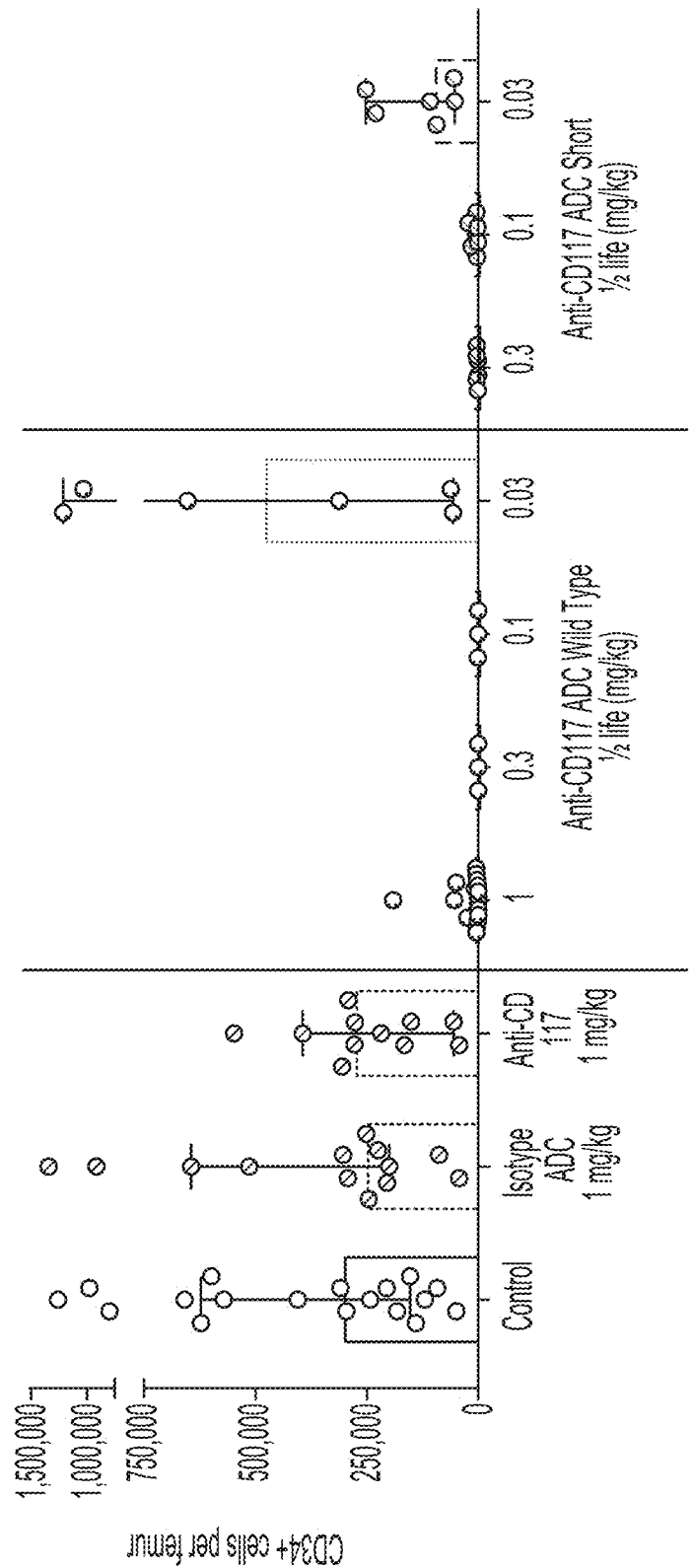

The results indicate that humanized NSG mice treated with both the Fc-modified CK6 variant antibody and the wild-type (unmodified Fc region) anti-CD117 ADC showed significant depletion of human HSPCs in the bone marrow, 21 days following a single administration of the ADC when compared to the controls (FIG. 7B). Further, flow cytometry data in FIG. 7A indicated that the wild-type anti-CD117-ADC significantly depleted human CD34+ cells in the bone marrow of humanized NSG mice compared to controls (i.e., an isotype ADC (1 mg/kg) and an anti-CD117 antibody (CK6) (1 mg/kg)).

Example 7. In Vivo HSC Depletion Assay Using an Anti-CD117-ADC

Figure 8A:
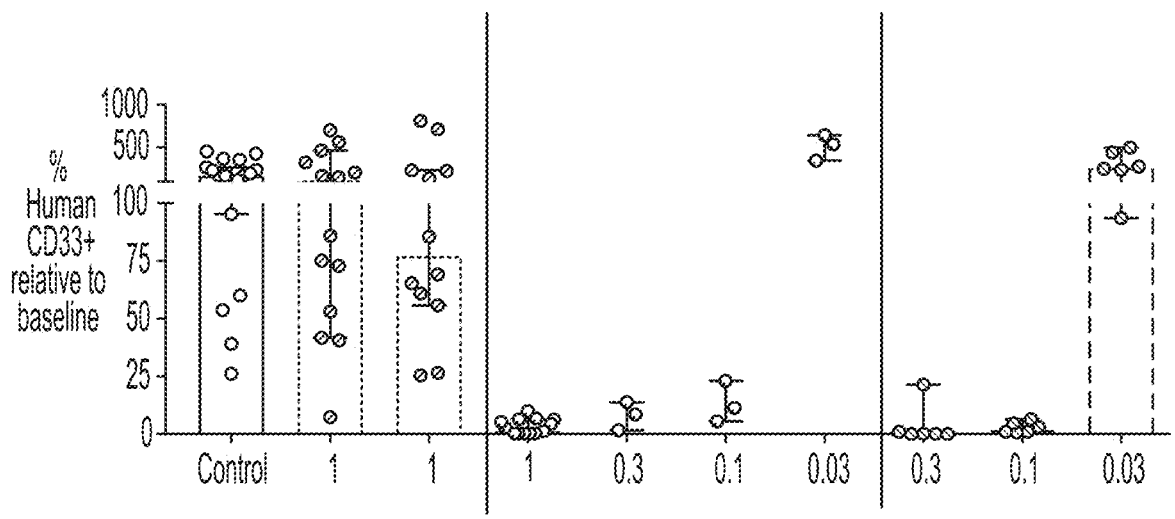
FIGS. 8A, 8B and 8C graphically depict the results of an in vivo human depletion assay showing that human peripheral lymphocytes are maintained 21 days after administration of a single dose of anti-CD117 ADC in a humanized mouse model. (A) Shows the percentage of human CD33+ cells (relative to baseline) maintained after 21 days in mice treated with various concentrations of a single dose of (i) a wild type anti-CD117-ADC (mg/kg), (ii) a CK6 variant anti-CD117-ADC with a shorter half life (mg/kg) or (iii) various controls (i.e., "control," "isotype-ADC (1 mg/kg)" and "Anti-CD117 (1 mg/kg)"). (B) Shows the percentage of human CD3+ cells (relative to baseline) maintained after 21 days in mice treated with various concentrations of a single dose of (i) a wild type anti-CD117-ADC (mg/kg), (ii) a CK6 variant anti-CD117-ADC with a shorter half life (mg/kg) or (iii) various controls (i.e., "control," "isotype-ADC (1 mg/kg)" and "Anti-CD117 (1 mg/kg)"). (C) Shows the percentage of human CD19+ cells (relative to baseline) maintained after 21 days in mice treated with various concentrations of a single dose of (i) a wild type anti-CD117-ADC (mg/kg), (ii) a CK6 variant anti-CD117-ADC with a shorter half life (mg/kg) or (iii) various controls (i.e., "control," "isotype-ADC (1 mg/kg)" and "Anti-CD117 (1 mg/kg)").
Figure 8B:
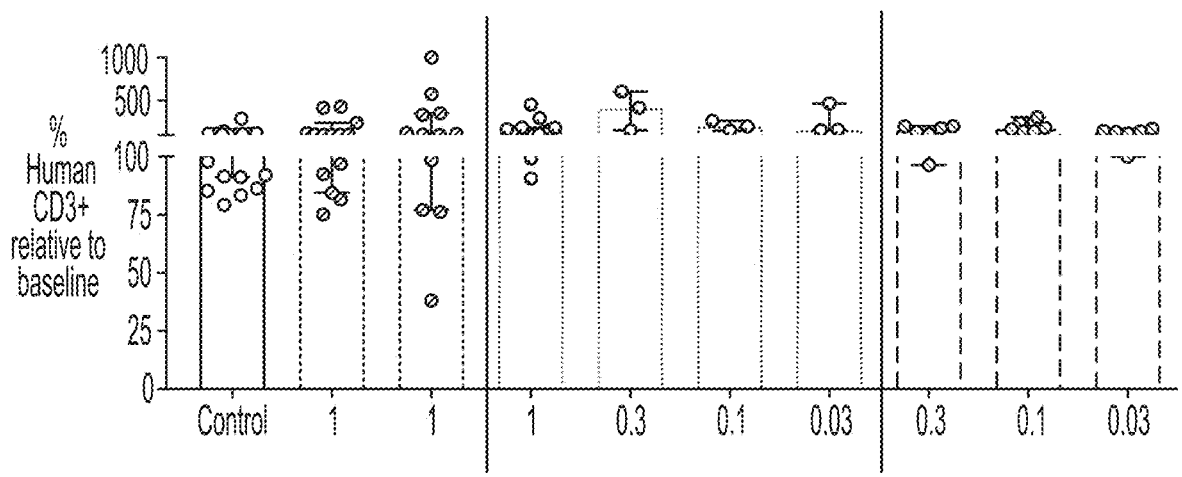
Figure 8C:
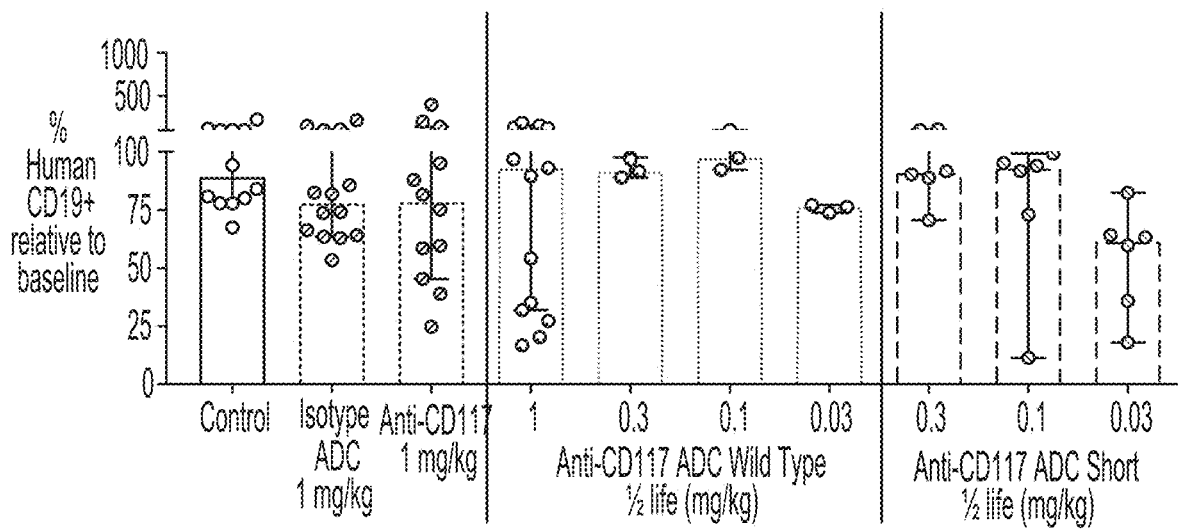
Figure 9A:
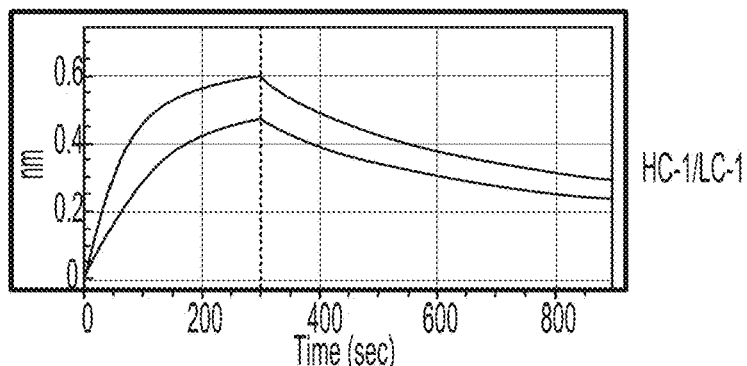
FIGS. 9A, 9B, 9C and 9D describe measurement of anti-CD117 antibody binding by Bio-Layer Interferometry (BLI) of the indicated purified IgG (sensor-associated) to purified human CD117 ectodomain (R&D Systems #332-SR) at concentrations of 33.3 nM (top trace) and 11 nM (bottom trace) as a function of time for the (A) HC-1/LC-1 (Ab1) antibody, (B) the HC-77/LC-77 (Ab 77) antibody, (C) the HC-79/LC-79 (Ab79) antibody, and (D) the HC-81/LC-81 (Ab81) antibody.
Figure 9B:
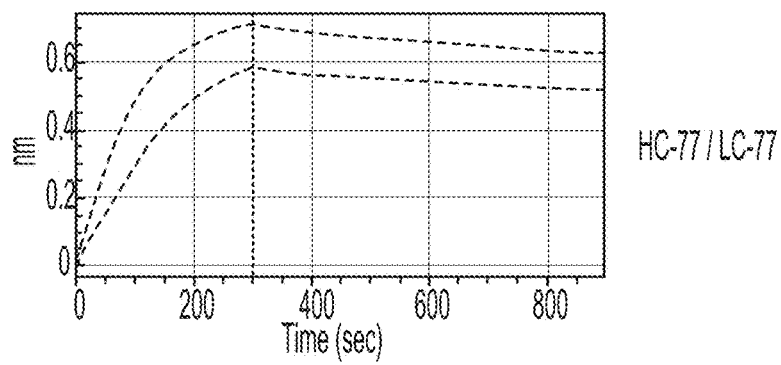
Figure 9C:
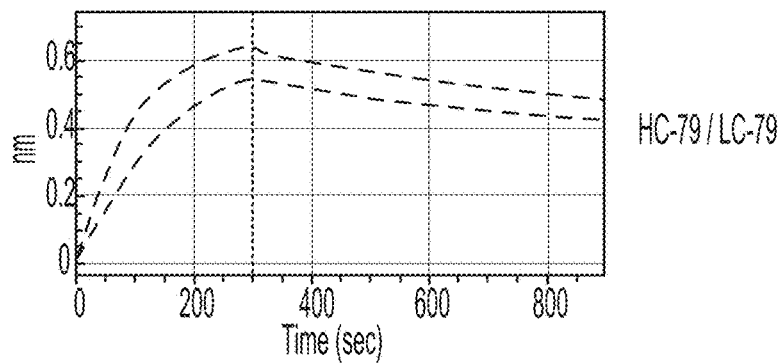
Figure 9D:
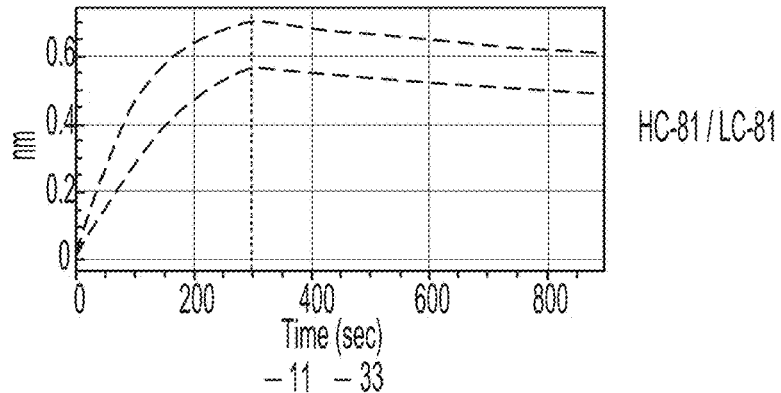

An additional experiment was performed to compare the Fc-modified CK6 variant antibody (i.e., an H435A Fc mutation; variant in this example refers to the Fc region) from Example 5 to a wild-type anti-CD117 ADC (CK6 antibody with an unsubstituted Fc region conjugated to an amatoxin). In vivo HSC depletion assays were conducted using humanized mice (purchased from Jackson Laboratories). The Fc-modified CK6 variant antibody (i.e., an H435A Fc mutation) from Example 5 was administered as a single injection of 1 mg/kg CD117-ADC, 0.3 mg/kg CD117-ADC, 0.1 mg/kg CD117-ADC, or 0.03 mg/kg CD117-ADC) to the humanized mouse model. In addition, a wild-type anti-CD117 ADC was similarly administered as a single injection of 1 mg/kg CD117-ADC, 0.3 mg/kg CD117-ADC, 0.1 mg/kg CD117-ADC, or 0.03 mg/kg CD117-ADC) to the humanized mice on day 0. Blood was collected on day 21 and examined by flow cytometry. The percentage of human CD33+(FIG. 8A), human CD3+(FIG. 8B), and human CD19+(FIG. 8C), of treated or control treated mice on day 21 relative to baseline are shown.

The results indicate that humanized NSG mice treated with the Fc-modified CK6 variant antibody and the wild-type anti-CD117 ADC showed significant depletion of human CD33+ myeloid cells (FIG. 8A) relative to baseline, 21 days following a single administration of the treatment regimen and indicate that both the anti-CD117 Fc-modified CK6 ADC and the wild-type anti-CD117 CK6 ADC depleted myeloid cells as a result of the depletion of early progenitor cells. Further, the results indicate that both the anti-CD117 Fc-modified CK6 ADC and the wild-type anti-CD117 CK6 ADC do not significantly deplete human peripheral lymphocytes, e.g., T cells (modeled as human CD3+ cells) and B cells (modeled as CD19+ cells) 21 days following a single administration of the treatment regimen.

Example 8. Identification of Novel Anti-CD117 Antibodies

A human Fab phage display library was created based on a derivative of the human CK6 antibody (i.e., HC-1/LC-1 (Ab1) in order to identify improved anti-CD117 antibodies that had better affinity properties than CK6 while maintaining the functional antagonistic and internalizing characteristics of CK6. The CK6 derivative used as the bases for the screen was Ab1, which is a variant of CK6 containing conservative amino acid substitutions within the light chain and heavy chain variable regions. Once the library was established, the screening process was performed according to standard phage display affinity maturation methodology known in the art. Briefly, the HC-1 was combined with a mixed donor-derived pool of human kappa light chains. Phage display selections were subsequently performed to selectively identify clones with improved off-rates after iterative rounds of panning. Antibodies were then screened to identify novel anti-CD117 antibodies with altered affinity to human CD117, e.g., an improved off rate of the antibody while maintaining kinetic characteristics of the CK6 antibody, including internalization.

To confirm binding to the desired target, purified antibodies were analyzed for binding to purified recombinant human CD117 ectodomain by bio-layer interferometry (BLI). Binding analysis of the antibodies identified from the phage display campaigns revealed a number of derivatives with improved off-rate kinetics as compared to HC-1/LC-1 (FIG. 1). The apparent kinetic values are provided in Table 4, which lists the apparent monovalent affinity ($K_D$), apparent association rate ($k_{on}$), and apparent dissociation rate ($k_{dis}$) of the indicated purified IgG to purified human CD117 ectodomain (R&D Systems #332-SR) as measured by BLI.

TABLE 4

| | $K_D$ (M) | $K_{on}$ (1/Ms) | $K_{dis}$ (1/s) |
|---|---|---|---|
| 001 (Ab1) | 2.81E-09 | 3.02E+05 | 8.48E-04 |
| 002 (Ab2) | 7.29E-10 | 3.70E+05 | 2.70E-04 |
| 003 (Ab3) | 1.02E-09 | 3.46E+05 | 3.52E-04 |
| 004 (Ab4) | 1.18E-09 | 3.45E+05 | 4.05E-04 |
| 005 (Ab5) | 1.21E-09 | 3.80E+05 | 4.61E-04 |
| 006 (Ab6) | 3.72E-09 | 3.15E+05 | 1.17E-03 |
| 007 (Ab7) | 9.90E-10 | 2.75E+05 | 2.72E-04 |
| 008 (Ab8) | 9.08E-10 | 2.90E+05 | 2.64E-04 |
| 009 (Ab9) | 1.51E-09 | 2.83E+05 | 4.27E-04 |
| 010 (Ab10) | 1.68E-09 | 3.48E+05 | 5.85E-04 |
| 011 (Ab11) | 1.41E-09 | 3.36E+05 | 4.74E-04 |
| 012 (Ab12) | 9.11E-10 | 2.94E+05 | 2.68E-04 |
| 013 (Ab13) | 1.55E-09 | 3.14E+05 | 4.88E-04 |
| 014 (Ab14) | 2.03E-09 | 2.84E+05 | 5.77E-04 |
| 015 (Ab15) | 9.79E-10 | 2.65E+05 | 2.60E-04 |
| 016 (Ab16) | 2.93E-09 | 3.24E+05 | 9.49E-04 |
| 017 (Ab17) | 6.72E-10 | 4.56E+05 | 3.06E-04 |
| 018 (Ab18) | 2.22E-08 | 2.21E+05 | 4.91E-03 |
| 019 (Ab19) | 2.35E-09 | 2.05E+05 | 4.81E-04 |
| 020 (Ab20) | 2.54E-10 | 7.94E+05 | 2.02E-04 |
| 021 (Ab21) | 7.15E-10 | 6.12E+05 | 4.37E-04 |
| 022 (Ab22) | 9.64E-11 | 2.29E+06 | 2.21E-04 |
| 023 (Ab23) | 1.49E-09 | 4.78E+05 | 7.13E-04 |
| 024 (Ab24) | 9.86E-10 | 1.11E+05 | 1.10E-04 |
| 025 (Ab25) | 5.20E-10 | 2.94E+06 | 1.53E-03 |
| 027 (Ab27) | 5.30E-10 | 7.12E+05 | 3.78E-04 |
| 028 (Ab28) | 4.03E-10 | 9.14E+05 | 3.68E-04 |

A subset of these antibodies were engineered to look at combinations of affinity modifying substitutions that had not been sampled in the phage display campaigns and may provide affinity benefit as cooperative sequence variations. Antibodies 77, 79, and 81 (Ab77, Ab79, and Ab81, respectively) representative examples of subsidiary derivatives and are described in more detail below.

Antibody 77 (Having HC-77/LC-77)

The heavy chain variable region (VH) amino acid sequence of Antibody 77 (Ab77) is provided below as SEQ ID NO: 7. The VH CDR amino acid sequences of Ab77 are underlined below and are as follows: TYWIG (VH CDR1; SEQ ID NO: 163); IIYPGDSDTRYSPSFQG (VH CDR2; SEQ ID NO: 2); and HGRGYNGYEGAFDI (VH CDR3; SEQ ID NO: 3).

```
Ab77 VH sequence
                                        (SEQ ID NO: 7)
QVQLVQSGAAVKKPGESLKISCKGSGYRFTTYWIGWVRQMPGKGLEWMG

IIYPGDSDTRYSPSFQGQVTISAGKSISTAYLQWSSLKASDTAMYYCAR

HGRGYNGYEGAFDIWGQGTMVTVSS
```

The light chain variable region (VL) amino acid sequence of Ab77 is provided below as SEQ ID NO 91. The VL CDR amino acid sequences of Ab77 underlined below and are as follows:

```
                                   (VL CDR1; SEQ ID NO: 164)
RASQGVISALA;

(VL CDR2; SEQ ID NO: 165)
DASILES;
and (VL CDR3; SEQ ID NO: 166)
QQFNSYPLT.
```

Ab77 VL sequence
(SEQ ID NO: 91)
DIQLTQSPSSLSASVGDRVTITC<u>RASQGVISALA</u>WYQQKPGKAPKLLIY <u>DASILES</u>GVPSRFSGSGSGTDFTLTISSLQPEDFATYYC<u>QQFNSYPLT</u>F

GGGTKVEIK

Antibody 79 (Having HC79/LC79)

The heavy chain variable region (VH) amino acid sequence of Ab79 is provided below as SEQ ID NO: 7. The VH CDR amino acid sequences of Ab79 are underlined below and are as follows:

(VH CDR1; SEQ ID NO: 163)
TYWIG;

(VH CDR2; SEQ ID NO: 2)
IIYPGDSDTRYSPSFQG;
and (VH CDR3; SEQ ID NO: 3)
HGRGYNGYEGAFDI.

Ab79 VH sequence
(SEQ ID NO: 7)
QVQLVQSGAAVKKPGESLKISCKGSGYRFT<u>TYWIG</u>WVRQMPGKGLEWMG <u>IIYPGDSDTRYSPSFQG</u>QVTISAGKSISTAYLQWSSLKASDTAMYYCAR <u>HGRGYNGYEGAFDI</u>WGQGTMVTVSS The light chain variable region (VL) amino acid sequence of Ab79 is provided below as SEQ ID NO: 93. The VL CDR amino acid sequences of Ab79 underlined below and are as follows:

(VL CDR1; SEQ ID NO: 167)
RASQGVGSALA;

(VL CDR2; SEQ ID NO: 165)
DASILES;
and (VL CDR3; SEQ ID NO: 166)
QQFNSYPLT.

Ab79 VL sequence
(SEQ ID NO: 93)
DIQLTQSPSSLSASVGDRVTITC<u>RASQGVGSALA</u>WYQQKPGKAPKLLIY <u>DASILES</u>GVPSRFSGSGSGTDFTLTISSLQPEDFATYYC<u>QQFNSYPLT</u>F

GGGTKVEIK

Antibody 81 (Having HC-81/LC-81)

The heavy chain variable region (VH) amino acid sequence of Ab81 is provided below as SEQ ID NO: 7. The VH CDR amino acid sequences of Ab81 underlined below and are as follows: TYWIG (VH CDR1; SEQ ID NO: 163); IIYPGDSDTRYSPSFQG (VH CDR2; SEQ ID NO: 2); and HGRGYNGYEGAFDI (VH CDR3; SEQ ID NO: 3).

Ab81 VH sequence
(SEQ ID NO: 7)
QVQLVQSGAAVKKPGESLKISCKGSGYRFT<u>TYW</u>

<u>IG</u>WVRQMPGKGLEWMG<u>IIYPGDSDTRYSPSFQG</u>

QVTISAGKSISTAYLQWSSLKASDTAMYYCAR<u>H</u>

<u>GRGYNGYEGAFDI</u>WGQGTMVTVSS

The light chain variable region (VL) amino acid sequence of Ab81 is provided below as SEQ ID NO 95. The VL CDR amino acid sequences of Ab81 underlined below and are as follows:

(VL CDR1; SEQ ID NO: 164)
RASQGVISALA;
and (VL CDR2; SEQ ID NO: 168)
DASTLES;

(VL CDR3; SEQ ID NO: 166)
QQFNSYPLT.

Ab81 VL sequence
(SEQ ID NO: 95)
DIQLTQSPSSLSASVGDRVTITC<u>RASQGVISALA</u>W

YQQKPGKAPKLLIY<u>DASTLES</u>GVPSRFSGSGSGTD

FTLTISSLQPEDFATYYC<u>QQFNSYPLT</u>FGGGTKVE

IK

This subset of clones consisting of library output iterations in the CDR1 and CDR2 of the light chain allowed for the analysis of cooperative substitutions in subsequent in vitro binding assays.

Example 9. In Vitro Antibody Binding Studies

Antibodies identified in Example 8 were tested for binding. Antibody binding studies were performed at 25 degrees celsius in 1×PBS supplemented with 0.1% w/v bovine serum albumin with a Pall ForteBio Octet Red96 using biolayer interferometry (BLI). The indicated purified human antibody (as an IgG1) was immobilized onto anti-human Fc biosensors (AHC; Pall ForteBio 18-5063) and incubated with 33.3 nM and 11 nM CD117 ectodomain (R&D Systems #332-SR)

The resulting binding intervals, which represented the association and dissociation curves were depicted in FIG. 9. The apparent monovalent affinity (KD), apparent association rate (kon), and apparent dissociation rate (kdis) are determined by local full fitting with a 1:1 binding mode as calculated by Fortebio data analysis software version 10 of the indicated purified IgG (i.e., the HC-77/LC-106 IgG; HC-109/LC-110 IgG; and HC-113/LC-114 IgG) to purified human CD117 ectodomain (R&D Systems #332-SR) were depicted in Table 5. Table 5 lists the apparent monovalent affinity ($K_D$), apparent association rate ($k_{on}$), and apparent dissociation rate ($k_{OFF}$) of the indicated purified IgG to purified human CD117 ectodomain (R&D Systems #332-SR). The results demonstrate a purified IgG (i.e., the HC-77/LC-77 IgG; HC-79/LC-79 IgG; and HC-81/LC-81 IgG) binds with high affinity to the purified human CD117 ectodomain and is characterized by a significantly slower kdis (1/s) when compared to the HC-1/LC-1 purified IgG.

TABLE 5

| Antibody | $K_D$ (M) | $K_{on}$ (1/Ms) | $K_{dis}$ (1/s) |
|---|---|---|---|
| HC-1/LC-1 (Ab1) (control) | $3.10 \times 10^{-9}$ | $4.20 \times 10^{5}$ | $1.30 \times 10^{-3}$ |
| HC-77/LC-77 (Ab77) | $6.84 \times 10^{-10}$ | $3.15 \times 10^{5}$ | $2.15 \times 10^{-4}$ |
| HC-79/LC-79 (Ab79) | $1.52 \times 10^{-9}$ | $3.16 \times 10^{5}$ | $4.78 \times 10^{-4}$ |
| HC-81/LC-81 (Ab81) | $8.77 \times 10^{-10}$ | $2.88 \times 10^{5}$ | $2.52 \times 10^{-4}$ |

As described in Table 5, each of antibodies Ab77, Ab79, and Ab81 had improved binding ($K_D$) compared to parent antibody Ab1. Surprisingly, the high level of affinity was maintained, while improving the dissocation rate.

Example 10. Identification of Anti-CD117 Antibody 85 (Ab85), Anti-CD117 Antibody 86 (Ab86), Anti-CD117 Antibody 87 (Ab87), Anti-CD117 Antibody 88 (Ab88), and Anti-CD117 Antibody 89 (Ab89)

In addition to the screen described in Examples 8 and 9, a second screen based on antibody CK6 was also performed. An scFv phage display library was created based on a derivative of the human CK6 antibody (as in Example 8 the CK6 variant was Ab1). Briefly, a small synthetic library of CDRH3 variants was generated to remove a potential deamidation site (NG) and was introduced into a large diversity library of either the IGHV5-51 or the IGHV1-46 human framework. This screen was a challenge given the position of the amino acid in the CDR3 region of the heavy chain. The synthetic library was combined with a large diversity library of the IGKV1-39 light chain human framework. Phage display selections were then performed to selectively identify clones with improved off-rates after iterative rounds of panning. Antibodies were then screened to identify novel anti-CD117 antibodies with improved affinity to human CD117. Certain antibodies, including the antibodies identified below, were identified using the screen.

Antibodies 85 (Ab85), 86 (Ab86), 87 (Ab87), 88 (Ab88), and 89 (Ab89) were identified in the screen as a novel therapeutic human anti-CD117 antibody. The heavy chain and light chain variable regions of Ab85, Ab86, Ab87, Ab88, and Ab89 (including the CDR domains) are described below in Table 6.

TABLE 6

| Antibody name | Backbone | Amino acid sequence |
|---|---|---|
| HC-85 | hIgG1 | EVQLVQSGAEVKKPGESLKISCKGSGYSFTNYWIGWV RQMPGKGLEWMAIINPRDSDTRYRPSFQGQVTISADK SISTAYLQWSSLKASDTAMYYCARHGRGYEGYEGAFDI WGQGTLVTVSS (SEQ ID NO: 143) |
| LC-85 | hKappa | DIQMTQSPSSLSASVGDRVTITCRSSQGIRSDLGWYQQ KPGKAPKLLIYDASNLETGVPSRFSGSGSGTDFTLTIS SLQPEDFATYYCQQANGFPLTFGGGTKVEIK (SEQ ID NO: 144) |
| HC-86 | hIgG1 | EVQLVQSGAEVKKPGESLKISCKGSGYSFTNYWIGWV RQMPGKGLEWMGIIYPGDSDIRYSPSLQGQVTISVDTS TSTAYLQWNSLKPSDTAMYYCARHGRGYNGYEGAFDI WGQGTLVTVSS (SEQ ID NO: 151) |
| LC-86 | hKappa | DIQMTQSPSSLSASVGDRVTITCRASQGIGDSLAWYQQ KPGKAPKLLIYDASNLETGVPSRFSGSGSGTDFTLTIS SLQPEDFATYYCQQLNGYPITFGQGTKVEIK (SEQ ID NO: 152) |
| HC-87 | hIgG1 | EVQLVQSGAEVKKPGESLKISCKGSGYSFTNYWIGWV RQMPGKGLEWMAIINPRDSDTRYRPSFQGQVTISADK SISTAYLQWSSLKASDTAMYYCARHGRGYEGYEGAFDI WGQGTLVTVSS (SEQ ID NO: 143) |
| LC-87 | hKappa | DIQMTQSPSSLSASVGDRVTITCRASQGIRNDLGWYQQ KPGKAPKLLIYDASSLESGVPSRFSGSGSGTDFTLTIS SLQPEDFATYYCQQLNGYPITFGQGTKVEIK (SEQ ID NO: 156) |
| HC-88 | hIgG1 | EVQLVQSGAEVKKPGESLKISCKGSGYSFTNYWIGWV RQMPGKGLEWMGIIYPGDSLTRYSPSFQGQVTISADKS ISTAYLQWSSLKASDTAMYYCARHGRGYNGYEGAFDI WGQGTLVTVSS (SEQ ID NO: 158) |
| LC-88 | hKappa | DIQMTQSPSSLSASVGDRVTITCRASQGIRNDLGWYQQ KPGKAPKLLIYDASSLESGVPSRFSGSGSGTDFTLTIS SLQPEDFATYYCQQLNGYPITFGQGTKVEIK (SEQ ID NO: 156) |
| HC-89 | hIgG1 | EVQLVQSGAEVKKPGESLKISCKGSGYSFTNYWIGWV RQMPGKGLEWMGIIYPGDSDTRYSPSFQGQVTISADK SISTAYLQWSSLKASDTAMYYCARHGRGYNGYEGAFDI WGQGTLVTVSS (SEQ ID NO: 160) |
| LC-89 | hKappa | DIQMTQSPSSLSASVGDRVTITCRASQGIGDSLAWYQQ KPGKAPKLLIYDASNLETGVPSRFSGSGSGTDFTLTIS SLQPEDFATYYCQQLNGYPITFGQGTKVEIK (SEQ ID NO: 152) |

Antibody HC-85/LC-85 (Ab 85)

The heavy chain variable region (VH) amino acid sequence of Ab85 is provided below as SEQ ID NO: 143. The VH CDR amino acid sequences of Ab85 underlined below and are as follows:

```
                                (VH CDR1; SEQ ID NO: 145)
    NYWIG;

(VH CDR2; SEQ ID NO: 146)
    IINPRDSDTRYRPSFQG;

and
                                (VH CDR3; SEQ ID NO: 147)
    HGRGYEGYEGAFDI.

Ab85 VH sequence
                                         (SEQ ID NO: 143)
    EVQLVQSGAEVKKPGESLKISCKGSGYSFTNYWIGWV

RQMPGKGLEWMAIINPRDSDTRYRPSFQGQVTISADK

SISTAYLQWSSLKASDTAMYYCARHGRGYEGYEGAFD

IWGQGTLVTVSS
```

The light chain variable region (VL) amino acid sequence of Ab85 is provided below as SEQ ID NO 144. The VL CDR amino acid sequences of Ab85 underlined below and are as follows:

```
                                (VL CDR1; SEQ ID NO: 148)
    RSSQGIRSDLG;

(VL CDR2; SEQ ID NO: 149)
    DASNLET;
    and
                                (VL CDR3; SEQ ID NO: 150)
    QQANGFPLT.

Ab85 VL sequence
                                         (SEQ ID NO: 144)
    DIQMTQSPSSLSASVGDRVTITCRSSQGIRSDLG

WYQQKPGKAPKLLIYDASNLETGVPSRFSGSGSG

TDFTLTISSLQPEDFATYYCQQANGFPLTFGGGT

KVEIK
```

Antibody HC-86/LC-86 (Ab86)

The heavy chain variable region (VH) amino acid sequence of Ab86 is provided below as SEQ ID NO: 151. The VH CDR amino acid sequences Ab86 underlined below and are as follows: NYWIG (VH CDR1; SEQ ID NO: 145); IIYPGDSDIRYSPSLQG (VH CDR2; SEQ ID NO: 153); and HGRGYNGYEGAFDI (VH CDR3; SEQ ID NO: 3).

```
Ab86 VH sequence
                             (SEQ ID NO: 151)
EVQLVQSGAEVKKPGESLKISCKGSYSFT NYW
IGWVRQMPGKGLEWMGIIYPGDSDIRYSPSLQG
QVTISVDTSTSTAYLQWNSLKPSDTAMYYCARH
GRGYNGYEGAFDIWGQGTLVTVSS
```

The light chain variable region (VL) amino acid sequence of Ab86 is provided below as SEQ ID NO 152. The VL CDR amino acid sequences of Ab86 underlined below and are as follows:

```
                             (VL CDR1; SEQ ID NO: 154)
RASQGIGDSLA;
                             (VL CDR2; SEQ ID NO: 149)
DASNLET;
and
                             (VL CDR3; SEQ ID NO: 155)
QQLNGYPIT.
Ab86 VL sequence
                             (SEQ ID NO: 152)
DIQMTQSPSSLSASVGDRVTITCRASQGIGDSLA
WYQQKPGKAPKLLIYDASNLETGVPSRFSGSGSG
TDFTLTISSLQPEDFATYYCQQLNGYPITFGQGT
KVEIK
```

Antibody HC-87/LC-87 (Ab87)

The heavy chain variable region (VH) amino acid sequence of Ab87 is provided below as SEQ ID NO: 143. The VH CDR amino acid sequences of Ab87 are underlined below and are as follows:

```
                             (VH CDR1; SEQ ID NO: 145)
NYWIG;
                             (VH CDR2; SEQ ID NO: 146)
IINPRDSDTRYRPSFQG;
and
                             (VH CDR3; SEQ ID NO: 147)
HGRGYEGYEGAFDI.
Ab87 VH sequence
                             (SEQ ID NO: 143)
EVQLVQSGAEVKKPGESLKISCKGSYSFTNYWIGW
VRQMPGKGLEWMAIINPRDSDTRYRPSFQGQVTISA
DKSISTAYLQWSSLKASDTAMYYCARHGRGYEGYEG
AFDIWGQGTLVTVSS
```

The light chain variable region (VL) amino acid sequence of Ab87 is provided below as SEQ ID NO 156. The VL CDR amino acid sequences of Ab87 underlined below and are as follows:

```
                             (VL CDR1; SEQ ID NO: 157)
RASQGIRNDLG;
                             (VL CDR2; SEQ ID NO: 5)
DASSLES;
and
                             (VL CDR3; SEQ ID NO: 155)
QQLNGYPIT.
Ab87 VL sequence
                             (SEQ ID NO: 156)
DIQMTQSPSSLSASVGDRVTITCRASQGIRNDLGW
YQQKPGKAPKLLIYDASSLESGVPSRFSGSGSTD
FTLTISSLQPEDFATYYCQQLNGYPITFGQGTKVE
IK
```

Antibody HC-88/LC-88 (Ab88)

The heavy chain variable region (VH) amino acid sequence of Ab88 is provided below as SEQ ID NO: 158. The VH CDR amino acid sequences of Ab88 are underlined below and are as follows:

```
                             (VH CDR1; SEQ ID NO: 145)
NYWIG;
                             (VH CDR2; SEQ ID NO: 159)
IIYPGDSLTRYSPSFQG;
and
                             (VH CDR3; SEQ ID NO: 3)
HGRGYNGYEGAFDI.
Ab88 VH sequence
                             (SEQ ID NO: 158)
EVQLVQSGAEVKKPGESLKISCKGSGYSFTNYWIGWVRQ
MPGKGLEWMGIIYPGDSLTRYSPSFQGQVTISADKSIST
AYLQWSSLKASDTAMYYCARHGRGYNGYEGAFDIWGQGT
LVTVSS
```

The light chain variable region (VL) amino acid sequence of Ab88 is provided below as SEQ ID NO: 156. The VL CDR amino acid sequences of Ab88 underlined below and are as follows:

```
                             (VL CDR1; SEQ ID NO: 157)
RASQGIRNDLG;
                             (VL CDR2; SEQ ID NO: 5)
DASSLES;
and
                             (VL CDR3; SEQ ID NO: 155)
QQLNGYPIT.
Ab88 VL sequence
                             (SEQ ID NO: 156)
DIQMTQSPSSLSASVGDRVTITCRASQGIRNDLGWYQQK
PGKAPKLLIYDASSLESGVPSRFSGSGSGTDFTLTISSL
QPEDFATYYCQQLNGYPITFGQGTKVEIK
```

Antibody HC-89/LC-89 (Ab89)

The heavy chain variable region (VH) amino acid sequence of Ab89 is provided below as SEQ ID NO: 160. The VH CDR amino acid sequences of Ab89 are underlined below and are as follows:

```
                                   (VH CDR1; SEQ ID NO: 145)
NYWIG;

(VH CDR2; SEQ ID NO: 2);
IIYPGDSDTRYSPSFQG
and (VH CDR3; SEQ ID NO: 3)
HGRGYNGYEGAFDI.

Ab89 VH sequence
                                   (SEQ ID NO:160)
EVQLVQSGAEVKKPGESLKISCKGSGYSFTNYWIG

WVRQMPGKGLEWMGIIYPGDSDTRYSPSFQGQVTI

SADKSISTAYLQWSSLKASDTAMYYCARHGRGYNG

YEGAFDIWGQGTLVTVSS
```

The light chain variable region (VL) amino acid sequence of Ab89 is provided below as SEQ ID NO: 152. The VL CDR amino acid sequences of Ab89 underlined below and are as follows:

```
                                   (VL CDR1; SEQ ID NO: 154)
RASQGIGDSLA;

(VL CDR2; SEQ ID NO: 149)
DASNLET;
and (VL CDR3; SEQ ID NO: 155)
QQLNGYPIT.

Ab89 VL sequence
                                   (SEQ ID NO: 152)
DIQMTQSPSSLSASVGDRVTITCRASQGIGDSLAW

YQQKPGKAPKLLIYDASNLETGVPSRFSGSGSGTD

FTLTISSLQPEDFATYYCQQLNGYPITFGQGTKVE

IK
```

Example 11. In Vitro Binding Studies of Antibody 85, Antibody 86, Antibody 87, Antibody 88, and Antibody 89

Figure 10A:
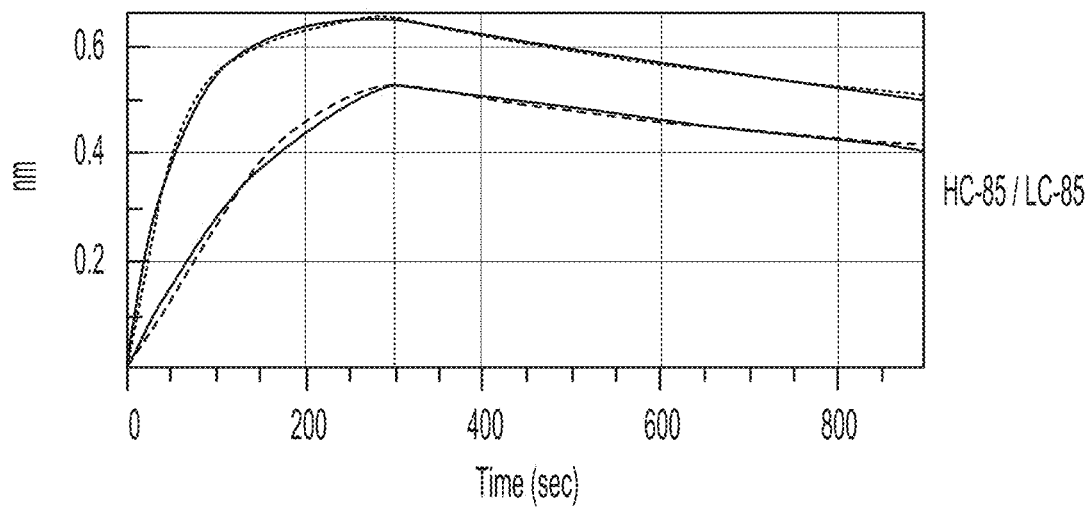
FIGS. 10A and 10B demonstrate the measurement of binding by Bio-Layer Interferometry (BLI) of the indicated purified IgG (sensor-associated) to purified human CD117 ectodomain (R&D Systems #332-SR) at concentrations of 33.3 nM (top traces) and 11 nM (bottom traces) as a function of time for the (A) HC-85/LC-85 antibody and the (B) HC-1/LC-1 antibody.
Figure 10B:
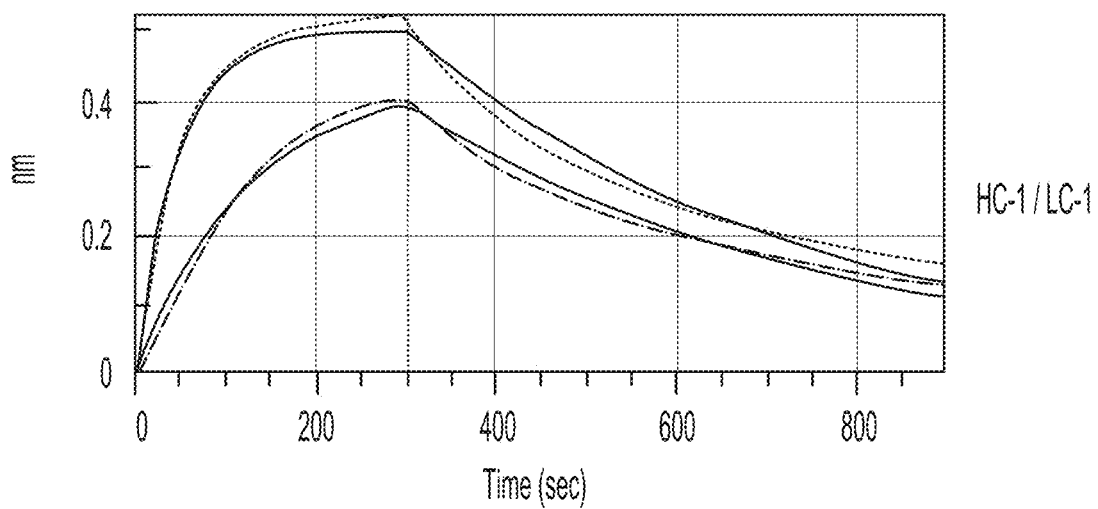

Ab85, Ab86, Ab87, Ab88, and Ab89 were further studied for binding characteristics using standard Octet binding. Antibody binding studies were performed at 25 degrees celsius in 1×PBS supplemented with 0.1% w/v bovine serum albumin with a Pall ForteBio Octet Red96 using biolayer interferometry (BLI). The indicated purified human antibody was immobilized onto anti-human Fc biosensors (AHC; Pall ForteBio 18-5063) and incubated with 33.3 nM (top traces) and 11 nM (bottom traces) CD117 ectodomain (R&D Systems #332-SR). The resulting binding intervals, which represented the association and dissociation curves were depicted in FIGS. 10A (i.e., HC-85/LC-85) and 10B (i.e., HC-1/LC-1). The apparent monovalent affinity ($K_D$), apparent association rate (kon), and apparent dissociation rate (kdis) of the indicated purified IgG (i.e., HC-85/LC-85) to purified human CD117 ectodomain (R&D Systems #332-SR) compared to a control (i.e., HC-1/LC-1) were depicted in Table 7. The results demonstrate a purified IgG (i.e., the HC-85/LC-85 IgG) binds with high affinity to the purified human CD117 ectodomain and is characterized by a slow kdis (1/s) relative to the parent Ab1 antibody. Thus, despite the modification in the HCDR3, binding affinity was improved, i.e., with a slower dissociation rate, and the demaidation site was removed.

TABLE 7

| | $K_D$ (M) | $K_{on}$ (1/Ms) | $K_{dis}$ (1/s) |
|---|---|---|---|
| HC-85/LC-85 (Ab85) | $8.35 \times 10^{-10}$ | $5.20 \times 10^5$ | $4.34 \times 10^{-4}$ |
| HC-1/LC-1 (Ab1) | $4.09 \times 10^{-9}$ | $5.56 \times 10^5$ | $2.27 \times 10^{-3}$ |

A comparison of the amino acid sequences of the heavy and light chain variable regions and CDRs of Ab85 and Ab1 is described in FIGS. 11A and 11B.

Example 12. Identification of Novel Anti-CD117 Antibodies

Having identified a number of improved anti-CD117 antibodies derived from anti-CD117 antibody CK6, combinations of antigen binding regions (variable regions) from antibodies identified in Examples 8-11 were then tested for binding.

To identify further anti-CD117 antibodies with advantageous therapeutic properties, heavy chain and light chain sequences disclosed here were mixed and matched to create novel anti-CD117 antibodies. The following antibodies were identified from this process as preferred anti-CD117 antibodies: HC-245/LC-245 (i.e., Ab245), HC-246/LC-246 (i.e., Ab246), HC-247/LC-247 (i.e., Ab247), HC-248/LC-248 (i.e., Ab248), and HC-249/LC-249 (i.e., Ab249).

TABLE 8

| Antibody name | Backbone | Amino acid sequence |
|---|---|---|
| HC-245 | hIgG1 | EVQLVQSGAEVKKPGESLKISCKGSGYRFTTSWIGWV RQMPGKGLEWMGIIYPGDSDTRYSPSFQGQVTISADK SISTAYLQWSSLKASDTAMYYCARHGLGYNGYEGAFDI WGQGTLVTVSS (SEQ ID NO: 98) |
| LC-245 | hKappa | DIQMTQSPSSLSASVGDRVTITCRASQGIGSALAWYQQ KPGKAPKLLIYDASTLESGVPSRFSGSGSGTDFTLTISS LQPEDFATYYCQQFNGYPLTFGQGTRLEIK (SEQ ID NO: 99) |
| HC-246 | hIgG1 | QVQLVQSGAAVKKPGESLKISCKGSGYRFTTYWIGWV RQMPGKGLEWMGIIYPGDSDTRYSPSFQGQVTISAGK SISTAYLQWSSLKASDTAMYYCARHGRGYNGYEGAFDI WGQGTMVTVSS (SEQ ID NO: 7) |

TABLE 8-continued

| Antibody name | Backbone | Amino acid sequence |
|---|---|---|
| LC-246 | hKappa | DIQMTQSPSSLSASVGDRVTITCRASQGIGSALAWYQQKPGKAPKLLIYDASTLESGVPSRFSGSGSGTDFTLTISSLQPEDFATYYCQQFNGYPLTFGQGTRLEIK (SEQ ID NO: 99) |
| HC-247 | hIgG1 | QVQLVQSGAAVKKPGESLKISCKGSGYRFTTYWIGWVRQMPGKGLEWMGIIYPGDSDTRYSPSFQGQVTISAGKSISTAYLQWSSLKASDTAMYYCARHGRGYNGYEGAFDIWGQGTMVTVSS (SEQ ID NO: 7) |
| LC-247 | hKappa | DIQMTQSPSSLSASVGDRVTITCRASRGISDYLAWYQQKPGKAPKLLIYDASNLETGVPSRFSGSGSGTDFTLTISSLQPEDFATYYCQQANSFPITFGQGTRLEIK (SEQ ID NO: 100) |
| HC-248 | hIgG1 | EVQLVQSGAEVKKPGESLKISCKGSGYRFTTSWIGWVRQMPGKGLEWMGIIYPGDSDTRYSPSFQGQVTISADKSISTAYLQWSSLKASDTAMYYCARHGLGYNGYEGAFDIWGQGTLVTVSS (SEQ ID NO: 98) |
| LC-248 | hKappa | DIQMTQSPSSLSASVGDRVTITCRASQGIGSALAWYQQKPGKAPKLLIYDASTLESGVPSRFSGSGSGTDFTLTISSLQPEDFATYYCQQLNGYPLTFGQGTRLEIK (SEQ ID NO: 101) |
| HC-249 | hIgG1 | EVQLVQSGAEVKKPGESLKISCKGSGYRFTTSWIGWVRQMPGKGLEWMGIIYPGDSDTRYSPSFQGQVTISADKSISTAYLQWSSLKASDTAMYYCARHGLGYNGYEGAFDIWGQGTLVTVSS (SEQ ID NO: 98) |
| LC-249 | hKappa | DIQMTQSPSSLSASVGDRVTITCRASQGIGSALAWYQQKPGKAPKLLIYDASNLETGVPSRFSGSGSGTDFTLTISSLQPEDFATYYCQQLNGYPLTFGQGTRLEIK (SEQ ID NO: 102) |

FIGS. 11C and 11D provide an alignment of the heavy and light chain variable regions of CK6 and Ab249.

Example 13: Kinetic Analysis of Affinity-Improved Anti-CD117 Antibodies

To differentiate amongst the affinity matured anti-CD117 antibodies, the monovalent binding kinetics were determined by biolayer interferometry in comparison to the CK6 derivative Ab1 (HC-1, LC-1). HC-77/LC-77 (i.e. Ab77), HC-79/LC-79 (i.e. Ab79), HC-81/LC-81 (i.e. Ab81), HC-85/LC-85 (i.e. Ab85), HC-245/LC-245 (i.e. Ab245), HC-246/LC-246 (i.e. Ab246), HC-247/LC-247 (i.e. Ab247), HC-248/LC-248 (i.e. Ab248), and HC-249/LC-249 (i.e. Ab249) and HC-1/LC-1 (i.e. Ab1) were immobilized onto anti-human Fc biosensors (AHC; Pall ForteBio 18-5063) and incubated with 33 nM and 11 nM CD117 purified ectodomain (R&D Systems #332-SR).

Figure 12A:
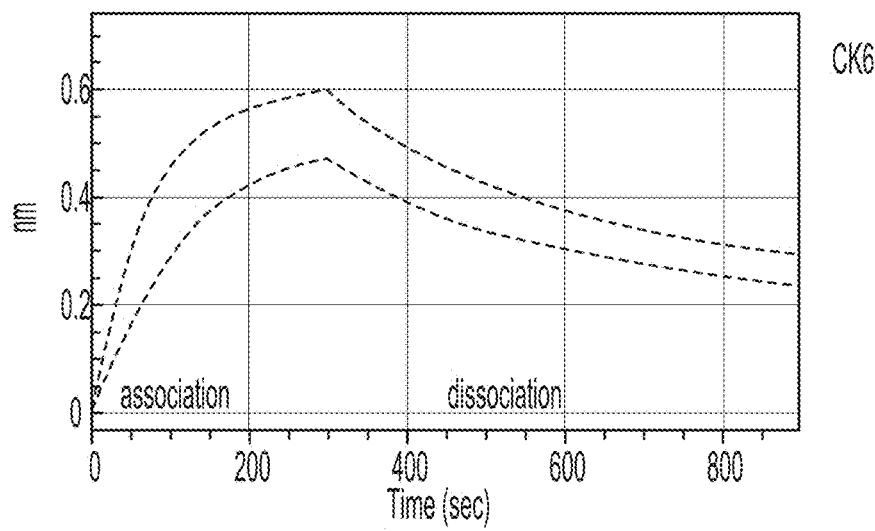
FIGS. 12A, 12B and 12C depict the binding by bio-layer interferometry (BLI) of the indicated purified IgG (sensor-associated) to 11 nm (bottom trace) and 33 nM (top trace) purified human CD117 ectodomain as a function of time for the (A) CK6 antibody, (B) the HC-85/LC-85 (Ab85) antibody and the (C) HC-249/LC-249 (Ab 249) antibody.
Figure 12B:
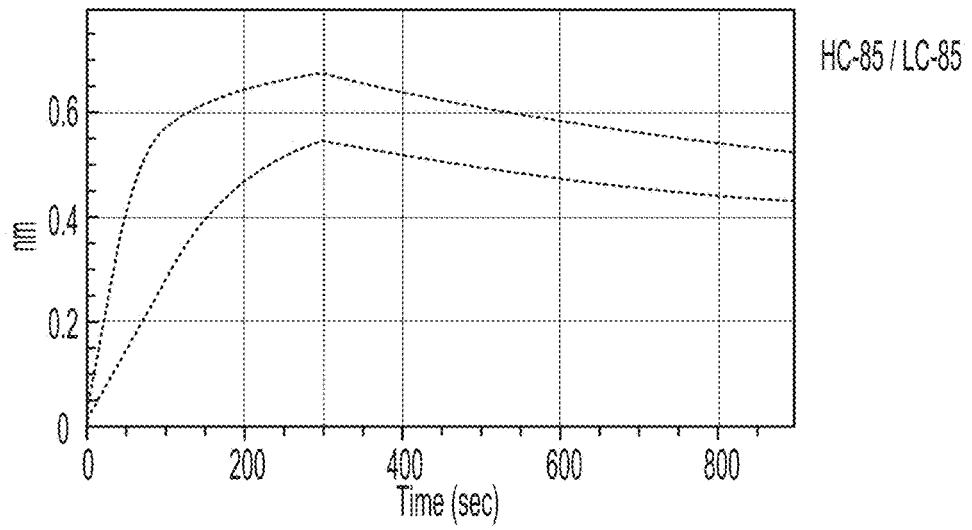
Figure 12C:
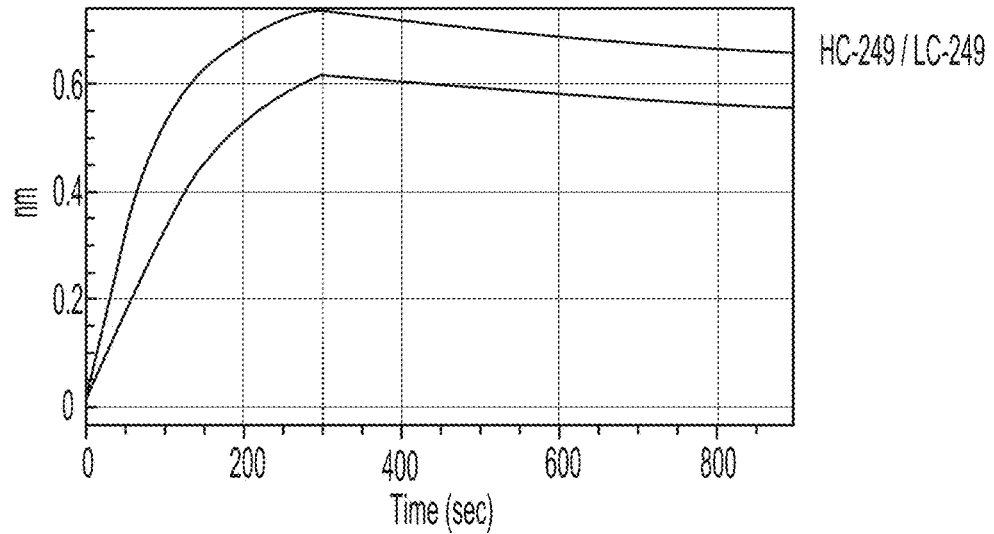
Figure 14A:
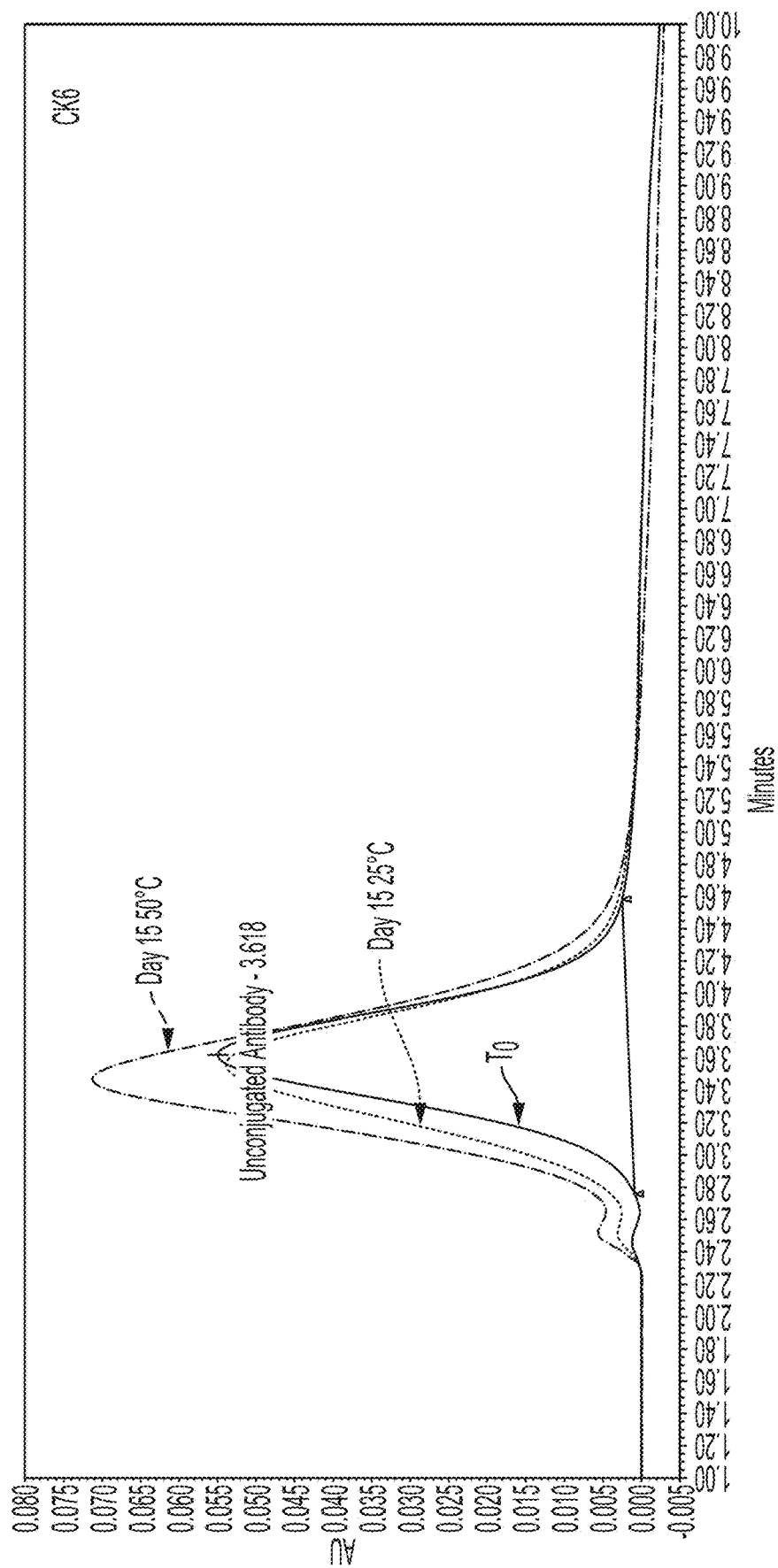
FIGS. 14A, 14B, 14C, 14D and 14E depict chromatograms demonstrating the elution profile of (A) the CK6 antibody, (B) the HC-77/LC-77 (Ab77) antibody, (C) the HC-79/LC-79 (Ab79) antibody, (D) the HC-81/LC-81 (Ab81) antibody, and (E) the HC-85/LC-85 (Ab85) antibody, under the indication incubation conditions (see legend) after analysis by hydrophobic interaction chromatography (HIC).
Figure 14B:
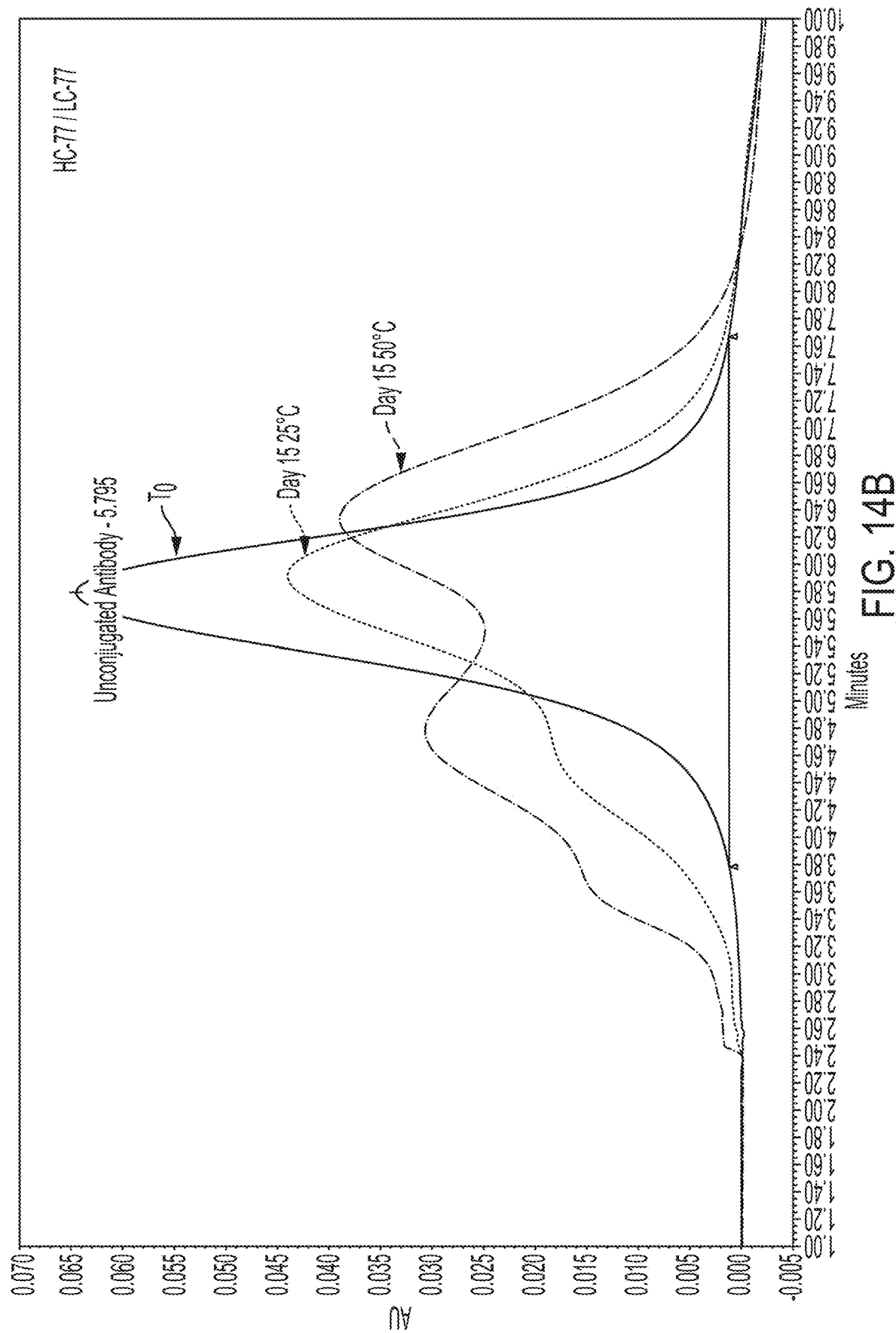
Figure 14C:
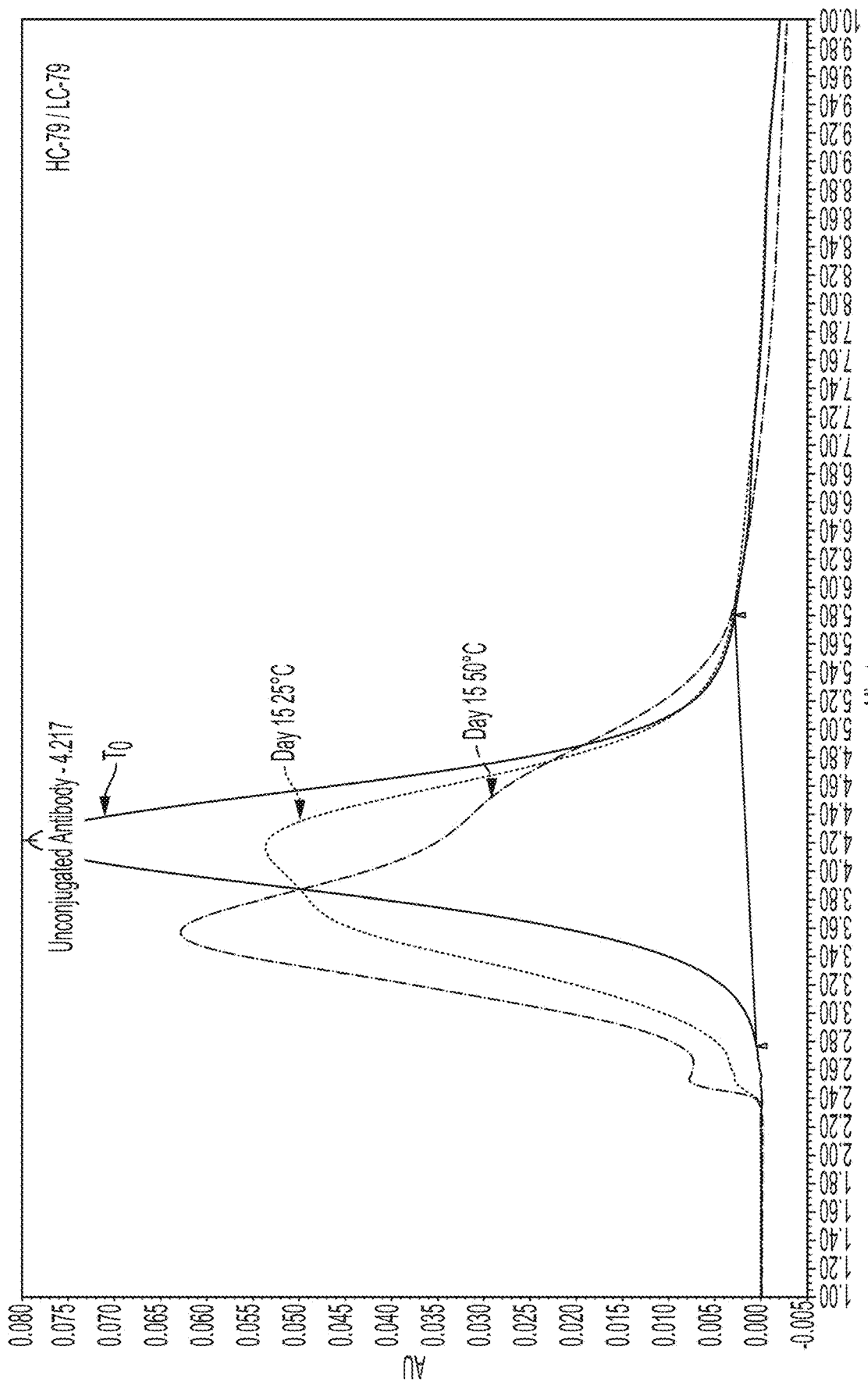
Figure 14D:
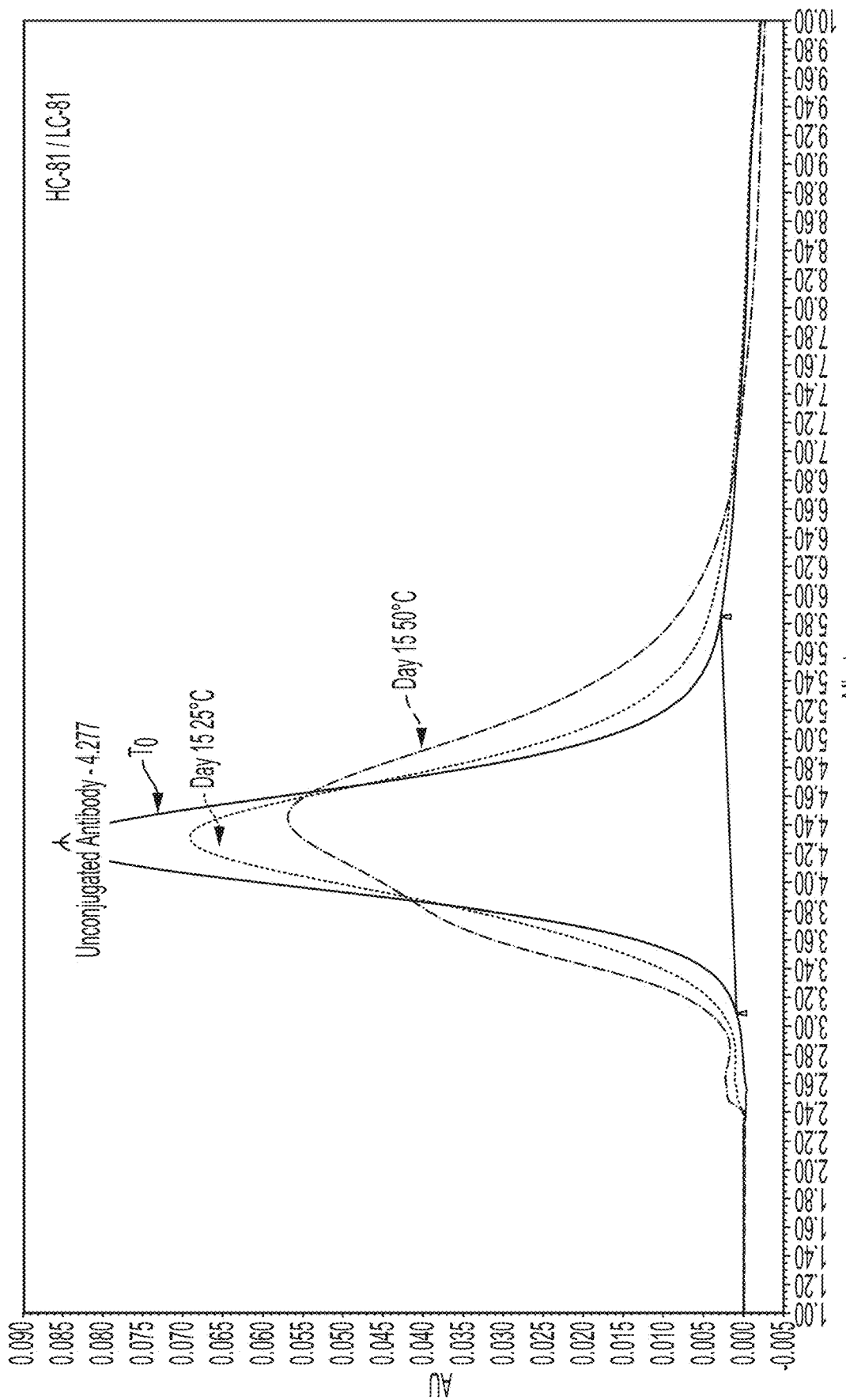
Figure 14E:
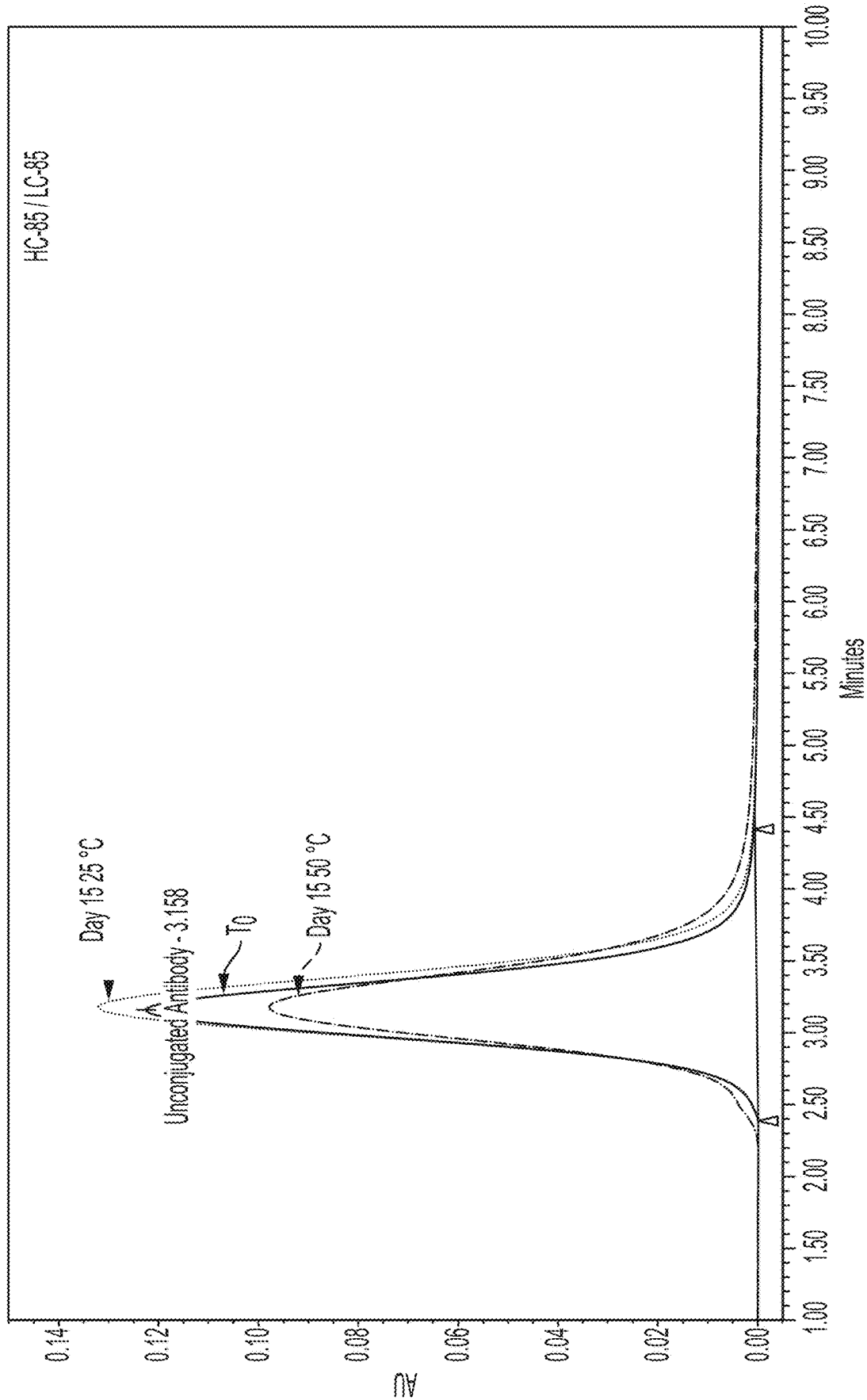

The apparent monovalent affinity (KD), apparent association rate (Kon) and apparent dissociation rate (kdis) are tabulated in Table 9. For each antibody the improvement in apparent dissocation rate compared to HC-1/LC-1 (i.e. Ab1) was calculated. The HC-249/LC-249 antibody (i.e. Ab249) demonstrated the most improved off-rate and the highest apparent monovalent affinity. The HC-85/LC-85 antibody (i.e. Ab85) had the highest apparent association rate amongst the set of antibodies tested in comparison to Ab1 and also had the deamidation site within the heavy chain CDR3 removed. The resulting sensorgrams, which represent the association and dissociation curves, are shown for CK6 derivative (HC-1/LC-1, i.e. Ab1), the HC-85/LC-85 antibody (i.e. Ab85), and the HC-249/LC-249 antibody (i.e. Ab249) (FIGS. 12A, 12B and 12C).

TABLE 9

| Antibody | $K_D$ (M) | $K_{on}$ (1/Ms) | $K_{dis}$ (1/s) | Fold improvement (off-rate) |
|---|---|---|---|---|
| Ab1 | $4.09 \times 10^9$ | $5.56 \times 10^5$ | $2.27 \times 10^{-3}$ | — |
| HC-77/LC-77 | $6.84 \times 10^{-10}$ | $3.15 \times 10^5$ | $2.15 \times 10^{-4}$ | 10.5 |
| HC-79/LC-79 | $1.52 \times 10^{-9}$ | $3.16 \times 10^5$ | $4.78 \times 10^{-4}$ | 4.7 |
| HC-81/LC-81 | $8.77 \times 10^{-10}$ | $2.88 \times 10^5$ | $2.52 \times 10^{-4}$ | 9 |
| HC-85/LC-85 | $8.35 \times 10^{-10}$ | $5.20 \times 10^5$ | $4.34 \times 10^{-4}$ | 5.2 |
| HC-245/LC-245 | $8.13 \times 10^{-10}$ | $3.50 \times 10^5$ | $2.85 \times 10^{-4}$ | 7.9 |
| HC-246/LC-246 | $7.08 \times 10^{-10}$ | $3.61 \times 10^5$ | $2.55 \times 10^{-4}$ | 8.9 |
| HC-247/LC-247 | $1.68 \times 10^{-9}$ | $3.74 \times 10^5$ | $6.30 \times 10^{-4}$ | 3.6 |
| HC-248/LC-248 | $9.22 \times 10^{-10}$ | $3.46 \times 10^5$ | $3.19 \times 10^{-4}$ | 7.1 |
| HC-249/LC-249 | $5.51 \times 10^{-10}$ | $3.44 \times 10^5$ | $1.89 \times 10^{-4}$ | 12 |

As described in Table 9, the off rate of Ab249 was significantly improved over the parent antibody, Ab1, where the rate was about 12 fold slower than the parent.

Example 14: Characterization of Charge Variants of Anti-CD117 Antibodies

Capillary isoelectric focusing was performed on a subset of affinity-improved anti-CD117 antibodies to determine if sequence differentiation impacted the biophysical properties of the antibodies. Briefly, 10-40 micrograms of antibody were subjected to 7- and 15-days incubation at 25 or 50 degrees Celsius and analyzed through a capillary electrophoresis method using the Maurice instrument manufactured by Protein Simple according to standard manufacturer instruction. Antibody samples migrate to their electrically neutral pH. The fraction of acidic variants was calculated based on absorbance peaks detected below the isoelectric point relative to the total injected sample.

The CK6 derivative Ab1 (HC-1/LC-1) exhibited 26% acidic species at the start of the assay and this fraction increased to 57% and 54% of total injected antibody after 7 days of incubation at 25 and 50 degrees Celsius, respectively. With extended incubation for 15 days, the fraction of acidic variants for CK6 increased to 68% and 78% total injected antibody at 25 and 50 degrees Celsius, respectively.

In comparison, the HC-85/LC-85 antibody (i.e., Ab85) demonstrated significantly lower starting fractions of acidic variants (6.9% at T0) and reduced accumulation of acidic variants at 25 degrees Celsius (16% at day 7; 18% at day 15) and at 50 degrees Celsius (36% at day 7; 50% at day 15).

The HC-249/LC-249 antibody (i.e, Ab249) exhibited higher fractions of acidic variants at the start of the experiment than Ab85 (31%), however, these fractions did not significantly increase following incubation at 25 degrees Celsius (35% at day 7; 23% at day 15). After stress at 50 degrees Celsius, the acidic species increased for Ab249 at both day 7 and day 15 (52% and 65%; respectively).

The antibodies tested in this example were tested as IgG1 antibodies with the same heavy and light constant regions described in SEQ ID NOs: 169 and 183, respectively. Thus, the observed variation in stability reflected in the percentage of acidic variant as tested was due to the variable regions.

Of all the antibodies analyzed, Ab85 had the lowest fraction of acidic variants and the least accumulation of these species following stress conditions as described in FIGS. 13A and 13B.

Example 15: Characterization of Hydrophobicity of Anti-CD117 Antibodies

A subset of the affinity improved anti-CD117 antibodies was evaluated after incubation at 25 or 50 degrees Celsius for 15 days by hydrophobic interaction chromatography (HIC). Briefly, 50 micrograms of the indicated antibody were injected onto a Tosoh TSKgel Phenyl-5PW 7.5 mm ID×7.5 cm 10-micron column (Catalog #07573) on a Waters ARC HPLC/UPLC system. For the CK6 variant (Ab1; HC-1/LC-1), peak broadening was observed after 15 days of incubation at 25 and 50 degrees Celsius. For affinity improved antibodies HC-77/LC-77 (i.e., Ab 77), HC-79/LC-79 (i.e., Ab79), and HC-81/LC-81 (i.e, Ab 81), significant peak broadening was evident in the chromatograms for both mild (25 degrees Celsius) and severe (50 degrees Celsius) conditions. Ab85 demonstrated minimal peak broadening after incubation at 25 or 50 degrees Celsius after 15 days, exhibiting the lowest change in hydrophobicity of the affinity improved anti-CD117 antibodies tested and compared to the CK6 variant Ab1 (HC-1/LC-1) as described in FIGS. 14A-14E. As described in Example 14, the antibodies contained the same constant region sequences.

Example 16: In Vitro Analysis of Affinity Improved Anti-CD117-ADCs Using an In Vitro Cell Killing Assay To evaluate the potency of affinity improved anti-CD117 antibodies as ADCs, Kasumi-1 cells were cultured for three days in the presence of the indicated anti-CD117-ADC (antibody conjugated to an amatoxin) or the control isotype ADC. Cell viability was measured by Celltiter Glo (FIG. 15).

To examine the potency of affinity improved anti-CD117 antibodies as ADCs on primary cells in vitro, human HSCs (i.e., isolated primary human CD34+ selected Bone Marrow Cells (BMCs), human CD34+ BMCs were cultured for five days with the indicated anti-CD117-ADC or the control isotype ADC in the presence of IL-6, TPO, and FLT-3 ligand. CD34+CD90+ cell counts were determined by flow cytometry (FIG. 16).

Figure 15:
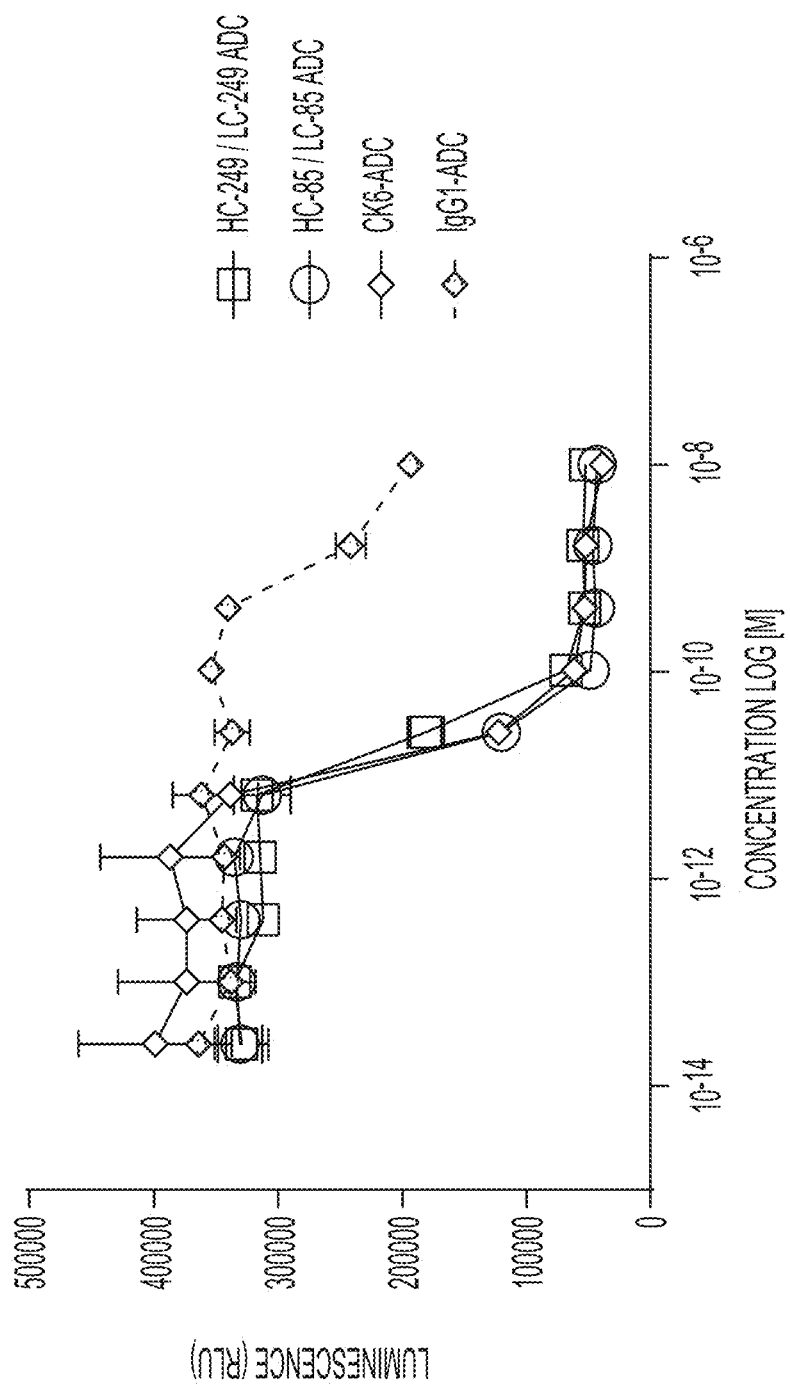
FIG. 15 graphically depicts the results of in vitro cell killing assays that show Kasumi-1 cell viability as measured in luminescene (RLU) by Celltiter Glo as a function of the indicated anti-CD117 ADC or control concentration. The IC50 (M) was determined by non-linear regression 4-parameter fit in Graphpad Prism.
Figure 16:
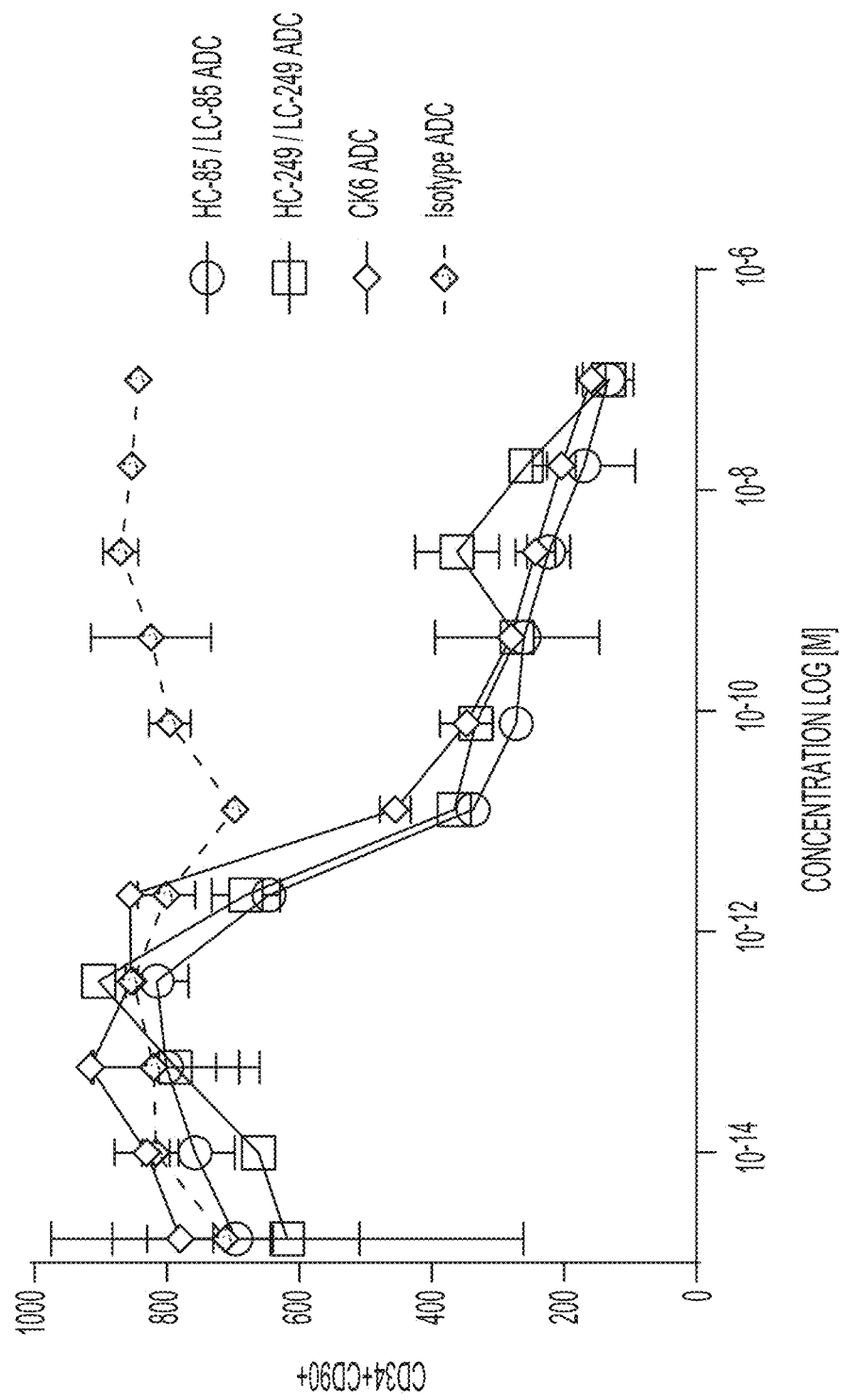
FIG. 16 graphically depicts the results of in vitro cell killing assays that show viable CD34+CD90+ cell count as a function of the indicated anti-CD117 ADC or control concentration. The IC50 (M) was determined by non-linear regression 4-parameter fit in Graphpad Prism.

As shown in FIGS. 15 and 16, both the HC-85/LC-85 ADC (i.e, Ab85) and the HC-249/LC-249 ADC (i.e, Ab249) were effective at killing Kasumi-1 ($1.76 \times 10^{-11}$ M and $2.5 \times 10^{-11}$M, respectively; see Table 10) and primary human CD34+ cells in vitro ($5.74 \times 10^{-12}$ M and $6.67 \times 10^{-12}$M, respectively; see Table 11) and the potency was similar to CK6 ($1.48 \times 10^{-11}$ M in Kasumi-1; $9.8 \times 10^{-12}$M in primary human CD34+CD90+ cells) (Tables 10 and 11).

Thus, the anti-CD117 antibodies Ab85 and Ab249 exhibited marked improvements in monovalent affinity (FIGS. 12B and 12C), superior biophysical behavior as measured by acidic variants and hydrophobicity under thermal stress (FIGS. 13A and 13B and FIGS. 14A-14E), and similar in vitro potency as ADCs in cytoxicity assays on Kasumi-1 (FIG. 15) and primary human CD34+CD90+ cells when compared to CK6 (FIG. 16). Further, Ab85 had an improved HC CDR3 domain as a potential deamidation site was removed without negatively impacting the characteristics of the antibody.

TABLE 10

| Antibody | IC50 (M) |
|---|---|
| CK6 | $1.48 \times 10^{-11}$ |
| HC-249/LC-249 | $2.50 \times 10^{-11}$ |
| HC-85/LC-85 | $1.76 \times 10^{-11}$ |

TABLE 11

| Antibody | IC50 | % efficacy | Antibody | IC50 | % efficacy |
|---|---|---|---|---|---|
| CK6 | $9.77 \times 10^{-12}$ | 70.80 | HC-245/LC-245 | $5.78 \times 10^{-12}$ | 76.43 |
| HC-77/LC-77 | $6.94 \times 10^{-12}$ | 54.38 | HC-246/LC-246 | $4.53 \times 10^{-12}$ | 67.82 |
| HC-79/LC-79 | $7.09 \times 10^{-12}$ | 63.37 | HC-247/LC-247 | $8.37 \times 10^{-12}$ | 55.43 |
| HC-81/LC-81 | $3.77 \times 10^{-12}$ | 68.74 | HC-248/LC-248 | $6.46 \times 10^{-12}$ | 47.80 |
| HC-85/LC-85 | $5.74 \times 10^{-12}$ | 71.18 | HC-249/LC-249 | $6.67 \times 10^{-12}$ | 52.01 |

Example 17: In Vivo HSC Depletion Assay Using an Affinity Improved Anti-CD117 ADCs An in vivo experiment was performed to evaluate the affinity improved antibody HC-85/LC-85 (i.e, Ab85) with an engineered Fc (i.e., an H435A Fc mutation). The H435A mutation is associated with a decrease in half life in antibodies in which it is introduced. This experiment was performed to determine how this mutation would impact the overall characteristics of an Ab85 ADC (Ab85 conjugated to an amatoxin via a cleavable linker).

Figure 17A:
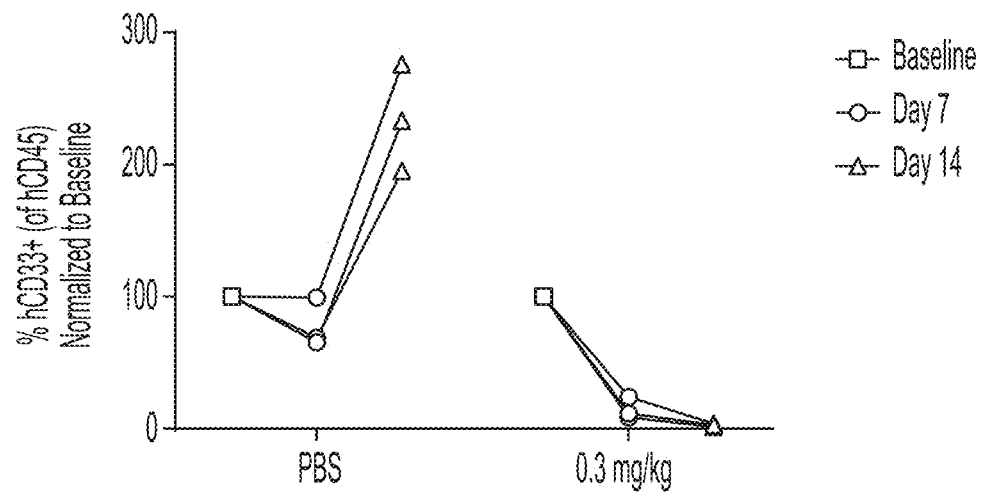
FIGS. 17A and 17B graphically depict the results of an in vivo cell depletion assay that shows a 0.3 mg/kg dose of the HC-85/LC-85 antibody (i.e., Ab85) ADC selectively depletes human HSCs in humanized NSG mice. (A) Shows the percent of human myeloid cells present in the peripheral blood of Ab85-ADC or control treated mice, expressed as a percent of that cell population prior to treatment (normalized to baseline) is shown for samples collected on day 0, 7, and 14. (B) Shows the absolute number of CD34+ cells in the bone marrow of the HC-85/LC-85-ADC (i.e., Ab85-ADC) or control treated mice 14 days after a single administration of the ADC or the control (i.e., PBS).
Figure 17B:
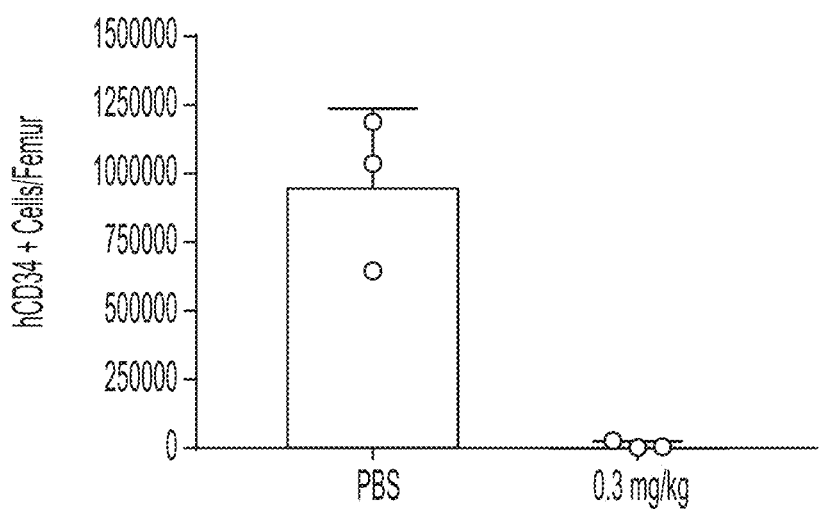

In vivo HSC depletion assays were conducted using humanized NSG mice (purchased from Jackson Laboratories). The Fc-modified Ab85 antibody (i.e., characterized by a H435A Fc mutation) was conjugated as an ADC and administered as a single injection of 0.3 mg/kg to the humanized mouse model. Blood was collected on days 0, 7, and 14 and examined by flow cytometry. The percentage of human CD33+ of treated or control treated mice relative to baseline are shown (FIG. 17A). Bone marrow was collected on day 14 and the absolute number of CD34+ cells was determined by flow cytometry (FIG. 17B).

The results indicate that humanized NSG mice treated with the Fc-modified Ab85 ADC showed significant depletion of human CD33+ myeloid cells relative to baseline, 7 and 14 days following a single administration of the treatment regimen and indicate that the Fc-modified Ab85 ADC depleted myeloid cells as a result of the depletion of early progenitor cells. In addition, humanized NSG mice treated with the Ab85 ADC showed significant depletion of human HSCs in the bone marrow, 14 days following a single administration of the ADC when compared to the control. Thus, Ab85 ADC with a modified Fc region was effective at selectively depleting CD34+ stem cells and CD33+ progenitor cells.

Example 18: CD117-Amanitin Antibody Drug Conjugates Effectively Deplete Human and Non-Human Primate HSCs Genotoxic conditioning prior to allogeneic and autologous hematopoietic stem cell (HSC) transplantation (HSCT) and the infusion of gene corrected autologous HSCs limits the use of these potentially curative treatments due to risks of regimen-related morbidities and mortality, including risks of infertility and secondary malignancies. CD117, which is specifically expressed on HSCs and progenitors is rapidly internalized and is an ideal target for an ADC-based approach to conditioning. As it has been previously shown that a single dose of an anti-CD117 ADC depleted >95% of bone marrow HSCs in a humanized mouse model and reduced disease burden while extending survival in an AML tumor model (Hartigan et al., Blood 2017 130:1894), the aim of this example was to develop a potent anti-CD117 ADC highly effective in eliminating host HSC with a short half-life and minimal adverse side effects in a non-human primate (NHP) model.

Figure 18:
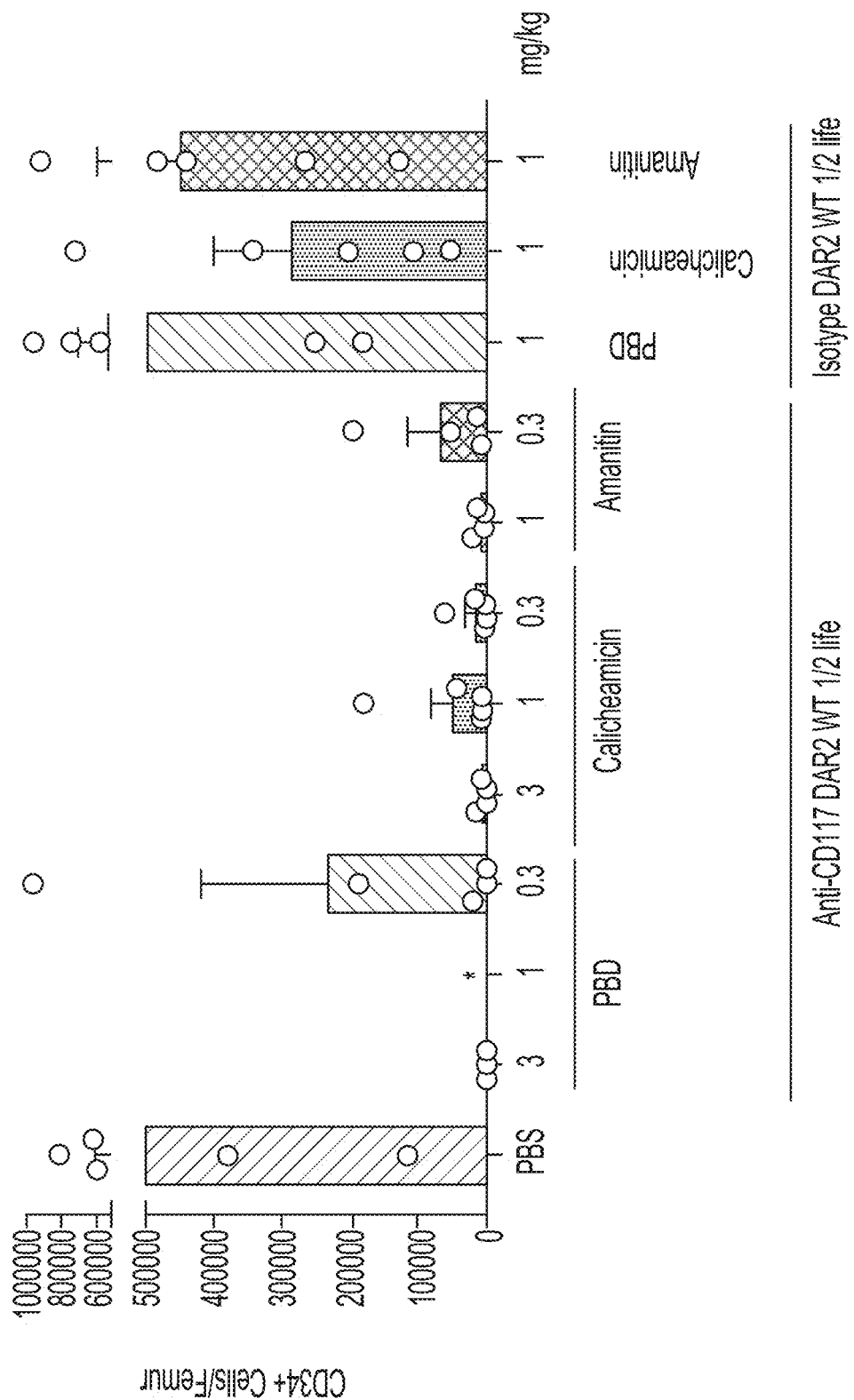
FIG. 18 graphically depicts the results of an in vitro toxicity assay using human bone marrow CD34+ cells for an anti-CD117 antibody (CK6) site specifically conjugated to various cytotoxic payloads. The results show that the anti-CD117 (CK6) antibody conjugated to amanitin resulted in a >90% depletion of human HSCs in humanized mice at 0.3 mg/kg. These results also show that the calicheamicin and amanitin ADCs demonstrate comparable depletion of HSCs FIG. 19 graphically depicts hematopoietic stem and progenitor cell number in bone marrow. The results show that a single dose of amanitin conjugated anti-CD117 (CD117-AM) eliminates bone marrow HSCs in cynomolgus monkeys. Male cynomolgus monkeys received a single i.v. dose of anti-CD117-AM, isotype-AM (IgG1-AM), or unconjugated anti-CD117 antibody. Bone marrow HSC counts were determined by flow cytometry 7 days post administration. The fraction of HSCs depleted after treatment with anti-CD117-AM, IgG1-AM, or unconjugated anti-CD117 was calculated relative to the PBS group.

The cytotoxic payloads a calicheamicin variant, a pyrrolobenzodiazepine (PBD), and an amanitin (AM) were site specifically conjugated to an anti-CD117 antibody (CK6; wild type half-life). The ADCs were titrated and evaluated for in vitro cytotoxicity using human bone marrow CD34+ cells (FIG. 18). The ADCs were administered in ascending doses to humanized NSG mice. HSC depletion and immunophenotype of the human cells in the peripheral blood was determined by flow cytometry at day 21 (data not shown). Anti-CD117 conjugated with the RNA polymerase II inhibitor amanitin (AM) resulted in >90% depletion of human HSCs in humanized NSG mice at 0.3 mg/kg. The AM-conjugates also demonstrated a broad therapeutic window in this model (therapeutic index of >120). These data also show that the calicheamicin and amanitin ADCs demonstrate comparable depletion of HSCs.

Amanitin-conjugate mediated NHP HSC depletion was evaluated in male cynomolgus monkeys in single ascending doses (3/group). HSC content in the bone marrow was monitored by flow cytometry and colony-forming unit (CFU) analysis on day 7 or 14 and 56 post dosing. Hematology and clinical chemistries were evaluated throughout the two-month study.

Figure 19:
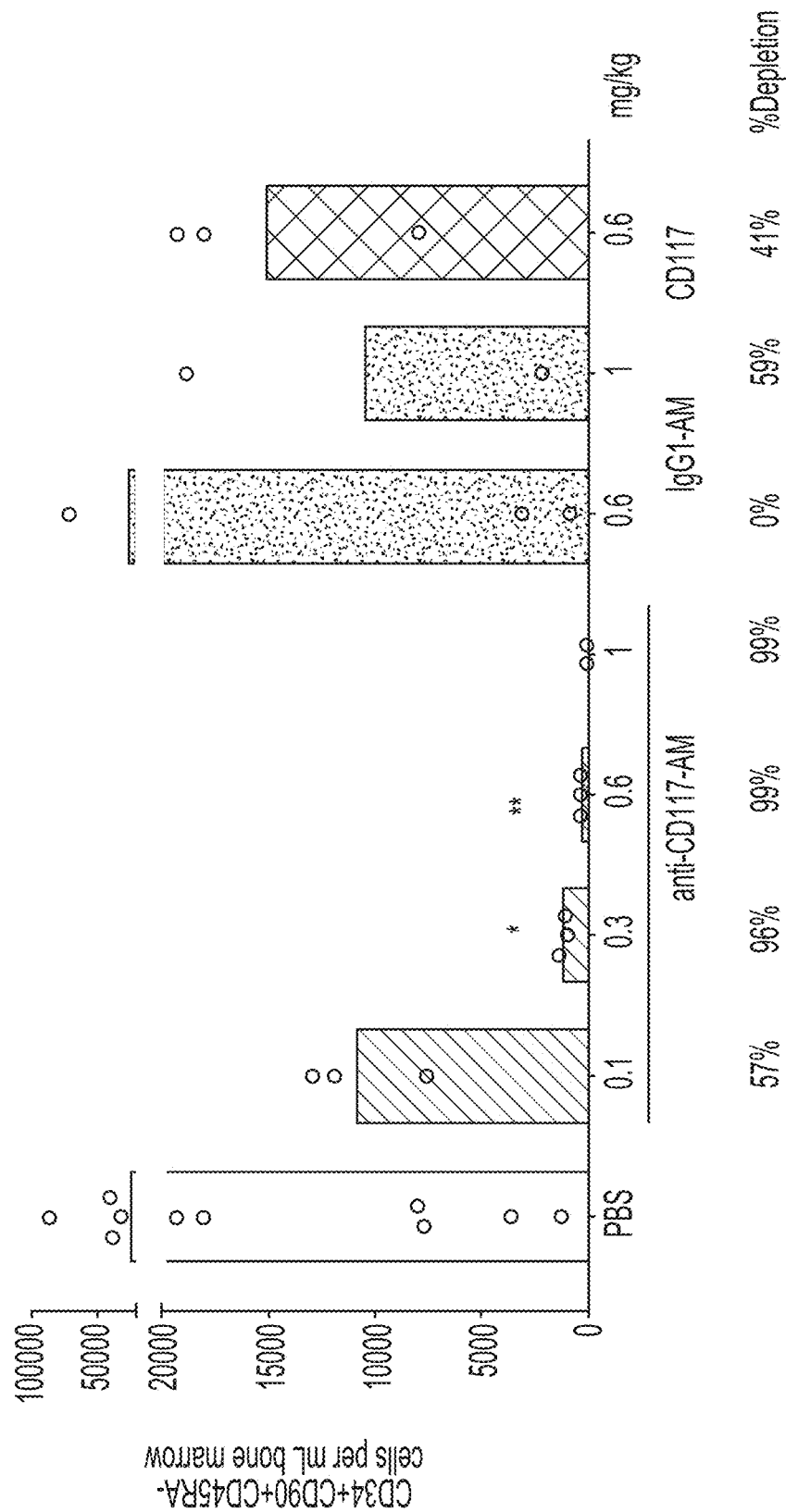

On-target, dose dependent decreases in phenotypic HSCs and CFUs were observed in the bone marrow at day 7 post anti-CD117-AM dosing with >95% HSC depletion observed with a single dose of 0.3 mg/kg (FIG. 19). In the periphery, a dose dependent transient decrease in reticulocytes was observed at day 4 with a neutrophil and monocyte nadir at day 18 (data not shown). The severity and duration of the depletion was also dose dependent. The anti-CD117-AM induced depletion was on target and amanitin dependent as the unconjugated antibody and isotype-AM had no effect (FIG. 19). Notably, white blood cell and lymphocyte counts were stable through day 56 (data not shown), demonstrating that this strategy will spare the adaptive immune system. Platelet nadir occurred 4-8 days post infusion and was dose dependent transient and reversible. This also occurred with the isotype-AM suggesting the effect was off-target.

Because the half-life of the anti-CD117-AM was 5 days, a second dose escalation study with anti-CD117-AM (HC-85; LC-85) engineered to have a short half-life (~18 h) was performed in NHP, as this may be more suitable for the transplant setting. The short half-life anti-CD117-AM demonstrated similar potency on all cell parameters at 0.3 mg/kg or with a fractionated dose (0.3/0.2 mg/kg Q3Dx2) and was well tolerated at the effective dose (FIG. 20). As expected, the fast half-life anti-CD117-AM was rapidly cleared with a half-life of 15-18 h. In conclusion, anti-CD117-AM exhibits potent elimination of NHP HSCs and progenitors in vivo.

Example 19: Anti-CD117 Antibody Drug Conjugates (ADCs) Conditioning Agents Have Profound In Vivo Anti-Leukemia Activity in Cell Line and Patient Derived Xenograft Models Allogeneic hematopoietic stem cell transplant (HSCT) is a potentially curative approach in patients with refractory or high risk hematologic malignancies. Prior to transplant, patients are conditioned with high dose chemotherapy or chemotherapy and total body irradiation which are associated with early and late morbidities and substantial risk of mortality. As a result, many eligible patients do not consider transplant and of those transplanted, 2/3 can only tolerate a reduced intensity conditioning which is associated with increased relapse rates. Thus, safer and more effective conditioning agents with improved disease control are urgently needed. To meet this need, we developed a novel antibody drug conjugate (ADC) conjugated to amanitin (AM) targeting CD117 which is expressed on hematopoietic stem and progenitor cells and acute myeloid leukemia (AML) and myelodysplastic syndrome (MDS) cells in >60% of patients. The aim of this example was to determine the anti-leukemia potency of anti-CD117 conjugated to amanitin, an agent previously shown to deplete primary human HSPCs in vitro and in vivo (Hartigan et al. Blood. 130; 1894 (2017)).

An ADC comprising the anti-CD117 antibody CK6 was conjugated to amanitin. The ADC was tested in three patient-derived xenografts (PDX) developed from FLT-3+ NPM1+ AML samples (J000106132 (FIG. 21A), J000106565 (FIG. 21B), J000106134 (FIG. 21C)) with varying growth kinetics (median survival of vehicle treated groups was 43 days (Table 12; see also FIG. 21A), 63 days (Table 13; see also FIG. 21B), 82 days (Table 14; see also FIG. 21C) post inoculation) that express CD117 (Jackson Laboratories).

TABLE 12

| ADC | Dose (mg/kg) | Median survival (Days) |
| --- | --- | --- |
| PBS | — | 43 |
| Anti-CD117-AM | 1 | 75.5 |
| Anti-CD117-AM | 0.3 | 55 |

TABLE 12-continued

| ADC | Dose (mg/kg) | Median survival (Days) |
| --- | --- | --- |
| Isotype-AM | 1 | 46 |
| Anti-CD117-naked | 1 | 43 |

TABLE 13

| ADC | Dose (mg/kg) | Median survival (Days) |
| --- | --- | --- |
| PBS | — | 82 |
| Anti-CD117-AM | 1 | >225 |
| Anti-CD117-AM | 0.3 | 179 |
| Isotype-AM | 1 | 75 |
| Anti-CD117-naked | 1 | 75 |

TABLE 14

| ADC | Dose (mg/kg) | Median survival (Days) |
| --- | --- | --- |
| PBS | — | 63 |
| Anti-CD117-AM | 1 | 106 |
| Anti-CD117-AM | 0.3 | 95 |
| Isotype-AM | 1 | 63 |
| Anti-CD117-naked | 1 | 63 |

Figure 21A:
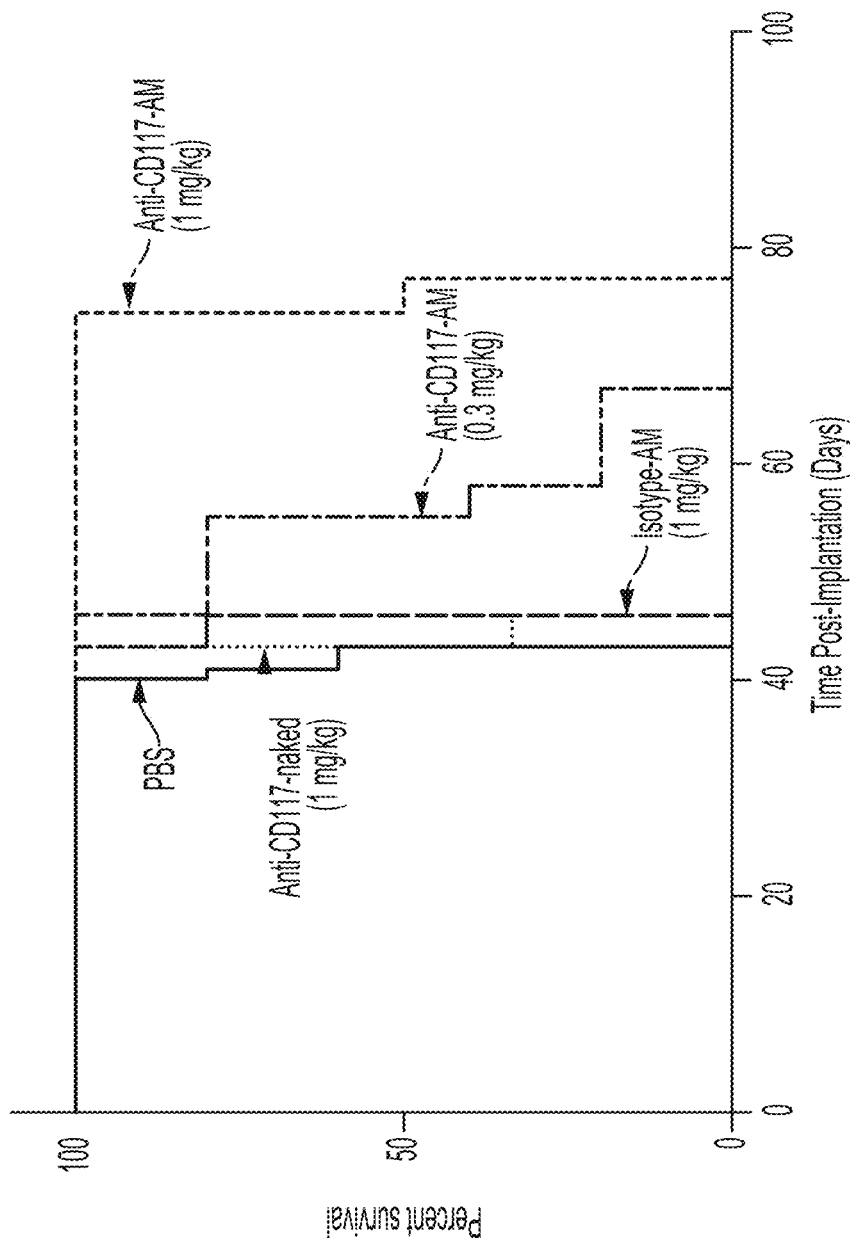
FIGS. 21A, 21B, and 21C graphically depict the results of a survival study using three AML-patient-derived xenografts developed from FLT-3+NPM1+AML samples showing survival was significantly increased in mouse models administered 0.3 mg/kg anti-CD117-amanitin or 1 mg/kg anti-CD117-amanitin. (A) Survival curve of AML-PDX developed from FLT-3+NPM1+AML sample J000106132 after single intravenous administration of ADCs (anti-CD117-AM, isotype-AM), an unconjugated anti-CD117 antibody or PBS (control). (B) Survival curve of AML-PDX developed from FLT-3+NPM1+AML sample J000106565 after single intravenous administration of ADCs (anti-CD117-AM, isotype-AM), an unconjugated anti-CD117 antibody or PBS (control). (C) Survival curve of AML-PDX developed from FLT-3+NPM1+AML sample J000106134 after single intravenous administration of ADCs (anti-CD117-AM, isotype-AM), an unconjugated anti-CD117 antibody or PBS (control).
Figure 21B:
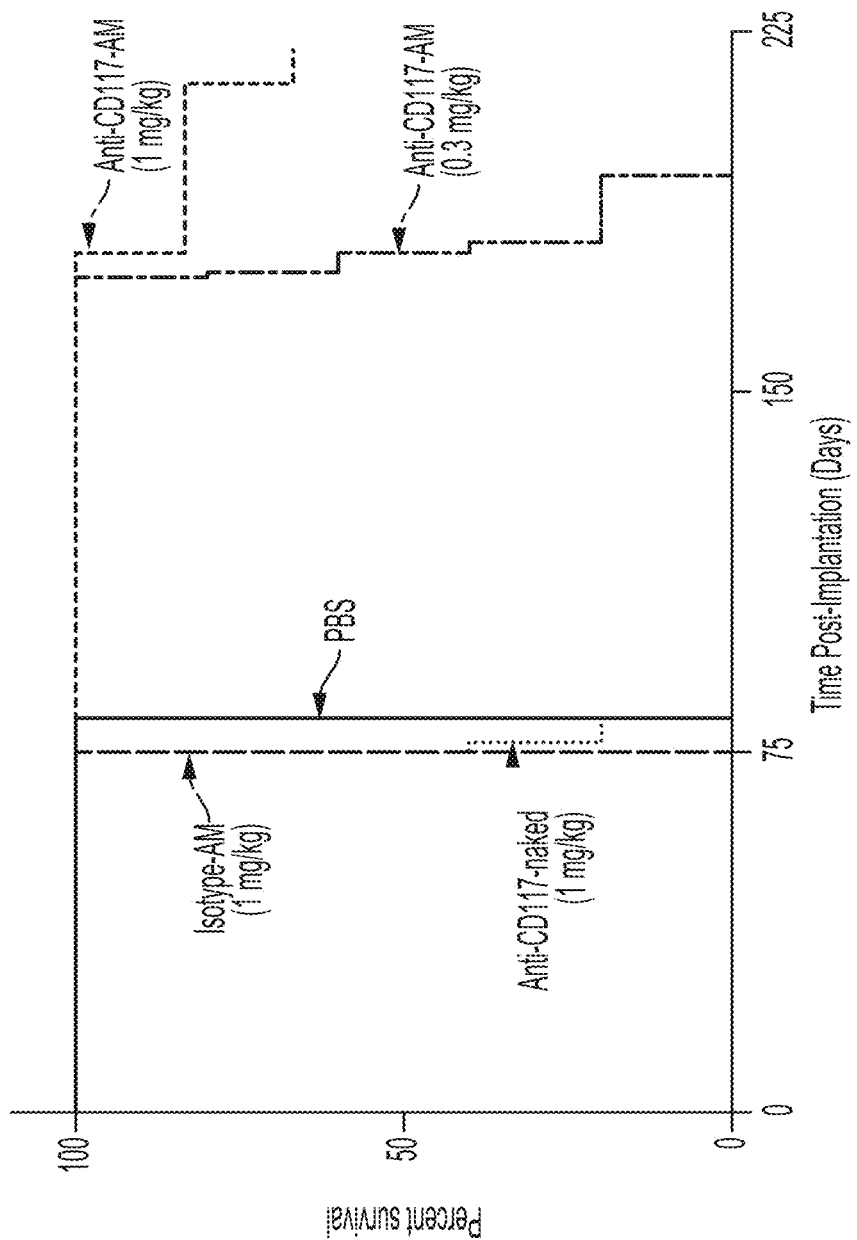
Figure 21C:
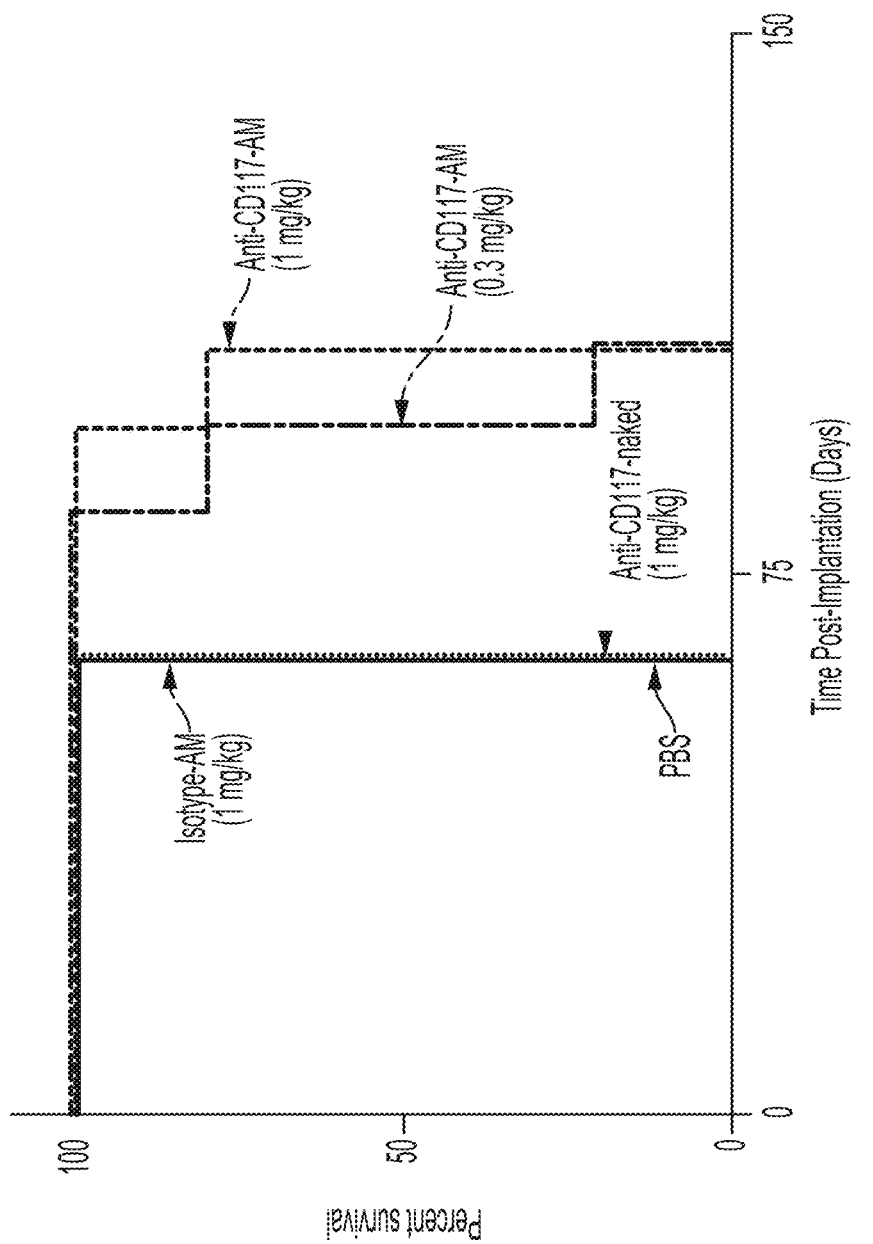

For the three PDX (J000106132 (FIG. 21A), J000106565 (FIG. 21B), J000106134 (FIG. 21C)), a single intravenous dose of ADCs (CD117-AM, isotype-AM (ISO-AM), unconjugated anti-CD117 antibody, or vehicle PBS) were administered to AML-PDX animals when 2-5% blasts were observed in the blood. With 4-5 mice/group/AML-PDX model, survival was significantly increased in recipients of 0.3 mg/kg CD117-AM and 1 mg/kg CD117-AM as compared to vehicle controls (Tables 12-14; FIGS. 21A-21C).

In addition to depletion of normal host HSPC, CD117-AM is a potent anti-leukemia agent based on these data in humanized murine models with established AML. Together with prior reports on the potency of CD117-AM as a conditioning agent, this non-genotoxic ADC (or variants of CK6 with improved properties described herein) may be useful in patients with active disease and in recipients of reduced dose conditioning who are at high risk of disease relapse.

Example 20. Identification of Novel Anti-CD117 Antibodies by Rat Immunization As a third strategy, to identify novel anti-CD117 antibodies, 5 rats were immunized with synthetic DNA coding for human CD117 ectodomain (aa26-524; P010721) and hybridoma fusions were prepared according to standard methods known in the art. Hybridomas were screened for binding to cell lines expressing human CD117 ectodomain (aa26-524; P010721) and cynomologus monkey CD117 ectodomain (aa26-521; F6V858) to identify antibodies which would proceed in screening. The following antibodies were identified as positive binders to both cell lines by flow cytometry: HC-17/LC-17 (i.e., Ab17), HC-18/LC-18 (i.e., Ab18), HC-19/LC-19 (i.e., Ab19), HC-20/LC-20 (i.e., Ab20), HC-21/LC-21 (i.e., Ab21), HC-22/LC-22 (i.e., Ab22), HC-23/LC-23 (i.e., Ab23), HC-24/LC-24 (i.e., Ab24), HC-25/LC-25 (i.e., Ab25), HC-27/LC-27 (i.e., Ab27), and HC-28/LC-28 (i.e., Ab28).

To confirm binding to the desired target, purified antibodies were analyzed for binding to purified recombinant CD117 ectodomain by bio-layer interferometry. Binding analysis of the antibodies identified from the rat immunizations reveals a wide set of association and dissociation kinetics as demonstrated in FIGS. 22 and 23. The apparent kinetic values are provided in Table 4 and Table 15. Table 15 provides a table listing the apparent monovalent affinity ($K_D$), apparent association rate ($k_{on}$), and apparent dissociation rate ($k_{dis}$) of the indicated purified IgG to purified rhesus CD117 ectodomain. As provided above, Table 4 provides a table listing the apparent monovalent affinity ($K_D$), apparent association rate ($k_{on}$), and apparent dissociation rate ($k_{dis}$) the indicated purified IgG (including the antibodies identified in this Example) to purified human CD117 ectodomain.

TABLE 15

| | $K_D$ (M) | $K_{on}$ (1/Ms) | $K_{dis}$ (1/s) |
| --- | --- | --- | --- |
| 017 (Ab17) | 5.62E−10 | 3.07E+05 | 1.73E−04 |
| 018 (Ab18) | 5.38E−08 | 2.21E+05 | 1.19E−02 |
| 019 (Ab19) | 2.34E−09 | 1.77E+05 | 4.15E−04 |
| 020 (Ab20) | 1.39E−09 | 4.21E+05 | 5.85E−04 |
| 021 (Ab21) | 8.69E−10 | 4.10E+05 | 3.57E−04 |
| 022 (Ab22) | 8.91E−11 | 1.74E+06 | 1.55E−04 |
| 023 (Ab23) | 7.62E−09 | 2.80E+05 | 2.14E−03 |
| 024 (Ab24) | 1.96E−08 | 3.97E+04 | 7.77E−04 |
| 025 (Ab25) | 8.10E−10 | 2.41E+06 | 1.95E−03 |
| 027 (Ab27) | 8.90E−10 | 3.09E+05 | 2.75E−04 |
| 028 (Ab28) | 3.60E−09 | 5.21E+05 | 1.87E−03 |

To confirm the species cross-reactivity of the antibodies identified in the screening of the rat hybridomas, purified antibodies were analyzed for binding to purified rhesus CD117 ectodomain by bio-layer interferometry. Binding analysis of the antibodies demonstrates strong cross-reactivity for the set of antibodies. Analysis of the apparent kinetic values for binding to rhesus antigen (Table 15) demonstrates strong correlation with the apparent association and dissociation rates observed for binding to the human antigen (Table 4).

TABLE 16

AMINO ACID SEQUENCE SUMMARY

| Sequence Identifier | Description | Amino Acid Sequence |
| --- | --- | --- |
| SEQ ID NO: 1 | CK6 CDR-H1 | SYWIG |
| SEQ ID NO: 2 | CK6 CDR-H2 Ab249 CDR-H2 | IIYPGDSDTRYSPSFQG |
| SEQ ID NO: 3 | CK6 CDR-H3 | HGRGYNGYEGAFDI |
| SEQ ID NO: 4 | CK6 CDR-L1 | RASQGISSALA |

TABLE 16-continued

AMINO ACID SEQUENCE SUMMARY

| Sequence Identifier | Description | Amino Acid Sequence |
|---|---|---|
| SEQ ID NO: 5 | CK6 CDR-L2 | DASSLES |
| SEQ ID NO: 6 | CK6 CDR-L3 | CQQFNSYPLT |
| SEQ ID NO: 7 | Heavy chain variable region of HC-1 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 8 | Light chain variable region of LC-1 | AIQLTQSPSSLSASVGDRVTITCRASQGVSSALAWY QQKPGKAPKLLIYDASSLESGVPSRFSGSGSGTDFT LTISSLQPEDFATYYCQQFNSYPLTFGGGTKVEIK |
| SEQ ID NO: 7 | Heavy chain variable region of HC-2 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 9 | Light chain variable region of LC-2 | DIQLTQSPSSLSASVGDRVTITCRASQGIRTDLGWY QQKPGKAPKLLIYDASSLESGVPSRFSGSGSGTDFT LTISSLQPEDFATYYCQQFNSYPLTFGGGTKVEIK |
| SEQ ID NO: 7 | Heavy chain variable region of HC-3 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 10 | Light chain variable region of LC-3 | AIRMTQSPSSLSASVGDRVTITCRASQGIRNDLAWY QQKPGKTPKLLIYDASSLESGVPSRFSGSGSGTDFT LTISSLQPEDFATYYCQQFNSYPLTFGGGTKVEIK |
| SEQ ID NO: 7 | Heavy chain variable region of HC-4 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 11 | Light chain variable region of LC-4 | AIQMTQSPSSLSASVGDRVTITCRASQGIRNDLGWY QQKPGKAPKLLIYDASSLESGVPSRFSGSGSGTDFT LTISSLQPEDFATYYCQQFNSYPLTFGGGTKVDIK |
| SEQ ID NO: 7 | Heavy chain variable region of HC-5 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 12 | Light chain variable region of LC-5 | NIQMTQSPSSLSASVGDRVTITCRASQAISDYLAWF QQKPGKAPKLLIYDASNLETGVPSRFSGSGSGTDFT LTISSLQPEDFATYYCQQLNSYPLTFGGGTKVEIK |
| SEQ ID NO: 7 | Heavy chain variable region of HC-6 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 13 | Light chain variable region of LC-6 | AIRMTQSPSSLSASVGDRVIIACRASQGIGGALAWY QQKPGNAPKVLVYDASTLESGVPSRFSGGGSGTDF TLTISSLQPEDFATYYCQQFNSYPLTFGGGTKLEIK |
| SEQ ID NO: 7 | Heavy chain variable region of HC-7 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 14 | Light chain variable region of LC-7 | DIAMTQSPPSLSAFVGDRVTITCRASQGIISSLAWYQ QKPGKAPKLLIYDASSLESGVPSRFSGSGSGTDFTL TIRSLQPEDFATYYCQQFNSYPLTFGGGTKLEIK |
| SEQ ID NO: 7 | Heavy chain variable region of HC-8 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 15 | Light chain variable region of LC-8 | DIQMTQSPSSLSASVGDRVTITCRASQGISSALAWY QQKAGKAPKVLISDASSLESGVPSRFSGSGSGTDFT LSISSLQPEDFATYYCQQFNGYPLTFGGGTKVDIK |

TABLE 16-continued

AMINO ACID SEQUENCE SUMMARY

| Sequence Identifier | Description | Amino Acid Sequence |
|---|---|---|
| SEQ ID NO: 7 | Heavy chain variable region of HC-9 amino acid sequence | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 16 | Light chain variable region of LC-9 | AIRMTQSPSSLSASVGDRVTITCQASQGIRNDLGWY QQKPGKAPKLLIYDASNLETGVPSRFSGSGSGTDFT FTISSLQPEDIATYYCQQFNSYPLTFGGGTKLEIK |
| SEQ ID NO: 7 | Heavy chain variable region of HC-10 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 17 | Light chain variable region of LC-10 | NIQMTQSPSSLSTSVGDRVTITCRASQGIGTSLAWY QQKPGKPPKLLIYDASSLESGVPSRLSGSGSGTDFT LTISSLQPEDFATYYCQQSNSYPITFGQGTRLEIK |
| SEQ ID NO: 7 | Heavy chain variable region of HC-11 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 18 | Light chain variable region of LC-11 | AIQLTQSPSSLSASVGDRVTITCRASQSIGDYLTWYQ QKPGKAPKVLIYGASSLQSGVPPRFSGSGSGTDFTL TVSSLQPEDFATYYCQQLNSYPLTFGGGTKLEIK |
| SEQ ID NO: 7 | Heavy chain variable region of HC-12 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 19 | Light chain variable region of LC-12 | DIQLTQSPSSLSASVGDRVTITCRASQGVRSTLAWY QQKPGKAPKLLIYDASILESGVPSRFSGSGSGTDFTL TISSLQPEDFATYYCQQFNGYPLTFGQGTRLEIK |
| SEQ ID NO: 7 | Heavy chain variable region of HC-13 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 20 | Light chain variable region of LC-13 | DIVMTQSPSSLSASVGDRVTITCRASQGIRNDLGWY QQKPGKAPKLLIYDASSLESGVPSRFSGSGSGTDFT LTISSLQPEDFATYYCQQFNSYPLTFGGGTKLEIK |
| SEQ ID NO: 7 | Heavy chain variable region of HC-14 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 21 | Light chain variable region of LC-14 | DIQLTQSPSSLSASVGDRVTITCRASQGISSFLAWYQ QKPGKAPKLLIYDASTLQSGVPSRFSGSASGTDFTL TISSLQPEDFATYYCQQLNGYPLTFGGGTKVEIK |
| SEQ ID NO: 7 | Heavy chain variable region of HC-15 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 22 | Light chain variable region of LC-15 | AIQLTQSPSSLSASVGDRVTITCRASQGIGSALAWYQ QKPGIGPKLLIYDASTLESGVPARFSGSGSRTDFTLTI TSLQPEDFATYYCQQFNGYPLTFGGGTKLEIK |
| SEQ ID NO: 7 | Heavy chain variable region of HC-16 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 23 | Light chain variable region of LC-16 | AIQLTQSPSSLSASVGDRVTITCRASQGITSALAWYQ EKPGKAPNLLIYDASSLESGVPSRFSGSGYGTDFTL TISSLQPEDFATYYCQQLNSYPLTFGGGTKVDIK |

TABLE 16-continued

AMINO ACID SEQUENCE SUMMARY

| Sequence Identifier | Description | Amino Acid Sequence |
|---|---|---|
| SEQ ID NO: 24 | Heavy chain variable region of HC-17 | QIQLVQSGPELRKPGESVKISCKASGYTFTDYAMYW VKQAPGKGLKWMGWINTYTGKPTYADDFKGRFVFS LEASANTANLQISNLKNEDTATYFCARARGLVDDYV MDAWGQGTSVTVSS |
| SEQ ID NO: 25 | Light chain variable region of LC-17 | SYELIQPPSASVTLGNTVSLTCVGDELSKRYAQWYQ QKPDKTIVSVIYKDSERPSGISDRFSGSSSGTTATLTI HGTLAEDEADYYCLSTYSDDNLPVFGGGTKLTVL |
| SEQ ID NO: 26 | Heavy chain variable region of HC-18 | EVQLQQYGAELGKPGTSVRLSCKVSGYNIRNTYIHW VNQRPGEGLEWIGRIDPTNGNTISAEKFKTKATLTAD TSSHTAYLQFSQLKSDDTAIYFCALNYEGYADYWGQ GVMVTGSS |
| SEQ ID NO: 27 | Light chain variable region of LC-18 | DIQMTQSPSFLSASVGDRVTINCKASQNINKYLNWY QQKVGEAPKRLIFKTNSLQTGIPSRFSGSGSGTDYT LTISSLQTEDVATYFCFQYNIGYTFGAGTKVELK |
| SEQ ID NO: 28 | Heavy chain variable region of HC-19 | EVQLQESGPGLVKPSQSLSLTCSVTGYSISSNYRWN WIRKFPGNKVEWMGYINSAGSTNYNPSLKSRISMTR DTSKNQFFLQVNSVTTEDTATYYCARSLRGYITDYS GFFDYWGQGVMVTVSS |
| SEQ ID NO: 29 | Light chain variable region of LC-19 | DIRMTQSPASLSASLGETVNIECLASEDIFSDLAWYQ QKPGKSPQLLIYNANSLQNGVPSRFSGSGSGTRYSL KINSLQSEDVATYFCQQYKNYPLTFGSGTKLEIK |
| SEQ ID NO: 30 | Heavy chain variable region of HC-20 | EVQLQQYGAELGKPGTSVRLSCKLSGYKIRNTYIHW VNQRPGKGLEWIGRIDPANGNTIYAEKFKSKVTLTAD TSSNTAYMQLSQLKSDDTALYFCAMNYEGYEDYWG QGVMVTVSS |
| SEQ ID NO: 31 | Light chain variable region of LC-20 | DIQMTQSPSFLSASVGDSVTINCKASQNINKYLNWY QQKLGEAPKRLIHKTDSLQTGIPSRFSGSGSGTDYT LTISSLQPEDVATYFCFQYKSGFMFGAGTKLELK |
| SEQ ID NO: 32 | Heavy chain variable region of HC-21 | QIQLVQSGPELKKPGESVKISCKASGYTFTDYAVYW VIQAPGKGLKWMGWINTYTGKPTYADDFKGRFVFSL ETSASTANLQISNLKNEDTATYFCARGAGMTKDYVM DAWGRGVLVTVS |
| SEQ ID NO: 33 | Light chain variable region of LC-21 | SYELIQPPSASVTLGNTVSLTCVGDELSKRYAQWYQ QKPDKTIVSVIYKDSERPSDISDRFSGSSSGTTATLTI HGTLAEDEADYYCLSTYSDDNLPVFGGGTKLTVL |
| SEQ ID NO: 34 | Heavy chain variable region of HC-22 | QVQLKESGPGLVQPSQTLSLTCTVSGFSLTSYLVHW VRQPPGKTLEWVGLMWNDGDTSYNSALKSRLSISR DTSKSQVFLKMHSLQAEDTATYYCARESNLGFTYW GHGTLVTVSS |
| SEQ ID NO: 35 | Light chain variable region of LC-22 | DIQMTQSPASLSASLEEIVTITCKASQGIDDDLSWYQ QKPGKSPQLLIYDVTRLADGVPSRFSGSRSGTQYSL KISRPQVADSGIYYCLQSYSTPYTFGAGTKLELK |
| SEQ ID NO: 36 | Heavy chain variable region of HC-23 | EVQLQQYGAELGKPGTSVRLSCKVSGYNIRNTYIHW VHQRPGEGLEWIGRIDPTNGNTISAEKFKSKATLTAD TSSNTAYMQFSQLKSDDTAIYFCAMNYEGYADYWG QGVMVTVSS |
| SEQ ID NO: 37 | Light chain variable region of LC-23 | DIQMTQSPSFLSASVGDRLTINCKASQNINKYLNWY QQKLGEAPKRLIFKTNSLQTGIPSRFSGSGSGTDYTL TISSLQPEDVATYFCFQYNIGFTFGAGTKLELK |
| SEQ ID NO: 38 | Heavy chain variable region of HC-24 | EVQLVESGGGLVQSGRSLKLSCAASGFTVSDYYMA WVRQAPTKGLEWVATINYDGSTTYHRDSVKGRFTIS RDNAKSTLYLQMDSLRSEDTATYYCARHGDYGYHY GAYYFDYWGQGVMVTVSS |
| SEQ ID NO: 39 | Light chain variable region of LC-24 | DIVLTQSPALAVSLGQRATISCRASQTVSLSGYNLIH WYQQRTGQQPKLLIYRASNLAPGIPARFSGSGSGTD FTLTISPVQSDDIATYYCQQSRESWTFGGGTNLEMK |
| SEQ ID NO: 40 | Heavy chain variable region of HC-25 | QIQLVQSGPELKKPGESVKISCKASGYTFTDYAIHWV KQAPGQGLRWMAWINTETGKPTYADDFKGRFVFSL EASASTAHLQISNLKNEDTATFFCAGGSHWFAYWG QGTLVTVSS |

TABLE 16-continued

AMINO ACID SEQUENCE SUMMARY

| Sequence Identifier | Description | Amino Acid Sequence |
|---|---|---|
| SEQ ID NO: 41 | Light chain variable region of LC-25 | SYELIQPPSASVTLENTVSITCSGDELSNKYAHWYQQKPDKTILEVIYNDSERPSGISDRFSGSSSGTTAILTIRDAQAEDEADYYCLSTFSDDDLPIFGGGTKLTVL |
| SEQ ID NO: 32 | Heavy chain variable region of HC-26 | QIQLVQSGPELKKPGESVKISCKASGYTFTDYAVYWVIQAPGKGLKWMGWINTYTGKPTYADDFKGRFVFSLETSASTANLQISNLKNEDTATYFCARGAGMTKDYVMDAWGRGVLVTVS |
| SEQ ID NO: 42 | Light chain variable region of LC-26 | SYELIQPPSTSVTLGNTVSLTCVGNELPKRYAYWFQQKPDQSIVRLIYDDDRRPSGISDRFSGSSSGTTATLTIRDAQAEDEAYYYCHSTYTDDKVPIFGGGTKLTVL |
| SEQ ID NO: 43 | Heavy chain variable region of HC-27 | EVQLVESGGGLVQPGRSMKLSCKASGFTFSNYDMAWVRQAPTRGLEWVASISYDGITAYYRDSVKGRFTISRENAKSTLYLQLVSLRSEDTATYYCTTEGGYVYSGPHYFDYWGQGVMVTVSS |
| SEQ ID NO: 44 | Light chain variable region of LC-27 | DIQMTQSPSSMSVSLGDTVTITCRASQDVGIFVNWFQQKPGRSPRRMIYRATNLADGVPSRFSGSRSGSDYSLTISSLESEDVADYHCLQYDEFPRTFGGGTKLELK |
| SEQ ID NO: 45 | Heavy chain variable region of HC-28 | EVQLQQYGAELGKPGTSVRLSCKVSGYKIRNTYIHWVNQRPGKGLEWIGRIDPANGNTIYAEKFKSKVTLTADTSSNTAYMQLSQLKSDDTALYFCAMNYEGYEDYWGQGVMVTVSS |
| SEQ ID NO: 46 | Light chain variable region of LC-28 | DIQMTQSPSFLSASVGDSVTINCKASQNINKYLNWYQQKLGEAPKRLIHKTNSLQPGFPSRFSGSGSGTDYTLTISSLQPEDVAAYFCFQYNSGFTFGAGTKLELK |
| SEQ ID NO: 47 | Heavy chain variable region of HC-29 | QVQLVQSGAEVKKPGASVKVSCKASGYTFTDYYIHWVRQAPGQGLEWMGWMNPHSGDTGYAQKFQGRVTMTRDTSTSTVYMELSSLRSEDTAVYYCARHGRGYNGYEGAFDIWGQGTLVTVSSAS |
| SEQ ID NO: 48 | Light chain variable region of LC-29 | DIQMTQSPSSLSASVGDRVTITCRASQGIGNELGWYQQKPGKAPKLLIYAASNLQSGVPSRFSGSGSGTDFTLTISSLQPEDFATYYCQQYDNLPLTFGQGTKVEIK |
| SEQ ID NO: 49 | Heavy chain variable region of HC-30 | QVQLVQSGAEVKKPGASVKVSCKASGYTFTGYYLHWVRQAPGQGLEWMGWINPNSGDTNYAQNFQGRVTMTRDTSTSTVYMELSSLRSEDTAVYYCARHGRGYNGYEGAFDIWGQGTLVTVSSAS |
| SEQ ID NO: 50 | Light chain variable region of LC-30 | DIQMTQSPSSLSASVGDRVTITCRASQGIRNDLGWYQQKPGKAPKLLIYDASSLESGVPSRFSGSGSGTDFTLTISSLQPEDFATYYCQQLNGYPLTFGGGTKVEIK |
| SEQ ID NO: 51 | Heavy chain variable region of HC-31 | QVQLVQSGAEVKKPGASVKVSCKASGYTFTGYYLHWVRQAPGQGLEWMGWINPNSGGTNYAQKFQGRVTMTRDTSTSTVYMELSSLRSEDTAVYYCARHGRGYEGYEGAFDIWGQGTLVTVSSAS |
| SEQ ID NO: 52 | Light chain variable region of LC-31 | DIQMTQSPSSLSASVGDRVTITCRASQGIRNDLGWYQQKPGKAPKLLIYDASELETGVPSRFSGSGSGTDFTLTISSLQPEDFATYYCQQLNGYPITFGQGTKVEIK |
| SEQ ID NO: 53 | Heavy chain variable region of HC-32 | QVQLVQSGAEVKKPGASVKVSCKASGYTFTSYYIHWVRQAPGQGLEWMGWLNPSGGGTSYAQKFQGRVTMTRDTSTSTVYMELSSLRSEDTAVYYCARHGRGYDGYEGAFDIWGQGTLVTVSSAS |
| SEQ ID NO: 54 | Light chain variable region of LC-32 | DIQMTQSPSSLSASVGDRVTITCRASQGIRNDLGWYQQKPGKAPKLLIYDASNLETGVPSRFSGSGSGTDFTLTISSLQPEDFATYYCQQLNGYPLTFGGGTKVEIK |
| SEQ ID NO: 55 | Heavy chain variable region of HC-33 | QVQLVQSGAEVKKPGASVKVSCKASGYTFSTYYMHWVRQAPGQGLEWMGIINPSGGSTSYAQKFQGRVTMTRDTSTSTVYMKLSSLRSEDTAVYYCARHGRGYEGYEGAFDIWGQGTLVTVSSAS |
| SEQ ID NO: 56 | Light chain variable region of LC-33 | DIQMTQSPSSLSASVGDRVTITCRASQGIRDDLGWYQQKPGKAPKLLIYDASNLETGVPSRFSGSGSGTDFTLTISSLQPEDFATYYCQQANGFPLTFGGGTKVEIK |

TABLE 16-continued

AMINO ACID SEQUENCE SUMMARY

| Sequence Identifier | Description | Amino Acid Sequence |
|---|---|---|
| SEQ ID NO: 57 | Heavy chain variable region of HC-34 | QVQLVQSGAEVKKPGASVKVSCKASGYTFTGYYIH WVRQAPGQGLEWMGIINPSGGNTNYAQNFQGRVT MTRDTSTSTVYMELSSLRSEDTAVYYCARHGRGYN AYEGAFDIWGQGTLVTVSSAS |
| SEQ ID NO: 58 | Light chain variable region of LC-34 | DIQMTQSPSSLSASVGDRVTITCRASQGIRNDLGWY QQKPGKAPKLLIYDASNLETGVPSRFSGSGSGTDFT LTISSLQPEDFATYYCQQVNGYPLTFGGGTKVEIK |
| SEQ ID NO: 59 | Heavy chain variable region of HC-35 | QVQLVQSGAEVKKPGASVKVSCKASGGTFSSYAIS WVRQAPGQGLEWMGVINPTVGGANYAQKFQGRVT MTRDTSTSTVYMELSSLRSEDTAVYYCARHGRGYN EYEGAFDIWGQGTLVTVSSAS |
| SEQ ID NO: 60 | Light chain variable region of LC-35 | DIQMTQSPSSLSASVGDRVTITCQASQDISDYLNWY QQKPGKAPKLLIYDASNLETGVPSRFSGSGSGTDFT LTISSLQPEDFATYYCQQGNSFPLTFGGGTKLEIK |
| SEQ ID NO: 61 | Heavy chain variable region of HC-36 | QVQLVQSGAEVKKLGASVKVSCKASGYTFSSYYMH WVRQAPGQGLEWMGVINPNGAGTNFAQKFQGRVT MTRDTSTSTVYMELSSLRSEDTAVYYCARHGRGYE GYEGAFDIWGQGTLVTVSSAS |
| SEQ ID NO: 50 | Light chain variable region of LC-36 | DIQMTQSPSSLSASVGDRVTITCRASQGIRNDLGWY QQKPGKAPKLLIYDASSLESGVPSRFSGSGSGTDFT LTISSLQPEDFATYYCQQLNGYPLTFGGGTKVEIK |
| SEQ ID NO: 62 | Heavy chain variable region of HC-37 | QVQLVQSGAEVKKPGASVKVSCKASGYTFTTYYMH WVRQAPGQGLEWMGWINPTGGGTNYAQNFQGRV TMTRDTSTSTVYMELSSLRSEDTAVYYCARHGRGY EGYEGAFDIWGQGTLVTVSSAS |
| SEQ ID NO: 63 | Light chain variable region of LC-37 | DIQMTQSPSSLSASVGDRVTITCRASQGIRNDVSWY QQKPGKAPKLLIYDASNLETGVPSRFSGSGSGTDFT LTISSLQPEDFATYYCQQLSGYPITFGQGTKLEIK |
| SEQ ID NO: 64 | Heavy chain variable region of HC-38 | QVQLVQSGAEVKKPGASVKVSCKASGYTFTSYYIH WVRQAPGQGLEWMGMINPSGGSTNYAQKFQGRVT MTRDTSTSTVYMELSSLRSEDTAVYYCARHGRGYN DYEGAFDIWGQGTLVTVSSAS |
| SEQ ID NO: 65 | Light chain variable region of LC-38 | DIQMTQSPSSLSASVGDRVTITCRASQSISDWLAWY QQKPGKAPKLLIYEASNLEGGVPSRFSGSGSGTDFT LTISSLQPEDFATYYCQQANSFPYTFGQGTKVEIK |
| SEQ ID NO: 66 | Heavy chain variable region of HC-39 | QVQLVQSGAEVKKPGASVKVSCKASGYIFSAYYIHW VRQAPGQGLEWMGIINPSGGSTRYAQKFQGRVTMT RDTSTSTVYMELSSLRSEDTAVYYCARHGRGYGGY EGAFDIWDQGTLVTVSSAS |
| SEQ ID NO: 67 | Light chain variable region of LC-39 | DIQMTQSPSSLSASVGDRVTITCRASQGIGDYVAWY QQKPGKAPKLLIYDASNLETGVPSRFSGSGSGTDFT LTISSLQPEDFATYYCQQLNGYPITFGQGTRLEIK |
| SEQ ID NO: 68 | Heavy chain variable region of HC-40 | EVQLVQSGAEVKKPGESLKISCKGSGYRFTSYWIG WVRQMPGKGLEWMGIIYPDDSDTRYSPSFQGQVTI SVDKSNSTAYLQWSSLKASDTAMYYCARHGRGYN GYEGAFDIWGQGTLVTVSSAS |
| SEQ ID NO: 69 | Light chain variable region of LC-40 | DIQMTQSPSSLSASVGDRVTITCRASQGISSYLAWY QQKPGKAPKLLIYDASNLETGVPSRFSGSGSGTYFT LTISSLQPEDFATYYCQQGASFPITFGQGTKVEIK |
| SEQ ID NO: 70 | Heavy chain variable region of HC-41 | EVQLVQSGAEVKKPGESLKISCKGSGSSFPNSWIAW VRQMPGKGLEWMGIIYPSDSDTRYSPSFQGQVTISA DKSISTAYLQWSSLEASDTAMYYCARHGRGYNGYE GAFDIWGQGTLVTVSSAS |
| SEQ ID NO: 71 | Light chain variable region of LC-41 | DIQMTQSPSSLSASVGDRVTITCRASQGIRNYLAWY QQKPGKAPKLLIYDASSLQSGVPSRFSGSGSGTDFT LTISSLQPEDFATYYCQQLNSYPLTFGGGTKVEIK |

TABLE 16-continued

AMINO ACID SEQUENCE SUMMARY

| Sequence Identifier | Description | Amino Acid Sequence |
|---|---|---|
| SEQ ID NO: 72 | Heavy chain variable region of HC-42 | EVQLVQSGAEVKKPGESLKISCKGSGYSFDSYWIG WVRQMPGKGLEWMGIMYPGDSDTRYSPSFQGQVT ISADKSISTAYLQWSSLKASDTAMYYCARHGRGYNA YEGAFDIWGQGTLVTVSSAS |
| SEQ ID NO: 73 | Light chain variable region of LC-42 | DIQMTQSPSSLSASVGDRVTITCRASQSINNWLAWY QQKPGKAPKLLIYDAFILQSGVPSRFSGSGSGTDFTL TISSLQPEDFATYYCLQLNSYPLTFGPGTKVDIK |
| SEQ ID NO: 74 | Heavy chain variable region of HC-43 | EVQLVQSGAEVKKPGESLKISCKGSGYSFTNWIAWV RQMPGKGLEWMGIIYPGDSETRYSPSFQGQVTISAD KSISTAYLQWSSLKASDTAMYYCARHGRGYYGYEG AFDIWGQGTLVTVSSAS |
| SEQ ID NO: 75 | Light chain variable region of LC-43 | DIQMTQSPSSLSASVGDRVTITCRASQGISDNLNWY QQKPGKAPKLLIYDASNLETGVPSRFSGSGSGTDFT LTISSLQPEDFATYYCQQAISFPLTFGQGTKVEIK |
| SEQ ID NO: 76 | Heavy chain variable region of HC-44 | EVQLVQSGAEVKKPGESLKISCKGSGYNFTSYWIG WVRQMPGKGLEWMGVIYPDDSETRYSPSFQGQVTI SADKSISTAYLQWSSLKASDTAMYYCARHGRGYNG YEGAFDIWGQGTLVTVSSAS |
| SEQ ID NO: 77 | Light chain variable region of LC-44 | DIQMTQSPSSLSASVGDRVTITCRASRDIRDDLGWY QQKPGKAPKLLIYDASNLETGVPSRFSGSGSGTDFT LTISSLQPEDFATYYCQQANSFPLTFGGGTKVEIK |
| SEQ ID NO: 78 | Heavy chain variable region of HC-45 | EVQLVQSGAEVKKPGESLKISCKGSGYTFNTYIGWV RQMPGKGLEWMGIIYPGDSGTRYSPSFQGQVTISA DKAISTAYLQWSSLKASDTAMYYCARHSRGYNGYE GAFDIWGQGTLVTVSSAS |
| SEQ ID NO: 79 | Light chain variable region of LC-45 | DIQMTQSPSSLSASVGDRVTITCRASQGISNYLAWY QQKPGKAPKLLIYDASNLETGVPSRFSGSGSGTDFT LTISSLQPEDFATYYCQQANSFPVTFGQGTKVEIK |
| SEQ ID NO: 80 | Heavy chain variable region of HC-46 | EVQLVQSGAEVKKPGESLKISCKGSGYNFTTYWIGW VRQMPGKGLEWMGIIHPADSDTRYNPSFQGQVTISA DKSISTAYLQWSSLKASDTAMYYCARHGRGYNGYE GAFDIWGQGTLVTVSSAS |
| SEQ ID NO: 81 | Light chain variable region of LC-46 | DIQMTQSPSSLSASVGDRVTITCRVSQGISSYLAWY QQKPGKAPKLLIYDASNLETGVPSRFSGSGSGTDFT LTISSLQPEDFATYYCQQANSFPLTFGGGTKVEIK |
| SEQ ID NO: 82 | Heavy chain variable region of HC-47 | EVQLVQSGAEVKKPGESLKISCKGSGYRFSNYWIA WVRQMPGKGLEWMGIIYPDNSDTRYSPSFQGQVTI SADKSISTAYLQWSSLKASDTAMYYCARHGRGYDG YEGAFDIWGQGTLVTVSSAS |
| SEQ ID NO: 83 | Light chain variable region of LC-47 | DIQMTQSPSSLSASVGDRVTITCRASQGIRSDLAWY QQKPGKAPKLLIYGASSLQSGVPSRFSGSGSGTDFT LTISSLQPEDFATYYCQQANSFPLSFGQGTKVEIK |
| SEQ ID NO: 84 | Heavy chain variable region of HC-48 | EVQLVQSGAEVKKPGESLKISCKGSGYRFASYWIG WVRQMPGKGLEWMGITYPGDSETRYNPSQGQVTIS ADKSISTAYLQWSSLKASDTAMYYCARHGRGYGGY EGAFDIWGQGTLVTVSSAS |
| SEQ ID NO: 85 | Light chain variable region of LC-48 | DIQMTQSPSSLSASVGDRVTITCRASQGIRNDLGWY QQKPGKAPKLLIYDASNLETGVPSRFSGSGSGTDFT LTISSLQPEDFATYYCQQANSFPLTFGGGTKVEIK |
| SEQ ID NO: 86 | Heavy chain variable region of HC-49 | EVQLVQSGAEVKKPGESLKISCKGSGYSFTSYWIGW VRQMPGKGLEWMGIIYPGDSDTRYSPSFQGQVTISA DKSISTAYLQWSSLKASDTAMYYCARHGRGYNGYE GAFDIWGQGTLVTVSSAS |
| SEQ ID NO: 87 | Light chain variable region of LC-49 | DIQMTQSPSSLSASVGDRVTITCRASQSISNWLAWY QQKPGKAPKLLIYDASNLETGVPSRFSGSGSGTDFT LTISSLQPEDFATYYCQQTNSFPLTFGQGTRLEIK |

TABLE 16-continued

AMINO ACID SEQUENCE SUMMARY

| Sequence Identifier | Description | Amino Acid Sequence |
|---|---|---|
| SEQ ID NO: 7 | Heavy chain variable region of HC-74 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 88 | Light chain variable region of LC-74 | DIQLTQSPSSLSASVGDRVTITCRASQGVISALAWYQ QKPGKAPKLLIYDASSLESGVPSRFSGSGSGTDFTL TISSLQPEDFATYYCQQFNSYPLTFGGGTKVEIK |
| SEQ ID NO: 7 | Heavy chain variable region of HC-75 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 89 | Light chain variable region of LC-75 | DIQLTQSPSSLSASVGDRVTITCRASQGIRSALAWYQ QKPGKAPKLLIYDASSLESGVPSRFSGSGSGTDFTL TISSLQPEDFATYYCQQFNSYPLTFGGGTKVEIK |
| SEQ ID NO: 7 | Heavy chain variable region of HC-76 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 90 | Light chain variable region of LC-76 | DIQLTQSPSSLSASVGDRVTITCRASQGVGSALAWY QQKPGKAPKLLIYDASSLESGVPSRFSGSGSGTDFT LTISSLQPEDFATYYCQQFNSYPLTFGGGTKVEIK |
| SEQ ID NO: 7 | Heavy chain variable region of HC-77 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 91 | Light chain variable region of LC-77 | DIQLTQSPSSLSASVGDRVTITCRASQGVISALAWYQ QKPGKAPKLLIYDASILESGVPSRFSGSGSGTDFTLTI SSLQPEDFATYYCQQFNSYPLTFGGGTKVEIK |
| SEQ ID NO: 7 | Heavy chain variable region of HC-78 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 92 | Light chain variable region of LC-78 | DIQLTQSPSSLSASVGDRVTITCRASQGIRSALAWYQ QKPGKAPKLLIYDASILESGVPSRFSGSGSGTDFTLTI SSLQPEDFATYYCQQFNSYPLTFGGGTKVEIK |
| SEQ ID NO: 7 | Heavy chain variable region of HC-79 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 93 | Light chain variable region of LC-79 | DIQLTQSPSSLSASVGDRVTITCRASQGVGSALAWY QQKPGKAPKLLIYDASILESGVPSRFSGSGSGTDFTL TISSLQPEDFATYYCQQFNSYPLTFGGGTKVEIK |
| SEQ ID NO: 7 | Heavy chain variable region of HC-80 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 94 | Light chain variable region of LC-80 | DIQLTQSPSSLSASVGDRVTITCRASQGISSALAWYQ QKPGKAPKLLIYDASILESGVPSRFSGSGSGTDFTLTI SSLQPEDFATYYCQQFNSYPLTFGGGTKVEIK |
| SEQ ID NO: 7 | Heavy chain variable region of HC-81 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 95 | Light chain variable region of LC-81 | DIQLTQSPSSLSASVGDRVTITCRASQGVISALAWYQ QKPGKAPKLLIYDASTLESGVPSRFSGSGSGTDFTL TISSLQPEDFATYYCQQFNSYPLTFGGGTKVEIK |
| SEQ ID NO: 7 | Heavy chain variable region of HC-82 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |

TABLE 16-continued

AMINO ACID SEQUENCE SUMMARY

| Sequence Identifier | Description | Amino Acid Sequence |
|---|---|---|
| SEQ ID NO: 96 | Light chain variable region of LC-82 | DIQLTQSPSSLSASVGDRVTITCRASQGIRSALAWYQ QKPGKAPKLLIYDASTLESGVPSRFSGSGSGTDFTL TISSLQPEDFATYYCQQFNSYPLTFGGGTKVEIK |
| SEQ ID NO: 7 | Heavy chain variable region of HC-83 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 97 | Light chain variable region of LC-83 | DIQLTQSPSSLSASVGDRVTITCRASQGVGSALAWY QQKPGKAPKLLIYDASTLESGVPSRFSGSGSGTDFT LTISSLQPEDFATYYCQQFNSYPLTFGGGTKVEIK |
| SEQ ID NO: 7 | Heavy chain variable region of HC-84 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 97 | Light chain variable region of LC-84 | DIQLTQSPSSLSASVGDRVTITCRASQGVGSALAWY QQKPGKAPKLLIYDASTLESGVPSRFSGSGSGTDFT LTISSLQPEDFATYYCQQFNSYPLTFGGGTKVEIK |
| SEQ ID NO: 98 | Heavy chain variable region of HC-245 | EVQLVQSGAEVKKPGESLKISCKGSGYRFTTSWIGW VRQMPGKGLEWMGIIYPGDSDTRYSPSFQGQVTISA DKSISTAYLQWSSLKASDTAMYYCARHGLGYNGYE GAFDIWGQGTLVTVSS |
| SEQ ID NO: 99 | Light chain variable region of LC-245 | DIQMTQSPSSLSASVGDRVTITCRASQGIGSALAWY QQKPGKAPKLLIYDASTLESGVPSRFSGSGSGTDFT LTISSLQPEDFATYYCQQFNGYPLTFGQGTRLEIK |
| SEQ ID NO: 7 | Heavy chain variable region of HC-246 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 99 | Light chain variable region of LC-246 | DIQMTQSPSSLSASVGDRVTITCRASQGIGSALAWY QQKPGKAPKLLIYDASTLESGVPSRFSGSGSGTDFT LTISSLQPEDFATYYCQQFNGYPLTFGQGTRLEIK |
| SEQ ID NO: 7 | Heavy chain variable region of HC-247 | QVQLVQSGAAVKKPGESLKISCKGSGYRFTTYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 100 | Light chain variable region of LC-247 | DIQMTQSPSSLSASVGDRVTITCRASRGISDYLAWY QQKPGKAPKLLIYDASNLETGVPSRFSGSGSGTDFT LTISSLQPEDFATYYCQQANSFPITFGQGTRLEIK |
| SEQ ID NO: 98 | Heavy chain variable region of HC-248 | EVQLVQSGAEVKKPGESLKISCKGSGYRFTTSWIGW VRQMPGKGLEWMGIIYPGDSDTRYSPSFQGQVTISA DKSISTAYLQWSSLKASDTAMYYCARHGLGYNGYE GAFDIWGQGTLVTVSS |
| SEQ ID NO: 101 | Light chain variable region of LC-248 | DIQMTQSPSSLSASVGDRVTITCRASQGIGSALAWY QQKPGKAPKLLIYDASTLESGVPSRFSGSGSGTDFT LTISSLQPEDFATYYCQQLNGYPLTFGQGTRLEIK |
| SEQ ID NO: 98 | Heavy chain variable region of HC-249 | EVQLVQSGAEVKKPGESLKISCKGSGYRFTTSWIGW VRQMPGKGLEWMGIIYPGDSDTRYSPSFQGQVTISA DKSISTAYLQWSSLKASDTAMYYCARHGLGYNGYE GAFDIWGQGTLVTVSS |
| SEQ ID NO: 102 | Light chain variable region of LC-249 | DIQMTQSPSSLSASVGDRVTITCRASQGIGSALAWY QQKPGKAPKLLIYDASNLETGVPSRFSGSGSGTDFT LTISSLQPEDFATYYCQQLNGYPLTFGQGTRLEIK |
| SEQ ID NO: 143 | Heavy chain variable region of Ab 85 | EVQLVQSGAEVKKPGESLKISCKGSGYSFTNYWIG WVRQMPGKGLEWMAIINPRDSDTRYRPSFQGQVTI SADKSISTAYLQWSSLKASDTAMYYCARHGRGYEG YEGAFDIWGQGTLVTVSS |
| NO: 144 | region of Ab 85 | QQKPGKAPKLLIYDASNLETGVPSRFSGSGSGTDFT LTISSLQPEDFATYYCQQANGFPLTFGGGTKVEIK |

TABLE 16-continued

AMINO ACID SEQUENCE SUMMARY

| Sequence Identifier | Description | Amino Acid Sequence |
| --- | --- | --- |
| SEQ ID NO: 145 | Ab85 CDR-H1 | NYWIG |
| SEQ ID NO: 146 | Ab85 CDR-H2 | IINPRDSDTRYRPSFQG |
| SEQ ID NO: 147 | Ab85 CDR-H3 | HGRGYEGYEGAFDI |
| SEQ ID NO: 148 | Ab85 CDR-L1 | RSSQGIRSDLG |
| SEQ ID NO: 149 | Ab85 CDR-L2<br>Ab249 CDR-L2 | DASNLET |
| SEQ ID NO: 150 | Ab85 CDR-L3 | QQANGFPLT |
| SEQ ID NO: 151 | Heavy chain variable region of Ab 86 | EVQLVQSGAEVKKPGESLKISCKGSGYSFTNYWIG WVRQMPGKGLEWMGIIYPGDSDIRYSPSLQGQVTIS VDTSTSTAYLQWNSLKPSDTAMYYCARHGRGYNGY EGAFDIWGQGTLVTVSS |
| SEQ ID NO: 152 | Light chain variable region of Ab 86 | DIQMTQSPSSLSASVGDRVTITCRASQGIGDSLAWY QQKPGKAPKLLIYDASNLETGVPSRFSGSGSGTDFT LTISSLQPEDFATYYCQQLNGYPITFGQGTKVEIK |
| SEQ ID NO: 145 | Ab86 CDR-H1 | NYWIG |
| SEQ ID NO: 153 | Ab86 CDR-H2 | IIYPGDSDIRYSPSLQG |
| SEQ ID NO: 3 | Ab86 CDR-H3 | HGRGYNGYEGAFDI |
| SEQ ID NO: 154 | Ab86 CDR-L1 | RASQGIGDSLA |
| SEQ ID NO: 149 | Ab86 CDR-L2 | DASNLET |
| SEQ ID NO: 155 | Ab86 CDR-L3 | QQLNGYPIT |
| SEQ ID NO: 143 | Heavy chain variable region of Ab 87 | EVQLVQSGAEVKKPGESLKISCKGSGYSFTNYWIG WVRQMPGKGLEWMAIINPRDSDTRYRPSFQGQVTI SADKSISTAYLQWSSLKASDTAMYYCARHGRGYEG YEGAFDIWGQGTLVTVSS |
| SEQ ID NO: 156 | Light chain variable region of Ab 87 | DIQMTQSPSSLSASVGDRVTITCRASQGIRNDLGWY QQKPGKAPKLLIYDASSLESGVPSRFSGSGSGTDFT LTISSLQPEDFATYYCQQLNGYPITFGQGTKVEIK |
| SEQ ID NO: 145 | Ab87 CDR-H1 | NYWIG |
| SEQ ID NO: 146 | Ab87 CDR-H2 | IINPRDSDTRYRPSFQG |
| SEQ ID NO: 147 | Ab87 CDR-H3 | HGRGYEGYEGAFDI |
| SEQ ID NO: 157 | Ab87 CDR-L1 | RASQGIRNDLG |
| SEQ ID NO: 5 | Ab87 CDR-L2 | DASSLES |
| SEQ ID NO: 155 | Ab87 CDR-L3 | QQLNGYPIT |
| SEQ ID NO: 158 | Heavy chain variable region of Ab 88 | EVQLVQSGAEVKKPGESLKISCKGSGYSFTNYWIG WVRQMPGKGLEWMGIIYPGDSLTRYSPSFQGQVTI SADKSISTAYLQWSSLKASDTAMYYCARHGRGYNG YEGAFDIWGQGTLVTVSS |

TABLE 16-continued

AMINO ACID SEQUENCE SUMMARY

| Sequence Identifier | Description | Amino Acid Sequence |
|---|---|---|
| SEQ ID NO: 156 | Light chain variable region of Ab 88 | DIQMTQSPSSLSASVGDRVTITCRASQGIRNDLGWY QQKPGKAPKLLIYDASSLESGVPSRFSGSGSGTDFT LTISSLQPEDFATYYCQQLNGYPITFGQGTKVEIK |
| SEQ ID NO: 145 | Ab88 CDR-H1 | NYWIG |
| SEQ ID NO: 159 | Ab88 CDR-H2 | IIYPGDSLTRYSPSFQG |
| SEQ ID NO: 3 | Ab88 CDR-H3 | HGRGYNGYEGAFDI |
| SEQ ID NO: 157 | Ab88 CDR-L1 | RASQGIRNDLG |
| SEQ ID NO: 5 | Ab88 CDR-L2 | DASSLES |
| SEQ ID NO: 155 | Ab88 CDR-L3 | QQLNGYPIT |
| SEQ ID NO: 160 | Heavy chain variable region of Ab89 | EVQLVQSGAEVKKPGESLKISCKGSGYSFTNYWIG WVRQMPGKGLEWMGIIYPGDSDTRYSPSFQGQVTI SADKSISTAYLQWSSLKASDTAMYYCARHGRGYNG YEGAFDIWGQGTLVTVSS |
| SEQ ID NO: 152 | Light chain variable region of Ab89 | DIQMTQSPSSLSASVGDRVTITCRASQGIGDSLAWY QQKPGKAPKLLIYDASNLETGVPSRFSGSGSGTDFT LTISSLQPEDFATYYCQQLNGYPITFGQGTKVEIK |
| SEQ ID NO: 145 | Ab89 CDR-H1 | NYWIG |
| SEQ ID NO: 2 | Ab89 CDR-H2 | IIYPGDSDTRYSPSFQG |
| SEQ ID NO: 3 | Ab89 CDR-H3 | HGRGYNGYEGAFDI |
| SEQ ID NO: 154 | Ab89 CDR-L1 | RASQGIGDSLA |
| SEQ ID NO: 149 | Ab89 CDR-L2 | DASNLET |
| SEQ ID NO: 155 | Ab89 CDR-L3 | QQLNGYPIT |
| SEQ ID NO: 161 | Heavy chain variable region amino acid sequence of CK6 | QVQLVQSGAAVKKPGESLKISCKGSGYRFTSYWIG WVRQMPGKGLEWMGIIYPGDSDTRYSPSFQGQVTI SAGKSISTAYLQWSSLKASDTAMYYCARHGRGYNG YEGAFDIWGQGTMVTVSS |
| SEQ ID NO: 162 | Light chain variable region amino acid sequence of CK6 | AIQLTQSPSSLSASVGDRVTITCRASQGISSALAWYQ QKPGKAPKLLIYDASSLESGVPSRFSGSGSGTDFTL TISSLQPEDFATYYCQQFNSYPLTFGGGTKVEIK |
| SEQ ID NO: 163 | Ab77 CDR-H1 | TYWIG |
| SEQ ID NO: 2 | Ab77 CDR-H2 | IIYPGDSDTRYSPSFQG |
| SEQ ID NO: 3 | Ab77 CDR-H3 | HGRGYNGYEGAFDI |
| SEQ ID NO: 164 | Ab77 CDR-L1 | RASQGVISALA |
| SEQ ID NO: 165 | Ab77 CDR-L2 | DASILES |
| SEQ ID NO: 166 | Ab77 CDR-L3 | QQFNSYPLT |
| SEQ ID NO: 163 | Ab79 CDR-H1 | TYWIG |
| SEQ ID NO: 2 | Ab79 CDR-H2 | IIYPGDSDTRYSPSFQG |
| SEQ ID NO: 3 | Ab79 CDR-H3 | HGRGYNGYEGAFDI |

TABLE 16-continued

AMINO ACID SEQUENCE SUMMARY

| Sequence Identifier | Description | Amino Acid Sequence |
|---|---|---|
| SEQ ID NO: 167 | Ab79 CDR-L1 | RASQGVGSALA |
| SEQ ID NO: 165 | Ab79 CDR-L2 | DASILES |
| SEQ ID NO: 166 | Ab79 CDR-L3 | QQFNSYPLT |
| SEQ ID NO: 163 | Ab81 CDR-H1 | TYWIG |
| SEQ ID NO: 2 | Ab81 CDR-H2 | IIYPGDSDTRYSPSFQG |
| SEQ ID NO: 3 | Ab81 CDR-H3 | HGRGYNGYEGAFDI |
| SEQ ID NO: 164 | Ab81 CDR-L1 | RASQGVISALA |
| SEQ ID NO: 168 | Ab81 CDR-L2 | DASTLES |
| SEQ ID NO: 166 | Ab81 CDR-L3 | QQFNSYPLT |
| SEQ ID NO: 169 | Heavy chain constant region (Wild type (WT)) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 170 | Heavy chain constant region with L234A, L235A (LALA) mutations (mutations in bold)* | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 171 | Heavy chain constant region with D265C mutation (mutation in bold)* | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVCVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 172 | Heavy chain constant region with H435A mutation (mutation in bold)* | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNAYTQKSLSLSPGK |

TABLE 16-continued

AMINO ACID SEQUENCE SUMMARY

| Sequence Identifier | Description | Amino Acid Sequence |
| --- | --- | --- |
| SEQ ID NO: 173 | Heavy chain constant region: modified Fc region with L234A, L235A, D265C mutations (mutations in bold)* | ASTKGPSVFPLAPSSKSTSGGTAALGCLVKDYFPEP VTVSWNSGALTSGVHTFPAVLQSSGLYSLSSVVTVP SSSLGTQTYICNVNHKPSNTKVDKKVEPKSCDKTHT CPPCPAPEAAGGPSVFLFPPKPKDTLMISRTPEVTC VVVCVSHEDPEVKFNWYVDGVEVHNAKTKPREEQY NSTYRVVSVLTVLHQDWLNGKEYKCKVSNKALPAPI EKTISKAKGQPREPQVYTLPPSRDELTKNQVSLTCL VKGFYPSDIAVEWESNGQPENNYKTTPPVLDSDGS FFLYSKLTVDKSRWQQGNVFSCSVMHEALHNHYTQ KSLSLSPGK |
| SEQ ID NO: 174 | Heavy chain constant region: modified Fc region with L234A, L235A, D265C, H435A mutations (mutations in bold)* | ASTKGPSVFPLAPSSKSTSGGTAALGCLVKDYFPEP VTVSWNSGALTSGVHTFPAVLQSSGLYSLSSVVTVP SSSLGTQTYICNVNHKPSNTKVDKKVEPKSCDKTHT CPPCPAPEAAGGPSVFLFPPKPKDTLMISRTPEVTC VVVCVSHEDPEVKFNWYVDGVEVHNAKTKPREEQY NSTYRVVSVLTVLHQDWLNGKEYKCKVSNKALPAPI EKTISKAKGQPREPQVYTLPPSRDELTKNQVSLTCL VKGFYPSDIAVEWESNGQPENNYKTTPPVLDSDGS FFLYSKLTVDKSRWQQGNVFSCSVMHEALHNAYTQ KSLSLSPGK |
| SEQ ID NO: 175 | Ab85 full length heavy chain sequence; constant region underlined | EVQLVQSGAEVKKPGESLKISCKGSGYSFTNYWIG WVRQMPGKGLEWMAIINPRDSDTRYRPSFQGQVTI SADKSISTAYLQWSSLKASDTAMYYCARHGRGYEG YEGAFDIWGQGTLVTVSSASTKGPSVFPLAPSSKST SGGTAALGCLVKDYFPEPVTVSWNSGALTSGVHTF PAVLQSSGLYSLSSVVTVPSSSLGTQTYICNVNHKP SNTKVDKKVEPKSCDKTHTCPPCPAPELLGGPSVFL FPPKPKDTLMISRTPEVTCVVVDVSHEDPEVKFNWY VDGVEVHNAKTKPREEQYNSTYRVVSVLTVLHQDW LNGKEYKCKVSNKALPAPIEKTISKAKGQPREPQVYT LPPSRDELTKNQVSLTCLVKGFYPSDIAVEWESNGQ PENNYKTTPPVLDSDGSFFLYSKLTVDKSRWQQGN VFSCSVMHEALHNHYTQKSLSLSPGK |
| SEQ ID NO: 176 | Ab85 full length heavy chain sequence; constant region underlined; modified Fc region with L234A, L235A mutations (mutations in bold)* | EVQLVQSGAEVKKPGESLKISCKGSGYSFTNYWIG WVRQMPGKGLEWMAIINPRDSDTRYRPSFQGQVTI SADKSISTAYLQWSSLKASDTAMYYCARHGRGYEG YEGAFDIWGQGTLVTVSSASTKGPSVFPLAPSSKST SGGTAALGCLVKDYFPEPVTVSWNSGALTSGVHTE PAVLQSSGLYSLSSVVTVPSSSLGTQTYICNVNHKP SNTKVDKKVEPKSCDKTHTCPPCPAPEAAGGPSVF LFPPKPKDTLMISRTPEVTCVVVDVSHEDPEVKFNW YVDGVEVHNAKTKPREEQYNSTYRVVSVLTVLHQD WLNGKEYKCKVSNKALPAPIEKTISKAKGQPREPQV YTLPPSRDELTKNQVSLTCLVKGFYPSDIAVEWESN GQPENNYKTTPPVLDSDGSFFLYSKLTVDKSRWQQ GNVFSCSVMHEALHNHYTQKSLSLSPGK |
| SEQ ID NO: 177 | Ab85 full length heavy chain sequence: constant region underlined; modified Fc region with L234A, L235A, D265C mutations (mutations in bold)* | EVQLVQSGAEVKKPGESLKISCKGSGYSFTNYWIG WVRQMPGKGLEWMAIINPRDSDTRYRPSFQGQVTI SADKSISTAYLQWSSLKASDTAMYYCARHGRGYEG YEGAFDIWGQGTLVTVSSASTKGPSVFPLAPSSKST SGGTAALGCLVKDYFPEPVTVSWNSGALTSGVHTF PAVLQSSGLYSLSSVVTVPSSSLGTQTYICNVNHKP SNTKVDKKVEPKSCDKTHTCPPCPAPEAAGGPSVF LFPPKPKDTLMISRTPEVTCVVVCVSHEDPEVKFNW YVDGVEVHNAKTKPREEQYNSTYRVVSVLTVLHQD WLNGKEYKCKVSNKALPAPIEKTISKAKGQPREPQV YTLPPSRDELTKNQVSLTCLVKGFYPSDIAVEWESN GQPENNYKTTPPVLDSDGSFFLYSKLTVDKSRWQQ GNVFSCSVMHEALHNHYTQKSLSLSPGK |
| SEQ ID NO: 178 | Ab85 full length heavy chain sequence (LALA-D265C-H435A mutant); constant region underlined | EVQLVQSGAEVKKPGESLKISCKGSGYSFTNYWIG WVRQMPGKGLEWMAIINPRDSDTRYRPSFQGQVTI SADKSISTAYLQWSSLKASDTAMYYCARHGRGYEG YEGAFDIWGQGTLVTVSSASTKGPSVFPLAPSSKST SGGTAALGCLVKDYFPEPVTVSWNSGALTSGVHTF PAVLQSSGLYSLSSVVTVPSSSLGTQTYICNVNHKP SNTKVDKKVEPKSCDKTHTCPPCPAPEAAGGPSVF LFPPKPKDTLMISRTPEVTCVVVCVSHEDPEVKFNW YVDGVEVHNAKTKPREEQYNSTYRVVSVLTVLHQD WLNGKEYKCKVSNKALPAPIEKTISKAKGQPREPQV YTLPPSRDELTKNQVSLTCLVKGFYPSDIAVEWESN GQPENNYKTTPPVLDSDGSFFLYSKLTVDKSRWQQ GNVFSCSVMHEALHNAYTQKSLSLSPGK |

TABLE 16-continued

AMINO ACID SEQUENCE SUMMARY

| Sequence Identifier | Description | Amino Acid Sequence |
|---|---|---|
| SEQ ID NO: 179 | Ab249 full length heavy chain sequence; constant region underlined | EVQLVQSGAEVKKPGESLKISCKGSGYRFTTSWIGW VRQMPGKGLEWMGIIYPGDSDTRYSPSFQGQVTISA DKSISTAYLQWSSLKASDTAMYYCARHGLGYNGYE GAFDIWGQGTLVTVSSASTKGPSVFPLAPSSKSTSG GTAALGCLVKDYFPEPVTVSWNSGALTSGVHTFPAV LQSSGLYSLSSVVTVPSSSLGTQTYICNVNHKPSNT KVDKKVEPKSCDKTHTCPPCPAPELLGGPSVFLFPP KPKDTLMISRTPEVTCVVVDVSHEDPEVKFNWYVDG VEVHNAKTKPREEQYNSTYRVVSVLTVLHQDWLNG KEYKCKVSNKALPAPIEKTISKAKGQPREPQVYTLPP SRDELTKNQVSLTCLVKGFYPSDIAVEWESNGQPEN NYKTTPPVLDSDGSFFLYSKLTVDKSRWQQGNVFS CSVMHEALHNHYTQKSLSLSPGK |
| SEQ ID NO: 180 | Ab249 full length heavy chain sequence; constant region underlined (LALA mutations)* | EVQLVQSGAEVKKPGESLKISCKGSGYRFTTSWIGW VRQMPGKGLEWMGIIYPGDSDTRYSPSFQGQVTISA DKSISTAYLQWSSLKASDTAMYYCARHGLGYNGYE GAFDIWGQGTLVTVSSASTKGPSVFPLAPSSKSTSG GTAALGCLVKDYFPEPVTVSWNSGALTSGVHTFPAV LQSSGLYSLSSVVTVPSSSLGTQTYICNVNHKPSNT KVDKKVEPKSCDKTHTCPPCPAPEAAGGPSVFLFP PKPKDTLMISRTPEVTCVVVDVSHEDPEVKFNWYVD GVEVHNAKTKPREEQYNSTYRVVSVLTVLHQDWLN GKEYKCKVSNKALPAPIEKTISKAKGQPREPQVYTLP PSRDELTKNQVSLTCLVKGFYPSDIAVEWESNGQPE NNYKTTPPVLDSDGSFFLYSKLTVDKSRWQQGNVE SCSVMHEALHNHYTQKSLSLSPGK |
| SEQ ID NO: 181 | Ab249 full length heavy chain sequence; constant region underlined (LALA-D265C mutations)* | EVQLVQSGAEVKKPGESLKISCKGSGYRFTTSWIGW VRQMPGKGLEWMGIIYPGDSDTRYSPSFQGQVTISA DKSISTAYLQWSSLKASDTAMYYCARHGLGYNGYE GAFDIWGQGTLVTVSSASTKGPSVFPLAPSSKSTSG GTAALGCLVKDYFPEPVTVSWNSGALTSGVHTFPAV LQSSGLYSLSSVVTVPSSSLGTQTYICNVNHKPSNT KVDKKVEPKSCDKTHTCPPCPAPEAAGGPSVFLFP PKPKDTLMISRTPEVTCVVVCVSHEDPEVKFNWYVD GVEVHNAKTKPREEQYNSTYRVVSVLTVLHQDWLN GKEYKCKVSNKALPAPIEKTISKAKGQPREPQVYTLP PSRDELTKNQVSLTCLVKGFYPSDIAVEWESNGQPE NNYKTTPPVLDSDGSFFLYSKLTVDKSRWQQGNVE SCSVMHEALHNHYTQKSLSLSPGK |
| SEQ ID NO: 182 | Ab249 full length heavy chain sequence; constant region underlined; (LALA-D265C-H435A mutations)* | EVQLVQSGAEVKKPGESLKISCKGSGYRFTTSWIGW VRQMPGKGLEWMGIIYPGDSDTRYSPSFQGQVTISA DKSISTAYLQWSSLKASDTAMYYCARHGLGYNGYE GAFDIWGQGTLVTVSSASTKGPSVFPLAPSSKSTSG GTAALGCLVKDYFPEPVTVSWNSGALTSGVHTFPAV LQSSGLYSLSSVVTVPSSSLGTQTYICNVNHKPSNT KVDKKVEPKSCDKTHTCPPCPAPEAAGGPSVFLFP PKPKDTLMISRTPEVTCVVVCVSHEDPEVKFNWYVD GVEVHNAKTKPREEQYNSTYRVVSVLTVLHQDWLN GKEYKCKVSNKALPAPIEKTISKAKGQPREPQVYTLP PSRDELTKNQVSLTCLVKGFYPSDIAVEWESNGQPE NNYKTTPPVLDSDGSFFLYSKLTVDKSRWQQGNVE SCSVMHEALHNAYTQKSLSLSPGK |
| SEQ ID NO: 183 | Light chain constant region | RTVAAPSVFIFPPSDEQLKSGTASVVCLLNNFYPREA KVQWKVDNALQSGNSQESVTEQDSKDSTYSLSSTL TLSKADYEKHKVYACEVTHQGLSSPVTKSFNRGEC |
| SEQ ID NO: 184 | Ab85 full length underlined light chain; constant region | DIQMTQSPSSLSASVGDRVTITCRSSQGIRSDLGWY QQKPGKAPKLLIYDASNLETGVPSRFSGSGSGTDFT LTISSLQPEDFATYYCQQANGFPLTFGGGTKVEIKRT VAAPSVFIFPPSDEQLKSGTASVVCLLNNFYPREAKV QWKVDNALQSGNSQESVTEQDSKDSTYSLSSTLTL SKADYEKHKVYACEVTHQGLSSPVTKSFNRGEC |
| SEQ ID NO: 185 | Ab249 light chain; constant region underlined | DIQMTQSPSSLSASVGDRVTITCRASQGIGSALAWY QQKPGKAPKLLIYDASNLETGVPSRFSGSGSGTDFT LTISSLQPEDFATYYCQQLNGYPLTFGQGTRLEIKRT VAAPSVFIFPPSDEQLKSGTASVVCLLNNFYPREAKV QWKVDNALQSGNSQESVTEQDSKDSTYSLSSTLTL SKADYEKHKVYACEVTHQGLSSPVTKSFNRGEC |
| SEQ ID NO: 186 | Ab249 HC-CDR1 | TSWIG |

TABLE 16-continued

AMINO ACID SEQUENCE SUMMARY

| Sequence Identifier | Description | Amino Acid Sequence |
|---|---|---|
| SEQ ID NO: 187 | Ab249 HC-CDR3 | HGLGYNGYEGAFDI |
| SEQ ID NO: 188 | Ab249 LC-CDR1 | RASQGIGSALA |
| SEQ ID NO: 189 | Ab249 LC-CDR3 | CQQLNGYPLT |

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

What is claimed is:

1. A method of depleting a population of CD117+ cells in a patient comrising administering to the patient an isolated anti-CD117 antibody, or antigen-binding fragment thereof, wherein the antibody, or antigen binding fragment thereof, comprises:
   (i) a heavy chain variable region comprising a CDR1 domain comprising the amino acid sequence as set forth in SEQ ID NO: 145, a CDR2 domain comprising the amino acid sequence as set forth in SEQ ID NO:153, and a CDR3 domain comprising the amino acid sequence as set forth in SEQ ID NO: 3; and a light chain variable region comprising a CDR1 domain comprising the amino acid sequence as set forth in SEQ ID NO: 154, a CDR2 domain comprising the amino acid sequence as set forth in SEQ ID NO:149, and a CDR3 domain comprising the amino acid sequence as set forth in SEQ ID NO: 155;
   (ii) a heavy chain variable region comprising the amino acid sequence as set forth in SEQ ID NO: 151, and a light chain variable region comprising the amino acid sequence as set forth in SEQ ID NO: 152;

(iii) a heavy chain variable region comprising a CDR1 domain comprising the amino acid sequence as set forth in SEQ ID NO: 145, a CDR2 domain comprising the amino acid sequence as set forth in SEQ ID NO: 146, and a CDR3 domain comprising the amino acid sequence as set forth in SEQ ID NO: 147; and a light chain variable region comprising a CDR1 domain comprising the amino acid sequence as set forth in SEQ ID NO: 157, a CDR2 domain comprising the amino acid sequence as set forth in SEQ ID NO: 5, and a CDR3 domain comprising the amino acid sequence as set forth in SEQ ID NO: 155;

(iv) a heavy chain variable region comprising the amino acid sequence as set forth in SEQ ID NO: 143, and a light chain variable region comprising the amino acid sequence as set forth in SEQ ID NO: 156;

(v) a heavy chain variable region comprising a CDR1 domain comprising the amino acid sequence as set forth in SEQ ID NO: 145, a CDR2 domain comprising the amino acid sequence as set forth in SEQ ID NO:159, and a CDR3 domain comprising the amino acid sequence as set forth in SEQ ID NO: 3; and a light chain variable region comprising a CDR1 domain comprising the amino acid sequence as set forth in SEQ ID NO: 157, a CDR2 domain comprising the amino acid sequence as set forth in SEQ ID NO:5, and a CDR3 domain comprising the amino acid sequence as set forth in SEQ ID NO: 155;

(vi) a heavy chain variable region comprising the amino acid sequence as set forth in SEQ ID NO: 158, and a light chain variable region comprising the amino acid sequence as set forth in SEQ ID NO: 156;

(vii) a heavy chain variable region comprising a CDR1 domain comprising the amino acid sequence as set forth in SEQ ID NO: 145, a CDR2 domain comprising the amino acid sequence as set forth in SEQ ID NO: 2, and a CDR3 domain comprising the amino acid sequence as set forth in SEQ ID NO: 3; and a light chain variable region comprising a CDR1 domain comprising the amino acid sequence as set forth in SEQ ID NO: 154, a CDR2 domain comprising the amino acid sequence as set forth in SEQ ID NO: 149, and a CDR3 domain comprising the amino acid sequence as set forth in SEQ ID NO: 155;

(viii) a heavy chain variable region comprising the amino acid sequence as set forth in SEQ ID NO: 160, and a light chain variable region comprising the amino acid sequence as set forth in SEQ ID NO: 152;

(ix) a heavy chain variable region comprising the amino acid sequence as set forth in SEQ ID NO: 98, and a light chain variable region comprising the amino acid sequence as set forth in SEQ ID NO: 102;

(x) a heavy chain variable region comprising a CDR1 domain comprising the amino acid sequence as set forth in SEQ ID NO: 186, a CDR2 domain comprising the amino acid sequence as set forth in SEQ ID NO: 2, and a CDR3 domain comprising the amino acid sequence as set forth in SEQ ID NO: 187; and a light chain variable region comprising a CDR1 domain comprising the amino acid sequence as set forth in SEQ ID NO: 188, a CDR2 domain comprising the amino acid sequence as set forth in SEQ ID NO: 149, and a CDR3 domain comprising the amino acid sequence as set forth in SEQ ID NO: 189;

(xi) a heavy chain variable region comprising the amino acid sequence as set forth in SEQ ID NO: 98, and a light chain variable region comprising the amino acid sequence as set forth in SEQ ID NO: 99;

(xii) a heavy chain variable region comprising the amino acid sequence as set forth in SEQ ID NO: 7, and a light chain variable region comprising the amino acid sequence as set forth in SEQ ID NO: 99;

(xiii) a heavy chain variable region comprising the amino acid sequence as set forth in SEQ ID NO: 7, and a light chain variable region comprising the amino acid sequence as set forth in SEQ ID NO: 100; or (xiv) a heavy chain variable region comprising the amino acid sequence as set forth in SEQ ID NO: 98, and a light chain variable region comprising the amino acid sequence as set forth in SEQ ID NO: 101.

2. The method of claim 1, wherein the antibody, or antigen binding fragment thereof, has a dissociation rate ($K_{OFF}$) of $1\times10^{-2}$ to $1\times10^{-3}$, $1\times10^{-3}$ to $1\times10^{-4}$, $1\times10^{-5}$ to $1\times10^{-6}$, $1\times10^{-6}$ to $1\times10^{-7}$ or $1\times10^{-7}$ to $1\times10^{-8}$ as measured by bio-layer interferometry (BLI).

3. The method of claim 1, wherein the antibody, or antigen binding fragment thereof, binds CD117 with a $K_D$ of about 100 nM or less, about 90 nM or less, about 80 nM or less, about 70 nM or less, about 60 nM or less, about 50 nM or less, about 40 nM or less, about 30 nM or less, about 20 nM or less, about 10 nM or less, about 8 nM or less, about 6 nM or less, about 4 nM or less, about 2 nM or less, about 1 nM or less as determined by a Bio-Layer Interferometry (BLI) assay.

4. The method of claim 1, wherein the antibody, or antigen-binding fragment thereof, is human.

5. The method of claim 1, wherein the antibody is an intact antibody.

6. method of claim 1, wherein the antibody is an IgG.

7. The method of claim 6, wherein the IgG is an IgG1 or an IgG4.

8. The method of claim 1, wherein the antibody, or antigen-binding fragment thereof, is a monoclonal antibody.

9. The method of claim 1, wherein the antibody, or antigen binding fragment thereof comprises an Fc region comprising at least one amino acid substitution selected from the group consisting of D265C, H435A, L234A, and L235A (numbering according to the EU index).

10. The method of claim 1, wherein the antibody, or antigen binding fragment thereof comprises an Fc region, wherein the Fc region comprises amino acid substitutions D265C, L234A, and L235A (numbering according to the EU index).

11. The method of claim 1, wherein the antibody, or antigen-binding portion thereof, is conjugated to a cytotoxin via a linker.

12. The method of claim 11, wherein the cytotoxin is selected from the group consisting of amatoxin, pseudomonas exotoxin A, deBouganin, diphtheria toxin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer.

13. The method of claim 12, wherein the amatoxin is selected from the group consisting of α-amanitin, β-amanitin, γ-amanitin, ε-amanitin, amanin, amaninamide, amanullin, amanullinic acid, and proamanullin.

14. A method depleting a population of CD117+ cells in a patient comprising administering to the patient an antibody drug conjugate (ADC) comprising an isolated anti-CD117 antibody conjugated to a cytotoxin via a linker, wherein the antibody comprises:

(i) a heavy chain variable region comprising a CDR1 domain comprising the amino acid sequence as set forth in SEQ ID NO: 145, a CDR2 domain comprising the amino acid sequence as set forth in SEQ ID NO:153, and a CDR3 domain comprising the amino acid sequence as set forth in SEQ ID NO: 3; and a light chain variable region comprising a CDR1 domain comprising the amino acid sequence as set forth in SEQ ID NO: 154, a CDR2 domain comprising the amino acid sequence as set forth in SEQ ID NO:149, and a CDR3 domain comprising the amino acid sequence as set forth in SEQ ID NO: 155;

(ii) a heavy chain variable region comprising the amino acid sequence as set forth in SEQ ID NO: 151, and a light chain variable region comprising the amino acid sequence as set forth in SEQ ID NO: 152;

(iii) a heavy chain variable region comprising a CDR1 domain comprising the amino acid sequence as set forth in SEQ ID NO: 145, a CDR2 domain comprising the amino acid sequence as set forth in SEQ ID NO: 146, and a CDR3 domain comprising the amino acid sequence as set forth in SEQ ID NO: 147; and a light chain variable region comprising a CDR1 domain comprising the amino acid sequence as set forth in SEQ ID NO: 157, a CDR2 domain comprising the amino acid sequence as set forth in SEQ ID NO: 5, and a CDR3 domain comprising the amino acid sequence as set forth in SEQ ID NO: 155;

(iv) a heavy chain variable region comprising the amino acid sequence as set forth in SEQ ID NO: 143, and a light chain variable region comprising the amino acid sequence as set forth in SEQ ID NO: 156;

(v) a heavy chain variable region comprising a CDR1 domain comprising the amino acid sequence as set forth in SEQ ID NO: 145, a CDR2 domain comprising the amino acid sequence as set forth in SEQ ID NO:159, and a CDR3 domain comprising the amino acid sequence as set forth in SEQ ID NO: 3; and a light chain variable region comprising a CDR1 domain comprising the amino acid sequence as set forth in SEQ ID NO: 157, a CDR2 domain comprising the amino acid sequence as set forth in SEQ ID NO:5, and a CDR3 domain comprising the amino acid sequence as set forth in SEQ ID NO: 155;

(vi) a heavy chain variable region comprising the amino acid sequence as set forth in SEQ ID NO: 158, and a light chain variable region comprising the amino acid sequence as set forth in SEQ ID NO: 156;

(vii) a heavy chain variable region comprising a CDR1 domain comprising the amino acid sequence as set forth in SEQ ID NO: 145, a CDR2 domain comprising the amino acid sequence as set forth in SEQ ID NO: 2, and a CDR3 domain comprising the amino acid sequence as set forth in SEQ ID NO: 3; and a light chain variable region comprising a CDR1 domain comprising the amino acid sequence as set forth in SEQ ID NO: 154, a CDR2 domain comprising the amino acid sequence as set forth in SEQ ID NO: 149, and a CDR3 domain comprising the amino acid sequence as set forth in SEQ ID NO: 155;

(viii) a heavy chain variable region comprising the amino acid sequence as set forth in SEQ ID NO: 160, and a light chain variable region comprising the amino acid sequence as set forth in SEQ ID NO: 152;

(ix) a heavy chain variable region comprising the amino acid sequence as set forth in SEQ ID NO: 98, and a light chain variable region comprising the amino acid sequence as set forth in SEQ ID NO: 102;

(x) a heavy chain variable region comprising a CDR1 domain comprising the amino acid sequence as set forth in SEQ ID NO: 186, a CDR2 domain comprising the amino acid sequence as set forth in SEQ ID NO: 2, and a CDR3 domain comprising the amino acid sequence as set forth in SEQ ID NO: 187; and a light chain variable region comprising a CDR1 domain comprising the amino acid sequence as set forth in SEQ ID NO: 188, a CDR2 domain comprising the amino acid sequence as set forth in SEQ ID NO: 149, and a CDR3 domain comprising the amino acid sequence as set forth in SEQ ID NO: 189;

(xi) a heavy chain variable region comprising the amino acid sequence as set forth in SEQ ID NO: 98, and a light chain variable region comprising the amino acid sequence as set forth in SEQ ID NO: 99;

(xii) a heavy chain variable region comprising the amino acid sequence as set forth in SEQ ID NO: 7, and a light chain variable region comprising the amino acid sequence as set forth in SEQ ID NO: 99;

(xiii) a heavy chain variable region comprising the amino acid sequence as set forth in SEQ ID NO: 7, and a light chain variable region comprising the amino acid sequence as set forth in SEQ ID NO: 100; or (xiv) a heavy chain variable region comprising the amino acid sequence as set forth in SEQ ID NO: 98, and a light chain variable region comprising the amino acid sequence as set forth in SEQ ID NO: 101.

15. The method of claim 14, wherein the cytotoxin is selected from the group consisting of an amatoxin, an auristatin, a maytansine, a maytansinoid, a pyrrolobenzodiazepine, and a pyrrolobenzodiazepine dimer.

16. A method of depleting a population of CD117+ cells in a patient comprising administering to the patient an antibody drug conjugate (ADC) represented by the formula Ab-Z-L-Am, wherein Ab is an antibody or antigen-binding fragment thereof that binds CD117, L is a linker, Z is a chemical moiety, and Am is an amatoxin, wherein the antibody or antigen-binding fragment thereof comprises:

(i) a heavy chain variable region comprising a CDR1 domain comprising the amino acid sequence as set forth in SEQ ID NO: 145, a CDR2 domain comprising the amino acid sequence as set forth in SEQ ID NO:153, and a CDR3 domain comprising the amino acid sequence as set forth in SEQ ID NO: 3; and a light chain variable region comprising a CDR1 domain comprising the amino acid sequence as set forth in SEQ ID NO: 154, a CDR2 domain comprising the amino acid sequence as set forth in SEQ ID NO:149, and a CDR3 domain comprising the amino acid sequence as set forth in SEQ ID NO: 155;

(ii) a heavy chain variable region comprising the amino acid sequence as set forth in SEQ ID NO: 151, and a light chain variable region comprising the amino acid sequence as set forth in SEQ ID NO: 152;

(iii) a heavy chain variable region comprising a CDR1 domain comprising the amino acid sequence as set forth in SEQ ID NO: 145, a CDR2 domain comprising the amino acid sequence as set forth in SEQ ID NO: 146, and a CDR3 domain comprising the amino acid sequence as set forth in SEQ ID NO: 147; and a light chain variable region comprising a CDR1 domain comprising the amino acid sequence as set forth in SEQ ID NO: 157, a CDR2 domain comprising the amino acid sequence as set forth in SEQ ID NO: 5, and a CDR3 domain comprising the amino acid sequence as set forth in SEQ ID NO: 155;

(iv) a heavy chain variable region comprising the amino acid sequence as set forth in SEQ ID NO: 143, and a light chain variable region comprising the amino acid sequence as set forth in SEQ ID NO: 156;

(v) a heavy chain variable region comprising a CDR1 domain comprising the amino acid sequence as set forth in SEQ ID NO: 145, a CDR2 domain comprising the amino acid sequence as set forth in SEQ ID NO:159, and a CDR3 domain comprising the amino acid sequence as set forth in SEQ ID NO: 3; and a light chain variable region comprising a CDR1 domain comprising the amino acid sequence as set forth in SEQ ID NO: 157, a CDR2 domain comprising the amino acid sequence as set forth in SEQ ID NO:5, and a CDR3 domain comprising the amino acid sequence as set forth in SEQ ID NO: 155;

(vi) a heavy chain variable region comprising the amino acid sequence as set forth in SEQ ID NO: 158, and a light chain variable region comprising the amino acid sequence as set forth in SEQ ID NO: 156;

(vii) a heavy chain variable region comprising a CDR1 domain comprising the amino acid sequence as set forth in SEQ ID NO: 145, a CDR2 domain comprising the amino acid sequence as set forth in SEQ ID NO: 2, and a CDR3 domain comprising the amino acid sequence as set forth in SEQ ID NO: 3; and a light chain variable region comprising a CDR1 domain comprising the amino acid sequence as set forth in SEQ ID NO: 154, a CDR2 domain comprising the amino acid sequence as set forth in SEQ ID NO: 149, and a CDR3 domain comprising the amino acid sequence as set forth in SEQ ID NO: 155;

(viii) a heavy chain variable region comprising the amino acid sequence as set forth in SEQ ID NO: 160, and a light chain variable region comprising the amino acid sequence as set forth in SEQ ID NO: 152;

(ix) a heavy chain variable region comprising the amino acid sequence as set forth in SEQ ID NO: 98, and a light chain variable region comprising the amino acid sequence as set forth in SEQ ID NO: 102;

(x) a heavy chain variable region comprising a CDR1 domain comprising the amino acid sequence as set forth in SEQ ID NO: 186, a CDR2 domain comprising the amino acid sequence as set forth in SEQ ID NO: 2, and a CDR3 domain comprising the amino acid sequence as set forth in SEQ ID NO: 187; and a light chain variable region comprising a CDR1 domain comprising the amino acid sequence as set forth in SEQ ID NO: 188, a CDR2 domain comprising the amino acid sequence as set forth in SEQ ID NO: 149, and a CDR3 domain comprising the amino acid sequence as set forth in SEQ ID NO: 189;

(xi) a heavy chain variable region comprising the amino acid sequence as set forth in SEQ ID NO: 98, and a light chain variable region comprising the amino acid sequence as set forth in SEQ ID NO: 99;

(xii) a heavy chain variable region comprising the amino acid sequence as set forth in SEQ ID NO: 7, and a light chain variable region comprising the amino acid sequence as set forth in SEQ ID NO: 99;

(xiii) a heavy chain variable region comprising the amino acid sequence as set forth in SEQ ID NO: 7, and a light chain variable region comprising the amino acid sequence as set forth in SEQ ID NO: 100; or (xiv) a heavy chain variable region comprising the amino acid sequence as set forth in SEQ ID NO: 98, and a light chain variable region comprising the amino acid sequence as set forth in SEQ ID NO: 101.

17. The method of claim 16, wherein the Am-L-Z is represented by formula (I)

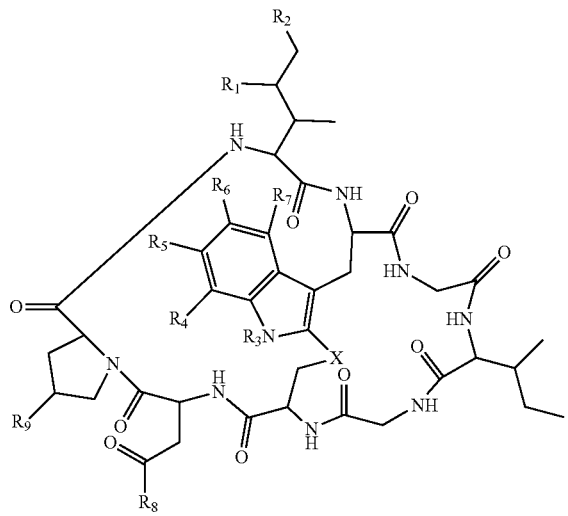

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$, $R_5$, $R_6$, and $R_7$ are each independently H, OH, $OR_C$, ORD, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;

L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, optionally substituted heteroarylene, a dipeptide, —(C═O)—, a peptide, or a combination thereof; and Z is a chemical moiety formed from a coupling reaction between a reactive substituent present on L and a reactive substituent present within the antibody or antigen-binding fragment thereof, wherein Am comprises exactly one $R_C$ substituent.

18. The method of claim 16, wherein Am-L-Z is represented by formula (IB),

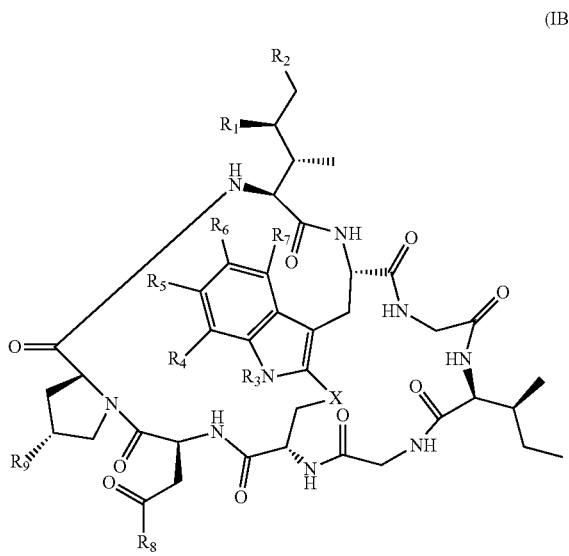

(IB)

wherein R$_1$ is H, OH, OR$_A$, or OR$_C$;
R$_2$ is H, OH, OR$_B$, or OR$_C$;
R$_A$ and R$_B$, when present, together with the oxygen atoms to which they are bound, combine to form an optionally substituted 5-membered heterocycloalkyl group;
R$_3$ is H, R$_C$, or R$_D$;
R$_4$, R$_5$, R$_6$, and R$_7$ are each independently H, OH, OR$_C$, OR$_D$, R$_C$, or R$_D$;
R$_8$ is OH, NH$_2$, OR$_C$, OR$_D$, NHR$_C$, or NR$_C$R$_D$;
R$_9$ is H, OH, OR$_C$, or OR$_D$;
X is —S—, —S(O)—, or —SO$_2$—;
R$_C$ is -L-Z;
R$_D$ is optionally substituted C$_1$-C$_6$ alkyl, optionally substituted C$_1$-C$_6$ heteroalkyl, optionally substituted C$_2$-C$_6$ alkenyl, optionally substituted C$_2$-C$_6$ heteroalkenyl, optionally substituted C$_2$-C$_6$ alkynyl, optionally substituted C$_2$-C$_6$ heteroalkynyl, optionally substituted cycloalkyl, optionally substituted heterocycloalkyl, optionally substituted aryl, or optionally substituted heteroaryl;
L is optionally substituted C$_1$-C$_6$ alkylene, optionally substituted C$_1$-C$_6$ heteroalkylene, optionally substituted C$_2$-C$_6$ alkenylene, optionally substituted C$_2$-C$_6$ heteroalkenylene, optionally substituted C$_2$-C$_6$ alkynylene, optionally substituted C$_2$-C$_6$ heteroalkynylene, optionally substituted cycloalkylene, optionally substituted heterocycloalkylene, optionally substituted arylene, optionally substituted heteroarylene, a dipeptide, —(C=O)—, a peptide, or a combination thereof; and
Z is a chemical moiety formed from a coupling reaction between a reactive substituent present on L and a reactive substituent present within the antibody or antigen-binding fragment thereof,
wherein Am comprises exactly one R$_C$ substituent.

19. The method of claim 18, wherein L-Z is

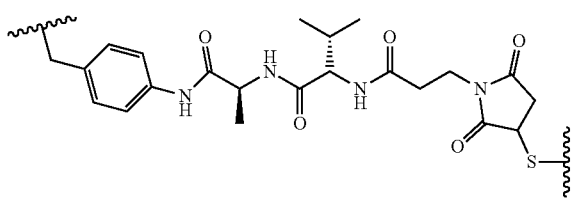

20. The method of claim 16, wherein the antibody or antigen-binding fragment thereof is conjugated to the amatoxin by way of a cysteine residue in the Fc domain of the antibody, or antigen-binding fragment thereof.

21. The method of claim 20, wherein the cysteine residue is introduced by way of a mutation in the Fc domain of the antibody or antigen-binding fragment thereof.

22. A method depleting a population of CD117+ cells in a patient comprising administering to the patient an antibody drug conjugate (ADC) represented by any one of the following:

(IV)

-continued
(IVA)
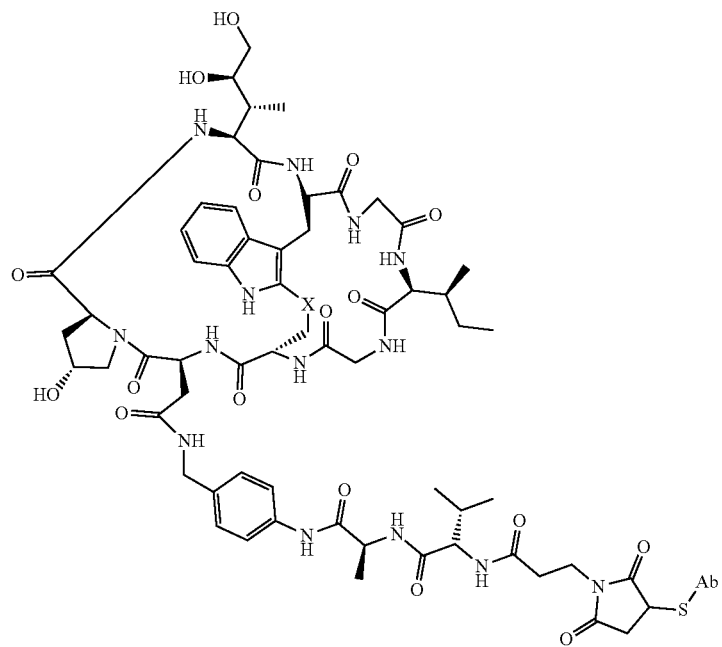
(IVB)
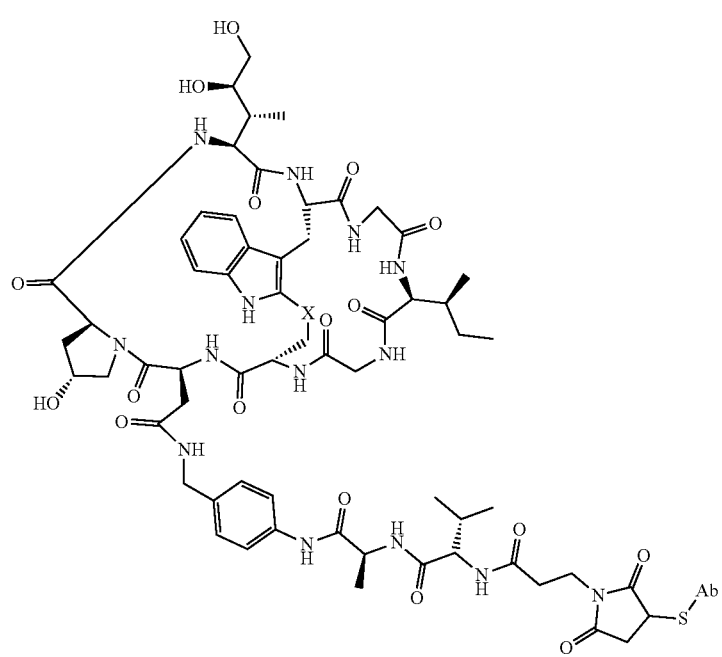

wherein X is S, SO, or SO$_2$, or

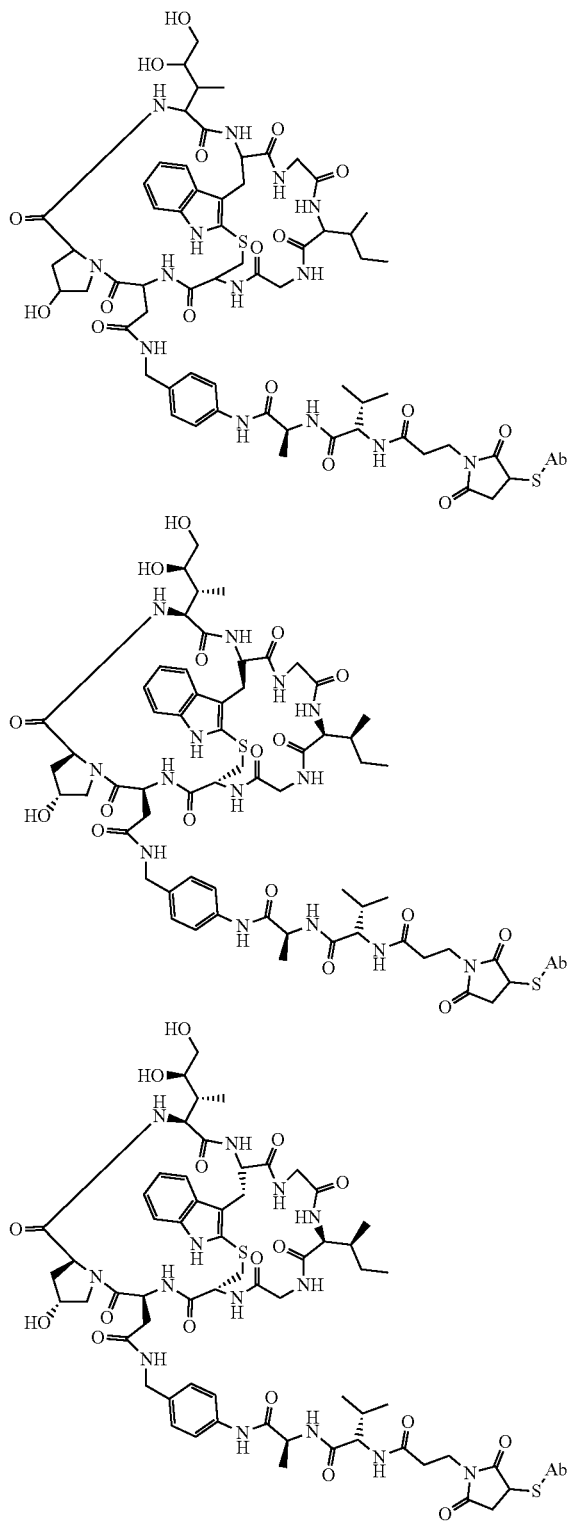

wherein Ab is an anti-CD117 antibody, or antigen-binding fragment thereof, comprising (i) a heavy chain variable region comprising a CDR1 domain comprising the amino acid sequence as set forth in SEQ ID NO: 145, a CDR2 domain comprising the amino acid sequence as set forth in SEQ ID NO:153, and a CDR3 domain comprising the amino acid sequence as set forth in SEQ ID NO: 3; and a light chain variable region comprising a CDR1 domain comprising the amino acid sequence as set forth in SEQ ID NO: 154, a CDR2 domain comprising the amino acid sequence as set forth in SEQ ID NO:149, and a CDR3 domain comprising the amino acid sequence as set forth in SEQ ID NO: 155;

(ii) a heavy chain variable region comprising the amino acid sequence as set forth in SEQ ID NO: 151, and a light chain variable region comprising the amino acid sequence as set forth in SEQ ID NO: 152;

(iii) a heavy chain variable region comprising a CDR1 domain comprising the amino acid sequence as set forth in SEQ ID NO: 145, a CDR2 domain comprising the amino acid sequence as set forth in SEQ ID NO: 146, and a CDR3 domain comprising the amino acid sequence as set forth in SEQ ID NO: 147; and a light chain variable region comprising a CDR1 domain comprising the amino acid sequence as set forth in SEQ ID NO: 157, a CDR2 domain comprising the amino acid sequence as set forth in SEQ ID NO: 5, and a CDR3 domain comprising the amino acid sequence as set forth in SEQ ID NO: 155;

(iv) a heavy chain variable region comprising the amino acid sequence as set forth in SEQ ID NO: 143, and a light chain variable region comprising the amino acid sequence as set forth in SEQ ID NO: 156;

(v) a heavy chain variable region comprising a CDR1 domain comprising the amino acid sequence as set forth in SEQ ID NO: 145, a CDR2 domain comprising the amino acid sequence as set forth in SEQ ID NO:159, and a CDR3 domain comprising the amino acid sequence as set forth in SEQ ID NO: 3; and a light chain variable region comprising a CDR1 domain comprising the amino acid sequence as set forth in SEQ ID NO: 157, a CDR2 domain comprising the amino acid sequence as set forth in SEQ ID NO:5, and a CDR3 domain comprising the amino acid sequence as set forth in SEQ ID NO: 155;

(vi) a heavy chain variable region comprising the amino acid sequence as set forth in SEQ ID NO: 158, and a light chain variable region comprising the amino acid sequence as set forth in SEQ ID NO: 156;

(vii) a heavy chain variable region comprising a CDR1 domain comprising the amino acid sequence as set forth in SEQ ID NO: 145, a CDR2 domain comprising the amino acid sequence as set forth in SEQ ID NO: 2, and a CDR3 domain comprising the amino acid sequence as set forth in SEQ ID NO: 3; and a light chain variable region comprising a CDR1 domain comprising the amino acid sequence as set forth in SEQ ID NO: 154, a CDR2 domain comprising the amino acid sequence as set forth in SEQ ID NO: 149, and a CDR3 domain comprising the amino acid sequence as set forth in SEQ ID NO: 155;

(viii) a heavy chain variable region comprising the amino acid sequence as set forth in SEQ ID NO: 160, and a light chain variable region comprising the amino acid sequence as set forth in SEQ ID NO: 152;

(ix) a heavy chain variable region comprising the amino acid sequence as set forth in SEQ ID NO: 98, and a light chain variable region comprising the amino acid sequence as set forth in SEQ ID NO: 102;

(x) a heavy chain variable region comprising a CDR1 domain comprising the amino acid sequence as set forth in SEQ ID NO: 186, a CDR2 domain comprising the amino acid sequence as set forth in SEQ ID NO: 2, and a CDR3 domain comprising the amino acid sequence as set forth in SEQ ID NO: 187; and a light chain variable region comprising a CDR1 domain comprising the amino acid sequence as set forth in SEQ ID NO: 188, a CDR2 domain comprising the amino acid sequence as set forth in SEQ ID NO: 149, and a CDR3 domain comprising the amino acid sequence as set forth in SEQ ID NO: 189;
(xi) a heavy chain variable region comprising the amino acid sequence as set forth in SEQ ID NO: 98, and a light chain variable region comprising the amino acid sequence as set forth in SEQ ID NO: 99;
(xii) a heavy chain variable region comprising the amino acid sequence as set forth in SEQ ID NO: 7, and a light chain variable region comprising the amino acid sequence as set forth in SEQ ID NO: 99;
(xiii) a heavy chain variable region comprising the amino acid sequence as set forth in SEQ ID NO: 7, and a light chain variable region comprising the amino acid sequence as set forth in SEQ ID NO: 100; or
(xiv) a heavy chain variable region comprising the amino acid sequence as set forth in SEQ ID NO: 98, and a light chain variable region comprising the amino acid sequence as set forth in SEQ ID NO: 101.

23. The method of claim 14, wherein the antibody or antigen-binding fragment thereof, comprises an Fc region comprising at least one amino acid substitution selected from the group consisting of D265C, H435A, L234A, and L235A (numbering according to the EU index).

24. The method of claim 14, wherein the antibody, or antigen binding fragment thereof, comprises an FC region, wherein the Fc region comprises D265C, L234A, and L235A (numbering according to the EU index).

25. The method of claim 14 further comprising:
administering to the patient a transplant comprising hematopoietic stem cells after administration of the ADC.

26. The method of claim 14, wherein the patient is suffering from a disorder selected from the group consisting of a stem cell disorders hemoglobinopathy disorder, myelodysplastic disorder, immunodeficiency disorder, a metabolic disorder, adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, juvenile rheumatoid arthritis and cancer.

\* \* \* \* \*

UNITED STATES PATENT AND TRADEMARK OFFICE
CERTIFICATE OF CORRECTION

PATENT NO. : 11,958,908 B2
APPLICATION NO. : 17/103866
DATED : April 16, 2024
INVENTOR(S) : Bradley R. Pearse et al.

Page 1 of 1

It is certified that error appears in the above-identified patent and that said Letters Patent is hereby corrected as shown below:

In the Claims

Claim 1, Column 375, Line 59 states:
a patient comrising administering to the patient an isolated"

Where it should state:
a patient comprising administering to the patient an isolated Claim 7, Column 378, Line 34 states:
7. The method of claim 6, wherein the IgG is an IgG1 or Where it should state:
7. The method of claim 1, wherein the IgG is an IgG1 or Claim 14, Column 378, Line 63 states:
14. A method depleting a population of CD117+ cells in Where it should state:
14. A method of depleting a population of CD117+ cells in Claim 17, Column 382, Line 39 states:
ORD, $R_C$, or $R_D$;

Where it should state:
OR$_D$, $R_C$, or $R_D$;

Signed and Sealed this
Seventeenth Day of December, 2024

Derrick Brent
*Acting Director of the United States Patent and Trademark Office*